United States Patent
Ohlmann et al.

(10) Patent No.: US 11,649,264 B2
(45) Date of Patent: *May 16, 2023

(54) METHODS AND PRODUCTS FOR GENETIC ENGINEERING

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); ECOLE NORMALE SUPERIEURE DE LYON, Lyons (FR); UNIVERSITE CLAUDE BERNARD LYON 1, Villeurbanne (FR)

(72) Inventors: Théophile Ohlmann, Tassin la Demi-Lune (FR); Philippe Mangeot, Lyons (FR); Emiliano Ricci, Lyons (FR)

(73) Assignees: Institut National De La Sante Et De La Recherche Medicale (INSERM), Paris (FR); Centre National De La Recherche Scientifique (CNRS), Paris (FR); Ecole Normale Superieure De Lyon, Lyons (FR); Universite De Claude Bernard Lyon 1, Villeurbanne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,405

(22) Filed: Feb. 12, 2021

(65) Prior Publication Data
US 2021/0284697 A1 Sep. 16, 2021

Related U.S. Application Data

(63) Continuation of application No. 15/769,534, filed as application No. PCT/EP2016/075289 on Oct. 20, 2016, now Pat. No. 10,968,253.

(30) Foreign Application Priority Data

Oct. 20, 2015 (EP) ..................................... 15306678

(51) Int. Cl.
| | | |
|---|---|---|
| C07K 14/005 | (2006.01) | |
| C12N 9/22 | (2006.01) | |
| C12N 7/00 | (2006.01) | |
| C12N 15/10 | (2006.01) | |
| C12N 15/113 | (2010.01) | |

(52) U.S. Cl.
CPC .............. C07K 14/005 (2013.01); C12N 7/00 (2013.01); C12N 9/22 (2013.01); C12N 15/102 (2013.01); C12N 15/113 (2013.01); C07K 2319/00 (2013.01); C07K 2319/43 (2013.01); C07K 2319/50 (2013.01); C12N 2310/20 (2017.05); C12N 2740/10023 (2013.01); C12N 2740/10042 (2013.01); C12N 2740/13023 (2013.01); C12N 2740/13042 (2013.01); C12N 2800/80 (2013.01)

(58) Field of Classification Search
CPC .............. C07K 14/005; C07K 2319/00; C07K 2319/43; C07K 2319/50; C12N 7/00; C12N 15/102; C12N 15/113; C12N 9/22; C12N 2310/20; C12N 2800/80; C12N 2740/10023; C12N 2740/13023; C12N 2740/13042; C12N 2740/10042; C12N 15/90

See application file for complete search history.

(56) References Cited

U.S. PATENT DOCUMENTS

| | | | |
|---|---|---|---|
| 2011/0189159 A1 | 8/2011 | Chatterjee | |
| 2011/0262483 A1* | 10/2011 | Haynes ................... | A61P 31/14 435/69.3 |
| 2012/0269840 A1* | 10/2012 | Barnett ................... | A61P 31/18 424/188.1 |
| 2016/0074427 A1 | 3/2016 | Kishimoto | |
| 2016/0340661 A1* | 11/2016 | Cong ...................... | A61P 27/02 |
| 2016/0367702 A1 | 12/2016 | Hoge | |
| 2019/0010518 A1 | 1/2019 | Quake | |

FOREIGN PATENT DOCUMENTS

| | | |
|---|---|---|
| WO | WO-1992/12237 | 7/1992 |
| WO | WO 1995/022617 | 8/1995 |
| WO | WO-2010/040023 | 4/2010 |
| WO | WO 2013/163628 | 10/2013 |
| WO | WO-2014/131833 | 4/2014 |
| WO | WO 2014/093595 | 6/2014 |
| WO | WO 2015/089247 | 6/2015 |
| WO | WO 2015/089486 | 6/2015 |
| WO | WO-2016/073433 | 5/2016 |
| WO | WO-2017/106822 | 6/2017 |

OTHER PUBLICATIONS

Cai et al., "Targeted genome editing by lentiviral protein transduction of zinc-finger and TAL-effector nucleases," Elife Sciences Publications (2014) 3:1-19.
Choi JG, Dang Y, Abraham S, Ma H, Zhang J, Guo H, Cai Y, Mikkelsen JG, Wu H, Shankar P, Manjunath N. Lentivirus prepacked with Cas9 protein for safer gene editing. Gene Ther. Jul. 2016 ;23(7) :627-33. doi: 10.1038/gt.2016.27. Epub Apr. 7, 2016.
Dale et al., Tracking and quantitation of fluorescent HIV during cell-cell transmission, Methods. Jan. 2011; 53(1): 20-26. DOI:10.1016/J.YMETH.2010.06.018.
Fenard D, Ingrao D, Seye A, Buisset J, Genries S, Martin S, Kichler A, Galy A. Vectofusin-1, a new viral entry enhancer, strongly promotes lentiviral transduction of human hematopoietic stem cells. Mol Ther Nucleic Acids. May 7, 2013;2:e90.

(Continued)

*Primary Examiner* — Rachel B Gill
(74) *Attorney, Agent, or Firm* — Morrison & Foerster LLP

(57) ABSTRACT

The present invention relates to a virus-derived particle comprising one or more Cas protein(s), as well as to kits and methods using the same for altering a target nucleic acid.

48 Claims, 25 Drawing Sheets

Specification includes a Sequence Listing.

(56) References Cited

OTHER PUBLICATIONS

Fu A, Tang R, Hardie J, Farkas ME, Rotella VM. Promises and pitfalls of intracellular delivery of proteins. Bioconjug Chem. Sep. 17, 2014;25(9):1602-8. Epub Sep. 2, 2014.
Garrone et al.: "A prime-boost Strategy Using Virus-Like Particles Pseudotyped for HCV Proteins Triggers Broadly Neutralizing Antibodies in Macaques", Science Tanslation Medicine. Aug. 3, 2011. vol. 3 Issue 94 94RA71.
Gori JL, Hsu PD, Maeder ML, Shen S, Welstead GG, Bumcrot D. Delivery and Specificity of CRISPR-Cas9 Genome Editing Technologies for Human Gene Therapy. Hum Gene Ther. Jul. 2015;26(7):443-51.
Hackett PB, Samia NV. Delivering the second revolution in site-specific nucleases. Elife. May 8, 2014;3:e02904.
Hill BD, Zak A, Khera E, Wen F. Engineering Virus-like Particles for Antigen and Drug Delivery. Curr Protein Pept Sci. 2018;19(1):112-127.
Horii et al: "Efficient generation of knockin mice by CRISPR/Cas system", Experimental Animals vol. 64, abstract, 2015.
Kaczmarczyk SJ, Sitaraman K, Young HA, Hughes SH, Chatterjee DK. Protein delivery using engineered virus-like particles. Proc Natl Acad Sci U SA. Oct. 11, 2011; 108(41): 16998-7003. Epub Sep. 26, 2011.
Kim et al., "Highly efficient Genome RNA-guided Research, genome vol. 24, editing pages in human 1012-1019, cells via 2014 delivery of purified Cas9 ribonucleoproteins," Genome Research (2014) 24:1012-1019.
Lafountaine et al: "Delivery and therapeutic applications of gene editing technologies ZFNs, TALENs, and :;RISPR/Cas9", International Journal of Pharmaceutics, vol. 494, pp. 180-194, Aug. 13, 2015.
Mangeot et al.: "Protein Transfer Into Human Cells by VSV-G-induced Nanovesicles", The American Society of Gene & Cell Therapy. Published Online Jul. 12, 2011. DOI: 10.1038/MT.2011.138.
Mateu MG. Assembly, Engineering and Applications of Virus-Based Protein Nanoparticles. Adv Exp Med Biol. 2016;940:83-120. Review. PubMed PMID: 27677510.
Oji et al: "Complex genome editing in mouse ES cells using the CRISPR/Cas system", Experimental Animals.
Qazi et al: "Programmed Self-Assembly of an Active P22-Cas9 Nanocarrier System", Molecular Phamaceutics, vol. 13, pp. 1191-1196, Mar. 7, 2016.
Ramakrishna et al: "Gene disruption by cell-penetrating peptide-mediated delivery of Cas9 protein and guide RNA", Genome Research, vol. 24, pp. 1020-1027, Apr. 2, 2014.
Sakuma T, Nishikawa A, Kume S, Chayama K, Yamamoto T. Multiplex genome engineering in human cells using all-in-one CRISPR/Cas9 vector system. Sci Rep. Jun. 23, 2014;4:5400.
Skipper KA, Mikkelsen JG. Delivering the Goods for Genome Engineering and Editing. Hum Gene Ther. Aug. 2015;26(8):486-97.
Sun et al: "Self-Assembled DNA Nanoclews for the Efficient Delivery of CRISPR-Cas9 for Genome Editing", I\Ngewandte Chemie International Edition, vol. 54, No. 41, pp. 12029-12033, Oct. 5, 2015.
Voelkel et al. "Protein transduction from retroviral Gag precursors", www.pnas.org/cgi/doi/10.1073/ pnas.0914517107, Apr. 27, 2010.
Cai et al., "Targeted genome editing by lentiviral protein transduction of ZFN and Cas9 proteins," Selected oral presentation (2014) A31:OR021.
Hochstrasser et al., "CasA mediates Cas3-catalyzed target degradation during CRISPR RNA-guided interference," PNAS (2014) 111(18):6618-6623.
Abe et al., "In vitro cell-free conversion of noninfectious moloney retrovirus particles to an infectious form by the addition of the vesicular stomatitis virus surrogate envelope G protein," J. Virol. 72(8):6356-6361 (1998) XP00913189C.

Aliyari et al., "RNA-based viral immunity initiated by the Dicer family of host immune receptors," Immunol Rev. (2009) 227(1):176-88.
Anastasov et al., Lentiviral vectors and exosomes as gene and protein delivery tools, in Methods in Molecular Biology, (2016) 1448: 49-61.
Brandler et al. "Recombinant vector derived from live attenuated measles virus: potential for flavivirus vaccines," Comp Immunol Microbiol Infect Dis. (2008) 31 (No. 2-3): 271-291.
Brown et al., "Assembly of hybrid bacteriophage Qbeta virus-like particles," Biochemistry. (2009) 48(47):11155-11157.
Cass et al., "The role of Cas8 in type I CRISPR interference," Biosci Rep. (2015) 5;35(3):e00197. (doi:10.1042/BSR20150043) (24 pages).
Cervera et al., "Generation of HIV-1 Gag VLPs by transient transfection of HEK 293 suspension cell cultures using an optimized animal-derived component free medium," J Biotechnol. (2013) 166(4): 152-65.
Chylinski et al. "The tracrRNA and Cas9 families of type II CRISPR-Cas immunity systems," RNA Biol. May 1, 2013; 10(5): 726-737.
Chylinski et al., "Classification and evolution of type II CRISPR-Cas systems," Nucleic Acids Res. (2014) 42(10):6091-105.
Cong et al., "Multiplex Genome Engineering Using CRISPR/Cas Systems," Science (2013) 339(6121): 819-823.
Cronin et al., "Altering the tropism of lentiviral vectors through pseudotyping," Curr Gene Ther. (2005) 5(4):387-98.
DiCarlo et al., "Genome engineering in *Saccharomyces cerevisiae* using CRISPR-Cas systems," Nucleic Acids Res. (2013) 41(7):4336-43.
Esvelt et al., "Orthogonal Cas9 proteins for RNA-guided gene regulation and editing," Nat Methods. (2013) 10(11):1116-21. doi: 10.1038/nmeth.2681 (18 pages).
Fabre et al., "CRISPR is an optimal target for the design of specific PCR assays for *Salmonella enterica* serotypes Typhi and Paratyphi A," PLoS Negl Trop Dis. (2014) 8(1):e2671 (11 pages).
Farboud et al. "Dramatic Enhancement of Genome Editing by CRISPR/Cas9 Through Improved Guide RNA Design," Genetics, (2015) 199(4); 959-971, (doi 10.1534/genetics.115.175166).
Fontana et al., "Rabies virus-like particles expressed in HEK293 cells," Vaccine. (2014) 32(24); 2799-804.
Gasiunas et al., "Cas9-crRNA ribonucleoprotein complex mediates specific DNA cleavage for adaptive immunity in bacteria," Proc Natl Acad Sci USA. (2012) 109(39):E2579-86.
Girard-Gagnepain et al., "Baboon envelope pseudotyped LVs outperform VSV-G-LVs for gene transfer into early-cytokine-stimulated and resting HSCs," Blood.(2014) 124 (8): 1221-1231.
Gong et al., "Mechanism of nonhomologous end-joining in mycobacteria: a low-fidelity repair system driven by Ku, ligase D and ligase C," Nat Struct Mol Biol. (2005) 12(4):304-12.
Gratz et al., "Highly specific and efficient CRISPR/Cas9-catalyzed homology-directed repair in *Drosophila*," Genetics. (2014) 196(4):961-71. doi:10.1534/genetics.113.160713.
Guibingua et al., "Cell surface heparan sulfate is a receptor for attachment of envelope protein-free retrovirus-like particles and VSV-G pseudotyped MLV-derived retrovirus vectors to target cells," Mol Ther. (2002) 5(5 Pt 1):538-46.
Guo et al., Efficient RNA/Cas9-mediated genome editing in Xenopus tropicalis, 2014, Development. (2014) 141(3):707-14.
Hai et al.,"One-step generation of knockout pigs by zygote injection of CRISPR/Cas system," (2014) Cell Res. 24: 372-375. doi: 10.1038/cr.2014.11.
Heler et al., "Cas9 specifies functional viral targets during CRISPR-Cas adaptation," Nature. (2015) 519(7542): 199-202.
Herbst-Kralovetz et al., "Norwalk virus-like particles as vaccines," Expert Rev Vaccines. (2010) 9(3): 299-307.
Hong et al.,"Novel recombinant hepatitis B virus vectors efficiently deliver protein and RNA encoding genes into primary hepatocytes," J Virol. (2013) 87(12):6615-24.
Hwang et al., "Heritable and precise zebrafish genome editing using a CRISPR-Cas system," PLoS One. (2013) 8(7):e68708 (9 pages).
Jalaguier et al., "Efficient production of HIV-1 virus-like particles from a mammalian expression vector requires the N-terminal capsid domain," PLoS One. (2011) 6(11):e28314 (13 pages).

(56) References Cited

OTHER PUBLICATIONS

Jao et al., "Efficient multiplex biallelic zebrafish genome editing using a CRISPR nuclease system," Proc Natl Acad Sci U S A. (2013) 110(34):13904-13909.

Jinek et al., "A Programmable Dual-RNA-Guided DNA Endonuclease in Adaptive Bacterial Immunity," Science. (2012) 337(6096):816-21.

Jinek et al., "RNA-programmed genome editing in human cells," Elife. (2013) 2:e00471. doi: 10.7554/eLife.00471 (9 pages).

Johnston et al., "High-throughput screening identifies compounds that enhance lentiviral transduction," Gene Ther. (2014) 21(12):1008-20.

Kajigaya et al., "Self-assembled B19 parvovirus capsids, produced in a baculovirus system, are antigenically and immunogenically similar to native virions," Proc Natl Acad Sci USA. (1991) 88(11):4646-50.

Kang et al., "Chimeric rabies virus-like particles containing membrane-anchored GM-CSF enhances the immune response against rabies virus," Viruses. (2015) 7(3): 1134-52. doi: 10.3390/v7031134.

Kieusseian et al., "Expression of Pitx2 in stromal cells is required for normal hematopoiesis," Blood. (2006) 107(2):492-500.

Kirnbauer et al., "Virus-like particles of bovine papillomavirus type 4 in prophylactic and therapeutic immunization," Virology. (1996) 219(1):37-44.

Kushnir et al., "Virus-like particles as a highly efficient vaccine platform: diversity of targets and production systems and advances in clinical development," Vaccine. (2012) 31(1):58-83.

Latham et al., "Formation of wild-type and chimeric influenza virus-like particles following simultaneous expression of only four structural proteins," J Virol. (2001) 75(13):6154-65.

Li et al., "Expression and self-assembly of empty virus-like particles of hepatitis E virus," J Virol. (1997) 71(10):7207-13.

Lin et al., "Enhanced homology-directed human genome engineering by controlled timing of CRISPR/Cas9 delivery," Elife. (2014) 15;3:e04766 (13 pages).

Lombardo et al., "TLR4-mediated survival of macrophages is MyD88 dependent and requires TNF-alpha autocrine signalling," J Immunol. (2007) 178(6): 3731-3739.

Ludwig et al., "Virus-like particles-universal molecular toolboxes," Curr Opin Biotechnol. (2007) 18(6):537-45.

Ma et al., "A guide RNA sequence design platform for the CRISPR/Cas9 system for model organism genomes," Biomed Res Int. (2013) ;2013:270805. doi: 10.1155/2013/270805 (4 pages).

Ma et al., "Generating rats with conditional alleles using CRISPR/Cas9," Cell Res. (2014) 24(1):122-5.

Maeder et al., "CRISPR RNA-guided activation of endogenous human genes," Nat Methods. (2013) 10(10):977-9.

Maetzig et al., "Retroviral protein transfer: falling apart to make an impact," Curr Gene Ther. (2012) 12(5):389-409.

Makarova et al., "Unification of Cas protein families and a simple scenario for the origin and evolution of CRISPR-Cas systems," Biol Direct. 2011; 6: 38 (27 pages).

Mali et al., "RNA-guided human genome engineering via Cas9," Science. (2013) 339(6121): 823-826.

Mangeot et al., "A universal transgene silencing method based on RNA interference," Nucleic Acids Res. (2004) 32(12):e102 (6 pages).

Mangeot et al., "Development of minimal lentivirus vectors derived from simian immunodeficiency virus (SIVmac251) and their use for gene transfer into human dendritic cells," J Virol. (2000) 74(18): 8307-8315.

Markowitz et al., "A safe packaging line for gene transfer: separating viral genes on two different plasmids," J. Virol. (1988) 62(4): 1120-1124.

Mashiko et al., "Feasibility for a large scale mouse mutagenesis by injecting CRISPR/Cas plasmid into zygotes," Dev Growth Differ. (2014) 56(1):122-9.

Mselli-Lakhal et al., "Gene transfer system derived from the caprine arthritis-encephalitis lentivirus," J Virol Methods. (2006) 136(1-2):177-184.

Murawski et al., "Newcastle disease virus-like particles containing respiratory syncytial virus G protein induced protection in BALB/c mice, with no evidence of immunopathology," J Virol. (2010) 84(2):1110-23.

Naskalska et al., "Virus Like Particles as Immunogens and Universal Nanocarriers," Pol J Microbiol. (2015) 64(1): 3-13.

Negre et al., "Characterization of novel safe lentiviral vectors derived from simian immunodeficiency virus (SIVmac251) that efficiently transduce mature human dendritic cells," (2000) Gene Ther. 7(19): 1613-1623.

Niu et al., "Generation of gene-modified cynomolgus monkey via Cas9/RNA-mediated gene targeting in one-cell embryos," Cell. (2014) 156(4): 836-43.

O'Connell et al., "Programmable RNA recognition and cleavage by CRISPR/Cas9," Nature. (2014) 516(7530): 263-266.

Ogasawara et al., "Recombinant viral-like particles of parvovirus B19 as antigen carriers of anthrax protective antigen," In Vivo. (2006) 20(3): 319-24.
Okimoto et al., "VSV-G envelope glycoprotein forms complexes with plasmid DNA and MLV retrovirus-like particles in cell-free conditions and enhances DNA transfection," Mol Ther. (2001) 4(3): 232-8.
Olsen, "Gene transfer vectors derived from equine infectious anemia virus," Gene Ther. (1998) 5(11):1481-1487.
Overballe-Petersen et al., "Bacterial natural transformation by highly fragmented and damaged DNA," Proc Natl Acad Sci USA. (2013) 110(49):19860-19865.
Peifang et al., "Enhanced activation of human T cell clones specific for virus-like particles expressing the HIV V3 loop in the presence of HIV V3 loop-specific polyclonal antibodies," Clin Exp Immunol. (1994) 97(3): 361-6.
Qi et al., "Repurposing CRISPR as an RNA-guided platform for sequence-specific control of gene expression," Cell. (2013) 152(5): 1173-83.
Quan et al., "Influenza M1 VLPs containing neuraminidase induce heterosubtypic cross-protection," Virology. (2012) 430(2): 127-35.
Ran et al., "Double nicking by RNA-guided CRISPR Cas9 for enhanced genome editing specificity," Cell. (2013) 154(6): 1380-9.
Rasmussen et al., "Characterization of virus-like particles produced by a recombinant baculovirus containing the gag gene of the bovine immunodeficiency-like virus," Virology. (1990) 178(2): 435-51.
Ruffing et al., "Assembly of viruslike particles by recombinant structural proteins of adeno-associated virus type 2 in insect cells," J Virol. (1992) 66(12):6922-6930.
Saenz et al., "Feline immunodeficiency virus-based lentiviral vectors," Cold Spring Harb Protoc. (2012) 2012(1):71-6.
Saenz et al., "Production, harvest, and concentration of feline immunodeficiency virus-based lentiviral vector from cells grown in CF10 or CF2 devices," Cold Spring Harb Protoc. (2012) 2012(1): 118-23.
Saenz et al., "Production and harvest of feline immunodeficiency virus-based lentiviral vector from cells grown in T75 tissue-culture flasks," Cold Spring Harb Protoc. (2012) 2012(1):124-125.
Samulski et al., "Helper-free stocks of recombinant adeno-associated viruses: normal integration does not require viral gene expression," J Virol. (1989) 63(9): 3822-8.
Sanjana et al., "Improved vectors and genome-wide libraries for CRISPR screening," Nat Methods. (2014) 11(8):783-784.
Shalem et al., "Genome-scale CRISPR-Cas9 knockout screening in human cells," Science. (2014) 343(6166): 84-87.
Sharma et al., "Noninfectious virus-like particles produced by Moloney murine leukemia virus-based retrovirus packaging cells deficient in viral envelope become infectious in the presence of lipofection reagents," Proc Natl Acad Sci USA. (1997) 94(20): 10803-10808.
Sinkunas et al., "Cas3 is a single-stranded DNA nuclease and ATP-dependent helicase in the CRISPR/Cas immune system," EMBO J. (2011) 30(7):1335-42.
Takahara et al., "A new retrovirus packaging cell for gene transfer constructed from amplified long terminal repeat-free chimeric proviral genes," J Virol. (1992) 66(6): 3725-3732.

(56) References Cited

OTHER PUBLICATIONS

Tomé-Amat et al., "Secreted production of assembled Norovirus virus-like particles from Pichia pastoris," Microb Cell Fact. (2014) 13:134-142.

Wagner et al., "Transfer of genes into embryonal carcinoma cells by retrovirus infection: efficient expression from an internal promoter," EMBO J. (1985) 4(3):663-6.

Walpita et al., "Mammalian Cell-Derived Respiratory Syncytial Virus-Like Particles Protect the Lower as well as the Upper Respiratory Tract," PLoS One. (2015) 10(7): e0130755 (18 pages).

Wang et al., "One-step generation of mice carrying mutations in multiple genes by CRISPR/Cas-mediated genome engineering," Cell. (2013) 153(4):910-918.

Wang et al., "Virus-like particles for the prevention of human papillomavirus-associated malignancies," Expert Rev Vaccines. (2013) 12(2):129-41.

Yang et al., "Effective gene targeting in rabbits using RNA-guided Cas9 nucleases," J Mol Cell Biol. (2014) 6(1):97-99.

Yang et al., "HIV-1 virus-like particles produced by stably transfected *Drosophila* S2 cells: a desirable vaccine component," J Virol. (2012) 86(14):7662-7676.

Yee et al., "A general method for the generation of high-titer, pantropic retroviral vectors: highly efficient infection of primary hepatocytes," Proc Natl Acad Sci USA. (1994) 91(20):9564-9568.

Yee et al., "Generation of high-titer pseudotyped retroviral vectors with very broad host range," Methods Cell Biol. (1994);43 Pt A: 99-112.

Zeltins, Andris. "Construction and characterization of virus-like particles: a review." Mol Biotechnol. (2013) 53(1): 92-107.

Zetsche et al., "Cpf1 is a single RNA-guided endonuclease of a class 2 CRISPR-Cas system," Cell. (2015) 163(3):759-71. http://dx.doi.org/10.1016/j.cell.2015.09.038.

Zhao et al., "BPV1 E2 protein enhances packaging of full-length plasmid DNA in BPV1 pseudovirions," Virology. (2000) 272(2): 382-93.

Zhu et al., "CRISPRseek: a bioconductor package to identify target-specific guide RNAs for CRISPR-Cas9 genome-editing systems," PLoS One. (2014) 9(9):e108424 (7 pages).

Zuris, John A., et al. "Cationic lipid-mediated delivery of proteins enables efficient protein-based genome editing in vitro and in vivo." Nature biotechnology 33.1 (2015): 73-80.

Aoki et al., "Protein transduction by pseudotyped lentivirus-like nanoparticles," Gene Therapy (2011) 1-6.

Zuris et al., "Efficient delivery of genome-editing proteins in vitro and in vivo," Nat Biotechnol (2015) 33(1):73-80.

* cited by examiner

Myd88-Cas 9 VLPs

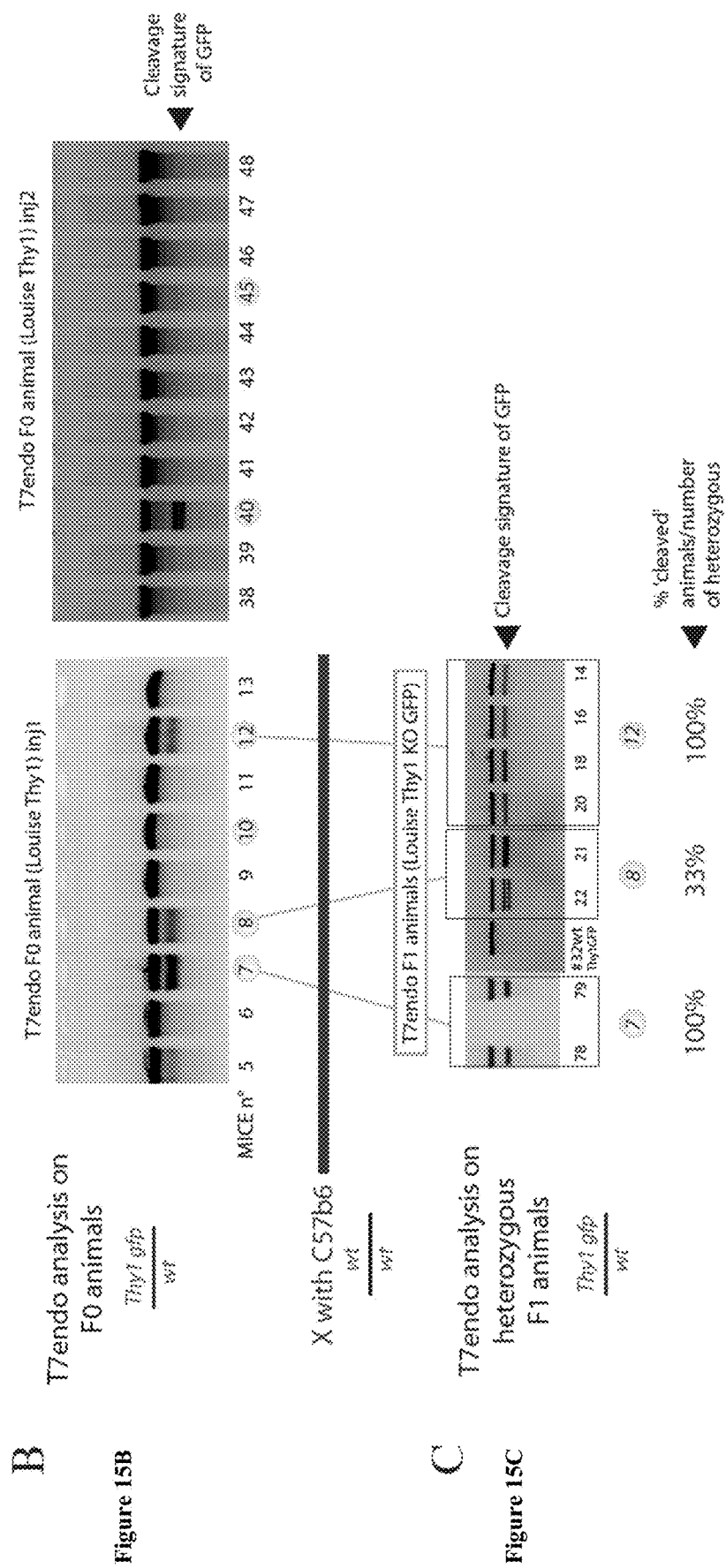

SEQUENCE LISTING

<160> NUMBER OF SEQ ID NOS: 40

<210> SEQ ID NO 1
<211> LENGTH: 25
<212> TYPE: DNA
<213> ORGANISM: Artificial Sequence
<220> FEATURE:
<223> OTHER INFORMATION: Synthetic YFPgRNA1f primer
<220> FEATURE:
<223> OTHER INFORMATION: YFPgRNA1f primer

<400> SEQUENCE: 1
caccgcgagg agctgttcac cgggg                                         25

<210> SEQ ID NO 2
<211> LENGTH: 25
<212> TYPE: DNA
<213> ORGANISM: Artificial Sequence
<220> FEATURE:
<223> OTHER INFORMATION: Synthetic YFPgRNA1r primer
<220> FEATURE:
<223> OTHER INFORMATION: YFPgRNA1r primer

<400> SEQUENCE: 2 aaaccccgg tgaacagctc ctcgc                                          25

<210> SEQ ID NO 3
<211> LENGTH: 25
<212> TYPE: DNA
<213> ORGANISM: Artificial Sequence
<220> FEATURE:
<223> OTHER INFORMATION: Synthetic YFPgRNA2f primer
<220> FEATURE:
<223> OTHER INFORMATION: YFPgRNA2f primer

<400> SEQUENCE: 3
caccgtcacc ataccggtag ccagc                                         25

<210> SEQ ID NO 4
<211> LENGTH: 25

```
<212> TYPE: DNA
<213> ORGANISM: Artificial Sequence
<220> FEATURE:
<223> OTHER INFORMATION: Synthetic YFPgRNA2r primer
<220> FEATURE:
<223> OTHER INFORMATION: YFPgRNA2r primer

<400> SEQUENCE: 4
aaacgctggc taccggtatg gtgac                                      25

<210> SEQ ID NO 5
<211> LENGTH: 25
<212> TYPE: DNA
<213> ORGANISM: Artificial Sequence
<220> FEATURE:
<223> OTHER INFORMATION: Synthetic hMyd88gRNA1f primer
<220> FEATURE:
<223> OTHER INFORMATION: hMyd88gRNA1f primer

<400> SEQUENCE: 5
caccggagac ctcaagggta gaggt                                      25

<210> SEQ ID NO 6
<211> LENGTH: 25
<212> TYPE: DNA
<213> ORGANISM: Artificial Sequence
<220> FEATURE:
<223> OTHER INFORMATION: Synthetic hMyd88gRNA1r primer
<220> FEATURE:
<223> OTHER INFORMATION: hMyd88gRNA1r primer

<400> SEQUENCE: 6
aaacacctct acccttgagg tctcc                                      25

<210> SEQ ID NO 7
<211> LENGTH: 25
<212> TYPE: DNA
<213> ORGANISM: Artificial Sequence
<220> FEATURE:
<223> OTHER INFORMATION: Synthetic hMyd88gRNA2f primer
<220> FEATURE:
<223> OTHER INFORMATION: hMyd88gRNA2f primer

<400> SEQUENCE: 7
caccggcagc catggcgggc ggtcc                                      25

<210> SEQ ID NO 8
<211> LENGTH: 25
<212> TYPE: DNA
<213> ORGANISM: Artificial Sequence
<220> FEATURE:
<223> OTHER INFORMATION: Synthetic hMyd88gRNA2r primer
<220> FEATURE:
<223> OTHER INFORMATION: hMyd88gRNA2r primer

<400> SEQUENCE: 8
aaacggaccg cccgccatgg ctgcc                                      25

<210> SEQ ID NO 9
<211> LENGTH: 25
<212> TYPE: DNA
<213> ORGANISM: Artificial Sequence
<220> FEATURE:
<223> OTHER INFORMATION: Synthetic mMyd88gRNA1f primer
<220> FEATURE:
<223> OTHER INFORMATION: mMyd88gRNA1f primer
```

<400> SEQUENCE: 9
caccggagcg tactggacgg caccg                                        25

<210> SEQ ID NO 10
<211> LENGTH: 25
<212> TYPE: DNA
<213> ORGANISM: Artificial Sequence
<220> FEATURE:
<223> OTHER INFORMATION: Synthetic mMyd88gRNA1r primer
<220> FEATURE:
<223> OTHER INFORMATION: mMyd88gRNA1r primer

<400> SEQUENCE: 10
aaaccggtgc cgtccagtac gctcc                                        25

<210> SEQ ID NO 11
<211> LENGTH: 25
<212> TYPE: DNA
<213> ORGANISM: Artificial Sequence
<220> FEATURE:
<223> OTHER INFORMATION: Synthetic mMyd88gRNA2f primer
<220> FEATURE:
<223> OTHER INFORMATION: mMyd88gRNA2f primer

<400> SEQUENCE: 11
caccggccca tctcctccgc cagca                                        25

<210> SEQ ID NO 12
<211> LENGTH: 25
<212> TYPE: DNA
<213> ORGANISM: Artificial Sequence
<220> FEATURE:
<223> OTHER INFORMATION: Synthetic  mMyd88gRNA2r primer
<220> FEATURE:
<223> OTHER INFORMATION: mMyd88gRNA2r primer

<400> SEQUENCE: 12
aaactgctgg cggaggagat gggcc                                        25

<210> SEQ ID NO 13
<211> LENGTH: 25
<212> TYPE: DNA
<213> ORGANISM: Artificial Sequence
<220> FEATURE:
<223> OTHER INFORMATION: Synthetic DDX3gRNA1f primer
<220> FEATURE:
<223> OTHER INFORMATION: DDX3gRNA1f primer

<400> SEQUENCE: 13
caccgaggga tgagtcatgt ggcag                                        25

<210> SEQ ID NO 14
<211> LENGTH: 25
<212> TYPE: DNA
<213> ORGANISM: Artificial Sequence
<220> FEATURE:
<223> OTHER INFORMATION: Synthetic DDX3gRNA1r primer
<220> FEATURE:
<223> OTHER INFORMATION: DDX3gRNA1r primer

<400> SEQUENCE: 14
aaacctgcca catgactcat ccctc                                        25

<210> SEQ ID NO 15
<211> LENGTH: 51
<212> TYPE: DNA

<213> ORGANISM: Artificial Sequence
<220> FEATURE:
<223> OTHER INFORMATION: Synthetic YFPf primer
<220> FEATURE:
<223> OTHER INFORMATION: YFPf primer

<400> SEQUENCE: 15
tctaatacga ctcactatag ggagaggtct atataagcag agctcgttta g        51

<210> SEQ ID NO 16
<211> LENGTH: 25
<212> TYPE: DNA
<213> ORGANISM: Artificial Sequence
<220> FEATURE:
<223> OTHER INFORMATION: Synthetic YFPr primer
<220> FEATURE:
<223> OTHER INFORMATION: YFPr primer

<400> SEQUENCE: 16
ggccatgata tagacgttgt ggctg                                      25

<210> SEQ ID NO 17
<211> LENGTH: 23
<212> TYPE: DNA
<213> ORGANISM: Artificial Sequence
<220> FEATURE:
<223> OTHER INFORMATION: Synthetic hMyd88f2 primer
<220> FEATURE:
<223> OTHER INFORMATION: hMyd88f2 primer

<400> SEQUENCE: 17
ttacgccccc cacatcaccc gcc                                        23

<210> SEQ ID NO 18
<211> LENGTH: 24
<212> TYPE: DNA
<213> ORGANISM: Artificial Sequence
<220> FEATURE:
<223> OTHER INFORMATION: Synthetic hMyd88r1 primer
<220> FEATURE:
<223> OTHER INFORMATION: hMyd88r1 primer

<400> SEQUENCE: 18
gtctccagtt gccggatctc caag                                       24

<210> SEQ ID NO 19
<211> LENGTH: 23
<212> TYPE: DNA
<213> ORGANISM: Artificial Sequence
<220> FEATURE:
<223> OTHER INFORMATION: Synthetic mMyd88f2 primer
<220> FEATURE:
<223> OTHER INFORMATION: mMyd88f2 primer

<400> SEQUENCE: 19
ggaaactcca caggcgagcg tac                                        23

<210> SEQ ID NO 20
<211> LENGTH: 26
<212> TYPE: DNA
<213> ORGANISM: Artificial Sequence
<220> FEATURE:
<223> OTHER INFORMATION: Synthetic mMyd88r2 primer
<220> FEATURE:
<223> OTHER INFORMATION: mMyd88r2 primer

<400> SEQUENCE: 20
ggcagtcctc ctcgatgcgc gacttc                                     26

<210> SEQ ID NO 21
<211> LENGTH: 119
<212> TYPE: DNA
<213> ORGANISM: Artificial Sequence
<220> FEATURE:
<223> OTHER INFORMATION: Synthetic Flag-DDX3 primer
<220> FEATURE:
<223> OTHER INFORMATION: Flag-DDX3 primer

<400> SEQUENCE: 21

```
actcgcttag cagcggaaga ctccgagttc tcggtactct tcagggatgg actacaagga      60
cgacgatgac aagagtcatg tggcagtgga aaatgcgctc gggctggacc agcaggtga      119
```

<210> SEQ ID NO 22
<211> LENGTH: 1958
<212> TYPE: PRT
<213> ORGANISM: Artificial Sequence
<220> FEATURE:
<223> OTHER INFORMATION: Synthetic GAG-Cas9 fusion protein
<220> FEATURE:
<223> OTHER INFORMATION: GAG-Cas9 fusion protein

<400> SEQUENCE: 22

```
Met Gly Gln Ala Val Thr Thr Pro Leu Ser Leu Thr Leu Asp His Trp
1               5                   10                  15

Lys Asp Val Glu Arg Thr Ala His Asn Leu Ser Val Glu Val Arg Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Pro Asp Ile Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Ile Ala Val Asp Pro Pro Pro Trp
                85                  90                  95

Val Arg Pro Phe Val His Pro Lys Pro Pro Leu Ser Leu Pro Pro Ser
            100                 105                 110

Ala Pro Ser Leu Pro Pro Glu Pro Pro Leu Ser Thr Pro Pro Gln Ser
        115                 120                 125

Ser Leu Tyr Pro Ala Leu Thr Ser Pro Leu Asn Thr Lys Pro Arg Pro
    130                 135                 140

Gln Val Leu Pro Asp Ser Gly Gly Pro Leu Ile Asp Leu Leu Thr Glu
145                 150                 155                 160

Asp Pro Pro Pro Tyr Arg Asp Pro Gly Pro Pro Ser Pro Asp Gly Asn
                165                 170                 175

Gly Asp Ser Gly Glu Val Ala Pro Thr Glu Gly Ala Pro Asp Pro Ser
            180                 185                 190

Pro Met Val Ser Arg Leu Arg Gly Arg Lys Glu Pro Pro Val Ala Asp
        195                 200                 205

Ser Thr Thr Ser Gln Ala Phe Pro Leu Arg Leu Gly Gly Asn Gly Gln
    210                 215                 220

Tyr Gln Tyr Trp Pro Phe Ser Ser Asp Leu Tyr Asn Trp Lys Asn
225                 230                 235                 240

Asn Asn Pro Ser Phe Ser Glu Asp Pro Ala Lys Leu Thr Ala Leu Ile
                245                 250                 255

Glu Ser Val Leu Leu Thr His Gln Pro Thr Trp Asp Asp Cys Gln Gln
            260                 265                 270
```

```
Leu Leu Gly Thr Leu Thr Gly Glu Glu Lys Gln Arg Val Leu Leu
            275                 280                 285

Glu Ala Arg Lys Ala Val Arg Gly Glu Asp Gly Arg Pro Thr Gln Leu
    290                 295                 300

Pro Asn Asp Ile Asn Asp Ala Phe Pro Leu Glu Arg Pro Asp Trp Asp
305                 310                 315                 320

Tyr Asn Thr Gln Arg Gly Arg Asn His Leu Val His Tyr Arg Gln Leu
                325                 330                 335

Leu Leu Ala Gly Leu Gln Asn Ala Gly Arg Ser Pro Thr Asn Leu Ala
                340                 345                 350

Lys Val Lys Gly Ile Thr Gln Gly Pro Asn Glu Ser Pro Ser Ala Phe
                355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ala Met Ser Phe Ile Trp Gln
385                 390                 395                 400

Ser Ala Pro Asp Ile Gly Arg Lys Leu Glu Arg Leu Glu Asp Leu Lys
                405                 410                 415

Ser Lys Thr Leu Gly Asp Leu Val Arg Glu Ala Glu Lys Ile Phe Asn
                420                 425                 430

Lys Arg Glu Thr Pro Glu Glu Arg Glu Arg Ile Arg Arg Glu Thr
                435                 440                 445

Glu Glu Lys Glu Glu Arg Arg Arg Ala Glu Asp Val Gln Arg Glu Lys
    450                 455                 460

Glu Arg Asp Arg Arg Arg His Arg Glu Met Ser Lys Leu Leu Ala Thr
465                 470                 475                 480

Val Val Ser Gly Gln Arg Gln Asp Arg Gln Gly Gly Glu Arg Arg Arg
                485                 490                 495

Pro Gln Leu Asp His Asp Gln Cys Ala Tyr Cys Lys Glu Lys Gly His
                500                 505                 510

Trp Ala Arg Asp Cys Pro Lys Lys Pro Arg Gly Pro Arg Gly Pro Arg
                515                 520                 525

Pro Gln Ala Ser Leu Leu Thr Arg Ser Ser Leu Tyr Pro Ala Leu Thr
    530                 535                 540

Pro Thr Gly Asp Tyr Lys Asp Asp Asp Lys Met Ala Pro Lys Lys
545                 550                 555                 560

Lys Arg Lys Val Gly Ile His Gly Val Pro Ala Ala Asp Lys Lys Tyr
                565                 570                 575

Ser Ile Gly Leu Asp Ile Gly Thr Asn Ser Val Gly Trp Ala Val Ile
                580                 585                 590

Thr Asp Glu Tyr Lys Val Pro Ser Lys Lys Phe Lys Val Leu Gly Asn
    595                 600                 605

Thr Asp Arg His Ser Ile Lys Lys Asn Leu Ile Gly Ala Leu Leu Phe
    610                 615                 620

Asp Ser Gly Glu Thr Ala Glu Ala Thr Arg Leu Lys Arg Thr Ala Arg
625                 630                 635                 640

Arg Arg Tyr Thr Arg Arg Lys Asn Arg Ile Cys Tyr Leu Gln Glu Ile
                645                 650                 655

Phe Ser Asn Glu Met Ala Lys Val Asp Asp Ser Phe Phe His Arg Leu
                660                 665                 670

Glu Glu Ser Phe Leu Val Glu Glu Asp Lys Lys His Glu Arg His Pro
                675                 680                 685
```

-continued

```
Ile Phe Gly Asn Ile Val Asp Glu Val Ala Tyr His Glu Lys Tyr Pro
    690                 695                 700
Thr Ile Tyr His Leu Arg Lys Lys Leu Val Asp Ser Thr Asp Lys Ala
705                 710                 715                 720
Asp Leu Arg Leu Ile Tyr Leu Ala Leu Ala His Met Ile Lys Phe Arg
                725                 730                 735
Gly His Phe Leu Ile Glu Gly Asp Leu Asn Pro Asp Asn Ser Asp Val
            740                 745                 750
Asp Lys Leu Phe Ile Gln Leu Val Gln Thr Tyr Asn Gln Leu Phe Glu
        755                 760                 765
Glu Asn Pro Ile Asn Ala Ser Gly Val Asp Ala Lys Ala Ile Leu Ser
770                 775                 780
Ala Arg Leu Ser Lys Ser Arg Arg Leu Glu Asn Leu Ile Ala Gln Leu
785                 790                 795                 800
Pro Gly Glu Lys Lys Asn Gly Leu Phe Gly Asn Leu Ile Ala Leu Ser
                805                 810                 815
Leu Gly Leu Thr Pro Asn Phe Lys Ser Asn Phe Asp Leu Ala Glu Asp
            820                 825                 830
Ala Lys Leu Gln Leu Ser Lys Asp Thr Tyr Asp Asp Asp Leu Asp Asn
        835                 840                 845
Leu Leu Ala Gln Ile Gly Asp Gln Tyr Ala Asp Leu Phe Leu Ala Ala
850                 855                 860
Lys Asn Leu Ser Asp Ala Ile Leu Leu Ser Asp Ile Leu Arg Val Asn
865                 870                 875                 880
Thr Glu Ile Thr Lys Ala Pro Leu Ser Ala Ser Met Ile Lys Arg Tyr
                885                 890                 895
Asp Glu His His Gln Asp Leu Thr Leu Leu Lys Ala Leu Val Arg Gln
            900                 905                 910
Gln Leu Pro Glu Lys Tyr Lys Glu Ile Phe Phe Asp Gln Ser Lys Asn
        915                 920                 925
Gly Tyr Ala Gly Tyr Ile Asp Gly Gly Ala Ser Gln Glu Glu Phe Tyr
930                 935                 940
Lys Phe Ile Lys Pro Ile Leu Glu Lys Met Asp Gly Thr Glu Glu Leu
945                 950                 955                 960
Leu Val Lys Leu Asn Arg Glu Asp Leu Leu Arg Lys Gln Arg Thr Phe
                965                 970                 975
Asp Asn Gly Ser Ile Pro His Gln Ile His Leu Gly Glu Leu His Ala
            980                 985                 990
Ile Leu Arg Arg Gln Glu Asp Phe Tyr Pro Phe Leu Lys Asp Asn Arg
        995                 1000                1005
Glu Lys Ile Glu Lys Ile Leu Thr Phe Arg Ile Pro Tyr Tyr Val Gly
    1010                1015                1020
Pro Leu Ala Arg Gly Asn Ser Arg Phe Ala Trp Met Thr Arg Lys Ser
1025                1030                1035                1040
Glu Glu Thr Ile Thr Pro Trp Asn Phe Glu Glu Val Val Asp Lys Gly
                1045                1050                1055
Ala Ser Ala Gln Ser Phe Ile Glu Arg Met Thr Asn Phe Asp Lys Asn
            1060                1065                1070
Leu Pro Asn Glu Lys Val Leu Pro Lys His Ser Leu Leu Tyr Glu Tyr
        1075                1080                1085
Phe Thr Val Tyr Asn Glu Leu Thr Lys Val Lys Tyr Val Thr Glu Gly
    1090                1095                1100
```

```
Met Arg Lys Pro Ala Phe Leu Ser Gly Glu Gln Lys Ala Ile Val
1105                1110                1115                1120

Asp Leu Leu Phe Lys Thr Asn Arg Lys Val Thr Val Lys Gln Leu Lys
                1125                1130                1135

Glu Asp Tyr Phe Lys Lys Ile Glu Cys Phe Asp Ser Val Glu Ile Ser
            1140                1145                1150

Gly Val Glu Asp Arg Phe Asn Ala Ser Leu Gly Thr Tyr His Asp Leu
            1155                1160                1165

Leu Lys Ile Ile Lys Asp Lys Asp Phe Leu Asp Asn Glu Glu Asn Glu
        1170                1175                1180

Asp Ile Leu Glu Asp Ile Val Leu Thr Leu Thr Leu Phe Glu Asp Arg
1185                1190                1195                1200

Glu Met Ile Glu Glu Arg Leu Lys Thr Tyr Ala His Leu Phe Asp Asp
                1205                1210                1215

Lys Val Met Lys Gln Leu Lys Arg Arg Arg Tyr Thr Gly Trp Gly Arg
                1220                1225                1230

Leu Ser Arg Lys Leu Ile Asn Gly Ile Arg Asp Lys Gln Ser Gly Lys
            1235                1240                1245

Thr Ile Leu Asp Phe Leu Lys Ser Asp Gly Phe Ala Asn Arg Asn Phe
        1250                1255                1260

Met Gln Leu Ile His Asp Asp Ser Leu Thr Phe Lys Glu Asp Ile Gln
1265                1270                1275                1280

Lys Ala Gln Val Ser Gly Gln Gly Asp Ser Leu His Glu His Ile Ala
                1285                1290                1295

Asn Leu Ala Gly Ser Pro Ala Ile Lys Lys Gly Ile Leu Gln Thr Val
                1300                1305                1310

Lys Val Val Asp Glu Leu Val Lys Val Met Gly Arg His Lys Pro Glu
            1315                1320                1325

Asn Ile Val Ile Glu Met Ala Arg Glu Asn Gln Thr Thr Gln Lys Gly
        1330                1335                1340

Gln Lys Asn Ser Arg Glu Arg Met Lys Arg Ile Glu Glu Gly Ile Lys
1345                1350                1355                1360

Glu Leu Gly Ser Gln Ile Leu Lys Glu His Pro Val Glu Asn Thr Gln
                1365                1370                1375

Leu Gln Asn Glu Lys Leu Tyr Leu Tyr Tyr Leu Gln Asn Gly Arg Asp
                1380                1385                1390

Met Tyr Val Asp Gln Glu Leu Asp Ile Asn Arg Leu Ser Asp Tyr Asp
            1395                1400                1405

Val Asp His Ile Val Pro Gln Ser Phe Leu Lys Asp Asp Ser Ile Asp
        1410                1415                1420

Asn Lys Val Leu Thr Arg Ser Asp Lys Asn Arg Gly Lys Ser Asp Asn
1425                1430                1435                1440

Val Pro Ser Glu Glu Val Val Lys Lys Met Lys Asn Tyr Trp Arg Gln
                1445                1450                1455

Leu Leu Asn Ala Lys Leu Ile Thr Gln Arg Lys Phe Asp Asn Leu Thr
                1460                1465                1470

Lys Ala Glu Arg Gly Gly Leu Ser Glu Leu Asp Lys Ala Gly Phe Ile
            1475                1480                1485

Lys Arg Gln Leu Val Glu Thr Arg Gln Ile Thr Lys His Val Ala Gln
        1490                1495                1500

Ile Leu Asp Ser Arg Met Asn Thr Lys Tyr Asp Glu Asn Asp Lys Leu
1505                1510                1515                1520
```

-continued

Ile Arg Glu Val Lys Val Ile Thr Leu Lys Ser Lys Leu Val Ser Asp
              1525                1530                1535

Phe Arg Lys Asp Phe Gln Phe Tyr Lys Val Arg Glu Ile Asn Asn Tyr
              1540                1545                1550

His His Ala His Asp Ala Tyr Leu Asn Ala Val Val Gly Thr Ala Leu
              1555                1560                1565

Ile Lys Lys Tyr Pro Lys Leu Glu Ser Glu Phe Val Tyr Gly Asp Tyr
              1570                1575                1580

Lys Val Tyr Asp Val Arg Lys Met Ile Ala Lys Ser Glu Gln Glu Ile
1585                1590                1595                1600

Gly Lys Ala Thr Ala Lys Tyr Phe Phe Tyr Ser Asn Ile Met Asn Phe
              1605                1610                1615

Phe Lys Thr Glu Ile Thr Leu Ala Asn Gly Glu Ile Arg Lys Arg Pro
              1620                1625                1630

Leu Ile Glu Thr Asn Gly Glu Thr Gly Glu Ile Val Trp Asp Lys Gly
              1635                1640                1645

Arg Asp Phe Ala Thr Val Arg Lys Val Leu Ser Met Pro Gln Val Asn
              1650                1655                1660

Ile Val Lys Lys Thr Glu Val Gln Thr Gly Gly Phe Ser Lys Glu Ser
1665                1670                1675                1680

Ile Leu Pro Lys Arg Asn Ser Asp Lys Leu Ile Ala Arg Lys Lys Asp
              1685                1690                1695

Trp Asp Pro Lys Lys Tyr Gly Gly Phe Asp Ser Pro Thr Val Ala Tyr
              1700                1705                1710

Ser Val Leu Val Val Ala Lys Val Glu Lys Gly Lys Ser Lys Lys Leu
              1715                1720                1725

Lys Ser Val Lys Glu Leu Leu Gly Ile Thr Ile Met Glu Arg Ser Ser
              1730                1735                1740

Phe Glu Lys Asn Pro Ile Asp Phe Leu Glu Ala Lys Gly Tyr Lys Glu
1745                1750                1755                1760

Val Lys Lys Asp Leu Ile Ile Lys Leu Pro Lys Tyr Ser Leu Phe Glu
              1765                1770                1775

Leu Glu Asn Gly Arg Lys Arg Met Leu Ala Ser Ala Gly Glu Leu Gln
              1780                1785                1790

Lys Gly Asn Glu Leu Ala Leu Pro Ser Lys Tyr Val Asn Phe Leu Tyr
              1795                1800                1805

Leu Ala Ser His Tyr Glu Lys Leu Lys Gly Ser Pro Glu Asp Asn Glu
              1810                1815                1820

Gln Lys Gln Leu Phe Val Glu Gln His Lys His Tyr Leu Asp Glu Ile
1825                1830                1835                1840

Ile Glu Gln Ile Ser Glu Phe Ser Lys Arg Val Ile Leu Ala Asp Ala
              1845                1850                1855

Asn Leu Asp Lys Val Leu Ser Ala Tyr Asn Lys His Arg Asp Lys Pro
              1860                1865                1870

Ile Arg Glu Gln Ala Glu Asn Ile Ile His Leu Phe Thr Leu Thr Asn
              1875                1880                1885

Leu Gly Ala Pro Ala Ala Phe Lys Tyr Phe Asp Thr Thr Ile Asp Arg
              1890                1895                1900

Lys Arg Tyr Thr Ser Thr Lys Glu Val Leu Asp Ala Thr Leu Ile His
1905                1910                1915                1920

Gln Ser Ile Thr Gly Leu Tyr Glu Thr Arg Ile Asp Leu Ser Gln Leu
              1925                1930                1935

Gly Gly Asp Lys Arg Pro Ala Ala Thr Lys Lys Ala Gly Gln Ala Lys
            1940                1945                1950

Lys Lys Lys Ala Arg Ala
    1955

<210> SEQ ID NO 23
<211> LENGTH: 511
<212> TYPE: PRT
<213> ORGANISM: Vesicular stomatitis virus
<220> FEATURE:
<223> OTHER INFORMATION: VSV-G protein
<220> FEATURE:
<223> OTHER INFORMATION: VSV-G protein

<400> SEQUENCE: 23

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

-continued

```
Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 24
<211> LENGTH: 1742
<212> TYPE: PRT
<213> ORGANISM: Artificial Sequence
<220> FEATURE:
<223> OTHER INFORMATION: Synthetic GAG PRO POL polyprotein
<220> FEATURE:
<223> OTHER INFORMATION: GAG PRO POL polyprotein

<400> SEQUENCE: 24

Met Gly Gln Ala Val Thr Thr Pro Leu Ser Leu Thr Leu Asp His Trp
1               5                   10                  15

Lys Asp Val Glu Arg Thr Ala His Asn Leu Ser Val Glu Val Arg Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Pro Asp Ile Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Ile Ala Val Asp Pro Pro Pro Trp
                85                  90                  95

Val Arg Pro Phe Val His Pro Lys Pro Pro Leu Ser Leu Pro Pro Ser
            100                 105                 110

Ala Pro Ser Leu Pro Pro Glu Pro Pro Leu Ser Thr Pro Gln Ser
        115                 120                 125

Ser Leu Tyr Pro Ala Leu Thr Ser Pro Leu Asn Thr Lys Pro Arg Pro
    130                 135                 140

Gln Val Leu Pro Asp Ser Gly Gly Pro Leu Ile Asp Leu Leu Thr Glu
145                 150                 155                 160
```

```
Asp Pro Pro Pro Tyr Arg Asp Pro Gly Pro Pro Ser Pro Asp Gly Asn
                165                 170                 175

Gly Asp Ser Gly Glu Val Ala Pro Thr Glu Gly Ala Pro Asp Pro Ser
            180                 185                 190

Pro Met Val Ser Arg Leu Arg Gly Arg Lys Glu Pro Pro Val Ala Asp
        195                 200                 205

Ser Thr Thr Ser Gln Ala Phe Pro Leu Arg Leu Gly Gly Asn Gly Gln
    210                 215                 220

Tyr Gln Tyr Trp Pro Phe Ser Ser Ser Asp Leu Tyr Asn Trp Lys Asn
225                 230                 235                 240

Asn Asn Pro Ser Phe Ser Glu Asp Pro Ala Lys Leu Thr Ala Leu Ile
                245                 250                 255

Glu Ser Val Leu Leu Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Glu Asp Gly Arg Pro Thr Gln Leu
    290                 295                 300

Pro Asn Asp Ile Asn Asp Ala Phe Pro Leu Glu Arg Pro Asp Trp Asp
305                 310                 315                 320

Tyr Asn Thr Gln Arg Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ala Met Ser Phe Ile Trp Gln
385                 390                 395                 400

Ser Ala Pro Asp Ile Gly Arg Lys Leu Glu Arg Leu Glu Asp Leu Lys
                405                 410                 415

Ser Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
        435                 440                 445

Glu Glu Lys Glu Glu Arg Arg Ala Glu Asp Val Gln Arg Glu Lys
    450                 455                 460

Glu Arg Asp Arg Arg His Arg Glu Met Ser Lys Leu Leu Ala Thr
465                 470                 475                 480

Val Val Ser Gly Arg Gln Asp Arg Gln Gly Gly Glu Arg Arg
                485                 490                 495

Pro Gln Leu Asp His Asp Gln Cys Ala Tyr Cys Lys Glu Lys Gly His
            500                 505                 510

Trp Ala Arg Asp Cys Pro Lys Lys Pro Arg Gly Pro Arg
        515                 520                 525

Pro Gln Ala Ser Leu Leu Thr Leu Asp Asp Thr Leu Asp Asp Gln Gly
    530                 535                 540

Gly Gln Gly Gln Glu Pro Pro Glu Pro Arg Ile Thr Leu Arg Val
545                 550                 555                 560

Gly Gly Gln Pro Val Thr Phe Leu Val Asp Thr Gly Ala Gln His Ser
                565                 570                 575
```

```
Val Leu Thr Gln Asn Pro Gly Pro Leu Ser Asp Lys Ser Ala Trp Val
            580                 585                 590

Gln Gly Ala Thr Gly Gly Lys Arg Tyr Arg Trp Thr Thr Asp Arg Arg
        595                 600                 605

Val His Leu Ala Thr Gly Lys Val Thr His Ser Phe Leu His Val Pro
    610                 615                 620

Asp Cys Pro Tyr Pro Leu Leu Gly Arg Asp Leu Leu Thr Lys Leu Lys
625                 630                 635                 640

Ala Gln Ile His Phe Glu Gly Ser Gly Ala Gln Val Val Gly Pro Met
                645                 650                 655

Gly Gln Pro Leu Gln Val Leu Thr Leu Asn Ile Glu Asp Glu Tyr Arg
            660                 665                 670

Leu His Glu Thr Ser Lys Gly Pro Asp Val Pro Leu Gly Ser Thr Trp
        675                 680                 685

Leu Ser Asp Phe Pro Gln Ala Trp Ala Glu Thr Gly Gly Met Gly Leu
    690                 695                 700

Ala Val Arg Gln Ala Pro Leu Ile Ile Pro Leu Lys Ala Thr Ser Thr
705                 710                 715                 720

Pro Val Ser Ile Lys Gln Tyr Pro Met Ser Gln Glu Ala Arg Leu Gly
                725                 730                 735

Ile Lys Pro His Ile Gln Arg Leu Leu Asp Gln Gly Ile Leu Val Pro
            740                 745                 750

Cys Gln Ser Pro Trp Asn Thr Pro Leu Leu Pro Val Lys Lys Pro Gly
        755                 760                 765

Thr Asn Asp Tyr Arg Pro Val Gln Asp Leu Arg Glu Val Asn Lys Arg
    770                 775                 780

Val Glu Asp Ile His Pro Thr Val Pro Asn Pro Tyr Asn Leu Leu Ser
785                 790                 795                 800

Gly Leu Pro Pro Ser His Gln Trp Tyr Thr Val Leu Asp Leu Lys Asp
                805                 810                 815

Ala Phe Phe Cys Leu Arg Leu His Pro Thr Ser Gln Ser Leu Phe Ala
            820                 825                 830

Phe Glu Trp Arg Asp Pro Glu Met Gly Ile Ser Gly Gln Leu Thr Trp
        835                 840                 845

Thr Arg Leu Pro Gln Gly Phe Lys Asn Ser Pro Thr Leu Phe Asp Glu
    850                 855                 860

Ala Leu His Arg Asp Leu Ala Asp Phe Arg Ile Gln His Pro Asp Leu
865                 870                 875                 880

Ile Leu Leu Gln Tyr Val Asp Asp Leu Leu Leu Ala Ala Thr Ser Glu
                885                 890                 895

Leu Asp Cys Gln Gln Gly Thr Arg Ala Leu Leu Gln Thr Leu Gly Asp
            900                 905                 910

Leu Gly Tyr Arg Ala Ser Ala Lys Lys Ala Gln Ile Cys Gln Lys Gln
        915                 920                 925

Val Lys Tyr Leu Gly Tyr Leu Leu Lys Glu Gly Gln Arg Trp Leu Thr
    930                 935                 940

Glu Ala Arg Lys Glu Thr Val Met Gly Gln Pro Thr Pro Lys Thr Pro
945                 950                 955                 960

Arg Gln Leu Arg Glu Phe Leu Gly Thr Ala Gly Phe Cys Arg Leu Trp
                965                 970                 975

Ile Pro Gly Phe Ala Glu Met Ala Ala Pro Leu Tyr Pro Leu Thr Lys
            980                 985                 990
```

-continued

```
Thr Gly Thr Leu Phe Glu Trp Gly Pro Asp Gln Gln Lys Ala Tyr Gln
        995                 1000                1005

Glu Ile Lys Gln Ala Leu Leu Thr Ala Pro Ala Leu Gly Leu Pro Asp
    1010                1015                1020

Leu Thr Lys Pro Phe Glu Leu Phe Val Asp Glu Lys Gln Gly Tyr Ala
1025                1030                1035                1040

Lys Gly Val Leu Thr Gln Lys Leu Gly Pro Trp Arg Arg Pro Val Ala
                1045                1050                1055

Tyr Leu Ser Lys Lys Leu Asp Pro Val Ala Ala Gly Trp Pro Pro Cys
            1060                1065                1070

Leu Arg Met Val Ala Ala Ile Ala Val Leu Thr Lys Asp Ala Gly Lys
        1075                1080                1085

Leu Thr Met Gly Gln Pro Leu Val Ile Leu Ala Pro His Ala Val Glu
    1090                1095                1100

Ala Leu Val Lys Gln Pro Pro Asp Arg Trp Leu Ser Asn Ala Arg Met
1105                1110                1115                1120

Thr His Tyr Gln Ala Leu Leu Leu Asp Thr Asp Arg Val Gln Phe Gly
                1125                1130                1135

Pro Ile Val Ala Leu Asn Pro Ala Thr Leu Leu Pro Leu Pro Glu Glu
            1140                1145                1150

Gly Leu Gln His Asp Cys Leu Asp Ile Leu Ala Glu Ala His Gly Thr
        1155                1160                1165

Arg Pro Asp Leu Thr Asp Gln Pro Leu Pro Asp Ala Asp His Thr Trp
    1170                1175                1180

Tyr Thr Asp Gly Ser Ser Phe Leu Gln Glu Gly Gln Arg Lys Ala Gly
1185                1190                1195                1200

Ala Ala Val Thr Thr Glu Thr Glu Val Val Trp Ala Lys Ala Leu Pro
                1205                1210                1215

Ala Gly Thr Ser Ala Gln Arg Ala Glu Leu Ile Ala Leu Thr Gln Ala
            1220                1225                1230

Leu Lys Met Ala Glu Gly Lys Lys Leu Asn Val Tyr Thr Asp Ser Arg
        1235                1240                1245

Tyr Ala Phe Ala Thr Ala His Ile His Gly Glu Ile Tyr Arg Arg Arg
    1250                1255                1260

Gly Leu Leu Thr Ser Glu Gly Lys Glu Ile Lys Asn Lys Asp Glu Ile
1265                1270                1275                1280

Leu Ala Leu Leu Lys Ala Leu Phe Leu Pro Lys Arg Leu Ser Ile Ile
                1285                1290                1295

His Cys Pro Gly His Gln Lys Gly Asn Arg Ala Glu Ala Arg Gly Asn
            1300                1305                1310

Arg Met Ala Asp Gln Ala Ala Arg Glu Val Ala Thr Arg Glu Thr Pro
        1315                1320                1325

Glu Thr Ser Thr Leu Leu Ile Glu Asn Ser Ala Pro Tyr Thr His Glu
    1330                1335                1340

His Phe His Tyr Thr Val Thr Asp Ile Lys Asp Leu Thr Lys Leu Gly
1345                1350                1355                1360

Ala Thr Tyr Asp Asp Ala Lys Lys Cys Trp Val Tyr Gln Gly Lys Pro
                1365                1370                1375

Val Met Pro Asp Gln Phe Thr Phe Glu Leu Leu Asp Phe Leu His Gln
            1380                1385                1390

Leu Thr His Leu Ser Phe Ser Lys Thr Lys Ala Leu Leu Glu Arg Asn
        1395                1400                1405
```

Tyr Cys Pro Tyr Tyr Met Leu Asn Arg Asp Arg Thr Leu Lys Asp Ile
1410                1415                1420

Thr Glu Thr Cys Gln Ala Cys Ala Gln Val Asn Ala Ser Lys Ser Ala
1425                1430                1435                1440

Val Lys Gln Gly Thr Arg Val Arg Gly His Arg Pro Gly Thr His Trp
            1445                1450                1455

Glu Ile Asp Phe Thr Glu Val Lys Pro Gly Leu Tyr Gly Tyr Lys Tyr
            1460                1465                1470

Leu Leu Val Phe Ile Asp Thr Phe Ser Gly Trp Val Glu Ala Phe Pro
            1475                1480                1485

Thr Lys Lys Glu Thr Ala Lys Val Val Thr Lys Lys Leu Leu Glu Glu
1490                1495                1500

Ile Phe Pro Arg Phe Gly Met Pro Gln Val Leu Gly Thr Asp Asn Gly
1505                1510                1515                1520

Pro Ala Phe Val Ser Lys Val Ser Gln Thr Val Ala Asp Leu Leu Gly
            1525                1530                1535

Val Asp Trp Lys Leu His Cys Ala Tyr Arg Pro Gln Ser Ser Gly Gln
            1540                1545                1550

Val Glu Arg Met Asn Arg Thr Ile Lys Glu Thr Leu Thr Lys Leu Thr
            1555                1560                1565

Leu Ala Thr Gly Ser Arg Asp Trp Val Leu Leu Pro Leu Ala Leu
            1570                1575                1580

Tyr Arg Ala Arg Asn Thr Pro Gly Pro His Gly Leu Thr Pro Tyr Glu
1585                1590                1595                1600

Ile Leu Tyr Gly Ala Pro Pro Leu Val Asn Phe Pro Asp Pro Asp
            1605                1610                1615

Met Ala Lys Val Thr His Asn Pro Ser Leu Gln Ala His Leu Gln Ala
            1620                1625                1630

Leu Tyr Leu Val Gln His Glu Val Trp Arg Pro Leu Ala Ala Ala Tyr
            1635                1640                1645

Gln Glu Gln Leu Asp Arg Pro Val Val Pro His Pro Phe Arg Val Gly
            1650                1655                1660

Asp Thr Val Trp Val Arg Arg His Gln Thr Lys Asn Leu Glu Pro Arg
1665                1670                1675                1680

Trp Lys Gly Pro Tyr Thr Val Leu Leu Thr Thr Pro Thr Ala Leu Lys
            1685                1690                1695

Val Asp Gly Ile Ala Ala Trp Ile His Ala Ala His Val Lys Ala Ala
            1700                1705                1710

Asp Thr Arg Ile Glu Pro Pro Ser Glu Ser Thr Trp Arg Val Gln Arg
            1715                1720                1725

Ser Gln Asn Pro Leu Lys Ile Arg Leu Thr Arg Gly Thr Ser
            1730                1735                1740

<210> SEQ ID NO 25
<211> LENGTH: 546
<212> TYPE: PRT
<213> ORGANISM: Baboon endogenous retrovirus
<220> FEATURE:
<223> OTHER INFORMATION: BAEV-G protein
<220> FEATURE:
<223> OTHER INFORMATION: BAEV-G protein

<400> SEQUENCE: 25

Met Gly Phe Thr Thr Lys Ile Ile Phe Leu Tyr Asn Leu Val Leu Val
1               5                   10                  15

```
Tyr Ala Gly Phe Asp Asp Pro Arg Lys Ala Ile Glu Leu Val Gln Lys
                20                  25                  30

Arg Tyr Gly Arg Pro Cys Asp Cys Ser Gly Gln Val Ser Glu Pro
            35                  40                  45

Pro Ser Asp Arg Val Ser Gln Val Thr Cys Ser Gly Lys Thr Ala Tyr
 50                  55                  60

Leu Met Pro Asp Gln Arg Trp Lys Cys Lys Ser Ile Pro Lys Asp Thr
 65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
            115                 120                 125

Thr Ser Asp Val Gln Val Leu Gly Ser Thr Asn Lys Leu Ile Gln Ser
130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
            195                 200                 205

Met Val Asp Ala Gln Thr Leu Asn Ile Leu Asn Ala Thr Tyr Asn Leu
            210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
            275                 280                 285

Pro Ser Tyr Asn Ser Thr Glu Glu Ile Asp Leu Gly His Val Ala Phe
290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
            355                 360                 365

His Phe Ile Tyr Arg Pro Lys Arg Ala Ile Gln Phe Ile Pro Leu Leu
            370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430
```

Asp Ser Leu Ala Glu Val Val Leu Gln Asn Arg Arg Gly Leu Asp Leu
            435                 440                 445

Leu Thr Ala Glu Gln Gly Gly Ile Cys Leu Ala Leu Gln Glu Lys Cys
        450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Thr Ile Gly Pro Cys Ile
        515                 520                 525

Phe Asn Arg Leu Thr Ala Phe Ile Asn Asp Lys Leu Asn Ile Ile His
        530                 535                 540

Ala Met
545

<210> SEQ ID NO 26
<211> LENGTH: 5877
<212> TYPE: DNA
<213> ORGANISM: Artificial Sequence
<220> FEATURE:
<223> OTHER INFORMATION: Synthetic sequence encoding Gag-Cas9 fusion
      protein
<220> FEATURE:
<223> OTHER INFORMATION: sequence encoding Gag-Cas9 fusion protein

<400> SEQUENCE: 26

```
atgggccagg ctgttaccac cccttaagt ttgactttag accactggaa ggatgtcgaa      60
cggacagccc acaacctgtc ggtagaggtt agaaaaaggc gctgggttac attctgctct    120
gcagaatggc caaccttcaa cgtcggatgg ccacgagacg cactttaa cccagacatt      180 attacacagg ttaagatcaa ggtcttctca cctggcccac atggacatcc ggatcaggtc    240
ccctacatcg tgacctggga agctatagca gtagaccccc ctccctgggt cagacccttc    300
gtgcacccta acctcccct ctctcttccc ccttcagccc cctctctccc acctgaaccc     360
ccactctcga ccccgcccca gtcctccctc tatccggctc tcacttctcc tttaaacacc    420
aaacctaggc tcaagtcct tcctgatagc ggaggaccac tcattgatct actcacggag     480
gaccctccgc cttaccggga cccagggcca ccctctcctg acgggaacgg cgatagcgga    540
gaagtggccc tacagaagg agcccctgac ccttccccaa tggtatcccg cctgcgggga    600 agaaagaac ccccgtggc ggattctact acctctcagg cgttcccct tcgcctggga       660 gggaatggac agtatcaata ctggccattt tcctcctctg acctctataa ctggaaaaat    720
aacaacccct ctttctccga ggacccagct aaattgacag ctttgatcga gtccgttctc    780
cttactcatc agcccacttg ggatgactgc aacagctat agggacccct gctgacggga    840
gaagaaaaac agcgagtgct cctagaggcc cgaaaggcgg ttcgagggga ggacggacgc    900
ccaactcagc tgcccaatga cattaatgat gcttttccct ggaacgtcc cgactgggac    960 tacaacaccc aacgaggtag gaaccaccta gtccactatc gccagttgct cctagcgggt  1020
ctccaaaacg cgggcagaag cccaccaat ttggccaagg taaagggat aacccaggga    1080 cctaatgagt ctccctcagc cttttagag agactcaagg aggcctatcg cagatacact    1140
ccttatgacc ctgaggaccc agggcaagaa ccaatgtgg ccatgtcatt catctggcag   1200
tccgccccgg atatcgggcg aaagttagag cggttagaag atttgaagag taagacctta  1260
```

```
ggagacttag tgagggaagc tgaaaagatc tttaataaac gagaaacccc ggaagaaaga    1320
gaggaacgta ttaggagaga aacagaggaa aaggaagaac gccgtagggc agaggatgtg    1380
cagagagaga aggagaggga ccgcagaaga catagagaaa tgagtaagtt gctggctact    1440
gtcgttagcg ggcagagaca ggatagacag ggagggagagc gaaggaggcc ccaactcgac    1500
cacgaccagt gtgcctactg caaagaaaag ggacattggg ctagagattg ccccaagaag    1560
ccaagaggac cccggggacc acgacccag gcctccctcc tgacgcgtag ttccctgtat    1620
ccagccctca cacctaccgg tgattacaaa gacgatgacg ataagatggc cccaaagaag    1680
aagcggaagg tcggtatcca cggagtccca gcagccgaca agaagtacag catcggcctg    1740
gacatcggca ccaactctgt gggctgggcc gtgatcaccg acgagtacaa ggtgcccagc    1800
aagaaattca aggtgctggg caacaccgac cggcacagca tcaagaagaa cctgatcgga    1860
gccctgctgt tcgacagcgg cgaaacagcc gaggccaccc ggctgaagag aaccgccaga    1920
agaagataca ccagacggaa gaaccggatc tgctatctgc aagagatctt cagcaacgag    1980
atggccaagg tggacgacag cttcttccac agactggaag agtccttcct ggtggaagag    2040
gataagaagc acgagcggca ccccatcttc ggcaacatcg tggacgaggt ggcctaccac    2100
gagaagtacc ccaccatcta ccacctgaga aagaaactgg tggacagcac cgacaaggcc    2160
gacctgcggc tgatctatct ggccctggcc cacatgatca agttccgggg ccacttcctg    2220
atcgagggcg acctgaaccc cgacaacagc gacgtggaca gctgttcat ccagctggtg    2280 cagacctaca accagctgtt cgaggaaaac cccatcaacg ccagcggcgt ggacgccaag    2340
gccatcctgt ctgccagact gagcaagagc agacggctgg aaaatctgat cgcccagctg    2400
cccggcgaga agaagaatgg cctgttcggc aacctgattg ccctgagcct gggcctgacc    2460
cccaacttca gagcaacttt cgacctggcc gaggatgcca aactgcagct gagcaaggac    2520
acctacgacg acgacctgga caacctgctg gcccagatcg gcgaccagta cgccgacctg    2580
tttctggccg ccaagaacct gtccgacgcc atcctgctga gcgacatcct gagagtgaac    2640
accgagatca ccaaggcccc cctgagcgcc tctatgatca gagatacga cgagcaccac    2700 caggacctga ccctgctgaa agctctcgtg cggcagcagc tgcctgagaa gtacaaagag    2760
attttcttcg accagagcaa gaacggctac gccggctaca ttgacggcgg agccagccag    2820
gaagagttct acaagttcat caagcccatc ctggaaaaga tggacggcac cgaggaactg    2880
ctcgtgaagc tgaacagaga ggacctgctg cggaagcagc ggaccttcga caacggcagc    2940
atcccccacc agatccacct gggagagctg cacgccattc tgcggcggca ggaagatttt    3000
tacccattcc tgaaggacaa ccgggaaaag atcgagaaga tcctgacctt ccgcatcccc    3060
tactacgtgg gccctctggc caggggaaac agcagattcg cctggatgac cagaaagagc    3120
gaggaaacca tcacccctg aacttcgag gaagtggtgg acaagggcgc ttccgcccag    3180
agcttcatcg agcggatgac caacttcgat aagaacctgc caacgagaa ggtgctgccc    3240 aagcacagcc tgctgtacga gtacttcacc gtgtataacg agctgaccaa agtgaaatac    3300
gtgaccgagg aatgagaaa gcccgccttc ctgagcggcg agcagaaaaa ggccatcgtg    3360
gacctgctgt tcaagaccaa ccggaaagtg accgtgaagc agctgaaaga ggactacttc    3420
aagaaaatcg agtgcttcga ctccgtggaa atctccggcg tggaagatcg gttcaacgcc    3480
tccctgggca cataccacga tctgctgaaa attatcaagg acaaggactt cctggacaat    3540
gaggaaaacg aggacattct ggaagatatc gtgctgaccc tgacactgtt tgaggacaga    3600
gagatgatcg aggaacggct gaaaacctat gcccacctgt tcgacgacaa agtgatgaag    3660
```

```
cagctgaagc ggcggagata caccggctgg ggcaggctga gccggaagct gatcaacggc    3720
atccgggaca agcagtccgg caagacaatc ctggatttcc tgaagtccga cggcttcgcc    3780
aacagaaact tcatgcagct gatccacgac gacagcctga cctttaaaga ggacatccag    3840
aaagcccagg tgtccggcca gggcgatagc ctgcacgagc acattgccaa tctggccggc    3900
agccccgcca ttaagaaggg catcctgcag acagtgaagg tggtggacga gctcgtgaaa    3960
gtgatgggcc ggcacaagcc cgagaacatc gtgatcgaaa tggccagaga gaaccagacc    4020
acccagaagg gacagaagaa cagccgcgag agaatgaagc ggatcgaaga gggcatcaaa    4080
gagctgggca gccagatcct gaaagaacac cccgtggaaa acacccagct gcagaacgag    4140
aagctgtacc tgtactacct gcagaatggg cgggatatgt acgtggacca ggaactggac    4200
atcaaccggc tgtccgacta cgatgtggac catatcgtgc ctcagagctt tctgaaggac    4260
gactccatcg acaacaaggt gctgaccaga agcgacaaga ccggggcaa gagcgacaac    4320 gtgccctccg aagaggtcgt gaagaagatg aagaactact ggcggcagct gctgaacgcc    4380
aagctgatta cccagagaaa gttcgacaat ctgaccaagg ccgagagagg cggcctgagc    4440
gaactggata aggccggctt catcaagaga cagctggtgg aaacccggca gatcacaaag    4500
cacgtggcac agatcctgga ctcccggatg aacactaagt acgacgagaa tgacaagctg    4560
atccgggaag tgaaagtgat cacccctgaag tccaagctgg tgtccgattt ccggaaggat    4620
ttccagtttt acaaagtgcg cgagatcaac aactaccacc acgcccacga cgcctacctg    4680
aacgccgtcg tgggaaccgc cctgatcaaa aagtaccca agctggaaag cgagttcgtg    4740
tacggcgact acaaggtgta cgacgtgcgg aagatgatcg ccaagagcga gcaggaaatc    4800
ggcaaggcta ccgccaagta cttcttctac agcaacatca tgaacttttt caagaccgag    4860
attaccctgg ccaacggcga gatccggaag cggcctctga tcgagacaaa cggcgaaacc    4920
ggggagatcg tgtgggataa gggccgggat tttgccaccg tgcggaaagt gctgagcatg    4980
ccccaagtga atatcgtgaa aaagaccgag gtgcagacag gcggcttcag caaagagtct    5040
atcctgccca gaggaacag cgataagctg atcgccagaa agaaggactg ggaccctaag    5100
aagtacggcg gcttcgacag ccccaccgtg gcctattctg tgctggtggt ggccaaagtg    5160
gaaaagggca gtccaagaa actgaagagt gtgaaagagc tgctggggat caccatcatg    5220
gaaagaagca gcttcgagaa gaatcccatc gactttctgg aagccaaggg ctacaaagaa    5280
gtgaaaaagg acctgatcat caagctgcct aagtactccc tgttcgagct ggaaaacggc    5340
cggaagagaa tgctggcctc tgccggcgaa ctgcagaagg gaaacgaact ggccctgccc    5400
tccaaatatg tgaacttcct gtacctggcc agccactatg agaagctgaa gggctccccc    5460
gaggataatg agcagaaaca gctgtttgtg gaacagcaca gcactacct ggacgagatc    5520 atcgagcaga tcagcgagtt ctccaagaga gtgatcctgg ccgacgctaa tctggacaaa    5580
gtgctgtccg cctacaacaa gcaccgggat aagcccatca gagagcaggc cgagaatatc    5640
atccacctgt ttaccctgac caatctggga gcccctgccg ccttcaagta ctttgacacc    5700
accatcgacc ggaagaggta caccagcacc aaagaggtgc tggacgccac cctgatccac    5760
cagagcatca ccggcctgta cgagacacgg atcgacctgt ctcagctggg aggcgacaag    5820
cgtcctgctg ctactaagaa agctggtcaa gctaagaaaa agaaagctag agcttga       5877
```

<210> SEQ ID NO 27
<211> LENGTH: 1641
<212> TYPE: DNA

<213> ORGANISM: baboon endogenous retrovirus
<220> FEATURE:
<223> OTHER INFORMATION: sequence encoding BAEV-G
<220> FEATURE:
<223> OTHER INFORMATION: sequence encoding BAEV-G

<400> SEQUENCE: 27

```
atgggctttta ccaccaagat tattttctg tataacctgg tgctggtgta tgcgggcttt      60
gatgatccgc gcaaagcgat tgaactggtg cagaaacgct atggccgccc gtgcgattgc     120
agcggcggcc aggtgagcga accgccgagc gatcgcgtga gccaggtgac ctgcagcggc     180
aaaaccgcgt atctgatgcc ggatcagcgc tggaaatgca aaagcattcc gaaagatacc     240
agcccgagcg gcccgctgca ggaatgcccg tgcaacagct atcagagcag cgtgcatagc     300
agctgctata ccagctatca gcagtgccgc agcggcaaca aaaccctatta taccgcgacc     360
ctgctgaaaa cccagaccgg cggcaccagc gatgtgcagg tgctgggcag caccaacaaa     420
ctgattcaga gcccgtgcaa cggcattaaa ggccagagca tttgctggag caccaccgcg     480
ccgattcatg tgagcgatgg cggcggcccg ctggatacca cccgcattaa aagcgtgcag     540
cgcaaactgg aagaaattca taaagcgctg tatccggaac tgcagtatca tccgctggcg     600
attccgaaag tgcgcgataa cctgatggtg gatgcgcaga ccctgaacat tctgaacgcg     660
acctataacc tgctgctgat gagcaacacc agcctggtgg atgattgctg gctgtgcctg     720
aaactgggcc cgccgacccc gctggcgatt ccgaacttc tgctgagcta tgtgacccgc     780
agcagcgata acattagctg cctgattatt ccgccgctgc tggtgcagcc gatgcagttt     840
agcaacagca gctgcctgtt tagcccgagc tataacagca ccgaagaaat tgatctgggc     900
catgtggcgt ttagcaactg caccagcatt accaacgtga ccggcccgat ttgcgcggtg     960
aacggcagcg tgtttctgtg cggcaacaac atggcgtata cctatctgcc gaccaactgg    1020
accggcctgt gcgtgctggc gaccctgctg ccggatattg atattattcc gggcgatgaa    1080
ccggtgccga ttccggcgat tgatcatttt atttatcgcc cgaaacgcgc gattcagttt    1140
attccgctgc tggcgggcct gggcattacc gcggcgttta ccaccggcgc gaccggcctg    1200
ggcgtgagcg tgacccagta taccaaactg agcaaccagc tgattagcga tgtgcagatt    1260
ctgagcagca ccattcagga tctgcaggat caggtggata gcctggcgga agtggtgctg    1320
cagaaccgcc gcgcctgga tctgctgacc gcggaacagg gcggcatttg cctggcgctg    1380
caggaaaaat gctgctttta tgtgaacaaa agcggcattg tgcgcgataa aattaaaacc    1440
ctgcaggaag aactggaacg ccgccgcaaa gatctggcga gcaacccgct gtggaccggc    1500
ctgcagggcc tgctgccgta tctgctgccg tttctgggcc cgctgctgac cctgctgctg    1560
ctgctgacca ttggcccgtg catttttaac cgcctgaccg cgtttattaa cgataaactg    1620
aacattattc atgcgatgta a                                              1641
```

<210> SEQ ID NO 28
<211> LENGTH: 1536
<212> TYPE: DNA
<213> ORGANISM: Vesicular stomatitis virus
<220> FEATURE:
<223> OTHER INFORMATION: sequence encoding VSV-G protein
<220> FEATURE:
<223> OTHER INFORMATION: sequence encoding VSV-G protein

<400> SEQUENCE: 28

```
atgaagtgcc ttttgtactt agccttttta ttcattgggg tgaattgcaa gttcaccata     60
gtttttccac acaaccaaaa aggaaactgg aaaaatgttc cttctaatta ccattattgc    120
```

```
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtatgga ccgaagtata taacacattc catccgatcc    300
ttcactccat ctgtagaaca atgcaaggaa agcattgaac aaacgaaaca aggaacttgg    360
ctgaatccag gcttccctcc tcaaagttgt ggatatgcaa ctgtgacgga tgccgaagca    420
gtgattgtcc aggtgactcc tcaccatgtg ctggttgatg aatacacagg agaatggggtt   480 gattcacagt tcatcaacgg aaaatgcagc aattacatat gccccactgt ccataactct    540
acaacctggc attctgacta aaggtcaaa gggctatgtg attctaacct catttccatg     600
gacatcacct tcttctcaga ggacggagag ctatcatccc tgggaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct aattcaggac gttgagagga tcttggatta ttccctctgc    900
caagaaacct ggagcaaaat cagagcgggt cttccaatct ctccagtgga tctcagctat    960
cttgctccta aaaacccagg aaccggtcct gctttcacca taatcaatgg taccctaaaa   1020
tactttgaga ccagatacat cagagtcgat attgctgctc caatcctctc aagaatggtc   1080
ggaatgatca gtggaactac cacagaaagg gaactgtggg atgactgggc accatatgaa   1140
gacgtggaaa ttgacccaa tggagttctg aggaccagtt caggatataa gtttcctttta  1200 tacatgattg gacatggtat gttggactcc gatcttcatc ttagctcaaa ggctcaggtg   1260
ttcgaacatc ctcacattca agacgctgct tcgcaacttc ctgatgatga gagtttattt   1320
tttggtgata ctgggctatc caaaaatcca atcgagcttg tagaaggttg gttcagtagt   1380
tggaaaagct ctattgcctc ttttttcttt atcatagggt taatcattgg actattcttg   1440
gttctccgag ttggtatcca tctttgcatt aaattaaagc acaccaagaa aagacagatt   1500
tatacagaca tagagatgaa ccgacttgga aagtaa                             1536
```

<210> SEQ ID NO 29  
<211> LENGTH: 9  
<212> TYPE: PRT  
<213> ORGANISM: Artificial Sequence  
<220> FEATURE:  
<223> OTHER INFORMATION: Synthetic cleavage sequence  
<220> FEATURE:  
<223> OTHER INFORMATION: cleavage sequence

<400> SEQUENCE: 29

Ser Ser Leu Tyr Pro Ala Leu Thr Pro  
1               5

<210> SEQ ID NO 30  
<211> LENGTH: 27  
<212> TYPE: DNA  
<213> ORGANISM: Artificial Sequence  
<220> FEATURE:  
<223> OTHER INFORMATION: Synthetic sequence encoding the cleavage  
      sequence of SEQ ID NO. 29  
<220> FEATURE:  
<223> OTHER INFORMATION: sequence encoding the cleavage sequence of SEQ  
      ID NO. 29

<400> SEQUENCE: 30
agttccctgt atccagccct cacacct                                        27

<210> SEQ ID NO 31
<211> LENGTH: 1401
<212> TYPE: PRT
<213> ORGANISM: Streptococcus
<220> FEATURE:
<223> OTHER INFORMATION: Cas9
<220> FEATURE:
<223> OTHER INFORMATION: Cas9

<400> SEQUENCE: 31

Met Ala Pro Lys Lys Lys Arg Lys Val Gly Ile His Gly Val Pro Ala
1               5                   10                  15

Ala Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

```
Ala Leu Val Arg Gln Gln Leu Pro Glu Lys Tyr Lys Glu Ile Phe Phe
            355                 360                 365

Asp Gln Ser Lys Asn Gly Tyr Ala Gly Tyr Ile Asp Gly Gly Ala Ser
370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
            435                 440                 445

Leu Lys Asp Asn Arg Glu Lys Ile Glu Lys Ile Leu Thr Phe Arg Ile
450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
            515                 520                 525

Leu Leu Tyr Glu Tyr Phe Thr Val Tyr Asn Glu Leu Thr Lys Val Lys
            530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
            595                 600                 605

Thr Tyr His Asp Leu Leu Lys Ile Ile Lys Asp Lys Asp Phe Leu Asp
610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
            675                 680                 685

Lys Gln Ser Gly Lys Thr Ile Leu Asp Phe Leu Lys Ser Asp Gly Phe
            690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
            755                 760                 765
```

-continued

```
Arg His Lys Pro Glu Asn Ile Val Ile Glu Met Ala Arg Glu Asn Gln
        770                 775                 780
Thr Thr Gln Lys Gly Gln Lys Asn Ser Arg Glu Arg Met Lys Arg Ile
785                 790                 795                 800
Glu Glu Gly Ile Lys Glu Leu Gly Ser Gln Ile Leu Lys Glu His Pro
                        805                 810                 815
Val Glu Asn Thr Gln Leu Gln Asn Glu Lys Leu Tyr Leu Tyr Tyr Leu
                820                 825                 830
Gln Asn Gly Arg Asp Met Tyr Val Asp Gln Glu Leu Asp Ile Asn Arg
            835                 840                 845
Leu Ser Asp Tyr Asp Val Asp His Ile Val Pro Gln Ser Phe Leu Lys
        850                 855                 860
Asp Asp Ser Ile Asp Asn Lys Val Leu Thr Arg Ser Asp Lys Asn Arg
865                 870                 875                 880
Gly Lys Ser Asp Asn Val Pro Ser Glu Glu Val Val Lys Lys Met Lys
                    885                 890                 895
Asn Tyr Trp Arg Gln Leu Leu Asn Ala Lys Leu Ile Thr Gln Arg Lys
                900                 905                 910
Phe Asp Asn Leu Thr Lys Ala Glu Arg Gly Gly Leu Ser Glu Leu Asp
            915                 920                 925
Lys Ala Gly Phe Ile Lys Arg Gln Leu Val Glu Thr Arg Gln Ile Thr
        930                 935                 940
Lys His Val Ala Gln Ile Leu Asp Ser Arg Met Asn Thr Lys Tyr Asp
945                 950                 955                 960
Glu Asn Asp Lys Leu Ile Arg Glu Val Lys Val Ile Thr Leu Lys Ser
                    965                 970                 975
Lys Leu Val Ser Asp Phe Arg Lys Asp Phe Gln Phe Tyr Lys Val Arg
                980                 985                 990
Glu Ile Asn Asn Tyr His His Ala His Asp Ala Tyr Leu Asn Ala Val
            995                 1000                1005
Val Gly Thr Ala Leu Ile Lys Lys Tyr Pro Lys Leu Glu Ser Glu Phe
        1010                1015                1020
Val Tyr Gly Asp Tyr Lys Val Tyr Asp Val Arg Lys Met Ile Ala Lys
1025                1030                1035                1040
Ser Glu Gln Glu Ile Gly Lys Ala Thr Ala Lys Tyr Phe Phe Tyr Ser
                    1045                1050                1055
Asn Ile Met Asn Phe Phe Lys Thr Glu Ile Thr Leu Ala Asn Gly Glu
                1060                1065                1070
Ile Arg Lys Arg Pro Leu Ile Glu Thr Asn Gly Glu Thr Gly Glu Ile
            1075                1080                1085
Val Trp Asp Lys Gly Arg Asp Phe Ala Thr Val Arg Lys Val Leu Ser
        1090                1095                1100
Met Pro Gln Val Asn Ile Val Lys Lys Thr Glu Val Gln Thr Gly Gly
1105                1110                1115                1120
Phe Ser Lys Glu Ser Ile Leu Pro Lys Arg Asn Ser Asp Lys Leu Ile
                    1125                1130                1135
Ala Arg Lys Lys Asp Trp Asp Pro Lys Lys Tyr Gly Gly Phe Asp Ser
                1140                1145                1150
Pro Thr Val Ala Tyr Ser Val Leu Val Val Ala Lys Val Glu Lys Gly
            1155                1160                1165
Lys Ser Lys Lys Leu Lys Ser Val Lys Glu Leu Leu Gly Ile Thr Ile
        1170                1175                1180
```

```
Met Glu Arg Ser Ser Phe Glu Lys Asn Pro Ile Asp Phe Leu Glu Ala
1185                1190                1195                1200

Lys Gly Tyr Lys Glu Val Lys Lys Asp Leu Ile Ile Lys Leu Pro Lys
            1205                1210                1215

Tyr Ser Leu Phe Glu Leu Glu Asn Gly Arg Lys Arg Met Leu Ala Ser
        1220                1225                1230

Ala Gly Glu Leu Gln Lys Gly Asn Glu Leu Ala Leu Pro Ser Lys Tyr
    1235                1240                1245

Val Asn Phe Leu Tyr Leu Ala Ser His Tyr Glu Lys Leu Lys Gly Ser
    1250                1255                1260

Pro Glu Asp Asn Glu Gln Lys Gln Leu Phe Val Glu Gln His Lys His
1265                1270                1275                1280

Tyr Leu Asp Glu Ile Ile Glu Gln Ile Ser Glu Phe Ser Lys Arg Val
        1285                1290                1295

Ile Leu Ala Asp Ala Asn Leu Asp Lys Val Leu Ser Ala Tyr Asn Lys
        1300                1305                1310

His Arg Asp Lys Pro Ile Arg Glu Gln Ala Glu Asn Ile Ile His Leu
        1315                1320                1325

Phe Thr Leu Thr Asn Leu Gly Ala Pro Ala Ala Phe Lys Tyr Phe Asp
        1330                1335                1340

Thr Thr Ile Asp Arg Lys Arg Tyr Thr Ser Thr Lys Glu Val Leu Asp
1345                1350                1355                1360

Ala Thr Leu Ile His Gln Ser Ile Thr Gly Leu Tyr Glu Thr Arg Ile
            1365                1370                1375

Asp Leu Ser Gln Leu Gly Gly Asp Lys Arg Pro Ala Thr Lys Lys
        1380                1385                1390

Ala Gly Gln Ala Lys Lys Lys Lys Ala
        1395                1400

<210> SEQ ID NO 32
<211> LENGTH: 4205
<212> TYPE: DNA
<213> ORGANISM: Streptococcus
<220> FEATURE:
<223> OTHER INFORMATION: encoding Cas9
<220> FEATURE:
<223> OTHER INFORMATION: encoding Cas9

<400> SEQUENCE: 32 atggcccaa agaagaagcg aaggtcggt atccacggag tcccagcagc cgacaagaag      60
tacagcatcg gcctggacat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct ccacagact ggaagagtcc    360 ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact cctgatcga gggcgacctg aaccccgaca cagcgacgt ggacaagctg     600 ttcatccagc tggtgcagac ctacaaccag ctgttcgagg aaaacccct caacgccagc    660 ggcgtggacg ccaaggccat cctgtctgcc agactgagca gagcagacg gctgaaaat     720 ctgatcgccc agctgcccgg cgagaagaag aatggcctgt cggcaacct gattgccctg    780
```

```
agcctgggcc tgaccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gccccctga cgcctctat gatcaagaga    1020
tacgacgagc accaccagga cctgaccctg ctgaaagctc tcgtgcggca gcagctgcct    1080
gagaagtaca aagagatttt cttcgaccag agcaagaacg ctacgccgg ctacattgac    1140
ggcggagcca gccaggaaga gttctacaag ttcatcaagc ccatcctgga aagatggac    1200
ggcaccgagg aactgctcgt gaagctgaac agagaggacc tgctgcggaa gcagcggacc    1260
ttcgacaacg gcagcatccc ccaccagatc cacctgggag agctgcacgc cattctgcgg    1320
cggcaggaag attttacccc attcctgaag gacaaccggg aaaagatcga agatcctg    1380
accttccgca tcccctacta cgtgggccct ctggccaggg aaacagcag attcgcctgg    1440
atgaccagaa agagcgagga aaccatcacc ccctggaact tcgaggaagt ggtggacaag    1500
ggcgcttccg cccagagctt catcgagcgg atgaccaact tcgataagaa cctgcccaac    1560
gagaaggtgc tgcccaagca cagcctgctg tacgagtact tcaccgtgta taacgagctg    1620
accaaagtga aatacgtgac cgagggaatg agaaagcccg ccttcctgag cggcgagcag    1680
aaaaaggcca tcgtggacct gctgttcaag accaaccgga agtgaccgt gaagcagctg    1740
aaagaggact acttcaagaa aatcgagtgc ttcgactccg tggaaatctc cggcgtggaa    1800
gatcggttca acgcctccct gggcacatac acgatctgc tgaaaattat caaggacaag    1860
gacttcctgg acaatgagga aaacgaggac attctggaag atatcgtgct gaccctgaca    1920
ctgtttgagg acagagagat gatcgaggaa cggctgaaaa cctatgccca cctgttcgac    1980
gacaaagtga tgaagcagct gaagcggcgg agatacaccg ctggggcag gctgagccgg    2040
aagctgatca acggcatccg ggacaagcag tccggcaaga caatcctgga tttcctgaag    2100
tccgacggct tcgccaacag aaacttcatg cagctgatcc acgacgacag cctgaccttt    2160
aaagaggaca tccagaaagc ccaggtgtcc ggccagggcg atagcctgca cgagcacatt    2220
gccaatctgg ccggcagccc cgccattaag aagggcatcc tgcagacagt gaaggtggtg    2280
gacgagctcg tgaaagtgat gggccggcac aagcccgaga acatcgtgat cgaaatggcc    2340
agagagaacc agaccaccca gaagggacag aagaacagcc gcgagagaat gaagcggatc    2400
gaagagggca tcaaagagct gggcagccag atcctgaaag aacacccgt ggaaaacacc    2460
cagctgcaga acgagaagct gtacctgtac tacctgcaga atgggcggga tatgtacgtg    2520
gaccaggaac tggacatcaa ccggctgtcc gactacgatg tggaccatat cgtgcctcag    2580
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca gagacagct ggtggaaacc    2820
cggcagatca caaagcacgt ggcacagatc ctggactccc ggatgaacac taagtacgac    2880
gagaatgaca agctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
```

| | |
|---|---:|
| agcgagcagg aaatcggcaa ggctaccgcc aagtacttct tctacagcaa catcatgaac | 3180 |
| tttttcaaga ccgagattac cctggccaac ggcgagatcc ggaagcggcc tctgatcgag | 3240 |
| acaaacggcg aaaccgggga gatcgtgtgg gataagggcc gggattttgc caccgtgcgg | 3300 |
| aaagtgctga gcatgcccca agtgaatatc gtgaaaaaga ccgaggtgca gacaggcggc | 3360 |
| ttcagcaaag agtctatcct gcccaagagg aacagcgata agctgatcgc cagaaagaag | 3420 |
| gactgggacc ctaagaagta cggcggcttc gacagcccca ccgtggccta ttctgtgctg | 3480 |
| gtggtggcca aagtggaaaa gggcaagtcc aagaaactga gagtgtgaa agagctgctg | 3540 |
| gggatcacca tcatggaaag aagcagcttc gagaagaatc ccatcgactt tctggaagcc | 3600 |
| aagggctaca agaagtgaa aaaggacctg atcatcaagc tgcctaagta ctccctgttc | 3660 |
| gagctggaaa acggccggaa gagaatgctg gcctctgccg gcgaactgca aagggaaac | 3720 |
| gaactggccc tgccctccaa atatgtgaac ttcctgtacc tggccagcca ctatgagaag | 3780 |
| ctgaagggct cccccgagga taatgagcag aaacagctgt tgtggaaca gcacaagcac | 3840 |
| tacctggacg agatcatcga gcagatcagc gagttctcca agagagtgat cctggccgac | 3900 |
| gctaatctgg acaaagtgct gtccgcctac aacaagcacc gggataagcc catcagagag | 3960 |
| caggccgaga atatcatcca cctgtttacc ctgaccaatc tgggagcccc tgccgccttc | 4020 |
| aagtactttg acaccaccat cgaccggaag aggtacacca gcaccaaaga ggtgctggac | 4080 |
| gccaccctga tccaccagag catcaccggc ctgtacgaga cacggatcga cctgtctcag | 4140 |
| ctgggaggcg acaagcgtcc tgctgctact aagaaagctg gtcaagctaa gaaaaagaaa | 4200 |
| gctag | 4205 |

<210> SEQ ID NO 33
<211> LENGTH: 12150
<212> TYPE: DNA
<213> ORGANISM: Artificial Sequence
<220> FEATURE:
<223> OTHER INFORMATION: Synthetic HIV-1 encapsidation construct
<220> FEATURE:
<223> OTHER INFORMATION: HIV-1 encapsidation construct

<400> SEQUENCE: 33

| | |
|---|---:|
| ttgattattg actagttatt aatagtaatc aattacgggg tcattagttc atagcccata | 60 |
| tatggagttc cgcgttacat aacttacggt aaatggcccg cctggctgac cgcccaacga | 120 |
| cccccgccca ttgacgtcaa taatgacgta tgttcccata gtaacgccaa tagggacttt | 180 |
| ccattgacgt caatgggtgg agtatttacg gtaaactgcc cacttggcag tacatcaagt | 240 |
| gtatcatatg ccaagtacgc cccctattga cgtcaatgac ggtaaatggc ccgcctggca | 300 |
| ttatgcccag tacatgacct tatgggactt tcctacttgg cagtacatct acgtattagt | 360 |
| catcgctatt accatggtga tgcggttttg gcagtacatc aatgggcgtg atagcggtt | 420 |
| tgactcacgg ggatttccaa gtctccaccc cattgacgtc aatgggagtt tgttttggca | 480 |
| ccaaaatcaa cgggactttc caaaatgtcg taacaactcc gccccattga cgcaaatggg | 540 |
| cggtaggcgt gtacggtggg aggtctatat aagcagagct cgtttagtga accgtcagat | 600 |
| cgcctggaga cgccatccac gctgttttga cctccataga agacaccggg accgatccag | 660 |
| cctccgcggc cgggaacggt gcattggaac gcggattccc cgtgccaaga gtgacgtaag | 720 |
| taccgcctat agagtctata ggcccacccc cttggcttct tatgcgacgg atcgatcccg | 780 |
| taataagctt cgaggtccgc ggccggccgc gttgacgcgc acggcaagag gcgaggggcg | 840 |
| gcgactggtg agagatgggt gcgagagcgt cagtattaag cggggagaa ttagatcgat | 900 |

```
gggaaaaaat tcggttaagg ccagggggaa agaaaaaata taaattaaaa catatagtat      960
gggcaagcag ggagctagaa cgattcgcag ttaatcctgg cctgttagaa acatcagaag     1020
gctgtagaca aatactggga cagctacaac catcccttca gacaggatca gaagaactta    1080
gatcattata taatacagta gcaaccctct attgtgtgca tcaaaggata gagataaaag    1140
acaccaagga agctttagac aagatagagg aagagcaaaa caaaagtaag aaaaaagcac    1200
agcaagcagc agctgacaca ggacacagca atcaggtcag ccaaaattac cctatagtgc    1260
agaacatcca ggggcaaatg gtacatcagg ccatatcacc tagaacttta aatgcatggg    1320
taaaagtagt agaagagaag gctttcagcc cagaagtgat acccatgttt tcagcattat    1380
cagaaggagc cacccccacaa gatttaaaca ccatgctaaa cacagtgggg ggacatcaag    1440
cagccatgca aatgttaaaa gagaccatca atgaggaagc tgcagaatgg gatagagtgc    1500
atccagtgca tgcagggcct attgcaccag gccagatgag agaaccaagg ggaagtgaca    1560
tagcaggaac tactagtacc cttcaggaac aaataggatg gatgacacat aatccaccta    1620
tcccagtagg agaaatctat aaaagatgga taatcctggg attaaataaa atagtaagaa    1680
tgtatagccc taccagcatt ctggacataa gacaaggacc aaaggaaccc tttagagact    1740
atgtagaccg attctataaa actctaagag ccgagcaagc ttcacaagag gtaaaaaatt    1800
ggatgacaga aaccttgttg gtccaaaatg cgaacccaga ttgtaagact attttaaaag    1860
cattgggacc aggagcgaca ctagaagaaa tgatgacagc atgtcaggga gtggggggac    1920
ccggccataa agcaagagtt ttggctgaag caatgagcca agtaacaaat ccagctacca    1980
taatgataca gaaaggcaat tttaggaacc aaagaaagac tgttaagtgt ttcaattgtg    2040
gcaaagaagg gcacatagcc aaaaattgca gggcccctag gaaaaagggc tgttggaaat    2100
gtggaaagga aggacaccaa atgaaagatt gtactgagag acaggctaat tttttaggga    2160
agatctggcc ttcccacaag ggaaggccag ggaattttct tcagagcaga ccagagccaa    2220
cagccccacc agaagagagc ttcaggtttg gggaagagac aacaactccc tctcagaagc    2280
aggagccgat agacaaggaa ctgtatcctt tagcttccct cagatcactc tttggcagcg    2340
accccctcgtc acaataaaga tagggggca attaaaggaa gctctattag atacaggagc    2400
agatgataca gtattagaag aaatgaattt gccaggaaga tggaaaccaa aaatgatagg    2460
gggaattgga ggttttatca agtaagaca gtatgatcag atactcatag aaatctgcgg    2520
acataaagct ataggtacag tattagtagg acctacacct gtcaacataa ttggaagaaa    2580
tctgttgact cagattggct gcactttaaa ttttcccatt agtcctattg agactgtacc    2640
agtaaaatta aagccaggaa tggatggccc aaaagttaaa caatggccat tgacagaaga    2700
aaaaataaaa gcattagtag aaatttgtac agaaatggaa aaggaaggaa aaatttcaaa    2760
aattgggcct gaaaatccat acaatactcc agtatttgcc ataaagaaaa aagacagtac    2820
taaatggaga aaattagtag atttcagaga acttaataag agaactcaag atttctggga    2880
agttcaatta ggaataccac atcctgcagg gttaaaacag aaaaaatcag taacagtact    2940
ggatgtgggc gatgcatatt tttcagttcc cttagataaa gacttcagga agtatactgc    3000
atttaccata cctagtataa acaatgagac accagggatt agatatcagt acaatgtgct    3060
tccacaggga tggaaaggat caccagcaat attccagtgt agcatgacaa aaatcttaga    3120
gccttttaga aaacaaaatc cagacatagt catctatcaa tacatggatg atttgtatgt    3180
aggatctgac ttagaaatag ggcagcatag aacaaaaata gaggaactga gacaacatct    3240
```

```
gttgaggtgg ggatttacca caccagacaa aaaacatcag aaagaacctc cattcctttg   3300
gatgggttat gaactccatc ctgataaatg gacagtacag cctatagtgc tgccagaaaa   3360
ggacagctgg actgtcaatg acatacagaa attagtggga aaattgaatt gggcaagtca   3420
gatttatgca gggattaaag taaggcaatt atgtaaactt cttaggggaa ccaaagcact   3480
aacagaagta gtaccactaa cagaagaagc agagctagaa ctggcagaaa acagggagat   3540
tctaaaagaa ccggtacatg gagtgtatta tgacccatca aaagacttaa tagcagaaat   3600
acagaagcag gggcaaggcc aatggacata tcaaatttat caagagccat ttaaaaatct   3660
gaaaacagga aagtatgcaa gaatgaaggg tgcccacact aatgatgtga aacaattaac   3720
agaggcagta caaaaaatag ccacagaaag catagtaata tggggaaaga ctcctaaatt   3780
taaattaccc atacaaaagg aaacatggga agcatggtgg acagagtatt ggcaagccac   3840
ctggattcct gagtgggagt ttgtcaatac ccctccctta gtgaagttat ggtaccagtt   3900
agagaaagaa cccataatag gagcagaaac tttctatgta gatggggcag ccaataggga   3960
aactaaatta ggaaaagcag gatatgtaac tgacagagga agacaaaaag ttgtccccct   4020
aacggacaca acaaatcaga agactgagtt acaagcaatt catctagctt tgcaggattc   4080
gggattagaa gtaaacatag tgacagactc acaatatgca ttgggaatca ttcaagcaca   4140
accagataag agtgaatcag agttagtcag tcaaataata gagcagttaa taaaaaagga   4200
aaaagtctac ctggcatggg taccagcaca caaaggaatt ggaggaaatg aacaagtaga   4260
taaattggtc agtgctggaa tcaggaaagt actattttta gatggaatag ataaggccca   4320
agaagaacat gagaaatatc acagtaattg gagagcaatg gctagtgatt ttaacctacc   4380
acctgtagta gcaaaagaaa tagtagccag ctgtgataaa tgtcagctaa aggggaagc   4440
catgcatgga caagtagact gtagcccagg aatatggcag ctagattgta cacatttaga   4500
aggaaaagtt atcttggtag cagttcatgt agccagtgga tatatagaag cagaagtaat   4560
tccagcagag acagggcaag aaacagcata cttcctctta aaattagcag gaagatggcc   4620
agtaaaaaca gtacatacag acaatggcag caatttcacc agtactacag ttaaggccgc   4680
ctgttggtgg gcggggatca agcaggaatt tggcattccc tacaatcccc aaagtcaagg   4740
agtaatagaa tctatgaata aagaattaaa gaaaattata ggacaggtaa gagatcaggc   4800
tgaacatctt aagacagcag tacaaatggc agtattcatc cacaatttta aaagaaaagg   4860
ggggattggg gggtacagtg caggggaaag aatagtagac ataatagcaa cagacataca   4920
aactaaagaa ttacaaaaac aaattacaaa aattcaaaat tttcgggttt attacaggga   4980
cagcagagat ccagtttgga aaggaccagc aaagctcctc tggaaaggtg aaggggcagt   5040
agtaatacaa gataatagtg acataaaagt agtgccaaga agaaaagcaa agatcatcag   5100
ggattatgga aaacagatgg caggtgatga ttgtgtggca agtagacagg atgaggatta   5160
acacatggaa ttctgcaaca actgctgttt atccatttca gaattgggtg tcgacatagc   5220
agaataggcg ttactcgaca gaggagagca agaaatggag ccagtagatc ctagactaga   5280
gccctggaag catccaggaa gtcagcctaa aactgcttgt accaattgct attgtaaaaa   5340
gtgttgcttt cattgccaag tttgtttcat gacaaaagcc ttaggcatct cctatggcag   5400
gaagaagcgg agacagcgac gaagagctca tcagaacagt cagactcatc aagcttctct   5460
atcaaagcag taagtagtac atgtaatgca acctataata gtagcaatag tagcattagt   5520
agtagcaata ataatagcaa tagttgtgtg gtccatagta atcatagaat ataggaaaat   5580
ggccgctgat cttcagacct ggaggaggag atatgaggga caattggaga agtgaattat   5640
```

```
ataaatataa agtagtaaaa attgaaccat taggagtagc acccaccaag gcaaagagaa    5700
gagtggtgca gagagaaaaa agagcagtgg gaataggagc tttgttcctt gggttcttgg    5760
gagcagcagg aagcactatg gcgcagcgt  caatgacgct gacggtacag gccagacaat    5820
tattgtctgg tatagtgcag cagcagaaca atttgctgag ggctattgag gcgcaacagc    5880
atctgttgca actcacagtc tggggcatca agcagctcca ggcaagaatc ctggctgtgg    5940
aaagatacct aaaggatcaa cagctcctgg ggatttgggg ttgctctgga aaactcattt    6000
gcaccactgc tgtgccttgg aatgctagtt ggagtaataa atctctggaa cagatttgga    6060
atcacacgac ctggatggag tgggacagag aaattaacaa ttacacaagc ttaatacact    6120
ccttaattga agaatcgcaa aaccagcaag aaaagaatga acaagaatta ttggaattag    6180
ataaatgggc aagtttgtgg aattggttta acataacaaa ttggctgtgg tatataaaat    6240
tattcataat gatagtagga ggcttggtag gtttaagaat agttttgct  gtactttcta    6300 tagtgaatag agttaggcag ggatattcac cattatcgtt tcagacccac ctcccaaccc    6360
cgaggggacc cgacaggccc gaaggaatag aagaagaagg tggagagaga cagagacaga    6420
gatccattcg attagtgaac ggatccttgg cacttatctg ggacgatctg cggagcctgt    6480
gcctcttcag ctaccaccgc ttgagagact tactcttgat tgtaacgagg attgtggaac    6540
ttctgggacg caggggggtgg gaagccctca aatattggtg gaatctccta caatattgga    6600
gtcaggagct aaagaatagt gctgttagct tgctcaatgc cacagccata gcagtagctg    6660
aggggacaga tagggttata gaagtagtac aaggagcttg tagagctatt cgccacatac    6720
ctagaagaat aagacagggc ttggaaagga ttttgctata agctcgaggc cgccccggtg    6780
accttcagac cttggcactg gaggtggccc ggcagaagcg cggcatcgtg atcagtgct    6840 gcaccagcat ctgctctctc taccaactgg agaactactg caactaggcc caccactacc    6900
ctgtccaccc ctctgcaatg aataaaacct ttgaaagagc actacaagtt gtgtgtacat    6960
gcgtgcatgt gcatatgtgg tgcgggggga acatgagtgg ggctggctgg agtggcgatg    7020
ataagctgtc aaacatgaga attaattctt gaagacgaaa gggcctcgtg atacgcctat    7080
ttttataggt taatgtcatg ataataatgg tttcttagtc tagaattaat tccgtgtatt    7140
ctatagtgtc acctaaatcg tatgtgtatg atacataagg ttatgtatta attgtagccg    7200
cgttctaacg acaatatgta caagcctaat tgtgtagcat ctggcttact gaagcagacc    7260
ctatcatctc tctcgtaaac tgccgtcaga gtcggtttgg ttggacgaac cttctgagtt    7320
tctggtaacg ccgtcccgca cccggaaatg gtcagcgaac caatcagcag ggtcatcgct    7380
agccagatcc tctacgccgg acgcatcgtg gccggcatca ccggcgccac aggtgcggtt    7440
gctggcgcct atatcgccga catcaccgat ggggaagatc gggctcgcca cttcgggctc    7500
atgagcgctt gtttcggcgt gggtatggtg gcaggccccg tggccggggg actgttgggc    7560
gccatctcct tgcatgcacc attccttgcg gcggcggtgc tcaacggcct caacctacta    7620
ctgggctgct tcctaatgca ggagtcgcat aagggagagc gtcgaatggt gcactctcag    7680
tacaatctgc tctgatgccg catagttaag ccagccccga cacccgccaa cacccgctga    7740
cgcgccctga cgggcttgtc tgctcccggc atccgcttac agacaagctg tgaccgtctc    7800
cgggagctgc atgtgtcaga ggttttcacc gtcatcaccg aaacgcgcga cgcaaaggg    7860 cctcgtgata cgcctatttt tataggttaa tgtcatgata ataatggttt cttagacgtc    7920
aggtggcact tttcggggaa atgtgcgcgg aaccccttatt tgtttatttt tctaaataca    7980
```

```
ttcaaatatg tatccgctca tgagacaata accctgataa atgcttcaat aatattgaaa    8040
aaggaagagt atgagtattc aacatttccg tgtcgccctt attccctttt ttgcggcatt    8100
ttgccttcct gttttttgctc acccagaaac gctggtgaaa gtaaaagatg ctgaagatca   8160
gttgggtgca cgagtgggtt acatcgaact ggatctcaac agcggtaaga tccttgagag    8220
ttttcgcccc gaagaacgtt ttccaatgat gagcactttt aaagttctgc tatgtggcgc    8280
ggtattatcc cgtattgacg ccgggcaaga gcaactcggt cgccgcatac actattctca    8340
gaatgacttg gttgagtact caccagtcac agaaaagcat cttacggatg gcatgacagt    8400
aagagaatta tgcagtgctg ccataaccat gagtgataac actgcggcca acttacttct    8460
gacaacgatc ggaggaccga aggagctaac cgcttttttg cacaacatgg gggatcatgt    8520
aactcgcctt gatcgttggg aaccggagct gaatgaagcc ataccaaacg acgagcgtga    8580
caccacgatg cctgtagcaa tggcaacaac gttgcgcaaa ctattaactg gcgaactact    8640
tactctagct tcccggcaac aattaataga ctggatggag gcggataaag ttgcaggacc    8700
acttctgcgc tcggcccttc cggctggctg gtttattgct gataaatctg gagccggtga    8760
gcgtgggtct cgcggtatca ttgcagcact ggggccagat ggtaagccct cccgtatcgt    8820
agttatctac acgacgggga gtcaggcaac tatgatgaa cgaaatagac agatcgctga    8880
gataggtgcc tcactgatta agcattggta actgtcagac caagtttact catatatact    8940
ttagattgat ttaaaacttc atttttaatt taaaaggatc taggtgaaga tcctttttga    9000
taatctcatg accaaaatcc cttaacgtga gttttcgttc cactgagcgt cagaccccgt    9060
agaaaagatc aaaggatctt cttgagatcc tttttttctg cgcgtaatct gctgcttgca    9120
aacaaaaaaa ccaccgctac cagcggtggt ttgtttgccg gatcaagagc taccaactct    9180
ttttccgaag gtaactggct tcagcagagc gcagatacca aatactgttc ttctagtgta    9240
gccgtagtta ggccaccact tcaagaactc tgtagcaccg cctacatacc tcgctctgct    9300
aatcctgtta ccagtggctg ctgccagtgg cgataagtcg tgtcttaccg ggttggactc    9360
aagacgatag ttaccggata aggcgcagcg gtcgggctga acggggggtt cgtgcacaca    9420
gcccagcttg gagcgaacga cctacaccga actgagatac ctacagcgtg agctatgaga    9480
aagcgccacg cttcccgaag ggagaaaggc ggacaggtat ccggtaagcg cagggtcgg    9540
aacaggagag cgcacgaggg agcttccagg gggaaacgcc tggtatcttt atagtcctgt    9600
cgggtttcgc cacctctgac ttgagcgtcg atttttgtga tgctcgtcag ggggcggag    9660
cctatggaaa aacgccagca acgcggcctt tttacggttc ctggccttt gctggccttt    9720
tgctcacatg ttctttcctg cgttatcccc tgattctgtg ataaccgta ttaccgcctt    9780
tgagtgagct gataccgctc gccgcagccg aacgaccgag cgcagcgagt cagtgagcga    9840
ggaagcggaa gagcgcccaa tacgcaaacc gcctctcccc gcgcgttggc cgattcatta    9900
atgcagctgt ggaatgtgtg tcagttaggg tgtggaaagt ccccaggctc ccagcaggc    9960
agaagtatgc aaagcatgca tctcaattag tcagcaacca ggtgtggaaa gtccccaggc   10020
tccccagcag gcagaagtat gcaaagcatg catctcaatt agtcagcaac catagtcccg   10080
cccctaactc cgcccatccc gcccctaact ccgcccagtt ccgcccattc tccgccccat   10140
ggctgactaa ttttttttat ttatgcagag gccgaggccg cctcggcctc tgagctattc   10200
cagaagtagt gaggaggctt ttttggaggc ctaggctttt gcaaaaagct tggacacaag   10260
acaggcttgc gagatatgtt tgagaatacc actttatccc gcgtcaggga gaggcagtgc   10320
gtaaaaagac gcggactcat gtgaaatact ggtttttagt gcgccagatc tctataatct   10380
```

```
cgcgcaacct attttcccct cgaacacttt ttaagccgta gataaacagg ctgggacact    10440
tcacatgagc gaaaaataca tcgtcacctg ggacatgttg cagatccatg cacgtaaact    10500
cgcaagccga ctgatgcctt ctgaacaatg gaaaggcatt attgccgtaa gccgtggcgg    10560
tctgtaccgg gtgcgttact ggcgcgtgaa ctgggtattc gtcatgtcga taccgtttgt    10620
atttccagct acgatcacga caaccagcgc gagcttaaag tgctgaaacg cgcagaaggc    10680
gatggcgaag gcttcatcgt tattgatgac ctggtggata ccggtggtac tgcggttgcg    10740
attcgtgaaa tgtatccaaa agcgcacttt gtcaccatct cgcaaaaacc ggctggtcgt    10800
ccgctggttg atgactatgt tgttgatatc ccgcaagata cctggattga acagccgtgg    10860
gatatgggcg tcgtattcgt cccgccaatc tccggtcgct aatcttttca acgcctggca    10920
ctgccgggcg ttgttctttt taacttcagg cgggttacaa tagtttccag taagtattct    10980
ggaggctgca tccatgacac aggcaaacct gagcgaaacc ctgttcaaac cccgctttaa    11040
acatcctgaa acctcgacgc tagtccgccg ctttaatcac ggcgcacaac cgcctgtgca    11100
gtcggccctt gatggtaaaa ccatccctca ctggtatcgc atgattaacc gtctgatgtg    11160
gatctggcgc ggcattgacc cacgcgaaat cctcgacgtc caggcacgta ttgtgatgag    11220
cgatgccgaa cgtaccgacg atgatttata cgatacggtg attggctacc gtggcggcaa    11280
ctggatttat gagtgggccc cggatctttg tgaaggaacc ttacttctgt ggtgtgacat    11340
aattggacaa actacctaca gagatttaaa gctctaaggt aaatataaaa tttttaaccc    11400
ggatctttgt gaaggaacct tacttctgtg gtgtgacata attggacaaa ctacctacag    11460
agatttaaag ctctaaggta aatataaaat ttttaagtgt ataatgtgtt aaactactga    11520
ttctaattgt ttgtgtattt tagattccaa cctatggaac tgatgaatgg gagcagtggt    11580
ggaatgcctt taatgaggaa aacctgtttt gctcagaaga aatgccatct agtgatgatg    11640
aggctactgc tgactctcaa cattctactc ctccaaaaaa gaagagaaag gtagaagacc    11700
ccaaggactt tccttcagaa ttgctaagtt ttttgagtca tgctgtgttt agtaatagaa    11760
ctcttgcttg ctttgctatt tacaccacaa aggaaaaagc tgcactgcta tacaagaaaa    11820
ttatggaaaa atattctgta acctttataa gtaggcataa cagttataat cataacatac    11880
tgttttttct tactccacac aggcatagag tgtctgctat taataactat gctcaaaaat    11940
tgtgtacctt tagcttttta atttgtaaag gggttaataa ggaatatttg atgtatagtg    12000
ccttgactag agatcataat cagccatacc acatttgtag aggttttact tgctttaaaa    12060
aacctcccac acctccccct gaacctgaaa cataaaatga atgcaattgt tgttgttggg    12120
ctgcaggaat taattcgagc tcgcccgaca                                     12150
```

<210> SEQ ID NO 34
<211> LENGTH: 10627
<212> TYPE: DNA
<213> ORGANISM: Artificial Sequence
<220> FEATURE:
<223> OTHER INFORMATION: Synthetic encoding HIV-1 GAG-CAS9 construct
<220> FEATURE:
<223> OTHER INFORMATION: encoding HIV-1 GAG-CAS9 construct

<400> SEQUENCE: 34

```
gcggccgctc tagagagctt ggcccattgc atacgttgta tccatatcat aatatgtaca    60
tttatattgg ctcatgtcca acattaccgc catgttgaca ttgattattg actagttatt    120
aatagtaatc aattacgggg tcattagttc atagcccata tatggagttc cgcgttacat    180
```

```
aacttacggt aaatggcccg cctggctgac cgcccaacga cccccgccca ttgacgtcaa    240
taatgacgta tgttcccata gtaacgccaa tagggacttt ccattgacgt caatgggtgg    300
agtatttacg gtaaactgcc cacttggcag tacatcaagt gtatcatatg ccaagtacgc    360
cccctattga cgtcaatgac ggtaaatggc ccgcctggca ttatgcccag tacatgacct    420
tatgggactt tcctacttgg cagtacatct acgtattagt catcgctatt accatggtga    480
tgcggttttg gcagtacatc aatgggcgtg gatagcggtt tgactcacgg ggatttccaa    540
gtctccaccc cattgacgtc aatgggagtt tgttttggca ccaaaatcaa cgggactttc    600
caaaatgtcg taacaactcc gccccattga cgcaaatggg cggtaggcgt gtacggtggg    660
aggtctatat aagcagagct cgtttagtga accgtcagat cgcctggaga cgccatccac    720
gctgttttga cctccataga agacaccggg accgatccag cctccggtcg accgatcctg    780
agaacttcag ggtgagtttg ggacccttg attgttcttt cttttcgct attgtaaaat    840
tcatgttata tggagggggc aaagttttca gggtgttgtt tagaatggga agatgtccct    900
tgtatcacca tggaccctca tgataatttt gtttctttca ctttctactc tgttgacaac    960
cattgtctcc tcttattttc ttttcatttt cttgtaactt tttcgttaaa ctttagcttg   1020
catttgtaac gaattttaa attcacttt gtttatttgt cagattgtaa gtactttctc   1080
taatcacttt tttttcaagg caatcagggt atattatatt gtacttcagc acagttttag   1140
agaacaattg ttataattaa atgataaggt agaatatttc tgcatataaa ttctggctgg   1200
cgtggaaata ttcttattgg tagaaacaac tacatcctgg tcatcatcct gcctttctct   1260
ttatggttac aatgatatac actgtttgag atgaggataa aatactctga gtccaaaccg   1320
ggcccctctg ctaaccatgt tcatgccttc ttcttttcc tacagctcct gggcaacgtg   1380
ctggttattg tgctgtctca tcattttggc aaagaattcc tcgagatggg tgcgagagcg   1440
tcggtattaa gcgggggaga attagataaa tgggaaaaaa ttcggttaag gccaggggga   1500
aagaaacaat ataaactaaa acatatagta tgggcaagca gggagctaga acgattcgca   1560
gttaatcctg gccttttaga gacatcagaa ggctgtagac aaatactggg acagctacaa   1620
ccatcccttc agacaggatc agaagaactt agatcattat ataatacaat agcagtcctc   1680
tattgtgtgc atcaaaggat agatgtaaaa gacaccaagg aagccttaga taagatagag   1740
gaagagcaaa acaaaagtaa gaaaaaggca cagcaagcag cagctgacac aggaaacaac   1800
agccaggtca gccaaaatta ccctatagtg cagaacctcc aggggcaaat ggtacatcag   1860
gccatatcac ctagaacttt aaatgcatgg gtaaaagtag tagaagagaa ggctttcagc   1920
ccagaagtaa tacccatgtt ttcagcatta tcagaaggag ccaccccaca agatttaaat   1980
accatgctaa acacagtggg gggacatcaa gcagccatgc aaatgttaaa agagaccatc   2040
aatgaggaag ctgcagaatg ggatagattg catccagtgc atgcagggcc tattgcacca   2100
ggccagatga gagaaccaag gggaagtgac atagcaggaa ctactagtac ccttcaggaa   2160
caaataggat ggatgacaca taatccacct atcccagtag gagaaatcta aaaagatgg   2220
ataatcctgg gattaaataa aatagtaaga atgtatagcc ctaccagcat tctggacata   2280
agacaaggac caaggaacc ctttagagac tatgtagacc gattctataa aactctaaga   2340
gccgagcaag cttcacaaga ggtaaaaaat tggatgacag aaaccttgtt ggtccaaaat   2400
gcgaacccag attgtaagac tattttaaaa gcattgggac caggagcgac actagaagaa   2460
atgatgacag catgtcaggg agtggggggga cccggccata agcaagagt tttggctgaa   2520
gcaatgagcc aagtaacaaa tccagctacc ataatgatac agaaaggcaa ttttaggaac   2580
```

```
caaagaaaga ctgttaagtg tttcaattgt ggcaaagaag ggcacatagc caaaaattgc    2640
agggccccta ggaaaaaggg ctgttggaaa tgtggaaagg aaggacacca aatgaaagat    2700
tgtactgaga gacaggctaa tttttagggg aagatctggc cttcccacaa gggaaggcca    2760 gggaatttc ttcagagcag accagagcca acagccccac cagaagagag cttcaggttt    2820
ggggaagaga caacaactcc ctctcagaag caggagccga tagacaagga actgtatcct    2880
ttagcttccc tcagatcact ctttggcagc gacccctcgt cacaaccggg gaccacgacc    2940
ccaggcaaag caagagtttt ggctgaagca atgagcaccg tgattacaa agacgatgac    3000 gataagatgg ccccaaagaa gaagcggaag gtcggtatcc acggagtccc agcagccgac    3060
aagaagtaca gcatcggcct ggacatcggc accaactctg tgggctgggc cgtgatcacc    3120
gacgagtaca aggtgcccag caagaaattc aaggtgctgg gcaacaccga ccggcacagc    3180
atcaagaaga acctgatcgg agccctgctg ttcgacagcg gcgaaacagc cgaggccacc    3240
cggctgaaga gaaccgccag aagaagatac accagacgga gaaccggat ctgctatctg    3300 caagagatct tcagcaacga gatggccaag gtggacgaca gcttcttcca cagactggaa    3360
gagtccttcc tggtggaaga ggataagaag cacgagcggc accccatctt cggcaacatc    3420
gtggacgagg tggcctacca cgagaagtac cccaccatct accacctgag aaagaaactg    3480
gtggacagca ccgacaaggc cgacctgcgg ctgatctatc tggccctggc ccacatgatc    3540
aagttccggg gccacttcct gatcgagggc gacctgaacc ccgacaacag cgacgtggac    3600
aagctgttca tccagctggt gcagacctac aaccagctgt tcgaggaaaa ccccatcaac    3660
gccagcggcg tggacgccaa ggccatcctg tctgccagac tgagcaagag cagacggctg    3720
gaaaatctga tcgcccagct gcccggcgag aagaagaatg gcctgttcgg caacctgatt    3780
gccctgagcc tgggcctgac ccccaacttc aagagcaact tcgacctggc cgaggatgcc    3840
aaactgcagc tgagcaagga cacctacgac gacgacctgg acaacctgct ggcccagatc    3900
ggcgaccagt acgccgacct gtttctggcc gccaagaacc tgtccgacgc catcctgctg    3960
agcgacatcc tgagagtgaa caccgagatc accaaggccc ccctgagcgc ctctatgatc    4020
aagagatacg acgagcacca ccaggacctg accctgctga aagctctcgt gcggcagcag    4080
ctgcctgaga gtacaaaga gattttcttc gaccagagca gaacggcta cgccggctac    4140 attgacggcg gagccagcca ggaagagttc tacaagttca tcaagcccat cctggaaaag    4200
atggacggca ccgaggaact gctcgtgaag ctgaacagag aggacctgct gcggaagcag    4260
cggaccttcg acaacggcag catccccac cagatccacc tgggagagct gcacgccatt    4320
ctgcggcggc aggaagattt ttacccattc ctgaaggaca accgggaaaa gatcgagaag    4380
atcctgacct tccgcatccc ctactacgtg ggccctctgg ccaggggaaa cagcagattc    4440
gcctggatga ccagaaagag cgaggaaacc atcaccccct ggaacttcga ggaagtggtg    4500
gacaagggcg cttccgccca gagcttcatc gagcggatga ccaacttcga taagaacctg    4560
cccaacgaga aggtgctgcc caagcacagc ctgctgtacg agtacttcac cgtgtataac    4620
gagctgacca aagtgaaata cgtgaccgag ggaatgagaa agcccgcctt cctgagcggc    4680
gagcagaaaa aggccatcgt ggacctgctg ttcaagacca ccggaaagt gaccgtgaag    4740 cagctgaaag aggactactt caagaaaatc gagtgcttcg actccgtgga aatctccggc    4800
gtggaagatc ggttcaacgc ctccctggc acataccacg atctgctgaa aattatcaag    4860
gacaaggact tcctggacaa tgaggaaaac gaggacattc tggaagatat cgtgctgacc    4920
```

```
ctgacactgt tgaggacag agagatgatc gaggaacggc tgaaaaccta tgcccacctg    4980
ttcgacgaca aagtgatgaa gcagctgaag cggcggagat acaccggctg ggcaggctg    5040 agccggaagc tgatcaacgg catccgggac aagcagtccg gcaagacaat cctggatttc    5100
ctgaagtccg acggcttcgc caacagaaac ttcatgcagc tgatccacga cgacagcctg    5160
acctttaaag aggacatcca gaaagcccag gtgtccggcc agggcgatag cctgcacgag    5220
cacattgcca atctgccggg cagccccgcc attaagaagg gcatcctgca gacagtgaag    5280
gtggtggacg agctcgtgaa agtgatgggc cggcacaagc ccgagaacat cgtgatcgaa    5340
atggccagag agaaccagac cacccagaag ggacagaaga cagccgcga gagaatgaag    5400 cggatcgaag agggcatcaa agagctgggc agccagatcc tgaaagaaca ccccgtggaa    5460
aacacccagc tgcagaacga gaagctgtac ctgtactacc tgcagaatgg gcgggatatg    5520
tacgtggacc aggaactgga catcaaccgg ctgtccgact acgatgtgga ccatatcgtg    5580
cctcagagct ttctgaagga cgactccatc gacaacaagg tgctgaccag aagcgacaag    5640
aaccggggca gagcgacaa cgtgcccctcc gaagaggtcg tgaagaagat gaagaactac    5700
tggcggcagc tgctgaacgc caagctgatt acccagagaa agttcgacaa tctgaccaag    5760
gccgagagag cggcctgag cgaactggat aaggccggct tcatcaagag acagctggtg    5820
gaaacccggc agatcacaaa gcacgtggca cagatcctgg actcccggat gaacactaag    5880
tacgacgaga atgacaagct gatccgggaa gtgaaagtga tcaccctgaa gtccaagctg    5940
gtgtccgatt tccggaagga tttccagttt tacaaagtgc gcgagatcaa caactaccac    6000
cacgcccacg acgcctacct gaacgccgtc gtgggaaccg ccctgatcaa aaagtaccct    6060
aagctggaaa gcgagttcgt gtacggcgac tacaaggtgt acgacgtgcg gaagatgatc    6120
gccaagagcg agcaggaaat cggcaaggct accgccaagt acttcttcta cagcaacatc    6180 atgaacttt tcaagaccga gattaccctg gccaacggcg agatccggaa gcggcctctg    6240
atcgagacaa acgcgaaac cggggagatc gtgtgggata agggccggga ttttgccacc    6300
gtgcggaaag tgctgagcat gccccaagtg aatatcgtga aaaagaccga ggtgcagaca    6360
ggcggcttca gcaaagagtc tatcctgccc aagaggaaca gcgataagct gatcgccaga    6420
aagaaggact gggacccta gaagtacggc ggcttcgaca gccccaccgt ggcctattct    6480
gtgctggtgg tggccaaagt ggaaaagggc aagtccaaga aactgaagag tgtgaaagag    6540
ctgctgggga tcaccatcat ggaaagaagc agcttcgaga gaatcccat cgactttctg    6600 gaagccaagg gctacaaaga agtgaaaaag gacctgatca tcaagctgcc taagtactcc    6660
ctgttcgagc tggaaaacgg ccggaagaga atgctggcct ctgccggcga actgcagaag    6720
ggaaacgaac tggccctgcc ctccaaatat gtgaacttcc tgtacctggc cagccactat    6780
gagaagctga agggctcccc cgaggataat gagcagaaac agctgtttgt ggaacagcac    6840
aagcactacc tggacgagat catcgagcag atcagcgagt ctccaagag agtgatcctg    6900 gccgacgcta atctggacaa agtgctgtcc gcctacaaca gcaccgggga taagcccatc    6960
agagagcagg ccgagaatat catccacctg tttaccctga ccaatctggg agcccctgcc    7020
gccttcaagt actttgacac caccatcgac cggaagaggt acaccagcac caaagaggtg    7080
ctggacgcca ccctgatcca ccagagcatc accggcctgt acgagacacg gatcgacctg    7140
tctcagctgg gaggcgacaa gcgtcctgct gctactaaga agctggtca gctaagaaa    7200 aagaaagcta gagcttgata tcctgcagac gcgtaggatc cgtcgaggaa ttcactcctc    7260
aggtgcaggc tgcctatcag aaggtggtgg ctggtgtggc caatgccctg gctcacaaat    7320
```

```
accactgaga tcttttccc tctgccaaaa attatgggga catcatgaag cccccttgagc   7380
atctgacttc tggctaataa aggaaattta ttttcattgc aatagtgtgt tggaattttt   7440
tgtgtctctc actcggaagg acatatggga gggcaaatca tttaaaacat cagaatgagt   7500
atttggttta gagtttggca acatatgccc atatgctggc tgccatgaac aaaggttggc   7560
tataaagagg tcatcagtat atgaaacagc cccctgctgt ccattcctta ttccatagaa   7620
aagccttgac ttgaggttag attttttta tattttgttt tgtgttattt ttttctttaa   7680
catccctaaa attttcctta catgttttac tagccagatt tttcctcctc tcctgactac   7740
tcccagtcat agctgtccct cttctcttat ggagatccct cgacggatcg ccgcaattc   7800
gtaatcatgt catagctgtt tcctgtgtga aattgttatc cgctcacaat tccacacaac   7860
atacgagccg gaagcataaa gtgtaaagcc tggggtgcct aatgagtgag ctaactcaca   7920
ttaattgcgt tgcgctcact gcccgctttc cagtcgggaa acctgtcgtg ccagctgcat   7980
taatgaatcg gccaacgcgc ggggagaggc ggtttgcgta ttgggcgctc ttccgcttcc   8040
tcgctcactg actcgctgcg ctcggtcgtt cggctgcggc gagcggtatc agctcactca   8100
aaggcggtaa tacggttatc cacagaatca ggggataacg caggaaagaa catgtgagca   8160
aaaggccagc aaaaggccag gaaccgtaaa aaggccgcgt tgctggcgtt tttccatagg   8220
ctccgccccc ctgacgagca tcacaaaaat cgacgctcaa gtcagaggtg gcgaaacccg   8280
acaggactat aaagatacca ggcgtttccc cctggaagct ccctcgtgcg ctctcctgtt   8340
ccgaccctgc cgcttaccgg atacctgtcc gcctttctcc cttcgggaag cgtggcgctt   8400
tctcatagct cacgctgtag gtatctcagt tcggtgtagg tcgttcgctc caagctgggc   8460
tgtgtgcacg aaccccccgt tcagcccgac cgctgcgcct tatccggtaa ctatcgtctt   8520
gagtccaacc cggtaagaca cgacttatcg ccactggcag cagccactgg taacaggatt   8580
agcagagcga ggtatgtagg cggtgctaca gagttcttga agtggtggcc taactacggc   8640
tacactagaa gaacagtatt tggtatctgc gctctgctga agccagttac cttcggaaaa   8700
agagttggta gctcttgatc cggcaaacaa accaccgctg gtagcggtgg tttttttgtt   8760
tgcaagcagc agattacgcg cagaaaaaaa ggatctcaag aagatccttt gatcttttct   8820
acggggtctg acgctcagtg gaacgaaaac tcacgttaag ggattttggt catgagatta   8880
tcaaaaagga tcttcaccta gatccttta aattaaaaat gaagttttaa atcaatctaa   8940
agtatatatg agtaaacttg gtctgacagt taccaatgct taatcagtga ggcacctatc   9000
tcagcgatct gtctatttcg ttcatccata gttgcctgac tccccgtcgt gtagataact   9060
acgatacggg agggcttacc atctggcccc agtgctgcaa tgataccgcg agacccacgc   9120
tcaccggctc cagatttatc agcaataaac cagccagccg gaagggccga gcgcagaagt   9180
ggtcctgcaa ctttatccgc ctccatccag tctattaatt gttgccggga agctagagta   9240
agtagttcgc cagttaatag tttgcgcaac gttgttgcca ttgctacagg catcgtggtg   9300
tcacgctcgt cgtttggtat ggcttcattc agctccggtt cccaacgatc aaggcgagtt   9360
acatgatccc ccatgttgtg caaaaaagcg gttagctcc ttcggtcctc cgatcgttgt   9420
cagaagtaag ttggccgcag tgttatcact catggttatg gcagcactgc ataattctct   9480
tactgtcatg ccatccgtaa gatgcttttc tgtgactggt gagtactcaa ccaagtcatt   9540
ctgagaatag tgtatgcggc gaccgagttg ctcttgcccg gcgtcaatac gggataatac   9600
cgcgccacat agcagaactt taaaagtgct catcattgga aaacgttctt cggggcgaaa   9660
```

```
actctcaagg atcttaccgc tgttgagatc cagttcgatg taacccactc gtgcacccaa    9720
ctgatcttca gcatctttta cttcaccag cgtttctggg tgagcaaaaa caggaaggca    9780
aaatgccgca aaaagggaa taagggcgac acggaaatgt tgaatactca tactcttcct    9840
ttttcaatat tattgaagca tttatcaggg ttattgtctc atgagcggat acatatttga    9900
atgtatttag aaaataaac aatagggt tccgcgcaca tttccccgaa aagtgccacc    9960
taaattgtaa gcgttaatat tttgttaaaa ttcgcgttaa attttttgtta aatcagctca   10020 ttttttaacc aataggccga aatcggcaaa atcccttata aatcaaaaga atagaccgag   10080
atagggttga gtgttgttcc agtttggaac aagagtccac tattaaagaa cgtggactcc   10140
aacgtcaaag ggcgaaaaac cgtctatcag ggcgatggcc cactacgtga accatcaccc   10200
taatcaagtt ttttgggtc gaggtgccgt aaagcactaa atcggaaccc taaagggagc   10260
ccccgattta gagcttgacg gggaaagccg gcgaacgtgg cgagaaagga agggaagaaa   10320 gcgaaggag cgggcgctag ggcgctggca agtgtagcgg tcacgctgcg cgtaaccacc   10380
acacccgccg cgcttaatgc gccgctacag ggcgcgtccc attcgccatt caggctgcgc   10440
aactgttggg aagggcgatc ggtgcgggcc tcttcgctat tacgccagct ggcgaaaggg   10500
ggatgtgctg caaggcgatt aagttgggta acgccagggt ttcccagtc acgacgttgt   10560 aaaacgacgg ccagtgagcg cgcgtaatac gactcactat agggcgaatt ggagctccac   10620
cgcggtg                                                            10627
```

<210> SEQ ID NO 35
<211> LENGTH: 20
<212> TYPE: DNA
<213> ORGANISM: Artificial Sequence
<220> FEATURE:
<223> OTHER INFORMATION: Synthetic GFP target sequence
<220> FEATURE:
<223> OTHER INFORMATION: GFP target sequence

<400> SEQUENCE: 35
cgaggagctg ttcaccgggg                                                 20

<210> SEQ ID NO 36
<211> LENGTH: 27
<212> TYPE: DNA
<213> ORGANISM: Artificial Sequence
<220> FEATURE:
<223> OTHER INFORMATION: Synthetic primer

<400> SEQUENCE: 36
attgcggaag ttcctcttct taccctg                                         27

<210> SEQ ID NO 37
<211> LENGTH: 27
<212> TYPE: DNA
<213> ORGANISM: Artificial Sequence
<220> FEATURE:
<223> OTHER INFORMATION: Synthetic primer

<400> SEQUENCE: 37
ttcctgggaa gggtggatta tgacggg                                         27

<210> SEQ ID NO 38
<211> LENGTH: 20
<212> TYPE: DNA
<213> ORGANISM: Artificial Sequence
<220> FEATURE:
<223> OTHER INFORMATION: Synthetic target sequence

```
<400> SEQUENCE: 38
cgaggagctg ttcaccgggg                                              20

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
tctgagtggc aaaggaccttt agg                                         23

<210> SEQ ID NO 40
<211> LENGTH: 26
<212> TYPE: DNA
<213> ORGANISM: Artificial Sequence
<220> FEATURE:
<223> OTHER INFORMATION: Synthetic primer

<400> SEQUENCE: 40
gaagtcgtgc tgcttcatgt ggtcgg                                       26
```

METHODS AND PRODUCTS FOR GENETIC ENGINEERING

CROSS REFERENCE TO RELATED APPLICATIONS

This application is a continuation of Non-Provisional application Ser. No. 15/769,534, filed Apr. 19, 2018, which is a National Stage application under 35 U.S.C. § 371 of International Application No. PCT/EP2016/075289, filed on Oct. 20, 2016, which claims priority to European Provisional Application No. 15306678, filed Oct. 20, 2015, the contents of which are incorporated herein by reference in their entirety.

SEQUENCE LISTING

The present application is being filed along with a Sequence Listing in electronic format. The Sequence Listing is provided as a file entitled 20210215_S114_CONT_US_INSERM_R.txt, which is 106,525 bytes in size. The information in the electronic format of the Sequence Listing is incorporated by reference in its entirety.

FIELD OF THE INVENTION

The present invention relates to the field of gene targeting by methods using viral-derived vector systems related to Clustered Regularly Interspaced Short Palindromic Repeats (CRISPR) and components thereof.

BACKGROUND OF THE INVENTION

Genome editing using targetable nucleases is an emerging technology for the precise genome modification of organisms ranging from bacteria to plants and animals, including humans. Its attraction is that it can be used for almost all organisms in which targeted genome modification has not been possible with other kinds of methods.

Improving protocols for expressing exogenous proteins within human cells is of major interest for research and medical purposes. In spite of the constant evolution of transfection methods and performances of viral vectors, the efficiency of these approaches can vary dramatically, especially in primary cells that are highly sensitive to modifications of their environment and may be altered in response to transfection agents/vectors. Moreover, delivering genetic information through the transfer of a coding integrative/non-integrative DNA may be responsible for adverse effects like the induction of unwanted stress signals or the unexpected insertion of an exogenous gene within the cellular genome, which is a serious issue for therapeutic applications, particularly in stem cells.

Recent approaches to targeted genome modification—zinc-finger nucleases (ZFNs) and transcription-activator like effector nucleases (TALENs)—have enabled researchers to generate permanent mutations by introducing double-stranded breaks to activate repair pathways. The capacity of designed nucleases, like ZFN and TALENs, to generate DNA double-stranded breaks at desired positions in the genome has created optimism for therapeutic translation of locus-directed genome engineering. However, these approaches are costly and time-consuming to engineer, limiting their widespread use, particularly for large scale, high-throughput studies.

More recently, a new tool based on a totally distinct and specific system, namely bacterial CRISPR-associated protein-9 nuclease (Cas9) from *Streptococcus pyogenes* has generated considerable interest.

To achieve site-specific DNA recognition and cleavage, Cas9 must be complexed with both a crRNA and a separate trans-activating crRNA (tracrRNA or trRNA), that is partially complementary to the crRNA (11). The tracrRNA is required for crRNA maturation from a primary transcript encoding multiple pre-crRNAs.

During the cleavage of target DNA, the HNH and RuvC-like nuclease domains cut both DNA strands, generating double-stranded breaks (DSBs) at sites defined by a 20-nucleotide guide sequence within an associated crRNA transcript that base pairs with the target DNA sequence. The HNH domain cleaves the target DNA strand that is complementary to the guide RNA, while the RuvC domain cleaves the non-complementary strand. The double-stranded endonuclease activity of Cas9 also requires that a short conserved sequence, (2-5 nts) known as protospacer-associated motif (PAM), follows immediately 3'- of the crRNA complementary sequence.

The simplicity of the type II CRISPR nuclease, with only three required components (Cas9 along with the crRNA and trRNA) made this system amenable to adaptation for genome editing. This potential was realized in 2012 by the Doudna and Charpentier laboratories (Jinek et al., 2012, Science, Vol. 337: 816-821). Based on the type II CRISPR system described previously, a simplified two-component system was developed by combining trRNA and crRNA into a single synthetic single guide RNA (sgRNA). The sgRNA-programmed Cas9 was shown to be as effective as Cas9 programmed with separate trRNA and crRNA in guiding targeted gene alterations.

Mainly, three different variants of the Cas9 nuclease have been adopted in genome-editing protocols. The first is wild-type Cas9, which can site-specifically cleave double-stranded DNA, resulting in the activation of the double-strand break (DSB) repair machinery. DSBs can be repaired by the cellular Non-Homologous End Joining (NHEJ) pathway (Overballe-Petersen et al., 2013, Proc Natl Acad Sci USA, Vol. 110: 19860-19865), resulting in insertions and/or deletions (indels) which disrupt the targeted locus. Alternatively, if a donor template with homology to the targeted locus is supplied, the DSB may be repaired by the homology-directed repair (HDR) pathway allowing for precise replacement mutations to be made (Overballe-Petersen et al., 2013, Proc Natl Acad Sci USA, Vol. 110: 19860-19865; Gong et al., 2005, Nat. Struct Mol Biol, Vol. 12: 304-312).

Cong and colleagues (Cong et al., 2013, Science, Vol. 339: 819-823) took the Cas9 system a step further towards increased precision by developing a mutant form, known as Cas9D10A, with only nickase activity. This means that Cas9D10A cleaves only one DNA strand, and does not activate NHEJ. Instead, when provided with a homologous repair template, DNA repairs are conducted via the high-fidelity HDR pathway only, resulting in reduced indel mutations (Cong et al., 2013, Science, Vol. 339: 819-823; Jinek et al., 2012, Science, Vol. 337: 816-821; Qi et al., 2013 Cell, Vol. 152: 1173-1183). Cas9D10A is even more appealing in terms of target specificity when loci are targeted by paired Cas9 complexes designed to generate adjacent DNA nicks (Ran et al., 2013, Cell, Vol. 154: 1380-1389).

The third variant is a nuclease-deficient Cas9 (Qi et al., 2013 Cell, Vol. 152: 1173-1183). Mutations H840A in the HNH domain and D10A in the RuvC domain inactivate cleavage activity, but do not prevent DNA binding. Therefore, this variant can be used to target in a sequence-specific manner any region of the genome without cleavage. Instead, by fusing with various effector domains, dCas9 can be used either as a gene silencing or activation tools. Furthermore, it can be used as a visualization tool by coupling the guide RNA or the Cas9 protein to a fluorophore or a fluorescent protein.

Following its initial demonstration in 2012 (9), the CRISPR/Cas9 system has been widely adopted by the scientific community. It has already been successfully used to target important genes in many cell lines and organisms, including human (Mali et al., 2013, Science, Vol. 339: 823-826), bacteria (Fabre et al., 2014, PLoS Negl. Trop. Dis., Vol. 8:e2671.), zebrafish (Hwang et al., 2013, PLoS One, Vol. 8:e68708.), C. elegans (Hai et al., 2014 Cell Res. doi: 10.1038/cr.2014.11.), bacteria (Fabre et al., 2014, PLoS Negl. Trop. Dis., Vol. 8:e2671.), plants (Mali et al., 2013, Science, Vol. 339: 823-826), Xenopus tropicalis (Guo et al., 2014, Development, Vol. 141: 707-714.), yeast (DiCarlo et al., 2013, Nucleic Acids Res., Vol. 41: 4336-4343.), Drosophila (Gratz et al., 2014 Genetics, doi:10.1534/genetics.113.160713), monkeys (Niu et al., 2014, Cell, Vol. 156: 836-843.), rabbits (Yang et al., 2014, J. Mol. Cell Biol., Vol. 6: 97-99.), pigs (Hai et al., 2014, Cell Res. doi: 10.1038/cr.2014.11.), rats (Ma et al., 2014, Cell Res., Vol. 24: 122-125.) and mice (Mashiko et al., 2014, Dev. Growth Differ. Vol. 56: 122-129.). Several groups have now taken advantage of this method to introduce single point mutations (deletions or insertions) in a particular target gene, via a single gRNA. Using a pair of gRNA-directed Cas9 nucleases instead, it is also possible to induce large deletions or genomic rearrangements, such as inversions or translocations. A recent exciting development is the use of the dCas9 version of the CRISPR/Cas9 system to target protein domains for transcriptional regulation, epigenetic modification, and microscopic visualization of specific genome loci.

The CRISPR/Cas9 system requires only the redesign of the crRNA to change target specificity. This contrasts with other genome editing tools, including zinc finger and TALENs, where redesign of the protein-DNA interface is required. Furthermore, CRISPR/Cas9 enables rapid genome-wide interrogation of gene function by generating large gRNA libraries for genomic screening.

Thus, the CRISPR/Cas9 technology can be easily adapted to any gene of interest and may offer unchallenged possibilities to alter genes (knock-out, knock-in, introduction of precise mutations). Its spread in the scientific community is amazingly rapid and has triggered a recent burst of scientific communications using it.

CRISPR's delivery is commonly performed by DNA transfection or through the use of viral vectors encoding Cas9, both methods being convenient but limited to certain cell types as well as being rather intrusive. Furthermore, maintenance of Cas9 expression for a long period is possibly toxic and at best not necessary, since Cas9-mediated cleavage occurs rapidly (Jinek et al., 2013, eLife, Vol. 2, e00471) and could even be toxic on long term. Other approaches have succeeded in exploiting recombinant Cas9 and synthetic RNAs to transfer the RNPc by Proteo transfection or by physical microinjection but these CRISPRs systems remain limited to target fragile primary cells.

There is a need in the art for improved tools and methods for gene editing by using CRISPR/Cas technology.

SUMMARY OF THE INVENTION

The present invention relates to products and methods for generating alterations in genomic nucleic acids; which alterations encompass mutations by introduction of nucleic acid insertion and nucleic acid deletion, which include knock-in and knock-out genomic alterations.

More precisely, this invention relates to products aimed at generating nucleic acid alteration events caused by CRISPR-Cas complexes, and especially caused by CRISPR-Cas9 complexes, as well as to methods using the same.

This invention relates to a virus-derived particle comprising one or more Cas protein(s), and especially Cas9 protein.

In some embodiments, the said virus-derived particle further comprises, or is further complexed with, one or more CRISPR-Cas system guide RNA(s).

In some embodiments, the said virus-derived particle further comprises, or is further complexed with a targeting nucleic acid.

In some embodiments, the said virus-derived particle is a retrovirus-derived particle, e.g. a lentivirus-derived vector particle.

This invention further pertains to a composition for altering a target nucleic acid in a eukaryotic cell, which composition comprises a virus-derived particle comprising one or more Cas protein(s), and especially Cas9 protein.

In some embodiments, the said composition further comprises, or alternatively is further complexed with, one or more CRISPR-Cas system guide RNA(s).

In some embodiments, the said composition further comprises a targeting nucleic acid.

This invention also concerns a kit comprising the required substances for preparing a virus-derived particle or a composition as defined above.

It also relates to genetically modified cells producing virus-derived particles as defined herein, especially cells which are under the form of stable cell lines.

This invention further relates to a fusion protein comprising (i) a viral protein that self assembles for generating a virus-derived particle, the said viral protein being fused to (ii) a Cas protein. In some embodiments, the said fusion protein comprises a cleavable site located between the said viral protein and the said Cas protein, and especially a cleavable site located between a Gag protein and a Cas9 protein.

It also pertains to nucleic acids and vector encoding the said fusion protein.

(A) Schematic representation of Cas9-VLPs assembly from HEK293T cells. 6 Steps are depicted:

(1) GAG-CAS9, GAG ProPol and a viral envelope protein are transfected in HEK293T cells in association with a construct encoding a guide RNA. GAG and the viral envelope tend to localize at the membrane where the assembly of a virus-derived particle (which may be also termed "Virus-Like Particle" or "VLP" herein) takes place (2). As concentration of GAG increases, mechanical forces induce the formation of a particle (3) that will bud from the producer cell after having incorporated all the actors of the CRISPR machinery (4). These particles can be concentrated and are stable at 4° C. more than 15 days. Due to the maturation process, the viral protease may have released most Cas9 proteins from the GAG platform within the particle (5). Exposed to target cells, VLPs will be able to bind and fuse the with cell membrane through an envelope/receptor interaction that thus depends on the envelope used to pseudotype particles and the considered target cell. After fusion with the cellular membrane, VLPs transfer their cargo within recipient cells which may include Cas9/gRNAs ribonucleocomplexes, free gRNAs or Cas9 possibly associated with non-protease GAG (not yet clarified). Fully active CRISPRs RNPc are nevertheless delivered into the nucleus of recipient cells (possibly due to a re-association of Cas9 and free gRNAs within the target cell) and mediate the cleavage of genomic-DNA in the very position specified by the gRNA (6).

(B) Molecular Design of the GAG-Cas9 coding construct. hCMVp (human cytomegalovirus early promoter) drives the expression of a mRNA incorporating an intron (rBG) and a poly adenylation (rBGpA) signal both deriving from the rabbit beta globin gene sequence. The construct consists of the fusion of the MLV-GAG polyprotein with the codon-optimized Cas9 sequence from Streptococcus pyogenes. Both moieties are separated by a MLV protease cleavage site (ps) and a flag-tag sequence fused to the Cas9 sequence.

Figure 2A:
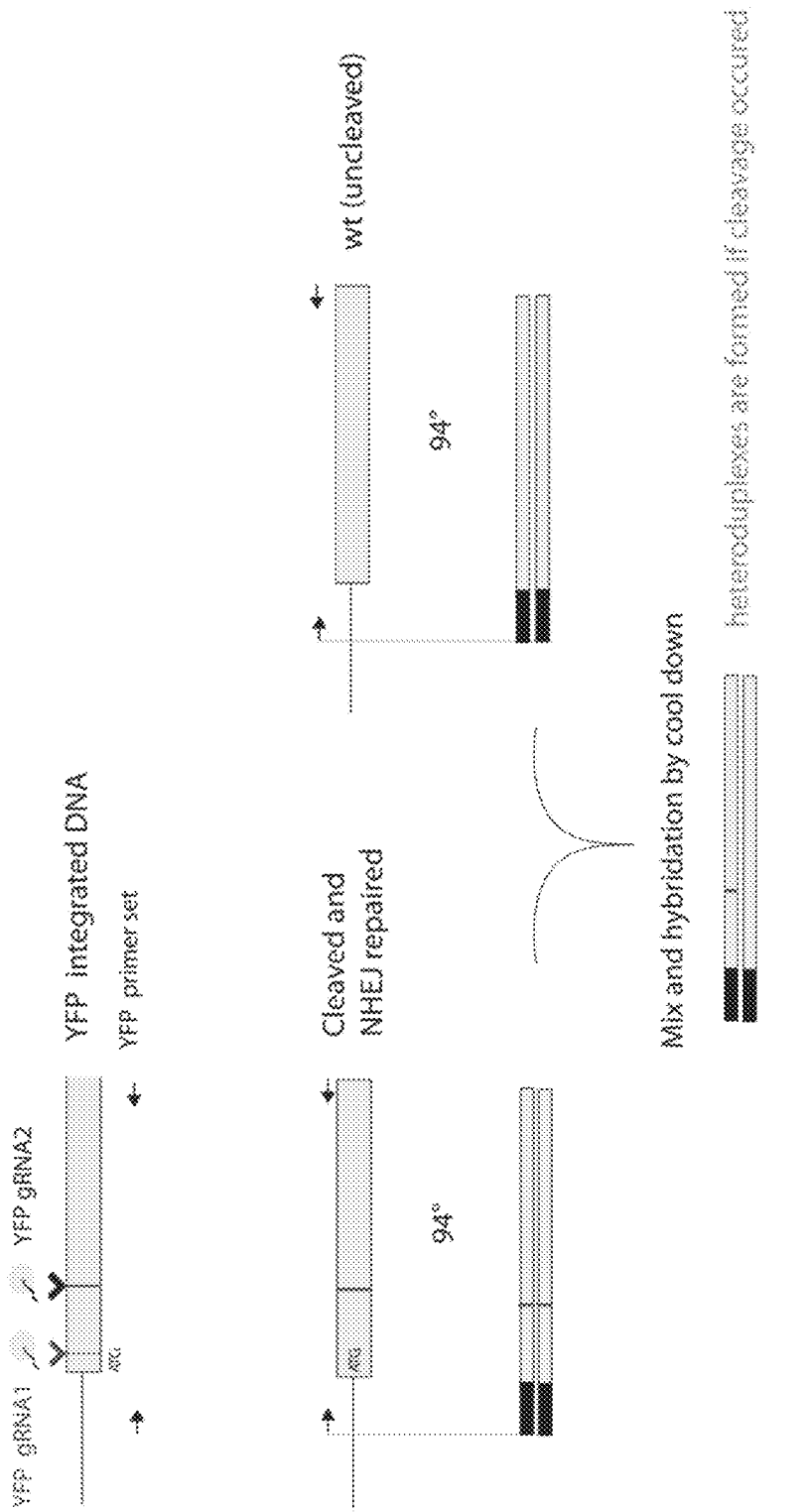
Figure 2B:
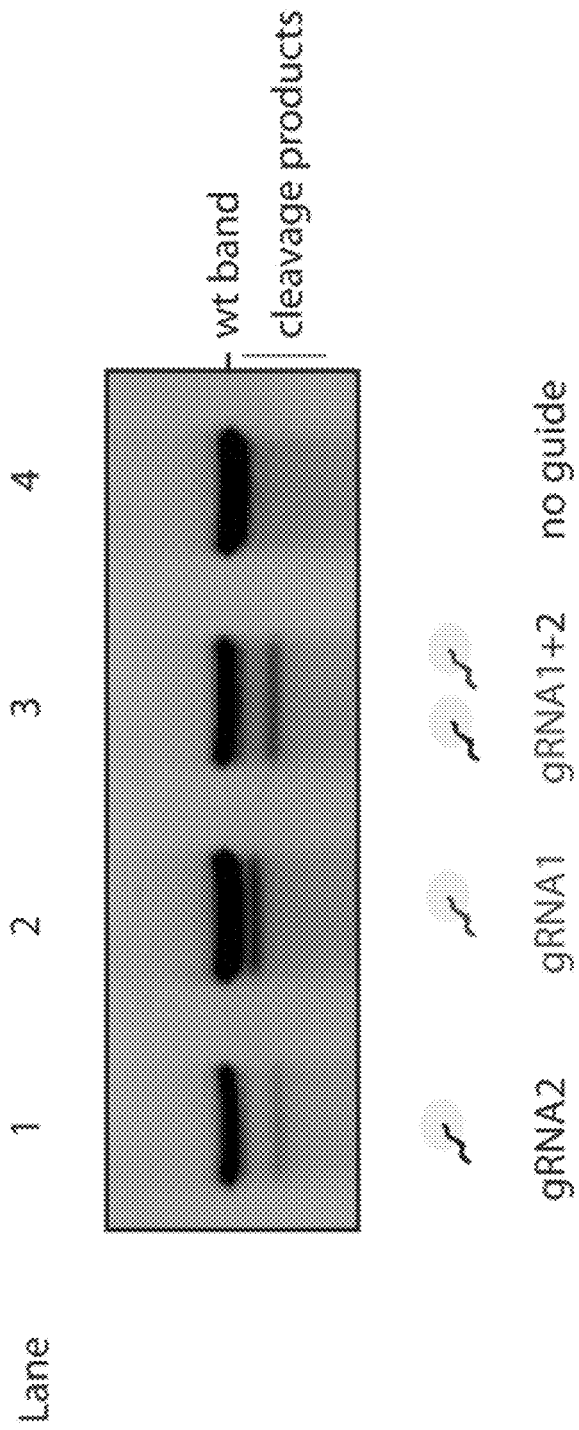

FIG. 2: Molecular validation of genetic cleavage by YFP-CRISPRs-VLPs (A) Localization of gRNAs recognition sites on the YFP gene, primers used and principle of the surveyor assay. L929 murine cells were lentitransduced with a YFP coding vector at low Multiplicity Of Infection (MOI). After 72 h, cells were next treated with VLPs loaded with gRNAs targeting the YFP gene at two different positions as indicated. To ascertain the cleavage of YFP, cells treated by Cas9-VLPs were lysed and genomic DNAs were extracted and analyzed by the S1 nuclease-based surveyor assay. The test detects heteroduplexes that are formed if two closely related ssDNA molecules hybridizes: S1 nuclease digestion is thus a proof that DNA was cleaved by Cas9.

(B) Surveyor assay on L929 cells treated by VLPs loaded with gRNAs2, 1, or a combination of both of them. Formation of heteroduplexes is detected for each rRNAs condition, revealing truncated versions of YFP whose size depends on the position of the gRNA on the YFP sequence.

Figure 3A:
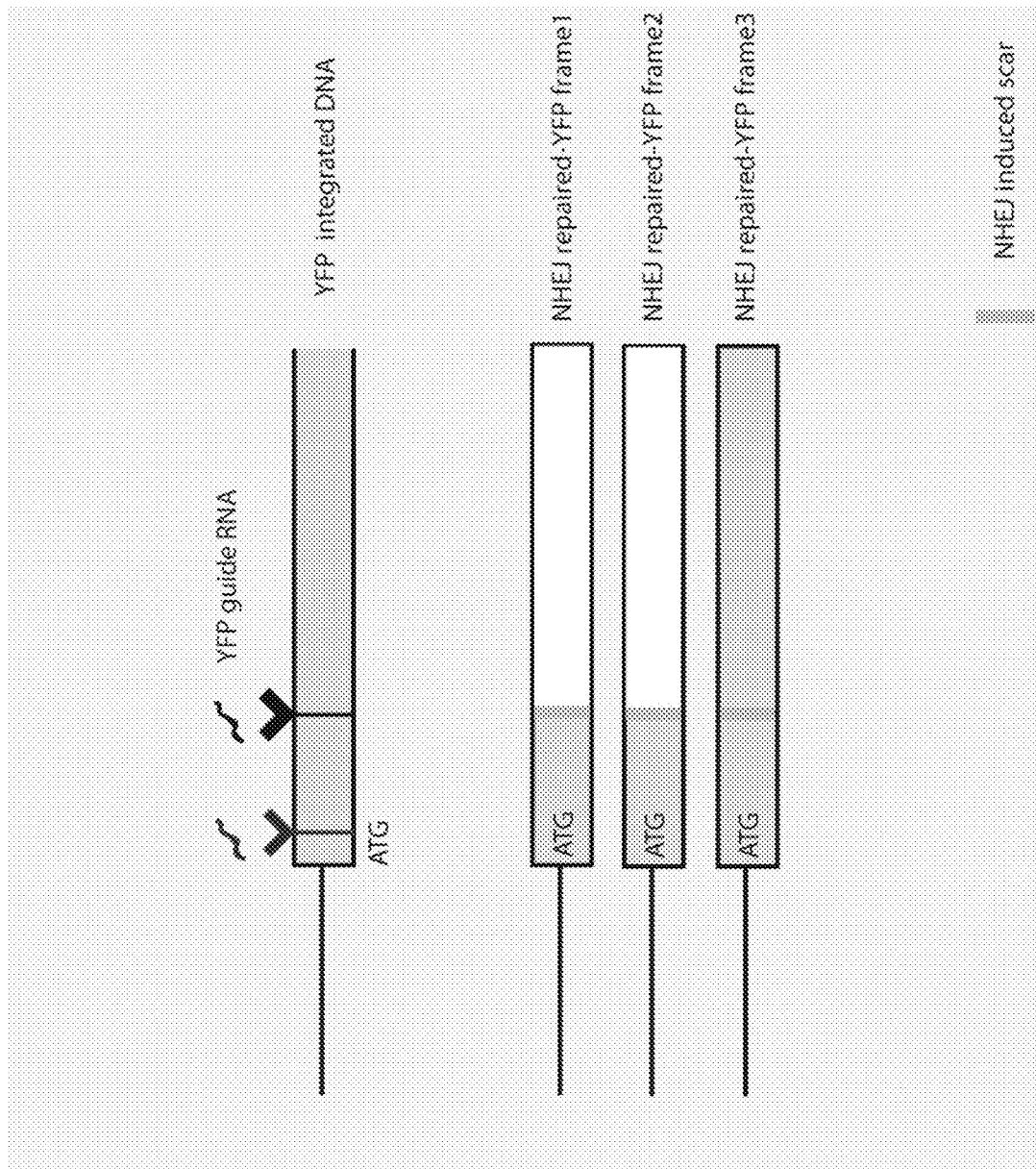
Figure 3B:
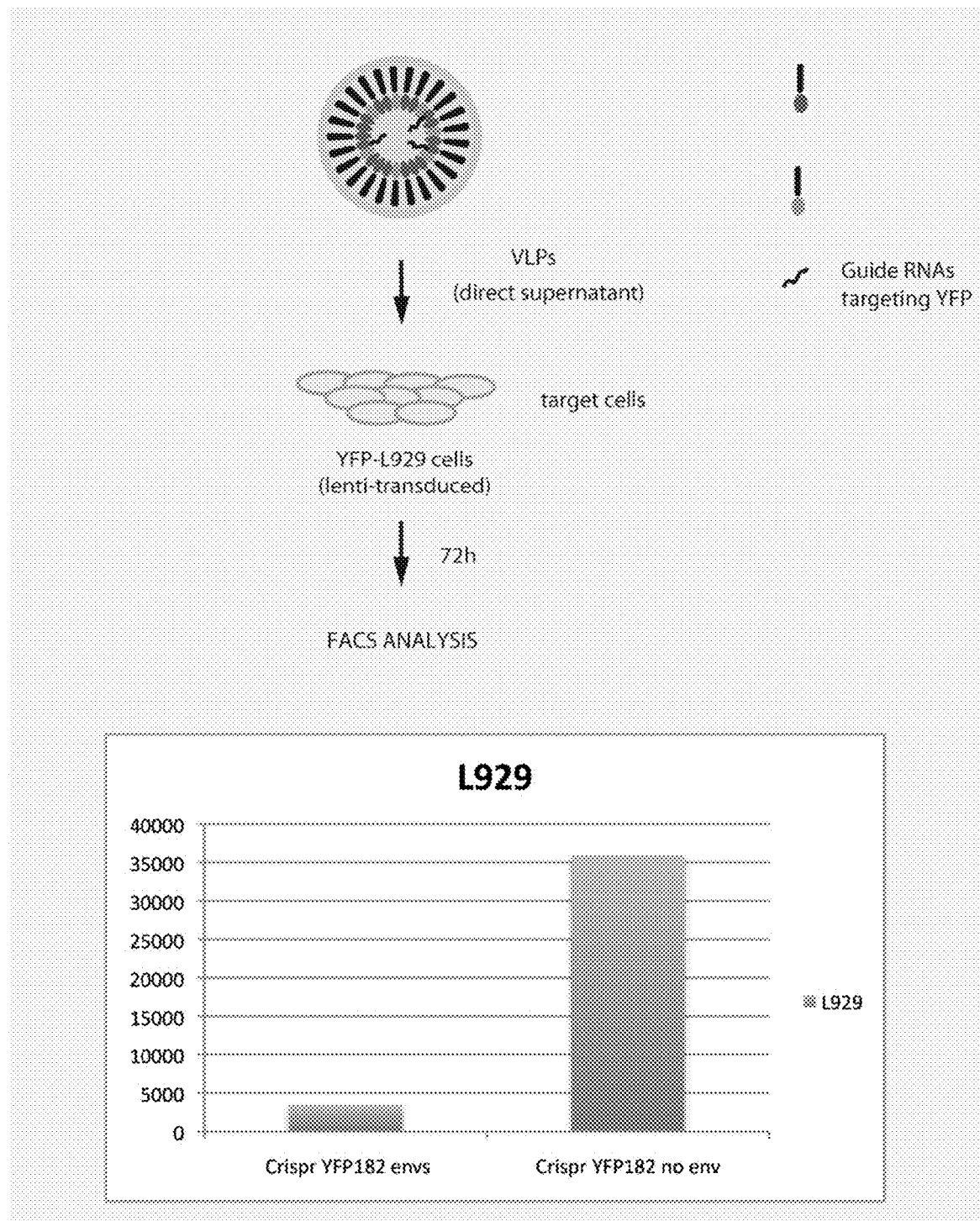

FIG. 3: CRISPR-mediated disruption of YFP in L929 murine cells by Cas9-VLPs.

(A) A guide RNA was raised to target YFP downstream the initiation codon ATG. After cleavage cells could repair this gap by NHEJ, a mechanism that could create small deletions and indels, a scar that could alter the YFP frame in some cells. 3 different versions of repaired YFP could thus be generated by the natural reparation machinery, only one of them restauring an in-frame YFP and a maintenance of the YFP phenotype. Accordingly, cleavage should induce a detectable but incomplete decrease of YFP in target cells.

(B) VLPs loaded with Cas9 and a guide RNAs targeting YFP were produced and directly introduced into the medium of YFP-L929 cells, a murine fibroblastic cell line # where YFP was stably integrated into the genome by lentivector transduction. Envelope-less VLPs were also produced and used as a negative control. 72 h after treatment cells were analyzed by flow cytometry (FACS) and global Mean Fluorescence Intensity (MFI) was monitored revealing the strong effect of YFP-breaking Cas9-VLPs on YFP L929 target cells. A 7-fold decrease of MFI was measured for cells treated by enveloped VLPs as compared with non treated YFP-cells or treated by env less VLPs*. We show here that Cas9-VLPs loaded with a specific guide RNA can be used without further concentration/purification process as CRISPR delivery agents.

Figure 4:
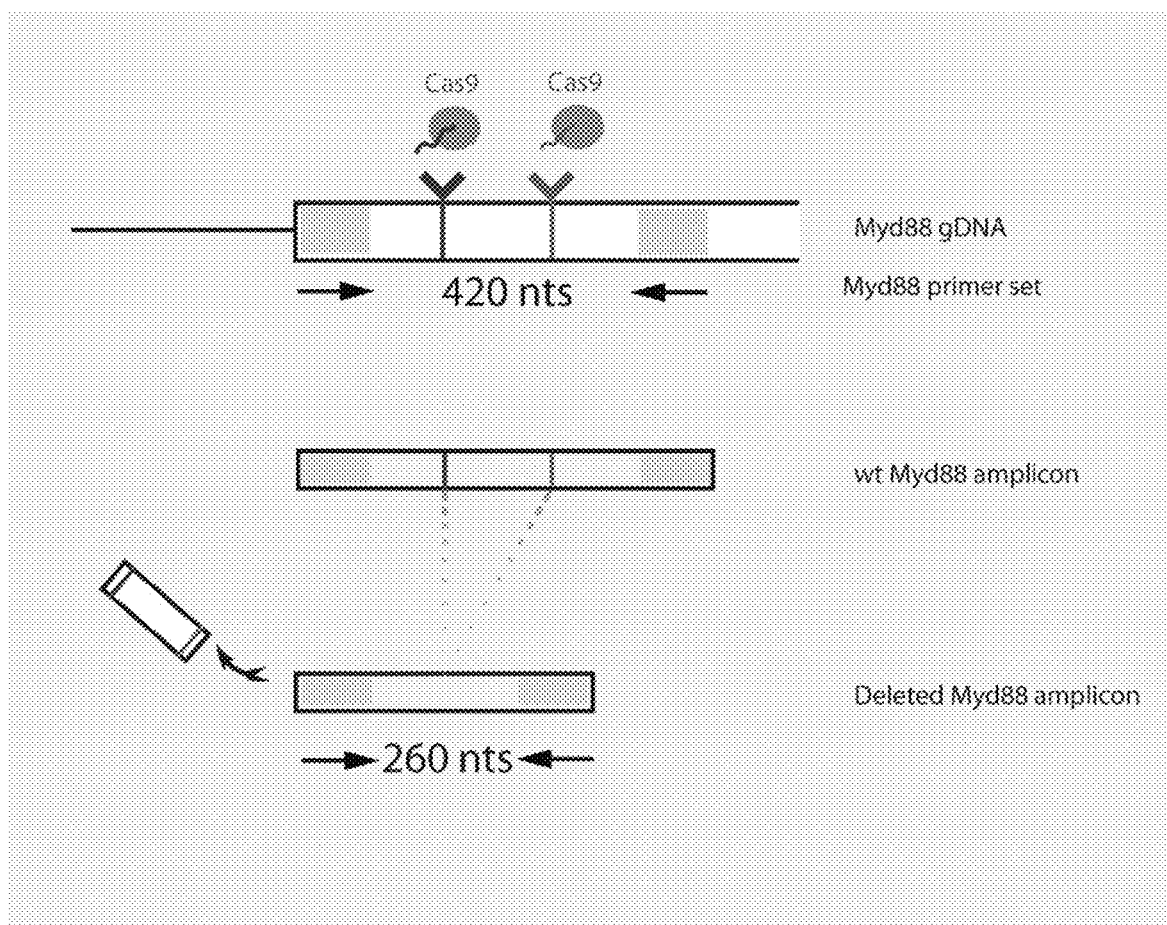
Figure 4:
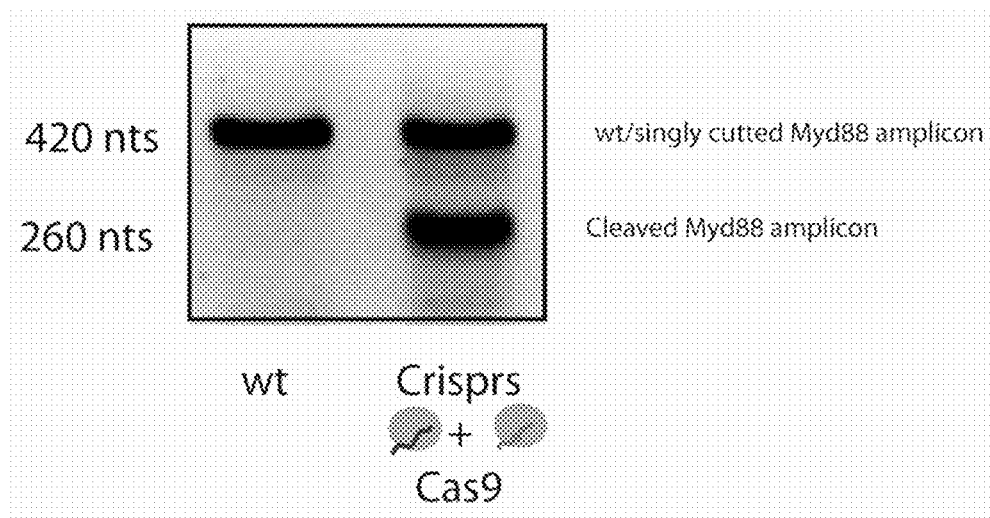
Figure 4:
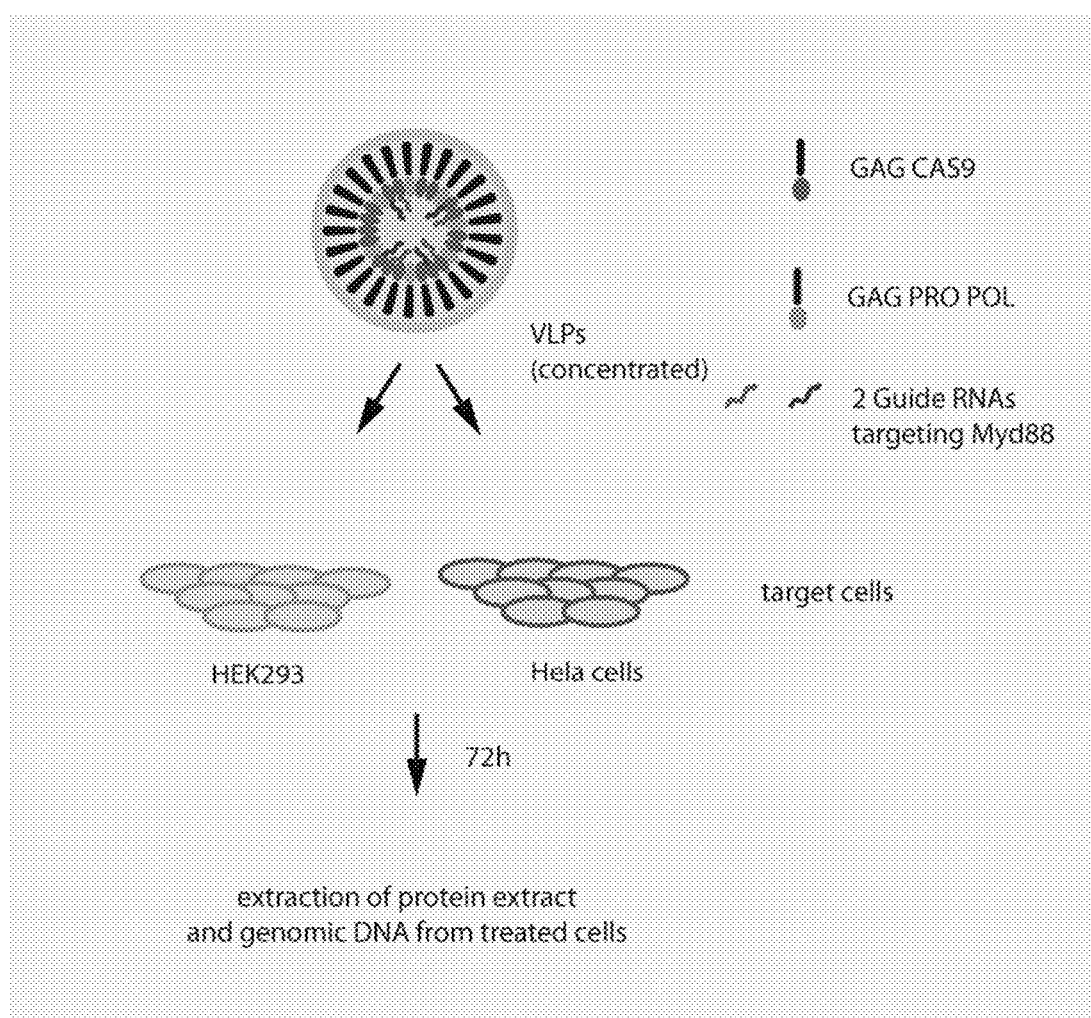
Figure 4:
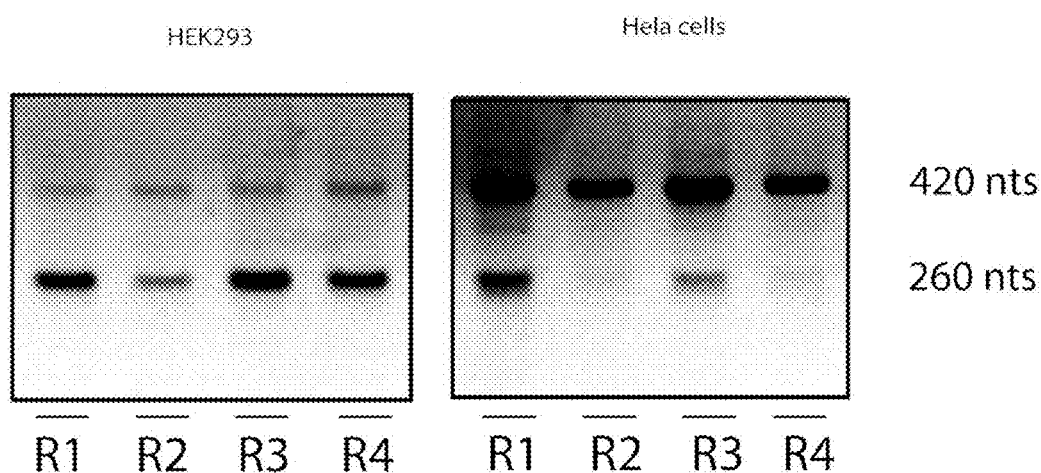

FIG. 4: Deletion of the Myd88 locus using conventional Cas9 delivery methods vs Cas9 VLPs (A) Schematic representation of the Myd88 genomic DNA and localization of the different tools used for the Myd88 cleaving assay. Two different CRISPRs sequences were designed against the human Myd88 gene as represented in purple and green. Grey boxes correspond to the regions where the two PCR primers hybridize. They have been optimized for the amplification of gMyd88 which generate an amplicon size of 420 nts. Should the CRISPRs system be active in target cells, a deletion of 160 nts occurs in some cells and can be repaired by NHEJ which gives rises to a 260 nts-in size truncated version of the gene.

(B) PCR-amplification of gMyd88 in wt-HEK or after transfection with both Myd88 CRISPRs and a Cas9 encoding plasmid. After extraction of genomic DNA, a PCR-assay was performed using the Myd88 primer set. In the population treated with CRISPRs components, two amplicons are generated corresponding to the uncleaved form of Myd88 (or a version which has been cleaved by a single CRISPR) and a double-cut version after cleavage of the gene at the two targeted positions. We can note that the Myd88 deletion does not affect all treated cells, indicating that the cleavage mediated by the transfected CRISPR components system is not complete.

(C) We also attempted to deliver both Myd88 guide RNAs by Cas9 loaded VLPs. For this VLPs were produced following the procedure described in FIG. 1 and different experimental procedures were explored, varying for the ratio of plasmid used and the nature of the envelope (R1-R4). After collecting and concentrating them, VLPs were introduced into the medium of HEK or Hela cells and efficiency of the Myd88 cleavage was next assessed by PCR.

(D) Myd88 amplification using the Myd88 primer set and the genomic DNA extracted from cells treated by VLPs. While all preparations were equally efficient in cleaving Myd88 in HEK cells (left panel), some differences can be appreciated in Hela cells, reflecting the importance of the envelope/ratio used. A particular protocol seems optimal (R1) for both cell types.

Figure 5:
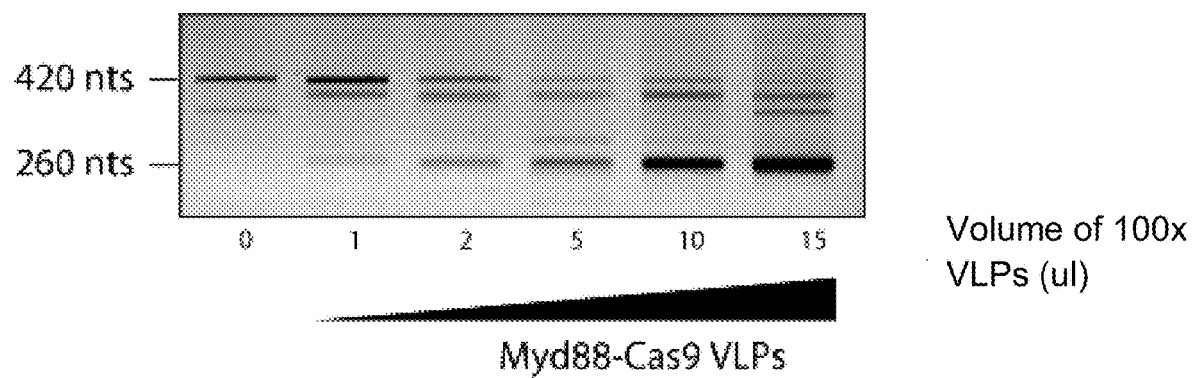

FIG. 5: Dose dependent cleavage of the Myd88 gene induced by Cas9-VLPs

Cas9-VLPs loaded with two gRNAs targeting the Myd88 gene were produced, concentrated and stored 15 days at 4° C. Increasing amount of VLPs were next added to the medium of HEK293T target cells plated in a 12-w plate (150000 cells/w). 20 h after VLP treatment, cells were lysed and genomic DNA was purified to analyze the genetic cleavage of the Myd88 locus. The signal revealing the deletion of Myd88 (260 nts) increases with the amount of VLPs introduced in the medium.

This shows that Cas9-VLPs are active in target cells less than 24 h after their introduction. We also noted that the VLP preparation can be stable at least 15 days at 4° C.

Figure 6:
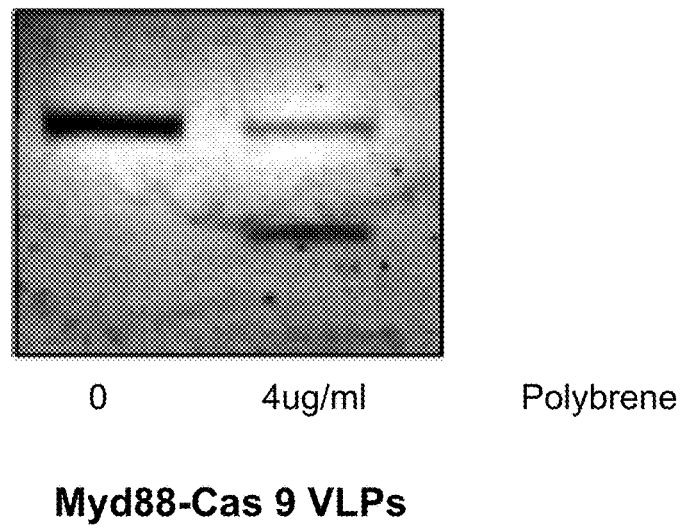

FIG. 6: Cleavage of the Myd88 gene in HEK targets by Cas9-VLPs is potentiated by polybrene.

Suboptimal doses of Cas9-VLPs loaded with two gRNAs targeting the Myd88 gene were introduced in the medium of 3×10e6 HEK target cells grown in complete medium supplemented or not with Hexadimethrine bromide (polybrene), a polycation favoring the contact of particles with target cells. 48 h after VLP treatment, cells were lysed and genomic DNA was purified to analyze the genetic cleavage of the Myd88 locus. In this condition where under-saturating amounts of VLPs were used, the Myd-88 cleavage is undetectable in cells cultivated in a standard medium but is strongly potentiated by polybrene addition.

FIG. 7: Cleavage of the Myd88 gene induced by Cas9-VLPs in human monocytes-derived macrophages Genotype (A) Cas9-VLPs loaded with two gRNAs targeting the Myd88 gene were concentrated and introduced in the medium of human monocytes-derived macrophages after 6 days of differentiation with Granulocyte-Macrophage Colony Stimulating Factor (GMCSF) (100000 cells per well i a 48-w plate). 48 h after treatment with VLPs, cells were lysed and genomic DNA was purified to analyze the genetic cleavage of the Myd88 locus. Under this condition, the Myd88 gene is cleaved with such high efficiency after treatment with VLPs that the wt sequence cannot even be detected by conventional PCR thus suggesting an almost complete cleavage mediated by Myd88-VLPs in primary non dividing cells.

Phenotype (B) According to Lombardo et al*, human macrophages massively die by apoptosis when cultivated without GMCSF, unless they are stimulated by a TLR-4 agonist like LPS. This resistance to apoptosis is LPS- and Myd88-dependent. To check whether VLPs treated cells lost their Myd88 function, we cultivated them without GMCSF (in RPMI medium) and stimulated them with LPS during 72 h. Upon this treatment WT macrophages resisted to GMCSF deprivation (compare condition 2 to condition 3) while macrophages treated with Myd88-cleaving Cas9-VLPs died massively (condition 4). This strongly suggests that VLPs treatment inactivated the Myd88 at the functional level.

Figure 8:
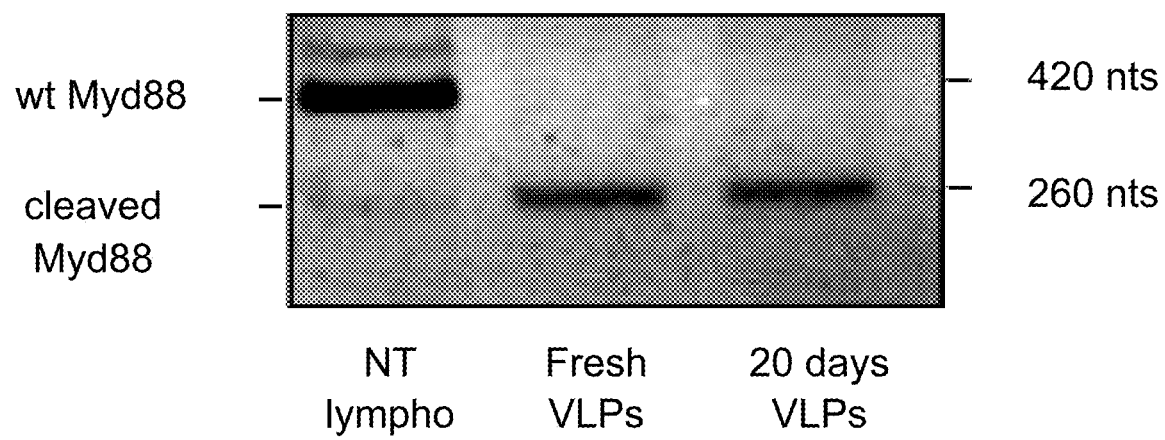

FIG. 8: Cleavage of the Myd88 gene induced by Cas9-VLPs in freshly-purified primary human lymphocytes.

Human purified lymphocytes (Ficoll/percoll) were plated at 40×10e6 cells/ml in 200 ul in a 48 w plate. Cells were next treated with a fresh preparation of Cas9-VLPs targeting Myd88 and an older one kept 20 days at 4° C., in a transduction medium supplemented with polybrene (4 ug/ml). After 2 h, 5000 of fresh medium was added to the transduction medium and cells where maintained in culture for 40 h before their lysis and genomic DNA extraction. Cleavage of Myd88 was next investigated by PCR revealing the wt or the cleaved form of Myd88. In both VLP conditions, the Myd88 gene was cleaved. 1 million of quiescent lymphocytes were genetically modified in less than 48 h with a single treatment of VLPs without any apparent toxicity.

Figure 9:
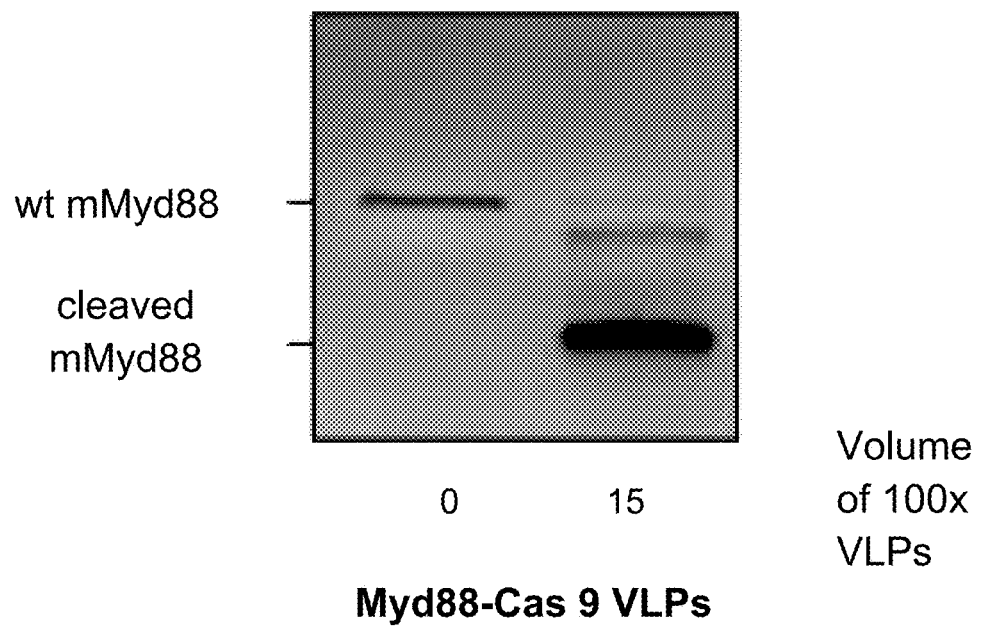

FIG. 9: Cleavage of the Myd88 gene induced by Cas9-VLPs in murine bone marrow-derived macrophages Macrophages were differentiated from bone marrow cells flushed-out from mouse femurs incubated during 8 days in MCSF containing medium. Cells were next treated with a fresh preparation of Cas9-VLPs targeting mMyd88 in a medium supplemented with polybrene (4 ug/ml). It is noteworthy that two new gRNAs were designed for this experiment that specifically targeted the murine gene.

Cells were cultivated 48 h before lysis and genomic DNA extraction. Cleavage of Myd88 was next investigated by PCR revealing the wt or the cleaved form of the murine Myd88 gene based on the design of the hMyd88 assay. A very efficient cleavage was detected by PCR in VLP-treated cells while bands corresponding to the complete or partially cleaved mMyd88 (by only one gRNA) appear faint.

FIG. 10: Targeted insertion of a flag-tag sequence in the endogenous DDX3 genomic locus mediated by 'all in one' Cas9-VLPs (A) schematic representation of the human DDX3 genomic locus and the different tools used in the experiment. The purple arrow represents the locus cleaved by the DDX3 CRISPR and the grey region an intronic region of DDX3. The FLAG IN rep primer (ssODN) is represented as a single strand DNA exhibiting 40 nt homology-repair arms, flanking the Flag-tag sequence, that are homologous to the DDX3 locus. Primers used in the PCR assay are represented. (B) Principle of the 'all in one' VLPs delivering the Cas9 protein, the gRNAs and the repair primer. VLPs targeting DDX3 were produced, centrifuged and stored at 4° C. VLPs were then combined with increasing doses of ssODNs and complexes added on HEK target cells cultivated in classic growing medium. Target cells were next lysed 72 h later for preparation of protein extracts and genomic DNA (C) Western-Blot analysis of cells treated with 'all in one' DDX3 VLPs. A Western-blot signal revealed by the flag antibody and corresponding to the DDX3 expected molecular weight (86 KDa) can be detected at the highest concentrations of ssODNs. This indicates that the Flag sequence was successfully inserted at the DDX3 locus of VLP-treated cells. This was further confirmed by PCR on the genomic DNA extracted from VLP-treated cells. Primers used (depicted in A) should amplify a DNA segment only if the Flag sequence is inserted in the DDX3 gene since the forward primer hybridizes to the Flag sequence and the reverse primer hybridizes to the intron of DDX3). As shown in lower panels, the genetic modification is obvious for higher concentration of primers and decreases with the dose but remains detectable—at the DNA level—for a concentration as low as 0.01 nmol/ml (lane 4). (D) Introduction of the Flag sequence upstream the endogenous locus of DDX3 in human monocyte-derived dendritic cells (Mo-derived DCs). VLPs and ssODN (5 nmol/ul final) were complexed and the mix used to treat Mo-derived DCs in a transduction medium containing polybrene (4 ug/ml). Genomic DNA analysis indicates that the flag sequence was successfully engrafted into the endogenous locus of DDX3 in human primary DCs by a single treatment of VLPs.

Figure 11:
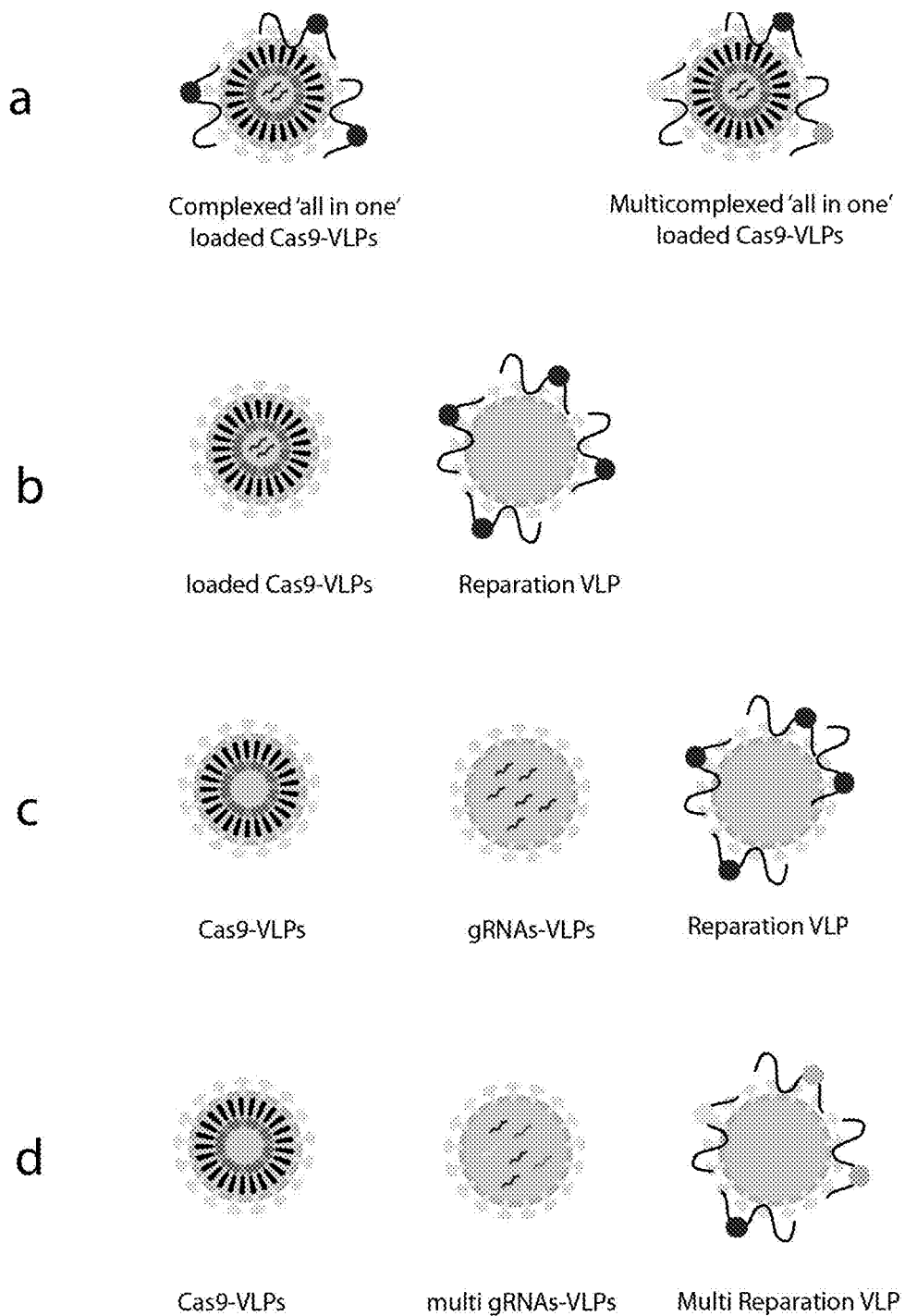

FIG. 11: Panel of possibilities using Nanoblades and their association with 'helper' VLPs We have shown that 'all in one' VLPs incorporating Cas9, gRNAs and possibly combined with a reparation ssDNA can be generated and deliver the complete package in recipient cells. This agent depicted in (a) is highly versatile in itself. Since VLPs can incorporate several gRNAs and may certainly be complexed after production with different reparation primers, many possibilities are offered to a scientist/company to create customized tools at low cost. As referenced in (Abe et al. J Virol 1998), VLPs of different nature may be complexed outside the cell after production and may complement each other, one helping the other to enter into the cell for example. Given this property of VLPs, we may imagine other ways to prepare an active agent to transfer the actors of the CRISPRs system by mixing particles, each of them being dedicated to a particular cargo. In (b) is proposed a system where could be mixed gRNA-Cas9-VLP and particles simply complexed by the reparation primer: the mixture of both types of particles would be in this case, the final active agent. To go further, gRNAs could also be packaged in a particular type of particle and combined after production with unloaded Cas9-VLPs to create a particle mixture able to deliver all the components. This system is depicted in (c). Considering the theoretical possibility to incorporate several gRNAs in VLPs, to choose different viral envelope to pseudotype each type of VLPs, and to associate them with different types of ssDNA, we may even imagine more complex agents, (d). While this segregation of CRISPRs components in different types of particles may certainly affect the global efficiency of the final agent, it may offer to a company producing nanoblades a vast panel of possibilities to improve the nanoblade service and render it costless. Should the (c) system be efficient enough, it only requires the preparation of a large well-titered batch of generic Cas9-VLPs to be associated with gRNAs particles customized specifically for each application. This system appears highly valuable from the industrial point of view, since a very precise molecular service is offered, which only necessitate the rapid costless preparation of the gRNAs-VLPs.

Figure 12A:
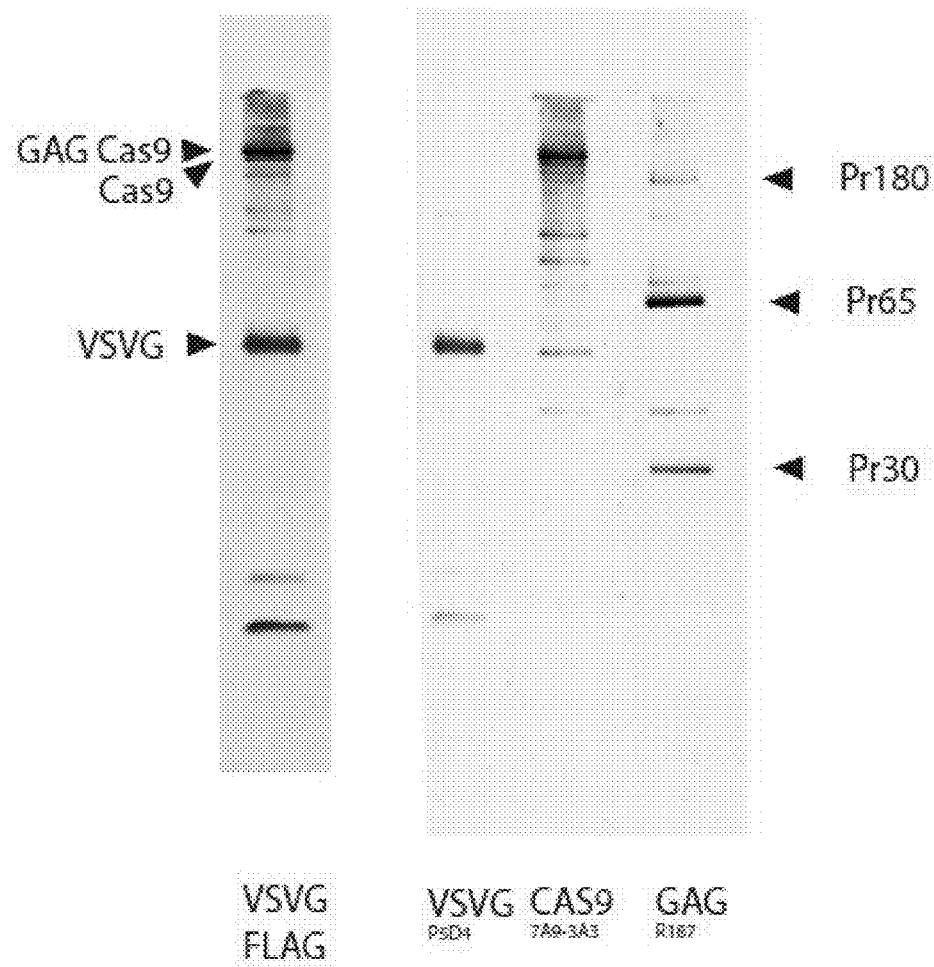
Figure 12B:
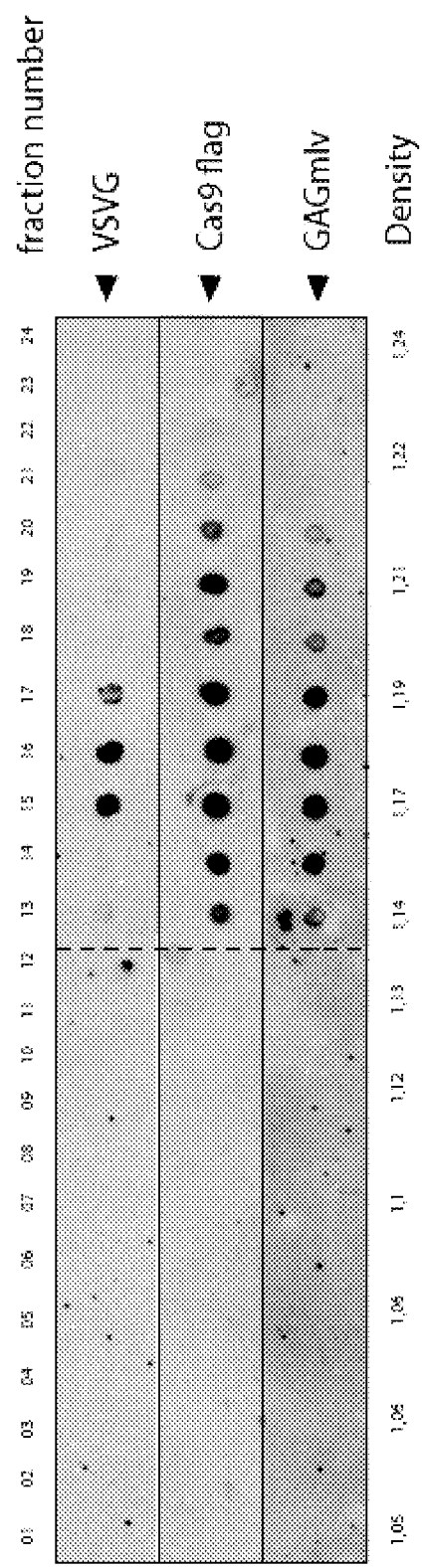

FIGS. 12A-12B: Western blot analysis and characterization of CAS9 Virus-derived particles separated on a discontinuous sucrose gradient.

FIG. 12A illustrates a Western blot gel electrophoresis. Lanes from left to right: (i) incubation with anti-Flag antibodies; (ii) incubation with anti-VSV-G antibodies; (iii) incubation with anti-CAS9 antibodies; (iv) incubation with anti-GAGmlv antibodies.

FIG. 12B illustrates a dot blots of fractions 1 to 24 collected after performing the separation of CAS9 virus-derived particles on a discontinuous sucrose gradient. Columns from left to right: fractions no 1 to no 24. Lanes from the upper part to the lower part of FIG. 12B: (i) incubation with anti-VSV-G antibodies; (ii) incubation with anti-CAS9 antibodies, (iii) incubation with anti-GAGmlv antibodies.

Figure 13:
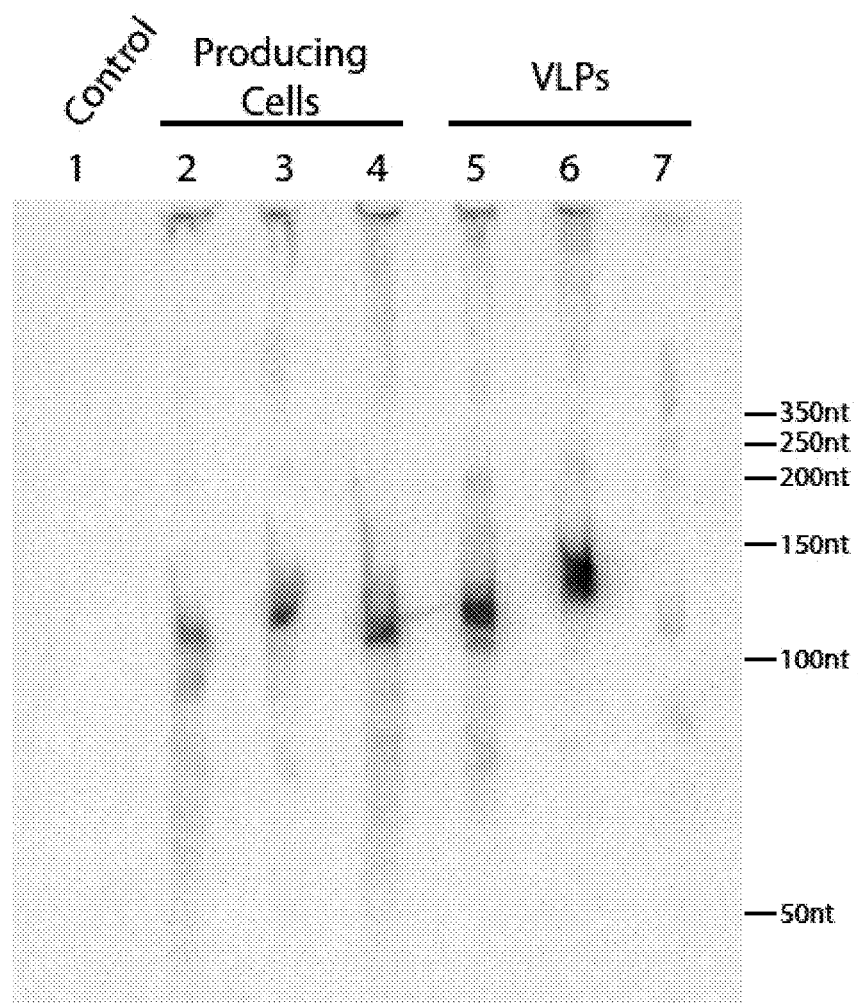

FIG. 13 Gag/Cas9 fusion actively loads guideRNAs within Virus-like particles (VLPs).

Northern blot directed against the conserved region of the guideRNA using total RNA extracted from producer cells (lanes 2 to 4) or the corresponding purified VLPs (lanes 5 to 7).

FIG. 14

Figure 14A:
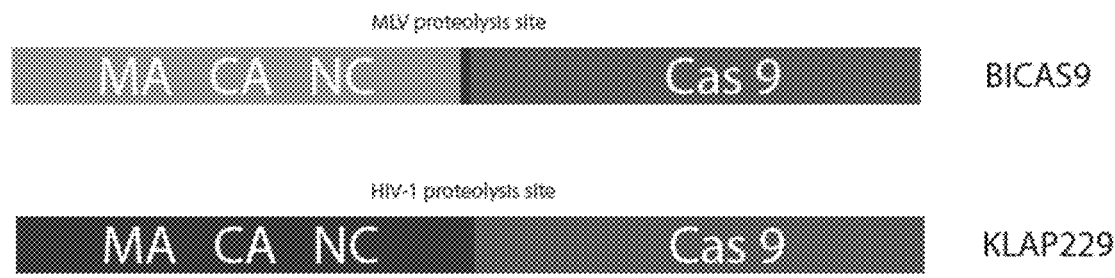

FIG. 14A: Schematic representation of the coding cassettes designed for the production of MLV-based VLPs or HIV-1-based VLPs. Both cassettes were incorporated in an eucaryotic expression vector equipped with the early hCMV promoter, the rabbit-Bglobin intron and the rabbit pA signal. Both systems were optimized by exploration and test of diverse proteolytic sites separating the GAG cassette from the Cas9 gene. MLV based VLPs were produced as described elsewhere while HIV-1 based VLPs were produced similarly except that an HIV-1 helper construct encoding GAG POL Tat Rev proteins was transfected instead of the MLV GAG POL plasmid. Production of HIV-1 VLPs follows the same procedure as compared with MLV-based VLPs.

Figure 14B:
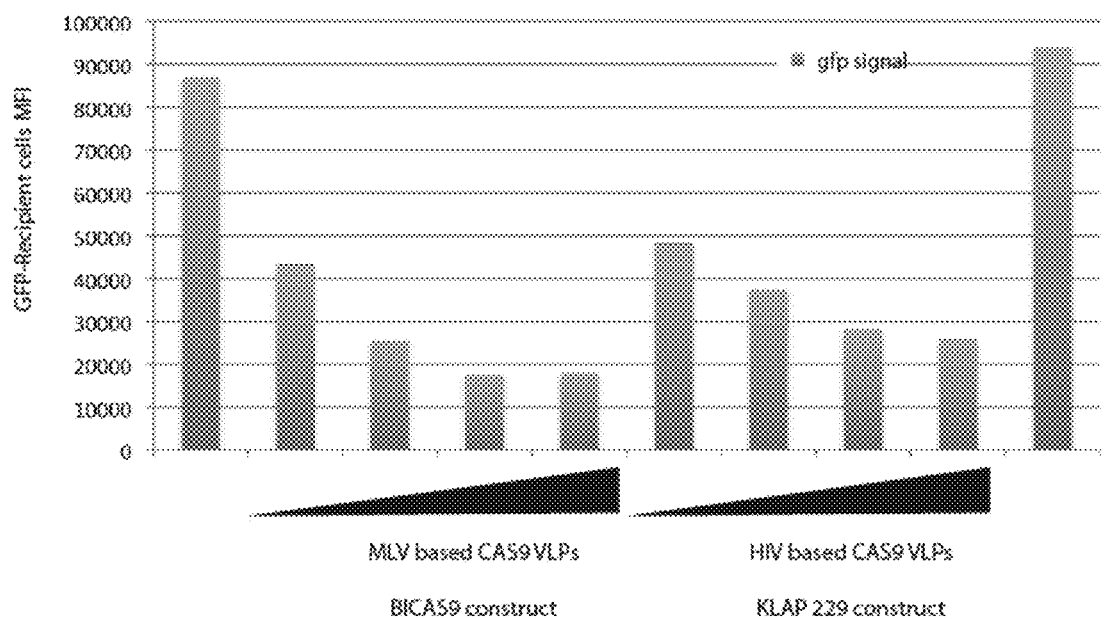

FIG. 14B: Concentrated VLPs engineered to incorporate a guide RNA targeting the GFP gene were used to transduce 30000 HEK293T cells expressing GFP. HIV-1 and MLV-based particles were produced with the same loaded gRNA (target sequence: CGAGGAGCTGTT-CACCGGGG—SEQ ID NO. 38). Recipient cells were plated the day before in a 96-w plate. Transduction medium was supplemented with polybrene (4 ug/ml). 72 hours after treatment with 3 increasing doses of each VLP-batch, fluorescence intensities were measured by a Fluorometer (Excitation 488, Emission 535). Fluorescence decrease was evident in VLPs-treated cells as compared with control non-treated cells (C), revealing the cleavage of the GFP gene within recipient cells. Results indicate that HIV-1 based VLPs are efficient in delivering the CRISPR/CAS9 system to a level slightly less efficient than MLV-based VLPs in these recipient cells (1,5-2 fold less efficient).

Figure 14C:
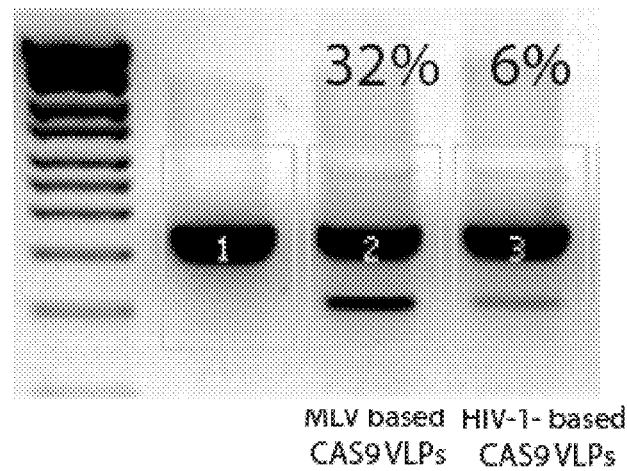

FIG. 14C: Cleavage of the WASP gene in primary human T cells stimulated with IL7. For this experiment, two guide RNAs targeting the human WASP gene were incorporated within HIV-1 or MLV-based VLPs before treatment of freshly purified T-cells stimulated with IL7. 500000 cells were plated in a 24 w plate in 400 ul of RPMI medium supplemented with polybrene (4 ug/ml) and IL-7. Concentrated HIV-1 or MLV VLPs (10 ul of VLP dosed at 1 uM CAS9) were added in the culture medium. WASP deletion by CRISPR-CAS9 was next measured by PCR in recipient cells 24 hours after treatment. Primer used for amplification of genomic WASP gene were:

forward: 5'-ATTGCGGAAGTTCCTCTTCTTACCCTG (SEQ ID NO. 36)

reverse: 5'-TTCCTGGGAAGGGTGGATTATGACGGG (SEQ ID NO. 37).

PCR conditions are: 95° C. 5 min followed by 25 cycles of (95° 30 sec-57° 30 sec-72° 30 sec) followed by 5 min at 72° C.

Amplicons were next loaded on a gel to reveal the state of WASP into VLP recipient T-cells: wt or cleaved. Gel analysis performed using the ImageJ software allowed a quantification of double-cutting efficiencies for MLV-based VLPs (32%) and HIV-1-based VLPs (6%).

Figure 15A:
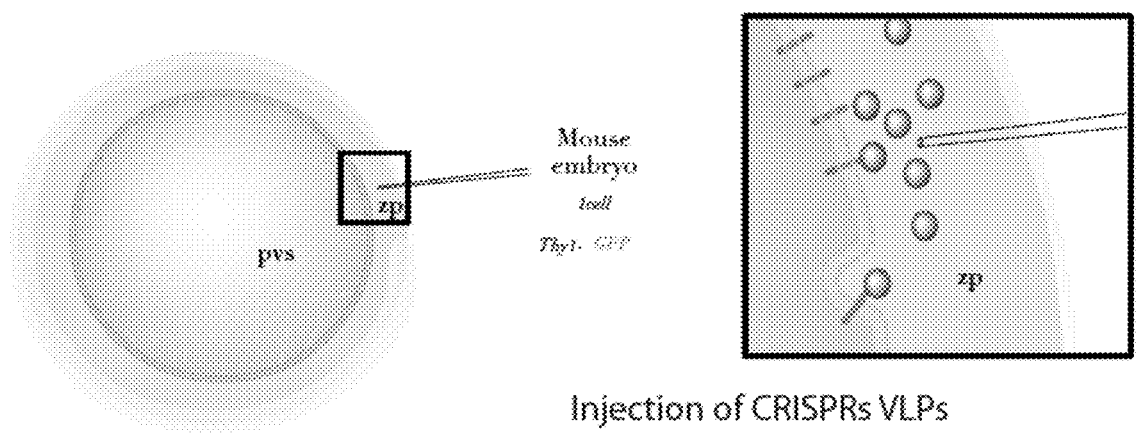
Figure 15D:
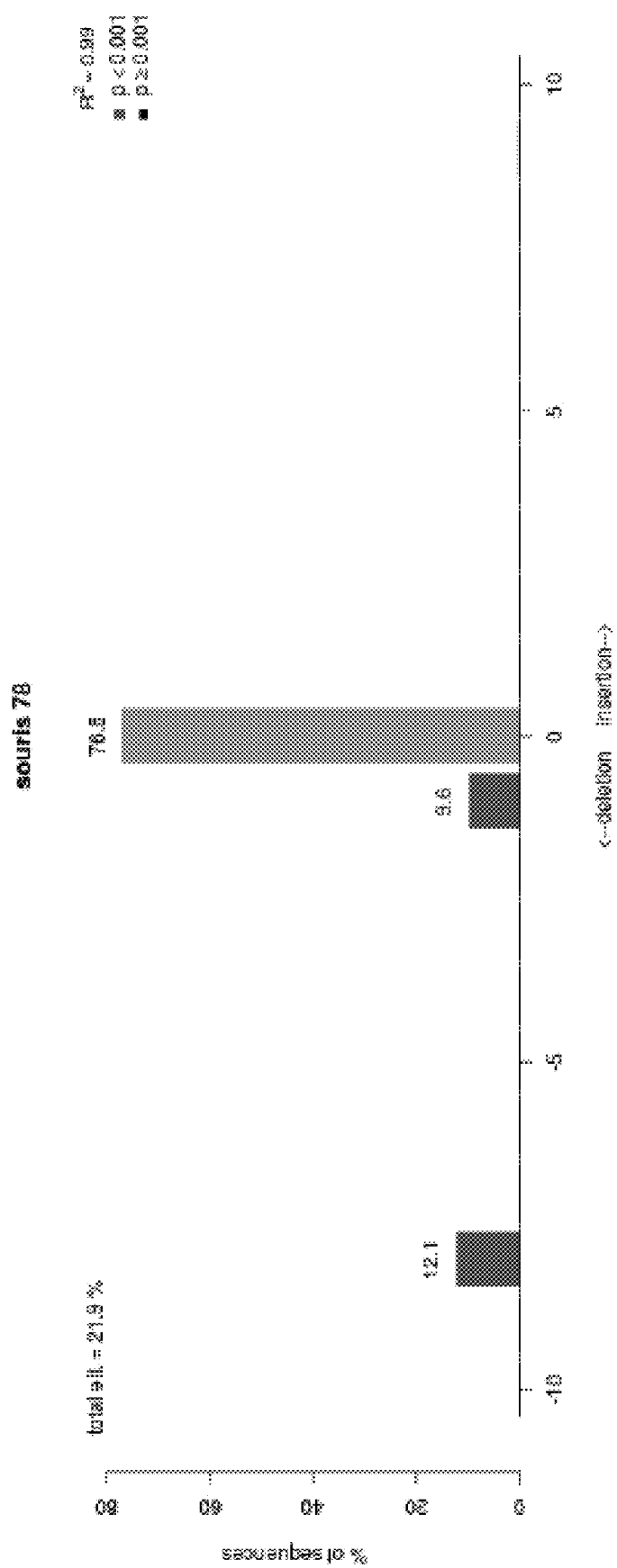
Figure 15E:
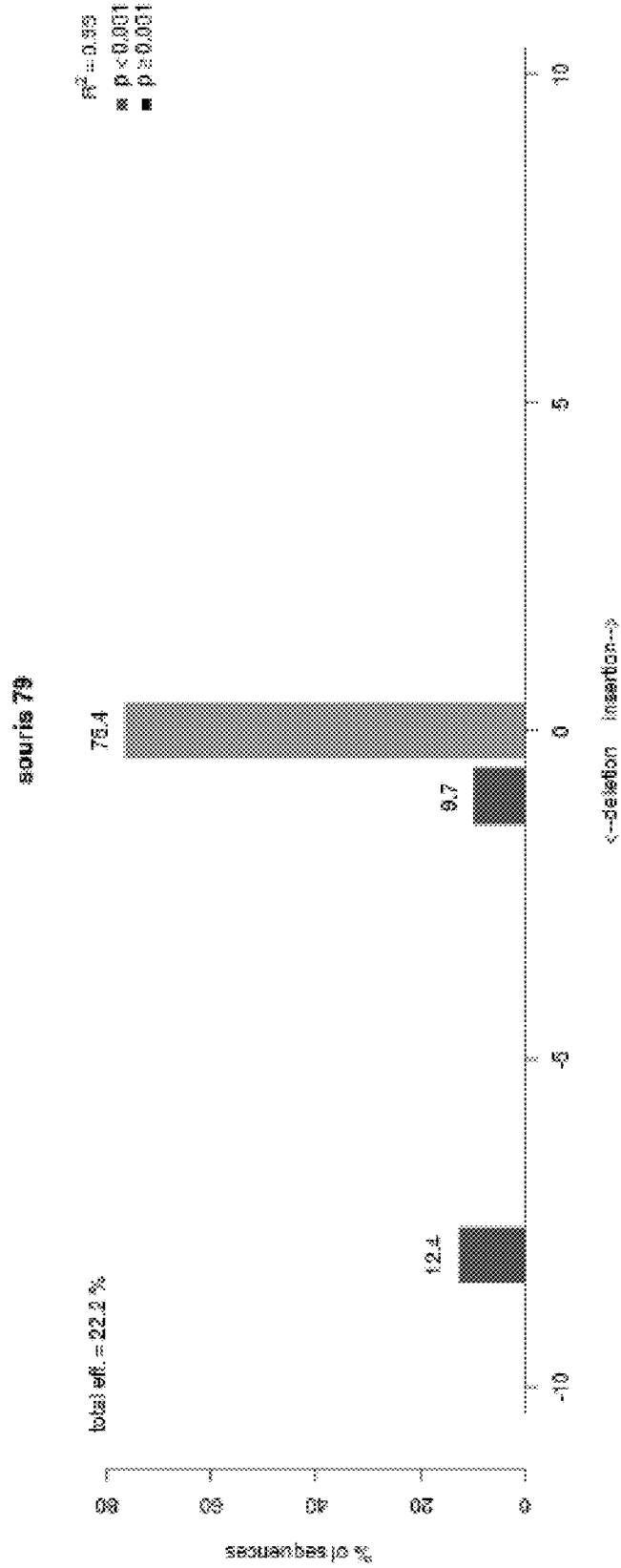
Figure 15F:
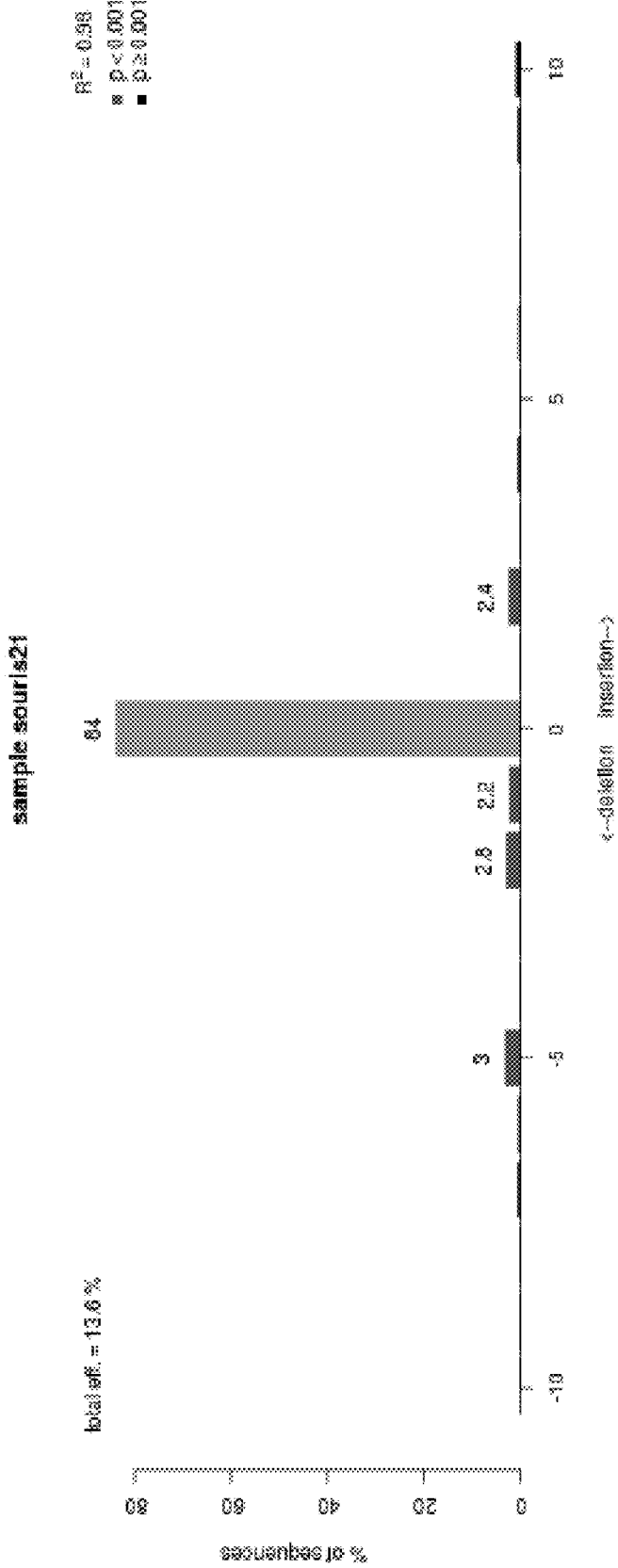
Figure 15G:
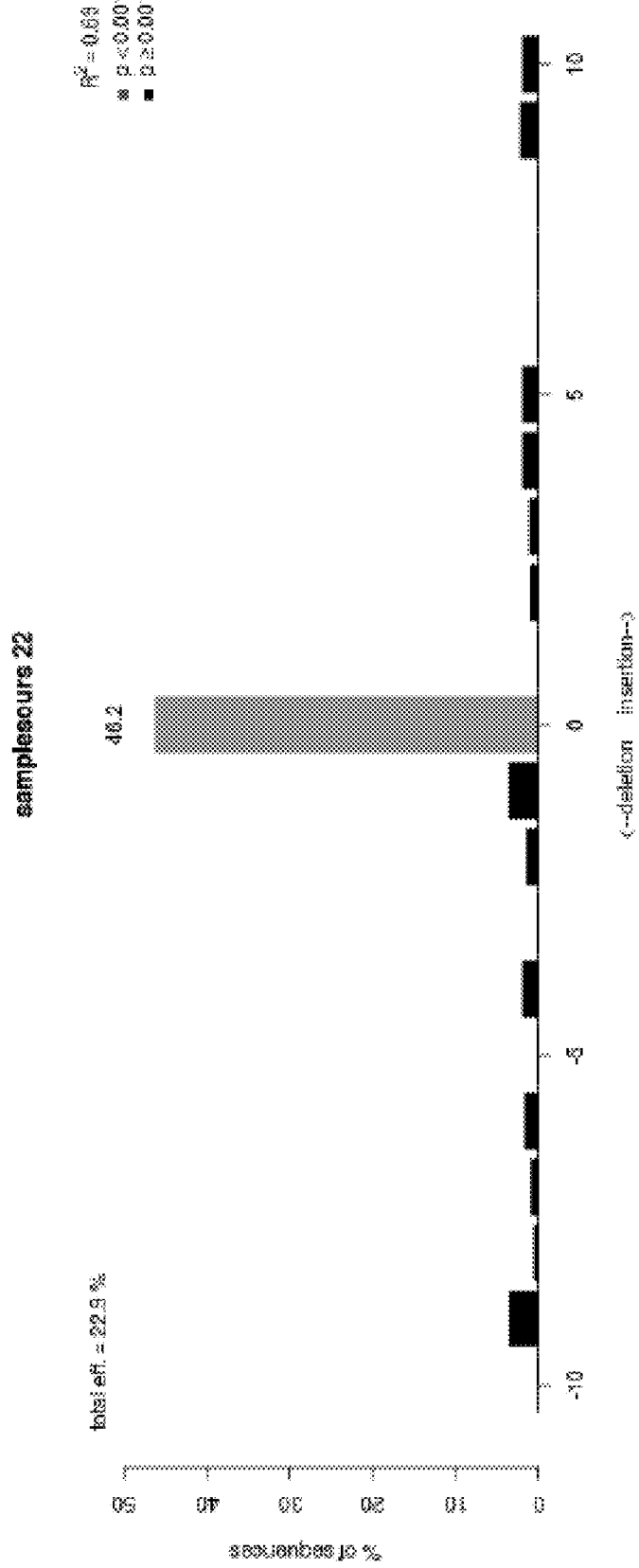

FIGS. 15A-15G: CRISPR delivery into Thy1-GFP mouse embryos by Cas9-containing virus-derived particles FIG. 15A illustrates the injection of CAS-containing virus-derived particles in the zona pellucida of Thy1-GFP mouse embryos.

FIG. 15B shows the results of cleaving the Thy1-GFP allele in the adult mice (F0) originating from the mouse embryos injected with CAS9-containing virus-derived particles FIG. 15C shows the alteration of the Thy1-GFP allele in the F1 mice originating from the F0 mice depicted in FIG. 15B.

FIGS. 15 D, E, F and G: Percent of GFP alteration in mice #78, #79, #21 and #22, respectively, as calculated from chromatograms wherein the results are compared with a non-treated Thy-GFP control mouse. In abscissa: percent of GFP alteration in F1 mice.

* % is never complete due to the fact that the chosen Thy1-GFP line carries several copies of GFP/allele (6 to 10). Results should be reproduced in a mouse line bearing one single constitutive GFP copy per allele, which is under preparation

DETAILED DESCRIPTION OF THE INVENTION

The present invention relates to the use of virus-derived particles to deliver CRISPR/Cas protein to target cells for generating targeted alteration(s) in the genome of an eukaryotic organism, preferably of a mammal, and especially of a human organism.

Surprisingly, the inventors have shown that the generation of a site-directed genome alteration, e.g. a site directed genome deletion or a site-directed genome insertion, may be successfully performed by delivering a Cas protein to the target cells through the use of viral vector particles wherein the said Cas protein has been packaged.

The present inventors have conceived a powerful method to transfer the CRISPRs active machinery within human and other mammalian cells, including primary cell types, by using versatile virus-derived particles (which are also termed "Virus Like Particles" or "VLPs" herein).

The inventors have shown that these VLPs ensure a transient and dose-dependent delivery of the CRISPR-RNPc (also termed "CRISPR-RiboNucleoProtein complex") into target cells and induce a robust and rapid cleavage of the desired targeted gene. As illustrated in the examples, when taking the Myd-88 gene as readout, the inventors have observed a complete cleavage of the latter gene in less than 6 hours in human cells, thus with a striking rapidity that may be attributed to the high efficiency of the virus-derived particles system described herein, which system comprises delivering directly a Cas protein, and most preferably a Cas9 protein, as well as CRISPR guide RNAs (also termed "gRNAs" herein) instead of performing a nucleic acid transfer of polynucleotides encoding Cas protein as it is the case for most already known CRISPRs delivery systems. As described in the examples herein, CRISPR guide RNAs are efficiently encapsulated in the CAS-containing VLPs. As it is also described in the examples, encapsulation of the CRISPR guide RNAs is highly subjected to the presence of the CAS protein in the VLPs.

The inventors have also shown that the CAS-containing VLPs may be prepared from a variety of virus-derived particles, and especially with virus-derived particles wherein the GAG protein contained therein may originate from a variety of viruses. Notably, it is described in the examples CAS-containing virus-derived particles comprising a MLV-derived GAG protein, as well as CAS-containing virus-derived particles comprising HIV1-derived GAG protein. It is shown herein that both kinds of CAS-containing virus-derived particles efficiently engineer a targeted gene, e.g., efficiently cleave a targeted gene.

Further, the inventors have shown that the GAG-containing virus-derived particles efficiently alter desired target sequences in vivo. Illustratively, it is shown in the examples that the GAG-containing virus-derived particles may be used to induce desired genomic alterations (e.g. induce a cleavage at a desired location in the genome) in living embryos. It is also shown herein that the genomic alterations performed in the living embryos are present in the resulting adult mammal and are then transferred to the subsequent generations.

The inventors findings are of a particular importance when considering that major gene expression processes (such as transcription and translation) are less active in some primary cells subsets that may be major targets for CRISPRs strategies and could therefore decrease the efficiency of conventional delivery methods like DNA transfection and conventional lentiviral vectors.

In this regard, the Cas9-virus-derived particles technology that has been conceived by the inventors appears as a tool of choice for genome editing, especially for genome editing in non-activated, non-dividing primary cells like lymphocytes, which poorly support transfection/transduction procedures, and display a low metabolism prior activation.

Further, according to the inventors results, the effect of the CRISPR RNPc is transient in the recipient target cell and is expected to exert its biological activity for at most a few hours after introduction of the RNPc through the contact of the virus-derived particles described herein with the target cells.

The transient delivery of CRIPSR components into target cells and the fact that this technology does not introduce plasmidic DNA in the target cells is expected to reduce the potential toxicity and also to reduce the risk of off-target cleavages.

Further, the fact that this technology does not introduce plasmidic DNA in the target cells allows avoiding the potential incorporation of exogenous-DNA in the target genome.

Illustratively, as it is shown in the examples, treatment of fragile human stem-CD34$^+$ cells or human lymphocytes with the virus-derived particles described herein has not induced detectable cell toxicity and has not led to cell-death, even after a massive input of the said virus-derived particles.

Notably, the present inventors have engineered a chimeric Cas9-protein upon fusion with the structural GAG protein of the murine leukemia virus to have the Cas9 protein packaged into MLV-derived VLPs or to HIV-1-derived VLPs.

This concept has thus been easily extended to other viral structural proteins like the GAG polyprotein from HIV-1 or the GAG polyprotein from Rous Sarcoma Virus (RSV) with success.

The virus-derived particles produced as described herein, are shown to efficiently transfer the CRISPR-RNPc into the desired target cells. Exploiting the technology of virus-derived particles described herein offers a large panel of viral envelopes that can be selected to pseudotype the said virus-derived particles, thus conferring particular properties to the preparation (tropism, complement resistance, robustness).

Insertion of the coding sequences of a Cas protein and one or more CRISPR gRNAs in expression cassettes, and especially the coding sequences of Cas9 and a specifically designed gRNA in expression cassettes, may also be performed in the backbone of recombinant viruses like Measles or certain Influenza strains, permissive to incorporation of foreign sequences. This allows an extensive diffusion of the active CRISPR RNPc in specific cells/tissues/organs permissive to the considered virus.

Beyond the exploitation of the Cas9 *Streptococcus pyogenes* endonuclease, the technology described herein is easily extended to Cas proteins from other organisms that can be alternatively fused with a structural viral protein. The growing cohort of Cas9-derivatives may also be delivered by the virus-derived particles described herein so as to achieve a large variety of genome alterations, such as cleaving only one DNA-strand, activating transcription and labelling precise genomic loci. The technology described herein also allows performing a Cas-based CRISPR strategy, especially a Cas9-based CRISPR strategy, for targeting intracellular mRNAs and induce their cleavage, as described by O'Connell et al. (2014, Nature, Vol. 516: 263-266), which is a technique involving small DNA sequences (PAMmers) provided in trans. The virus-derived particles technology described herein may be adapted to this RNA targeting approach by a simple combination of particles with ssDNA PAMmers on the model of the flaging-DDX3 strategy described in the examples (See also FIG. 10 herein).

The possibility to combine the virus-derived particles described herein, after their production, with ssDNA or even dsDNA offers vast possibilities in terms of industrial developments and rapid and costless customizations for various nucleic acid engineering purposes. Moreover, it is to note that viral-derived nanoparticles differing for their envelope or their proteic/nucleic cargo can trans-complement when combined as a mixture, as it was described in another technical context by Abe et al. (1998, J Virol, Vol. 72: 6356-6361).

A plurality of ways of combining the virus-derived particles of the invention and to transfer the CRISPRs effect into target cells are described elsewhere in the present specification. Some of these various embodiments are depicted in FIG. 11 herein. Preliminary data indicate that the virus-derived particles comprising a Cas protein, especially a Cas9 protein, may be combined with vesicles incorporating one or more CRISPR gRNA(s) when these virus-derived particles and vesicles are prepared and used as taught in another technical context by Mangeot et al. (2011, Mol Ther J Am Soc Gene Ther, Vol. 19: 1956-1666), and that the CRISPRs action is efficient in cells treated by the resulting mixture of the Cas-containing virus-derived particles and the gRNA(s)-containing vesicles. The opportunity to segregate the CRISPRs components in different types of particles may be of high interest from an industrial point of view and offers versatile technical solutions for generating the desired nucleic acid alteration(s).

The Cas-containing virus-derived particles described herein, especially the Cas9-containing virus-derived particles, may be easily produced in large amounts in the absence of gRNAs, to obtain VLP batches that are carefully dosed and quality-controlled. These Cas9-VLPs can later be combined in a custom-dependent manner with gRNA(s)-containing vesicles and/or targeting nucleic acid-containing vesicles, so as to complement the system by specific gRNAs or specific reparation template, or both.

As it is fully illustrated in the present specification, the Cas-containing virus-derived particles technology that is described herein offers new possibilities to the CRISPR community and notably upgrade the available toolbox to target challenging cell-types and explore innovative therapeutic CRISPR-based approaches for in/ex vivo gene therapy.

Thus, the inventors have successfully packaged a Cas protein into virus-derived particles by conceiving packaging cells expressing a cleavable fusion protein between (i) a viral structural protein and (ii) the said Cas protein. Thus, the present invention relates to a virus-derived particle comprising one or more Cas protein(s).

As used herein, a virus-derived particle means a particle formed from the assembly of viral structural proteins which are associated so as to form the particle core that will be later enveloped with a membrane, (which virus-derived particle does not contain any nucleic acid encoding a nucleic acid or a protein of interest). Thus, in contrast to most of the virus-derived particles known in the art, which are designed for delivering expression nucleic acids in the transduced cells, a virus-derived particle as described herein is designed for delivering proteins, and optionally non-coding nucleic acids in the transduced cells, i.e. at least a Cas protein. As it is described in detail in the present specification, a virus-derived particle according to the invention may also contain one or more non-coding nucleic acids, which non-coding nucleic acids encompass CRISPR-Cas system guide RNA(s) and targeting nucleic acids. For the sake of clarity, it may arise that a virus-derived particle as described herein may contain traces of coding nucleic acids originating from the cells that are used for producing them, such as traces of mRNAs or plasmidic DNA originating from the said producing cells. The small amount of coding nucleic acids that may in some occasions be present within the virus-derived particles are generally passively encapsulated. However, it shall be clearly understood that the virus-derived particles described herein are not at all dedicated to transport any coding nucleic acid of interest but, as described in detail throughout the entire specification, these virus-derived particles are in contrast only dedicated to transport proteins, mainly one or more proteins having a Cas endonuclease activity, and in some embodiments also non-coding nucleic acids of interest, namely (i) one or more CRISPR-guide RNA(s) and/or one or more targeting nucleic acid(s).

As shown in the examples herein, the said cleavable fusion protein between (i) a viral structural protein and (ii) the said Cas protein is successfully incorporated in the virus-derived particles that are produced by the packaging cells and the resulting virus-derived particles successfully deliver the Cas protein to the target cells for altering the target cells genome through site-directed genomic DNA cleavage and, in some embodiments, also nucleic acid insertion by homologous recombination. As shown in the examples herein, the said fusion protein contributes to the formation of the virus-derived particles wherein it is associated with the viral structural proteins.

The inventors have notably shown that successful genomic alteration is obtained by using these virus-derived particles in combination with one or more CRIPSR-Cas system guide RNA(s), and in particular by using virus-derived particles further containing the said one or more CRIPSR-Cas system guide RNA(s) inside the said particles.

As shown in the examples, the virus-derived particles described herein have been successfully used for disrupting or deleting various genes, both in vitro and in vivo, so as to generate organisms wherein the said various genes have been knocked-out.

As it is also shown in the examples, the virus-derived particles described herein have been successfully used for the targeted insertion of nucleic acids of interest in the genome of target cells, so as to generate knock-in organisms.

As experimentally illustrated herein, the inventors have fused a Cas9 protein with the GAG protein of Murine Leukemia Virus and have used this construct to produce functional Cas9-loaded virus-derived particles delivering the Cas9 activity into recipient cells.

As further experimentally illustrated herein, the inventors have fused a Cas9 protein with the GAG protein of HIV-1 and have used this construct to produce functional Cas9-loaded virus-derived particles delivering the Cas9 activity into recipient cells.

Moreover it is shown in the examples herein that the guide RNAs can also be incorporated successfully in virus-derived particles, creating a fully active CRISPR-RNPc within viral like particles that can be transmitted into recipient cells. The experimental results of the inventors illustrate the high efficiency of these Cas-containing virus-derived particles. These virus-derived particles are fully able to deliver CRISPRs in different cells types, including primary cells, without apparent toxicity. Cleavage efficiency of the genomic target nucleic acid is remarkably close to 100% in human naive lymphocytes simply treated by the said virus-derived particles cleaving the human (hMyd88) gene.

The present invention relates to a virus-derived particle comprising one or more Cas protein(s). Various embodiments of the virus-derived particles described in the present specification are illustrated in FIG. 11.

Virus-Derived Particles

As used herein, a virus-derived particle consists of a virus-like particle formed by one or more virus-derived protein(s), which virus-derived particle is substantially devoid of any nucleic acid encoding a nucleic acid or a protein of interest, or alternatively is devoid of any nucleic acid encoding a nucleic acid or a protein of interest. Notably, a virus-derived particle according to the invention is substantially devoid of any nucleic acid encoding a viral nucleic acid or a viral protein of interest, or alternatively is devoid of any nucleic acid encoding a viral nucleic acid or a viral protein of interest. A virus-derived particle according to the invention is replication-incompetent.

Virus-Derived Particles

Any virus suitable for gene therapy may be used, including but not limited to adeno-associated virus ("AAV"); adenovirus; herpes virus; lentivirus and retrovirus. Adeno-associated virus ("AAV") may be selected in a group comprising AAV1, AAV6, AAV7, AAV8, AAV9 or rh10, which AAV are particularly suitable for use in human subjects.

The general methods that are known in the art for producing viral vector particles, which generally contain coding nucleic acids of interest, may also be used for producing the virus-derived particles according to the present invention, which do not contain coding nucleic acids of interest.

Conventional viral vector particles encompass retroviral, lentiviral, adenoviral and adeno-associated viral vector particles that are well known in the art. For a review of various viral vector particles that may be used, the one skilled in the art may notably refer to Kushnir et al. (2012, Vaccine, Vol. 31: 58-83), Zeltons (2013, Mol Biotechnol, Vol. 53: 92-107), Ludwig et al. (2007, Curr Opin Biotechnol, Vol. 18(no 6): 537-55) and Naskalaska et al. (2015, Vol. 64 (no 1): 3-13). Further, references to various methods using virus-derived particles for delivering proteins to cells are found by the one skilled in the art in the article of Maetzig et al. (2012, Current Gene therapy, Vol. 12: 389-409) as well as the article of Kaczmarczyk et al. (2011, Proc Natl Acad Sci USA, Vol. 108 (no 41): 16998-17003).

Generally, a virus-derived particle that is used according to the invention, which virus-derived particle may also be termed "Virus-Like Particle" or "VLP", is formed by one or more virus-derived structural protein(s) and/or one more virus-derived envelope protein.

A virus-derived particle that is used according to the present invention is replication incompetent in a host cell wherein it has entered.

In preferred embodiments, a virus-derived particle is formed by one or more retrovirus-derived structural protein(s) and optionally one or more virus-derived envelope protein(s).

In preferred embodiments, the virus-derived structural protein is a retroviral gag protein or a peptide fragment thereof. As it is known in the art, Gag and Gag/pol precursors are expressed from full length genomic RNA as polyproteins, which require proteolytic cleavage, mediated by the retroviral protease (PR), to acquire a functional conformation. Further, Gag, which is structurally conserved among the retroviruses, is composed of at least three protein units: matrix protein (MA), capsid protein (CA) and nucleocapsid protein (NC), whereas Pol consists of the retroviral protease, (PR), the retrotranscriptase (RT) and the integrase (IN).

In some embodiments, a virus-derived particle comprises a retroviral Gag protein but does not comprise a Pol protein.

As it is known in the art, the host range of retroviral vector, including lentiviral vectors, may be expanded or altered by a process known as pseudotyping. Pseudotyped lentiviral vectors consist of viral vector particles bearing glycoproteins derived from other enveloped viruses. Such pseudotyped viral vector particles possess the tropism of the virus from which the glycoprotein is derived.

In some embodiments, a virus-derived particle is a pseudotyped virus-derived particle comprising one or more viral structural protein(s) or viral envelope protein(s) imparting a tropism to the said virus-derived particle for certain eukaryotic cells. A pseudotyped virus-derived particle as described herein may comprise, as the viral protein used for pseudotyping, a viral envelope protein selected in a group comprising VSV-G protein, Measles virus HA protein, Measles virus F protein, Influenza virus HA protein, Moloney virus MLV-A protein, Moloney virus MLV-E protein, Baboon Endogenous retrovirus (BAEV) envelope protein, Ebola virus glycoprotein and foamy virus envelope protein, or a combination of two or more of these viral envelope proteins.

A well-known illustration of pseudotyping viral vector particles consists of the pseudotyping of viral vector particles with the vesicular stomatitis virus glycoprotein (VSV-G). For the pseudotyping of viral vector particles, the one skilled in the art may notably refer to Yee et al. (1994, Proc Natl Acad Sci, USA, Vol. 91: 9564-9568) Cronin et al. (2005, Curr Gene Ther, Vol. 5(no 4): 387-398).

For producing virus-derived particles, and more precisely VSV-G pseudotypes virus-derived particles, for delivering protein(s) of interest into target cells, the one skilled in the art may refer to Mangeot et al. (2011, Molecular Therapy, Vol. 19 (no 9): 1656-1666).

In some preferred embodiments, the VSV-G protein which is used for pseudotyping a virus-derived particle of the invention has the amino acid sequence of SEQ ID NO. 23, that may be encoded by a nucleic acid comprising the sequence of SEQ ID NO. 28.

In some preferred embodiments, the BAEV-G (BAEV) protein which is used for pseudotyping a virus-derived particle of the invention has the amino acid sequence of SEQ ID NO. 25, that may be encoded by a nucleic acid comprising the sequence of SEQ ID NO. 27.

Thus, in some embodiments, a virus-derived particle further comprises a viral envelope protein, wherein either (i) the said viral envelope protein originates from the same virus as the viral structural protein, e.g. originates from the same virus as the viral Gag protein, or (ii) the said viral envelope protein originates from a virus distinct from the virus from which originates the viral structural protein, e.g. originates from a virus distinct from the virus from which originates the viral Gag protein.

As it is readily understood by the one skilled in the art, a virus-derived particle that is used according to the invention may be selected in a group comprising Moloney murine leukemia virus-derived vector particles, Bovine immunodeficiency virus-derived particles, Simian immunodeficiency virus-derived vector particles, Feline immunodeficiency virus-derived vector particles, Human immunodeficiency virus-derived vector particles, Equine infection anemia virus-derived vector particles, Caprine arthritis encephalitis virus-derived vector particle, Baboon endogenous virus-derived vector particles, Rabies virus-derived vector particles, Influenza virus-derived vector particles, Norovirus-derived vector particles, Respiratory syncytial virus-derived vector particles, Hepatitis A virus-derived vector particles, Hepatitis B virus-derived vector particles, Hepatitis E virus-derived vector particles, Newcastle disease virus-derived vector particles, Norwalk virus-derived vector particles, Parvovirus-derived vector particles, Papillomavirus-derived vector particles, Yeast retrotransposon-derived vector particles, Measles virus-derived vector particles, and bacteriophage-derived vector particles.

In particular, a virus-derived particle that is used according to the invention is a retrovirus-derived particle. Such retrovirus may be selected among Moloney murine leukemia virus, Bovine immunodeficiency virus, Simian immunodeficiency virus, Feline immunodeficiency virus, Human immunodeficiency virus, Equine infection anemia virus, and Caprine arthritis encephalitis virus.

In another embodiment, a virus-derived particle that is used according to the invention is a lentivirus-derived particle. Lentiviruses belong to the retroviruses family, and have the unique ability of being able to infect non-dividing cells.

Such lentivirus may be selected among Bovine immunodeficiency virus, Simian immunodeficiency virus, Feline immunodeficiency virus, Human immunodeficiency virus, Equine infection anemia virus, and Caprine arthritis encephalitis virus.

For preparing Moloney murine leukemia virus-derived vector particles, the one skilled in the art may notably refer to the methods disclosed by Sharma et al. (1997, Proc Natl Acad Sci USA, Vol. 94: 10803+-10808), Guibingua et al. (2002, Molecular Therapy, Vol. 5(no 5): 538-546). Moloney murine leukemia virus-derived (MLV-derived) vector particles may be selected in a group comprising MLV-A-derived vector particles and MLV-E-derived vector particles.

For preparing Bovine Immunodeficiency virus-derived vector particles, the one skilled in the art may notably refer to the methods disclosed by Rasmussen et al. (1990, Virology, Vol. 178(no 2): 435-451)

For preparing Simian immunodeficiency virus-derived vector particles, including VSV-G pseudotyped SIV virus-derived particles, the one skilled in the art may notably refer to the methods disclosed by Mangeot et al. (2000, Journal of Virology, Vol. 71(no 18): 8307-8315), Negre et al. (2000, Gene Therapy, Vol. 7: 1613-1623) Mangeot et al. (2004, Nucleic Acids Research, Vol. 32 (no 12), e102)

For preparing Feline Immunodeficiency virus-derived vector particles, the one skilled in the art may notably refer to the methods disclosed by Saenz et al. (2012, Cold Spring Harb Protoc, (1): 71-76; 2012, Cold Spring Harb Protoc, (1): 124-125; 2012, Cold Spring Harb Protoc, (1): 118-123).

For preparing Human immunodeficiency virus-derived vector particles, the one skilled in the art may notably refer to the methods disclosed by Jalaguier et al. (2011, PlosOne, Vol. 6(no 11), e28314), Cervera et al. (J Biotechnol, Vol. 166(no 4): 152-165), Tang et al. (2012, Journal of Virology, Vol. 86(no 14): 7662-7676)

For preparing Equine infection anemia virus-derived vector particles, the one skilled in the art may notably refer to the methods disclosed by Olsen (1998, Gene Ther, Vol. 5(no 11): 1481-1487).

For preparing Caprine arthritis encephalitis virus-derived vector particles, the one skilled in the art may notably refer to the methods disclosed by Mselli-Lakhal ety al. (2006, J Virol Methods, Vol. 136(no 1-2): 177-184).

For preparing Baboon endogenous virus-derived vector particles, the one skilled in the art may notably refer to the methods disclosed by Girard-Gagnepain et al. (2014, Blood, Vol. 124(no 8): 1221-1231)

For preparing Rabies virus-derived vector particles, the one skilled in the art may notably refer to the methods disclosed by Kang et al. (2015, Viruses, Vol. 7: 1134-1152, doi:10.3390/v7031134), Fontana et al. (2014, Vaccine, Vol. 32(no 24): 2799-27804) or to the PCT application published under no WO 2012/0618.

For preparing Influenza virus-derived vector particles, the one skilled in the art may notably refer to the methods disclosed by Quan et al. (2012, Virology, Vol. 430: 127-135) and to Latham et al. (2001, Journal of Virology, Vol. 75(no 13): 6154-6155).

For preparing Norovirus-derived vector particles, the one skilled in the art may notably refer to the methods disclosed by Tome-Amat et al., (2014, Microbial Cell Factories, Vol. 13: 134-142).

For preparing Respiratory syncytial virus-derived vector particles, the one skilled in the art may notably refer to the methods disclosed by Walpita et al. (2015, PlosOne, DOI: 10.1371/journal.pone.0130755)

For preparing Hepatitis B virus-derived vector particles, the one skilled in the art may notably refer to the methods disclosed by Hong et al. (2013, Vol. 87(no 12): 6615-6624).

For preparing Hepatitis E virus-derived vector particles, the one skilled in the art may notably refer to the methods disclosed by Li et al. (1997, Journal of Virology, Vol. 71(no 10): 7207-7213).

For preparing Newcastle disease virus-derived vector particles, the one skilled in the art may notably refer to the methods disclosed by Murawski et al. (2010, Journal of Virology, Vol. 84(no 2): 1110-1123)

For preparing Norwalk virus-derived vector particles, the one skilled in the art may notably refer to the methods disclosed by Herbst-Kralovetz et al. (2010, Expert Rev Vaccines, Vol. 9(no 3): 299-307).

For preparing Parvovirus-derived vector particles, the one skilled in the art may notably refer to the methods disclosed by Ogasawara et al. (2006, In Vivo, Vol. 20: 319-324)

For preparing Papillomavirus-derived vector particles, the one skilled in the art may notably refer to the methods disclosed by Wang et al. (2013, Expert Rev Vaccines, Vol. 12(no 2): doi: 10.1586/erv.0.12.151)

For preparing Yeast retrotransposon-derived vector particles, the one skilled in the art may refer to the methods disclosed by Peifang et al. (1994, Clin Exp Immunol, Vol. 97(no 3): 361-366) or to the U.S. Pat. No. 6,060,064

For preparing Measles virus-derived vector particles, the one skilled in the art may notably refer to the methods disclosed by Brandler et al. (2008, Vol. 31(no 2-3): 271-291).

For preparing bacteriophage-derived vector particles, and in particular Q-beta virus-like particles, the one skilled in the art may notably refer to the methods disclosed by Brown et al. (2009, Biochemistry, Vol. 48(no 47): 11155-11157).

A virus-derived particle that is used herein comprises a Gag protein, and most preferably a Gag protein originating from a virus selected in a group comprising Rous Sarcoma Virus (RSV) Feline Immunodeficiency Virus (FIV), Simian Immunodeficiency Virus (SIV), Moloney Leukemia Virus (MLV) and Human Immunodeficiency Viruses (HIV-1 and HIV-2) especially Human Immunodeficiency Virus of type 1 (HIV-1).

In some embodiments, a virus-derived particle may also comprise one or more viral envelope protein(s). The presence of one or more viral envelope protein(s) may impart to the said virus-derived particle a more specific tropism for the cells which are targeted, as it is known in the art. The one or more viral envelope protein(s) may be selected in a group comprising envelope proteins from retroviruses, envelope proteins from non-retroviral viruses, and chimeras of these viral envelope proteins with other peptides or proteins. An example of a non-lentiviral envelope glycoprotein of interest is the lymphocytic choriomeningitis virus (LCMV) strain WE54 envelope glycoprotein. These envelope glycoproteins increase the range of cells that can be transduced with retroviral derived vectors.

In some preferred embodiments, the virus-derived particle comprises a Gag protein originating from a virus selected in a group comprising Rous Sarcoma Virus (RSV) and Moloney Leukemia Virus (MLV).

In some preferred embodiments, a virus-derived particle that is used herein, further comprises a pseudotyping viral envelope protein, and most preferably a VSV-G protein.

Cas Protein

A virus-derived particle comprises a Cas protein. The said Cas protein may be selected in a group comprising a type I Cas protein, a type II Cas protein and a type III Cas protein.

For using a type I, type II or type III Cas protein, the one skilled in the art may refer to Chylinski et al. (2014, Nucleic Acids Research, Vol. 42(no 10): 6091-6105), Sinkunas et al.

(2011, The EMBO Journal, Vol. 30(no 7): 1335-1342), Aliyari et al. (2009, Immunological Reviews, Vol. 227(no 1): 176-188), Cass et al. (Biosci Rep, doi:10.1042/BSR20150043), Makarova et al. (2011, Biology Direct, Vol. 6: 38), Gasiunas et al. (2012, Proc Natl Acad Sci USA, Vol. 109(no 39): E2579-E2586), Heler et al. (2015, Nature, Vol. 519(no 7542): 199-202), Esvelt et al. (2013, Nat Methods, Vol. 10(no 11): doi:10.138/nmeth.2681) or Chylinski et al. (2013, Biology, Vol. 10(no 5): 726-737).

In some embodiments, the Cas protein may consist of the Type II Cas protein named Cpf1 which is disclosed by Zeische et al. (2015, Cell, dx.doi.org/10.1016/j.cell.2015.09.038, in Press).

Preferably, a virus-derived protein comprises a type II Cas protein. A type II Cas protein is most preferably a Cas9 protein.

Most preferably, the Cas protein which is contained inside a virus-derived particle as described herein is a Cas9 protein, or an homolog or a derivative thereof. The Cas9 protein may be selected in a group comprising a Cas9 protein originating from *Streptococcus thermophilus* and a Cas9 protein originating from *Streptococcus pyogenes*, or an homolog thereof or a derivative thereof. Cas9 protein originating from *Streptococcus thermophilus* is described notably by Gasiunas et al. (2012, Proc Natl Acad Sci USA, Vol. 109(no 39): E2579-E2586). Cas9 protein originating from *Streptococcus pyogenes* is described notably by Heler et al. (2015, Nature, Vol. 519(no 7542): 199-202) and Sanjana et al. (2014, Nat Methods, Vol. 11(no 18): 783-784).

A Cas9 protein that may be used according to the present invention encompasses proteins which are homologs, variants or derivatives of the naturally occurring Cas9 proteins, such as the Cas9 proteins described by Cong et al. (2013, *Science*, Vol. 339: 819-823).

A Cas9 protein as well as vectors encoding a Cas9 protein are commercially available from Sigma-Aldrich Company. Cas9 protein and variants thereof that may be used in virus-derived particles described herein are also described in the PCT applications published under no WO 2013/163628, WO 2014/093595, WO 2015/089247 and WO 2015/089486.

In some embodiments, Cas9 protein is produced so as to be incorporated in the virus-derived particles during their formation. Illustratively, Cas9 may be encoded by a nucleic acid sequence inserted in an expression vector contained in the virus-derived particles producing cells. In preferred embodiments, the Cas9-encoding nucleic acid is placed under the control of regulatory sequences allowing its overexpression in the producing cells. In some embodiments, the Cas9 protein consists of the protein of SEQ ID NO. 31, which is encoded by the nucleic acid sequence of SEQ ID NO. 32.

In some embodiments of a virus-derived particle described herein, the Cas protein is produced and integrated within the said virus-derived particle as a fusion protein between (i) a viral structural protein and (ii) the said Cas protein. In some of these embodiments, the Cas protein is produced and integrated within the said virus-derived particle as a GAG-Cas9 fusion protein. As it has been ascertained by the present inventors, such a fusion protein is successfully integrated within the resulting virus-derived particle and the Cas moiety is fully active, i.e. the Cas moiety possesses its endonuclease activity. According to those embodiments, the embedded Cas protein is released inside the target cells following the entering of the virus-derived particles.

In other embodiments, a Cas protein comprised in a virus-derived particle is initially produced as a cleavable fusion protein between (i) a viral structural protein and (ii) a Cas protein. An illustration of such a cleavable fusion protein is the cleavable GAG-Cas9 protein that is described in the examples herein. According to these other embodiments, the said cleavable fusion protein is integrated within the resulting virus-derived particle at the time of its production by the producing cells. Then, part or all of the said fusion proteins may be cleaved in the final virus-derived particles, leading to a population of virus-derived particles comprising (i) a part of the virus-derived particles wherein none the said cleavable fusion protein has been cleaved, (ii) a part of the virus-derived particles wherein at least a part of the said cleavable fusion proteins have been cleaved, leading the release of Cas protein moiety inside the virus-derived particles and (iii) a part of the virus-derived particles wherein all or almost all of the said cleavable fusion proteins have been cleaved, leading the release of all or almost all of the Cas protein moieties inside the virus-derived particles. In some preferred embodiments, a cleavable GAG-Cas9 protein is the GAG-Cas9 protein having the amino acid sequence of SEQ ID NO. 22, that may be encoded by a sequence of SEQ ID NO. 26. In other embodiments, it may be used a cleavable GAG-Cas9 protein encoded by the nucleic acid sequence of SEQ ID NO. 34 (that may be termed "KLAP229" herein).

Thus, in a virus-derived particle that may be used according to the invention, the Cas protein, typically the Cas9 protein, may be present either as (i) a non-cleavable fusion protein, typically a non-cleavable Gag-Cas9 fusion protein, as (ii) a cleavable fusion protein, typically a cleavable Gag-Cas9 fusion protein, as (iii) a Cas protein, typically a Cas9 protein, resulting from the proteolytic cleavage of the said fusion protein, or (iv) both the fusion protein and the Cas protein. It shall be understood that a virus-derived particle as used herein is produced in packaging cells that notably express a protein between (i) a viral structural protein and (ii) a Cas protein, typically a cleavable Gag-Cas9 fusion protein, which encompasses the cleavable fusion protein between (i) a viral structural protein and (ii) a Cas protein, typically the cleavable Gag-Cas9 fusion protein. The cleavable fusion protein is incorporated as such in the virus-derived particle and is then at least partly cleaved in the virus-derived particle so as to release the Cas protein, which is functional in the virus-derived particle as it is shown in the examples herein. However, because the Cas protein is initially incorporated in the virus-derived particles under the form of the said cleavable fusion protein, there are a number of intermediate states wherein the Cas protein is partly present under the form of the cleavable fusion protein and partly present as a free Cas protein resulting from the cleavage of the cleavable fusion protein.

In preferred embodiments, the fusion protein comprises a proteolysis cleavage site located between the viral structural protein moiety and the Cas protein moiety, typically between the Gag protein moiety and the Cas9 protein moiety. Proteolytic sites, which may also be termed protease sites, are well known form the one skilled in the art. A protease site that may be contained in the cleavable fusion protein may be a site that is cleavable by a protease selected in a group comprising trypsin (EC 3.4.21.4), chymotrypsin (EC 3.4.21.1), endoproteinase Glu C (EC 3.4.21.19), endoproteinase Lys-C (EC 3.4.21.50), pepsin (EC 3.4.23.1), elastase (EC 3.4.21.36) abd carboxypeptidase (EC 3.4.17.1).

In some embodiments, the protease cleavage site is selected in a group comprising the amino acid sequences SSLYPALTP (SEQ ID N° 29), that may be encoded by a sequence comprising SEQ ID NO. 30.

Protease cleavable fusion protein between Gag and a protein of interest, as well as vectors for expressing such fusion proteins are notably described by Voelkel et al. (2010, Proc Natl Acad Sci USA, Vol. 107(no 17): 7805-7810), to which the one skilled in the art may refer.

As described in the examples herein, some embodiments of a virus-derived particles are formed in packaging cells expressing a Gag-Pro-Pol viral protein. Without wishing to be bound by any particular theory, the inventors believe that in these embodiments, the Pro protein (i.e. the viral protease) is released in the virus-derived particles and cleaves the fusion protein, typically the Gag Cas fusion protein, especially the Gag-Cas9 fusion protein, so as to generate the free Cas protein, especially the free Cas9 protein. In some preferred embodiments, the Gag-Pro-Pol protein has the amino acid sequence of SEQ ID NO. 24.

However, as it is also illustrated in the examples herein, A functional Cas protein, typically a functional Cas9 protein, is released in the target cells in the embodiments wherein the virus-derived particles are devoid of any viral protease, e.g.; when the virus-derived particles are formed in packaging cells that express a viral structural protein (e.g. Gag) and optionally one or more viral envelope protein (e.g. VSV-G and/or BAEV-G).

Guide RNAs

For generating a site-directed alteration in a target nucleic acid, when using a virus-derived particle as described herein, one or more CRISPR-Cas guide RNAs are required.

The number of CRISPR-Cas guide RNAs, which may also be termed "guide RNAs" or "gRNAs", may vary depending of the kind of alteration(s) to the target nucleic acids which is(are) sought. A single guide RNA may be used in combination with a virus-derived particle for generating a single DNA cleavage event in the target nucleic acid. Two or more guide RNAs may be used in combination with a virus-derived particle for generating two or more cleavage events in the target nucleic acids, or alternatively to generate cleavage event(s) in a plurality of target nucleic acids.

Methods for designing guide RNAs that, when combined with a Cas protein, generate the cleavage of a target nucleic acid, are well known from the one skilled in the art. As it is well known in the art, a guide RNA is a polynucleotide having sufficient complementarity with a target nucleic acid to hybridize with the said target nucleic acid and direct sequence-specific binding of a CRISPR complex to the said target nucleic acid.

Various tools are readily available to the one skilled in the art for designing guide RNAs, which include the tool marketed under the name GenCRISPR™ gRNA constructs by the Company GenScript (United States). The GenCRISPR™ gRNA constructs collection comprise about six guide RNAs to specifically target each of about 20,000 genes in the human genome. Guide RNAs may also be designed according to the teachings of Ran et al. (2013, Cell, Vol. 154: 1380-1389), Mail et al. (2013, Science, Vol. 339: 823-826), Wang et al. (2013, Cell, Vol. 153: 910-918), Jao et al. (2013, Proc Natl Acad Sic USA, Vol. 110: 13904-13909), Cong et al. (2013, Science, Vol. 339: 819-823), Shalem et al. (2014, Science, Vol. 343: 84-87), Maeder et al. (2013, Nat Methods; Vol. 10: 977-979), Qi et al. (2013, Cell, Vol. 152: 1173-1183), Farboud et al. (2015, Genetics, doi 10.1534/genetics.115.175166) or Ma et al. (2013, BioMed research International, Vol. 2013, Article ID 270805, doi.org/10.1155/2013/270805).

In some embodiments, a virus-derived particle as described herein further comprises one or more CRISPR-Cas guide RNA(s). Each guide RNA hybridizes with a specific target sequence comprised in a target nucleic acid.

In some embodiments, a virus-derived particle as described herein comprises a single guide RNA. Such embodiments of a virus-derived particle allow generating a single cleavage at a desired location of the target nucleic acid.

In some other embodiments, a virus-derived particle as described herein comprises two distinct guide RNAs, each guide RNA hybridizing with a specific target sequence comprised in the same target nucleic acid, so as to generate two cleavage events at the sites recognized by the respective two distinct guide RNAs. Such embodiments allow introducing a deletion of the polynucleotide framed by the two cleavage sites within the target nucleic acid. When a template nucleic acid of interest is further added, such embodiments allow the insertion of a desired exogenous nucleic acid of interest in the nucleic acid target, between these two cleavage sites.

In some preferred embodiments, the one or more guide RNAs are comprised inside the virus-derived particle. Typically, the virus-derived particles are produced by packaging cells expressing (i) the required viral structural protein(s) (e.g. Gag), (ii) the one or more viral envelope protein(s) (e.g. VSV-G and/or BAEV-G), (iii) the Cas fusion protein (e.g. a Gag-Cas9 fusion protein) and (iv) the one or more CRISPR-Cas guide RNAs. According to these embodiments, the one or more guide RNAs are incorporated within the virus-derived particles while these are produced by the packaging cells. In these embodiments wherein the virus-derived particles comprise a Cas protein, especially a Cas9 protein, and one or more guide RNA(s), the said virus-derived particles comprise CRISPR-Cas ribonucleoprotein complexes which are complexes of the Cas protein with a guide RNA.

According to some of these embodiments, the said virus-derived particles comprise one or more kinds of complexes of a Cas protein and a guide RNA, wherein each CRISPR-Cas complex comprise a single Cas protein complexed with a single guide RNA. In some of these embodiments wherein a plurality of cleavages of a target nucleic acid is sought, the said virus-derived particles comprise the same number of kinds of CRISPR-Cas complexes, each kind of CRIPSR-Cas complex being specific for generating a DNA cleavage at a desired location of a target nucleic acid to which the corresponding guide RNA hybridize.

In further preferred embodiments, the one or more guide RNAs are initially produced by specific packaging cells expressing the said one or more guide RNAs and also expressing the viral protein(s) which are required for producing other viral particles or other viral vesicles (or other Virus-Like Particles or VLPs). Then, the guide RNA(s)-containing viral particles are brought into contact with a virus-derived particle comprising a Cas protein, so as to generate, by complementation, the final virus-derived particles comprising both a Cas protein and the one or more guide RNAs that were initially contained in the said other viral particles. for obtaining these virus-derived particles by complementation, the one skilled in the art may notably refer to Abe et al. (1998, Journal of Virology, Vol. 72(no 8): 6356-6361). Illustratively, Gag-based Virus-derived particles comprising a Cas protein which are described herein may be brought into contact with VSV-G-based viral particles comprising one or more CRSIPS-Cas guide RNAs, so as to obtain final virus-derived particles comprising the said Cas protein and the said one or more CRISPR-Cas guide RNAs and wherein the said final virus-derived particles consist of VSV-G pseudotyped Gag-based VLPs.

In some other embodiments part of all of the said one or more guide RNAs are not comprised inside the virus-derived particles but are instead complexed with these virus-derived particles. According to these other embodiments, the guide RNAs which are complexed with the virus-derived particles also enter into the target cells with the virus-derived particles to which these guide RNAs are complexed.

Targeting Nucleic Acids

For the purpose of altering a target nucleic acid by using virus-derived particles as described herein, especially when an alteration of the target nucleic acid by homologous recombination is sought, it is further made use of a targeting nucleic acid in combination with these virus-derived particles.

Methods for targeting nucleic acids for the purpose of altering their sequence by homologous recombination are well known from the one skilled in the art. Typically, a homologous repair donor nucleic acid comprises (i) a first sequence that is homologous to a first locus of the targeted genomic sequence and (ii) a second sequence that is homologous to a second locus of the genomic sequence. Generally, for the purpose of altering a target nucleic acid by homologous recombination, the said first sequence (i) and the said second sequence (ii) are located at each side of the cleavage site created by the CRISPR-Cas/guide RNA(s) complex.

Methods for performing alterations in a target nucleic acid through homologous recombination by using a CRISPR-Cas system are well known in the art. The one skilled in the art may notably refer to Jinek et al. (2013, eLife, Vol. 2: e00471, doi: 10.754/eLife.00471) and Lin et al. (2014, eLife, Vol. 3: e04766, DOI:10.7554/eLife.04766).

Typically, an Homologous Recombination template nucleic acid, which may also be termed a template nucleic acid herein, comprises an exogenous sequence of variable length, flanked at its 5' and 3' ends, respectively, by sequences that hybridizes to the target nucleic acid. If the exogenous sequence that will be inserted in the genome is below 50 nt long, the flanking hybridizing sequences, also called homology recombination arms, should range from 20 to 50 nucleotides in length. If the exogenous sequence to insert is longer than 100 nt, the homology recombination arms should be considerably longer (around 800 bp).

The targeting nucleic acid, or template nucleic acid, may have any suitable length, such as about 10, 15, 20, 25, 50, 75, 100, 150, 200, 500, 1000 or more nucleotides in length. When optimally aligned, a targeting nucleic acid might overlap with one or more nucleotides of a target sequence, e.g. about or more than about 1, 5, 10, 15, 20 or more nucleotides.

Based on the general knowledge from the one skilled in the art, practically the sole requirement for designing a targeting nucleic acid for the purpose of homologous recombination is the prior knowledge of the nucleic sequence of the target nucleic acid.

In some embodiments, a targeting nucleic acid is comprised inside a virus-derived particle as described herein. According to these embodiments, the virus-derived particle comprising a Cas protein, one or more guide RNAs and one or more targeting nucleic acids are preferably produced by packaging cells that express the said Cas protein, the required viral proteins, the required guide RNAs and the requited targeting nucleic acid(s).

In some other embodiments, a targeting nucleic acid is not comprised inside the virus-derived particle but is complexed to the virus-derived particles.

Nucleic Acid Expression Vectors

As already stated elsewhere in the present specification, a virus-derived particle as described herein is produced in cells, also named packaging cells herein, which express the required proteins, i.e. at least a fusion viral structural protein/Cas protein and one or more viral proteins required for forming the viral particles, which may also be termed Virus-Like Particles or VLPs. In preferred embodiments, the packaging cells also express one or more CRISPR-Cas guide RNAs and, when necessary, also a targeting nucleic acid (also termed template nucleic acid).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in eukaryotic cells generally comprise promoters, enhancers, and termination and polyadenylation signals. In some embodiments, "expression vectors" are used in order to permit pseudotyping of the viral envelope proteins.

Generally, vectors for expressing the required proteins or nucleic acids are vector suitable for expressing nucleic sequences within the desired host cells that are used as packaging cells. Preferably, the packaging cells are mammalian cells. Notably, vectors for expressing the required proteins or nucleic acids comprise an open reading frame which is placed under the control of regulatory elements that are functional in the packaging cell wherein their expression is sought. Notably, these vectors comprise, for each protein or nucleic acid to be expressed, an open reading frame which is placed under the control of a suitable promoter sequence, as well as a polyadenylation sequence.

The packaging cell line provides the viral proteins required for particle assembly (Markowitz et al., 1988, J. Virol., Vol. 62:1120).

As it is well known in the art, a nucleic acid vector is introduced into the packaging cell by any of a variety of techniques (e.g., calcium phosphate co-precipitation, lipofection, electroporation). The viral proteins produced by the packaging cell mediate the insertion of the viral protein(s) and of the Cas protein into virus-derived particles, which are then released into the culture supernatant.

The nucleic acid vectors used may be derived from a retrovirus (e.g., a lentivirus). Retrovirus vectors suitable for producing the virus-derived particles described herein allow (1) transfection of the packaging vectors and envelope vectors into the host cell to form a packaging cell line that produces the virus-derived particles essentially free from packaging vector RNA, and (2) the packaging of the Cas protein and optionally also of the CRISPR guide RNA(s) and eventually of a targeting nucleic acid into the virus-derived particles.

Vectors and packaging cells for use according to the present invention are illustrated in the examples herein.

Illustratively, a vector for expressing the viral structural protein/Cas protein, e.g. a Gag-Cas9 protein, may be prepared by the one skilled in the art as taught by Voelkel et al. (2010, Proc Natl Acad Sci USA, Vol. 107: 7805-7810).

Illustratively, a vector for expressing the viral structural protein, e.g. a Gag protein or a Gag-Pro-Pol fusion protein, and optionally also a viral envelope protein, e.g. a VSV-G protein or a BAEV-G protein, may be prepared by the one skilled in the art according to the teachings of Negre et al. (2000, Gene Ther, Vol. 7: 1613-1623) and of Yee et al. (1994, Methods Cell Biol, Vol. 43 PtA: 99-112).

Illustratively, a vector for expressing a CRISPR guide RNA may be prepared as taught by Kieusseian et al. (2006, Blood, Vol. 107: 492-500).

Packaging Cells

The host cell is a cell into which a vector of interest may be introduced and wherein it may be replicated, and, in the case of an expression vector, in which one or more vector-based genes may be expressed.

Any suitable permissive or packaging cell known in the art may be employed in the production of the virus-derived particles described herein. Mammalian cells or insect cells are preferred. Examples of cells useful for the production of the virus-derived particles in the practice of the invention include, for example, human cell lines, such as VERO, WI38, MRC5, A549, HEK293, HEK293T, B-50 or any other HeLa cells, HepG2, Saos-2, HuH7, and HT1080 cell lines.

Illustrative cell lines for use as packaging cells are insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred insect cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93 (2000); and Samulski et al., U.S. Pat. No. 6,204,059.

The cells may be supplied with any one or more of the stated functions already incorporated, e.g., a cell line with one or more vector functions incorporated extra-chromosomally or integrated into the cell's chromosomal DNA, a cell line with one or more packaging functions incorporated extra-chromosomally or integrated into the cell's chromosomal DNA, or a cell line with helper functions incorporated extra-chromosomally or integrated into the cell's chromosomal DNA. A packaging cell line is a suitable host cell transfected by one or more nucleic acid vectors that, under achievable conditions, produces virus-derived particles comprising a Cas protein and, in some embodiments, also one or more CRIPSR guide RNA(s) and eventually also a targeting nucleic acid.

As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi+ sequence (designated as A-psi), and a 5'-LTR-env-3'-LTR fragment that is also A-psi located at another chromosomal site.

A number of cell types can be used, which encompasses:
a) NIH-3T3 murine cells which are currently widely used as packaging cells producing recombinant retroviruses in clinical use (Takahara et al., Journal of Virology, (June 1992), 66 (6) 3725-32).
b) TK⁻ cell lines have already been described, including NIH-3T3 TK cells (F. Wagner et al., EMBO Journal (1985), Vol. 4 (no 3): 663-666); these cells can be killed when they are cultivated in selective culture media such as HAT. If they are complemented for the kinase thymidine function, for example those from the HSV1-TK virus, they can grow in a selective medium; such lines thus offer the possibility of using the HSV1-TK gene as a selection gene. The gene coding for the thymidine kinase of HSV1 or one of its functional derivatives is also widely used as a transgene as a pro-drug transforming ganciclovir or acyclovir into a drug which is cytotoxic for the cell, and it can thus be applied to selective cell destruction, for example of cancerous cells (see, for example, International patent application WO 95/22617).

Illustratively, the packaging cells may be the well-known HEK293T cell line, as shown in the examples herein.

The present invention also relates to a cell line for producing a virus-derived particle as described herein, comprising:
one or more nucleic acids encoding the proteins required for forming the said virus-derived particle, and
a nucleic acid comprising an expression cassette encoding a viral structural protein-Cas fusion protein.

In some embodiments, a nucleic acid encoding a protein required for forming the said virus-derived particle encompasses a nucleic acid encoding a viral structural protein, such as a Gag protein.

In some embodiments, the said cell line also comprises a nucleic acid encoding a viral envelope protein, such as a viral envelope protein selected in a group comprising a VSV-G protein and a BAEV-G protein.

In some embodiments, the said cell line further comprises nucleic acid(s) encoding one or more CRISPR guide RNA(s).

In some embodiments, the said cell line further comprises nucleic acid(s) encoding one or more targeting nucleic acid(s).

Compositions and Kits

The present invention provides virus-derived particles compositions and kits suitable for use in therapy (in vivo or ex vivo) that are described herein.

In some embodiments, the said compositions comprise virus-derived particles comprising a Cas protein, especially a Cas9 protein, and is devoid of a guide RNA and of a targeting nucleic acid. In these embodiments, the gRNA(s) or the targeting nucleic acid are absent from the virus-derived particles, either as nucleic acids located inside the said virus-derived particles or as nucleic acids complexed with the said virus-derived particles.

The present invention relates to a composition for altering a target nucleic acid in a eukaryotic cell, which composition comprises at least one virus-derived particle as described in the present specification.

In some embodiments, the said composition further comprises one or more CRISPR-Cas system guide RNA(s).

In some of these embodiments, the said one or more CRISPR-Cas system guide RNA(s) is(are) comprised in virus-derived particles.

In some other embodiments, the said one or more CRISPR-Cas system guide RNA(s) is(are) complexed with the said virus-derived particles.

In some embodiments of the compositions, the said compositions comprise (i) Cas-containing virus-derived particles in combination with (ii) vesicles comprising gRNA(s) and/or targeting nucleic acid(s). According to some of these embodiments, each gRNA present in the composition is comprised in a specific kind vesicles. According to some other of these embodiments, more than one gRNA, which includes all gRNA(s), are comprised in a specific kind of vesicles. In some of these embodiments, a targeting nucleic acid is comprised in a specific kind of vesicles. In some other of these embodiments, when more than one targeting nucleic acid is present in the composition, all the targeting nucleic acids are all comprised in a specific kind of vesicles. In still further embodiments, the whole gRNA(s) and targeting nucleic acid(s) present in the composition are all comprised in the same vesicles.

A "specific kind" of vesicle, as used herein is defined uniquely as regards its specific content in gRNA(s) and/or targeting nucleic acid(s), irrespective of the structural features of the vesicle itself.

Most preferably, the said vesicles are comprised of viral proteins. In some embodiments, the said vesicles have the same structural features of viral proteins as the virus-derived particles containing a Cas protein that are described in the present specification. In some other embodiments, the said vesicles are mainly or fully composed of viral envelope proteins, such as, for example, VSV-G or BAEV-G.

When present in a composition according to the invention, the Cas-containing virus-derived particles and the gRNA(s)—and/or targeting nucleic acid—containing vesicles trans-complement so as to efficiently generate the desired nucleic acid alteration(s) in the target cells. Such a trans-complementation in another technical context is taught by Mangeot et al. (2011, Ther J am Soc Gene Ther, Vol. 19: 1656-1666).

Compositions as described herein encompass pharmaceutical compositions that are used for the purpose of performing a method of gene therapy in mammals in need thereof, which includes non-human mammals and human individuals in need thereof.

Compositions of the invention may be formulated for delivery to animals for veterinary purposes (e.g., livestock such as cattle, pigs, etc), and other non-human mammalian subjects, as well as to human subjects. The virus-derived particles may be formulated with a physiologically acceptable carrier for use in gene transfer and gene therapy applications.

In some embodiments, the said composition further comprises one or more transduction helper compounds. The transduction helper compounds are preferably selected in a group comprising cationic polymers, as described notably by Zuris et al. (2015, Nat Biotechnol, Vol. 33(no 1): 73-80). The transduction helper compound may be selected in a group comprising polybrene (that may be also termed hexadimethrine bromide), protamine sulfate, 12-myristate 13-acetate (also termed phorbol myristate acetate or PMA, as described by Johnston et al., 2014, Gene Ther, Vol. 21(12): 1008-1020), vectofusin (as described by Fenard et al., 2013, Molecular Therapy Nucleic Acids, Vol. 2: e90), poloxamer P338 (as described by Anastasov et al., 2016, Lentiviral vectors and exosomes as gene and protein delivery tools, in Methods in Molecular Biology, Vol. 1448: 49-61), RetroNectin® Reagent (commercialized by Clontech Laboratories Inc.), Viral Plus® transduction enhancer (commercialized by Applied Biological Materials Inc.), TransPlus® Virus Transduction Enhancer (commercialized by Cliniosciences), Lentiboost® (commercialized by Sirion Biotech), or ExpressMag® Transduction System (commercialized by Sigma-Aldrich). As shown in the examples herein, the said cationic transduction helper compound may consist of polybrene.

The virus-derived particles may be formulated in a conventional manner using one or more physiologically acceptable carriers or excipients. The virus-derived particles may be formulated for parenteral administration by injection, e.g., by bolus injection or continuous infusion. Formulations for injection may be presented in unit dosage form, e.g., in ampoules or in multi-dose containers, with an added preservative. The virus-derived particles compositions may take such forms as suspensions, solutions or emulsions in oily or aqueous vehicles, and may contain formulation agents such as suspending, stabilizing and/or dispersing agents. Liquid preparations of the virus-derived particles compositions may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts. Alternatively, the compositions may be in powder form for constitution with a suitable vehicle, e.g., sterile pyrogen-free water, before use.

The virus-derived particles compositions of the invention may be administered to a subject at therapeutically effective doses to generate the desired genome alteration in a target nucleic acid contained in a target cell, in a target tissue or organ or in a target organism, particularly a target mammal, which encompasses a target non-human mammal and a human individual. A therapeutically effective dose refers to an amount of the pharmaceutical composition sufficient to result in amelioration of symptoms caused by the occurrence of the desired genome alteration event in the target nucleic acid.

In an embodiment, an amount of virus-derived particles composition of the invention is administered at a dose unit that is in the range of about 0.1-5 micrograms (μg)/kilogram (kg). To this end, a virus-derived particles composition of the invention may be formulated in doses in the range of about 7 mg to about 350 mg to treat to treat an average subject of 70 kg in body weight. The amount of virus-derived particles composition of the invention that may be administered may be selected in a group comprising 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg or 5.0 mg/kg. The dose of virus-derived particles in a unit dosage of the composition may be selected in a group comprising 7 mg, 8 mg, 9 mg, 10 mg, 20 mg, 25 mg, 30 mg, 35 mg, 40 mg, 45 mg, 50 mg, 55 mg, 60 mg, 65 mg, 70 mg, 75 mg, 80 mg, 85 mg 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg, especially for treating an average subject of 70 kg in body weight. These doses can be given once or repeatedly, such as daily, every other day, weekly, biweekly, or monthly. In some embodiments, a virus-derived particles composition may be administered to a subject in one dose, or in two doses, or in three doses, or in four doses, or in five doses, or in six doses or more. The interval between dosages may be determined based the practitioner's determination that there is a need thereof.

The virus-derived particles compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

A virus-derived particles composition may be in liquid or solid (e.g. lyophilized) form.

Kits

The present invention further relates to kits for preparing the virus-derived particles described in the present specification.

This invention concerns a kit for preparing virus-derived particles for altering a target nucleic acid in a eukaryotic cell comprising:
- a nucleic acid comprising an expression cassette encoding a GAG-Cas fusion protein, and
- a nucleic acid comprising one or more expression cassette(s) encoding virus-like assembly protein(s), In some embodiments, the said kit further comprises a nucleic acid comprising an expression cassette encoding a pseudotyping viral envelope protein.

In some embodiments of the said kit, the virus-derived assembly protein is a virus-derived Gag protein.

In some embodiments, the said Gag protein is encoded by an expression cassette selected in a group comprising an expression cassette encoding a GAG-PRO-POL polyprotein and an expression cassette encoding a GAG protein.

In some embodiments, the said kit further comprises one or more nucleic acid(s) encoding a CRISPR-Cas system guide RNA In certain embodiments of the said kit, the said nucleic acids are localized in an eukaryotic cell as a result of its transfection into the said eukaryotic cell. In some of these embodiments, the said nucleic acids are under the form of nucleic acid vectors in the said eukaryotic cells, which cells may also be termed packaging cells herein. In some other of these embodiments, part or all of these nucleic acids are integrated in the genome of these eukaryotic cells, which cells may also be termed packaging cells herein.

Thus, in some embodiments of a kit according to the invention, the said eukaryotic cell consists of a packaging cell line.

The kits of the present invention may optionally comprise different containers (e.g., vial, ampoule, test tube, flask or bottle) for each individual composition or element comprised therein. The kit may contain additional reagents, such as buffers, diluents and the like, for formulation the individual components. Each component will generally be suitable as aliquoted in its respective container or provided in a concentrated form.

Instructions for using the kit according to the methods described herein may be included. The instructional material may comprise a publication, a recording, a diagram, or any other medium of expression which can be used to communicate the usefulness of the method of the invention in the kit for assessment of oocyte quality. A package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

Methods for Altering a Target Nucleic Acid

The virus-derived particles as well as the compositions comprising them may be used for gene therapy.

A further aspect of the invention is a method of treating subjects with the virus-derived particles according to the invention or with compositions comprising them.

Administration of the virus-derived particles to a human subject or an animal in need thereof can be by any means known in the art for administering virus vectors.

Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

This invention also relates to a method for altering a target nucleic acid comprising at least a target sequence in an eukaryotic cell, comprising the steps of:
a) bringing into contact the said eukaryotic cell with virus-derived particles as described herein, or with a composition as described in the present specification, and
b) collecting the said eukaryotic cell having an altered target nucleic acid.

In some embodiments, the virus-derived particles, or compositions comprising them, are administered directly to the subject, in vivo. In some other embodiments, subject's cells are provided, and then the said cells are transduced in vitro with the virus-derived particles, or with a composition comprising them. In a further method step, the transduced subject's cells are administered back to the body of the subject.

In some embodiments, said method is performed in vitro or ex vivo.

The present invention also relates to a composition as described in the present specification, for its use for preventing or treating any disease or disorder that is amenable to gene therapy.

The present invention provides for methods for preventing or treating any disease or disorder that is amenable to gene therapy. In one embodiment, "treatment" or "treating" refers to an amelioration of a disease or disorder, or at least one discernible symptom thereof. In another embodiment, "treatment" or "treating" refers to an amelioration of at least one measurable physical parameter associated with a disease or disorder, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both. Other conditions, including cancer, immune disorders, and veterinary conditions, may also be treated.

Types of diseases and disorders that can be treated by methods of the present invention include, but are not limited to, age-related macular degeneration; diabetic retinopathy; infectious diseases e.g., HIV pandemic flu, category 1 and 2 agents of biowarfare, or any new emerging viral infection; autoimmune diseases; cancer; multiple myeloma; diabetes; systemic lupus erythematosus (SLE); hepatitis C; multiple sclerosis; Alzheimer's disease; parkinson's disease; amyotrophic lateral sclerosis (ALS), huntington's disease; epilepsy; chronic obstructive pulmonary disease (COPD); joint inflammation, arthritis; myocardial infarction (MI); congestive heart failure (CHF); hemophilia A; or hemophilia B.

Infectious diseases that can be treated or prevented by the methods of the present invention are caused by infectious agents including, but not limited to, viruses, bacteria, fungi, protozoa, helminths, and parasites. The invention is not limited to treating or preventing infectious diseases caused by intracellular pathogens. Many medically relevant microorganisms have been described extensively in the literature, e.g., see C. G. A Thomas, Medical Microbiology, Bailliere Tindall, Great Britain 1983, the entire contents of which are hereby incorporated herein by reference.

Types of cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The present invention is further illustrated, without being in any way limited to, the examples below.

EXAMPLES

A. Materials and Methods
A.1. Constructs

The GAG-Cas9 coding plasmid was designed as described in (Voelkel et al., 2010). The codon-optimized sequence of flag-Cas9 from Streptococcus pyogenes was PCR-amplified using the lentiCRISPR plasmid (Addgene plasmid 4953) as a template. This last construct was a gift from F. Zhang laboratory (Shalem et al., 2014, Science, Vol. 343: 84-87). Flag-Cas9 was next inserted downstream the Murine Leukemia Virus GAG sequence (MA-CA-NC). Frames were harmonized to generate a polyprotein. Both moieties were separated by a MLV-protease cleavage site that releases flag-Cas9 from GAG during the viral maturation process. This chimeric protein was expressed under control of the hCMV promoter and is equipped with an intron and a poly A signal both derived from the rabbit beta-Globin mRNA. The expression plasmid encoding the GagProPol polyprotein of MLV (Negre et al., 2000, Gene Ther, Vol. 7: 1613-1623) and the VSVG coding plasmid (Yee et al., 1994, Methods Cell Biol, Vol. 43 PtA: 99-112) were described elsewhere.

The gRNA coding plasmids termed as «CRIZI»derives from a previously described lentiviral construct (Kieusseian et al., 2006, Blood, Vol. 107: 492-500) in which was inserted the U6 cassette from the lentiCRISPR plasmid. Cloning of CRISPR gRNA sequences in CRIZI was performed between BsmBI sites upstream the U6 promoter following the procedure described by the authors. Sequences of gRNAs used in this study were designed using the Crispseek software (potential off-targets>3 mismatches) (Zhu et al., 2014, PloS One, Vol. 9: e108424). Primer sequences are given for each gRNA:

YFP (SEQ ID NO. 1)
YFPgRNA1f    caccgCGAGGAGCTGTTCACCGGGG (SEQ ID NO. 2)
YFPgRNA1r    aaacCCCCGGTGAACAGCTCCTCGc (SEQ ID NO. 3)
YFPgRNA2f    caccgTCACCATACCGGTAGCCAGC (SEQ ID NO. 4)
YFPgRNA2r    aaacGCTGGCTaccggtATGGTGAc Myd88

(SEQ ID NO. 5)
hMyd88gRNA1fcaccgGAGACCTCAAGGGTAGAGGT (SEQ ID NO. 6)
hMyd88gRNA1raaacACCTCTACCCTTGAGGTCTCc (SEQ ID NO. 7)
hMyd88gRNA2fcaccgGCAGCCATGGCGGGCGGTCC (SEQ ID NO. 8)
hMyd88gRNA2raaacGGACCGCCCGCCATGGCTGCc (SEQ ID NO. 9)
mMyd88gRNA1fcaccggagcgtactggacggcaccg (SEQ ID NO. 10)
mMyd88gRNA1raaaccggtgccgtccagtacgctcc (SEQ ID NO. 11)
mMyd88gRNA2fcaccggcccatctcctccgccagca (SEQ ID NO. 12)
mMyd88gRNA2raaactgctggcggaggagatgggcc

DDX3

(SEQ ID NO. 13)
DDX3gRNA1f    CACCGAGGGATGAGTCATGTGGCAG (SEQ ID NO 14)
DDX3gRNA1r    AAACCTGCCACATGACTCATCCCTC

A.2. Production of VLPs

Cas9-VLP referred as a preparation of VLPs incorporating one of several gRNAs targeting a specific gene. Preparation of VLPs requires a cotransfection of several plasmids. VLPs were produced upon transfection of Lenti-X™ 293T (Clontech) using JetPei (Polyplus) following the manufacturer instructions. The JetPrime transfection agent (Polyplus) or the Calcium phosphate method (CalPhos mammalian kit, Clontech) may be used as well.

Classical ratio of the plasmids mixed in the JetPei transfection recipe are: GAG-Cas9 (20%), GagProPol (20%), VSV-G or other envelope (20%) and gRNAs encoding constructs (40%).

For Cas9Myd88VLPs, two different gRNA were introduced in the recipe to achieve copackaging of both RNA-species in the nascent VLPs. HEK293T cells plated at 3×10e6 cells/10 cm-plate 24 h prior transfection were transfected with a mix containing:

- R1: 4 ug of GAG-Cas9, 4 ug of GagProPol, 2 ug of VSVG, 2 ug of BaEV envelope (Girard-Gagnepain et al., 2014), 2 ug of Myd88-gRNA1 coding plasmid, 2 ug of Myd88-gRNA2 coding plasmid.
- R2: 6 ug of GAG-Cas9, 6 ug of GagProPol, 4 ug of VSVG, 4 ug of Myd88-gRNA1 coding plasmid, 4 ug of Myd88-gRNA2 coding plasmid.
- R3: 4 ug of GAG-Cas9, 8 ug of GagProPol, 2 ug of VSVG, 2 ug of BaEV envelope, 2 ug of Myd88-gRNA1 coding plasmid, 2 ug of Myd88-gRNA2 coding plasmid.
- R4: 4-6 ug of GAG-Cas9, 2 ug of VSVG, 2 ug of BaEV envelope, 5 ug of Myd88-gRNA1 coding plasmid, 5 ug of Myd88-gRNA2 coding plasmid.

40 hours after transfection, VLP-containing supernatants were collected and clarified by a short centrifugation (2000 g, 3 min). Clarified Cas9-YFPVLPs were used directly to transduce L929 cells. Cas9-h-h/mMyd88VLPs and Cas9-DDX3VLPs were pelleted by ultracentrifugation 1 h at 35000 rpm in a SW41-rotor and re-suspended in ice-cold PBS by overnight gentle agitation. 10 ml of supernatant were concentrated to produce 100 ul of concentrated VLPs in ice-cold PBS (concentration fold: 100×). Concentrated VLPs batches were stored at −80° C. and were shown to be stable at least 2 weeks at 4° C. after thawing. Filtration of VLP-containing supernatant can be performed with a 0.45 um-in-size pore filter before centrifugation/transduction.

A.3. ProteoTransduction Procedure Using Cas9-VLPs

3×10e5 L929-YFP cells were transduced with Cas9-YFPVLPs by addition of 400 ul of clarified VLP-containing supernatant in 400 ul of medium in a 6 well plate. After two hours, medium was supplemented with 2 ml of DMEM 10% FCS.

Transduction of primary cells was classically performed in 48-well plates upon addition of 5-20 ul of 100×VLPs in 300 ul of medium. After two hours, this transduction medium was supplemented by 0.5 ml of fresh culture medium. Polybrene addition was shown to potentialize proteotransduction when used at a final concentration of 4 ug/ml in the transduction medium.

A.4. PCR-Based Genotyping Assays

Genomic-DNA extraction of cells treated by VLPs was achieved using the Nucleospin Tissue Kit (Machery Nagel) according to the manufacturer instructions. DNA preparations were performed 24-48 h after VLP-treatment but additional experiments indicate that cleavage was complete in HEK293T recipient cells as soon as 6 h after exposure with VLPs.

PCR amplifications of Myd88 were performed in 50 ul using the GOTAQ polymerase (Promega). 100 ng of cellular genomic DNA was used as a template for a PCR reaction as follow: 94° C. 5 min, 3 cycles (94° C. 30 sec, 68° C. 30 sec), 3 cycles (94° C. 30 sec, 64° C. 30 sec, 72° C., 30 sec), 27 cycles (94° C. 30 sec, 57° C. 30 sec, 72° C. 30 sec), 72° C. 5 min, 12° C. PCR amplicons were analysed in Ethidium Bromide stained 2.5% agarose gels.

A.5. Primers used for genotyping analysis (5'-NNN-3'):

YFP (surveyor assay)

|  |  |
|---|---|
| | (SEQ ID NO. 15) |
| YFPf | tcTAATACGACTCACTATAGGGAGAGGTCTATATAAGCAGAGCTCGTTTAG |

A.5. Primers used for genotyping analysis (5'-NNN-3'):

|  |  |
|---|---|
| | (SEQ ID NO. 16) |
| YFPr | GGCCATGATATAGACGTTGTGGCTG |

Myd88

|  |  |
|---|---|
| | (SEQ ID NO. 17) |
| hMyd88f2 | TTACGCCCCCCACATCACCCGCC |
| | (SEQ ID NO. 18) |
| hMyd88r1 | GTCTCCAGTTGCCGGATCTCCAAG |
| | (SEQ ID NO. 19) |
| mMyd88f2 | ggaaactccacaggcgagcgtac |
| | (SEQ ID NO. 20) |
| mMyd88r2 | ggcagtcctcctcgatgcgcgacttc |

A.6. Combination of Cas9-DDX3VLPs with ssDNA 15 ul of concentrated Cas9-DDX3VLPs were mixed in 10 ul of PBS containing 8 ug/ml of polybrene. This mixture was next supplemented with 5 ul of each dilutions of the Flag-DDX3 primer, best results being obtained with the higher concentration (5 ul of primer at 100 µmol/ul). This 'all in one' complex was incubated 15 min at 4° C. and the 30 ul were added in the medium (400 ul+polybrene 4 ug/ml) of HEK293T cultivated in a 12-well-plate (200000 cells plated the day before). After two hours, the transduction medium was supplemented with 1ml of DMEM 10% FCS. 40 hours after VLP-treatment, cells were splitted for amplification and analysis of the genetic insertion of the flag sequence upstream the DDX3 gene and WB analysis were performed 72 hours latter.

A.7. Sequence of the Flag-DDX primer (HPLC -purified):

(SEQ ID NO. 21)
5'-ACTCGCTTAGCAGCGGAAGACTCCGAGTTCTCGGTACTCTTCAGGGA

TGGACTACAAGGACGACGATGACAAGAGTCATGTGGCAGTGGAAAATGCG

CTCGGGCTGGACCAGCAGGTGA-3'

Example 1: Cleavage of the YFP Gene by Cas9-YFPVLPs

Molecular engineering of viral structures allows the generation of viruses/VLPs that can incorporate a protein of interest. Amongst numerous examples can be cited the design of an HIV-1 clone incorporating a fluorescent gene allowing an easy monitoring of infection (Dale et al., 2011, Methods San Diego Calif., Vol. 53: 20-26), VLPs harboring viral epitopes useful for vaccination purposes in animal (Garrone et al., 2011, Sci Transl Med, Vol. 3: 94ra71), or VLPs used to deliver their proteic functional cargo in recipient cells (Voelkel et al., 2010, Proc Natl Acad Sci USA, Vol. 107: 7805-7810), (Mangeot et al., 2011, Mol Ther J Am Soc Gene Ther, Vol. 19: 1656-1666). To achieve the production of efficient Cas9-VLPs, Cas9 was fused to the structural GAG protein of murine Leukemia Virus (MLV) as previously described (Voelkel et al., 2010, Supra). Basically, expression of this chimeric protein with a viral protease (Pro) and an envelope in HEK293T cells is expected to produce VLPs incorporating a Cas9 moiety in their viral core, Cas9 being cleaved from the GAG platform by the viral protease.

Figure 1A:
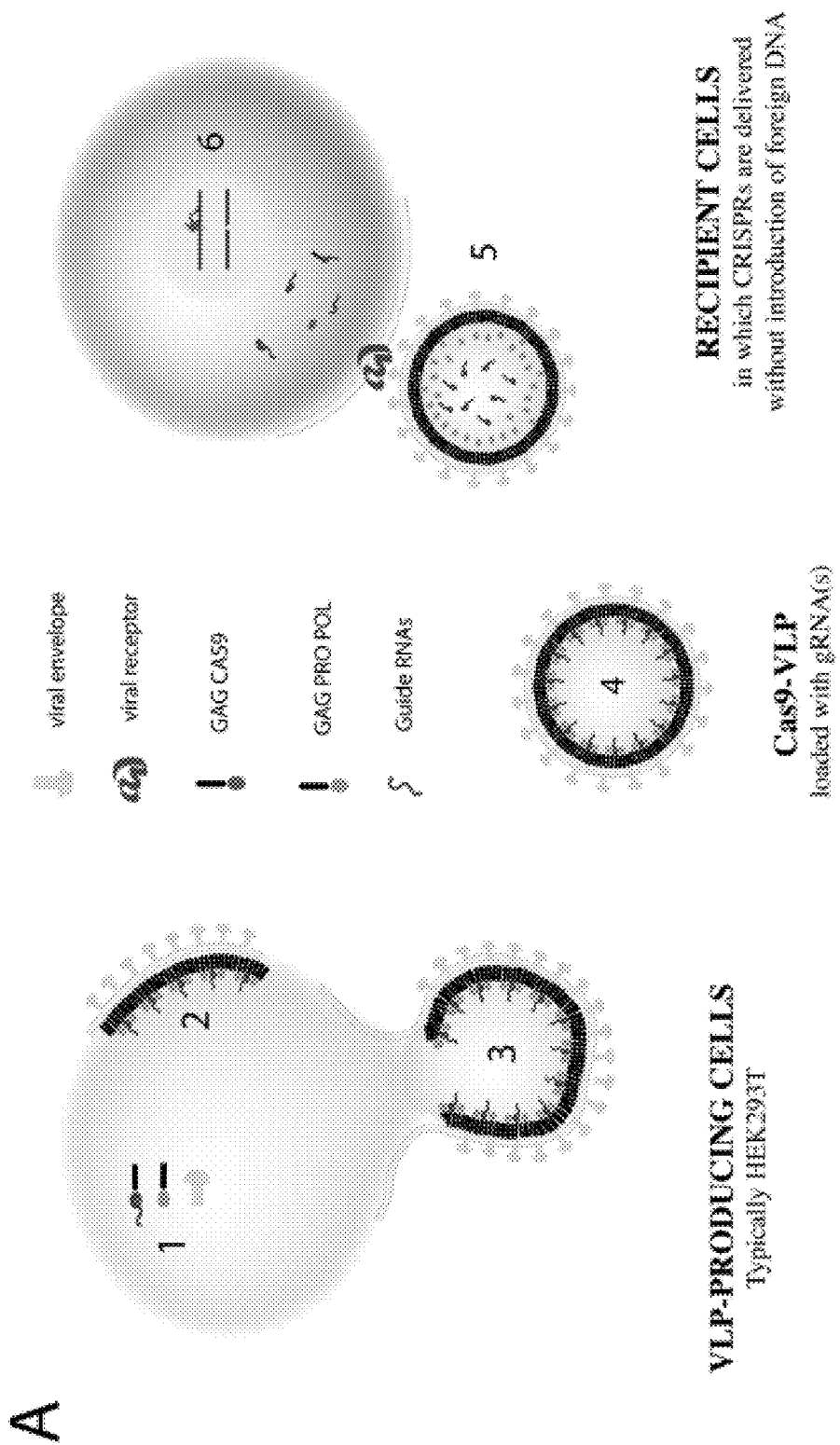
FIG. 1: Molecular Basis of Cas9-VLP assembly and transfer of CRISPRs-components into recipient cells.
Figure 1B:
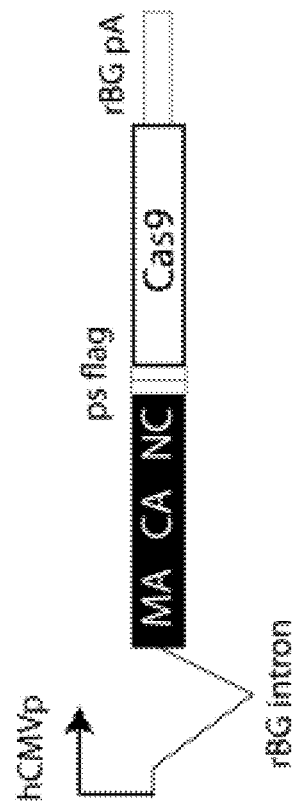

Considering the affinity of Cas9 for gRNAs, we further assumed that expression of gRNAs in VLP-producing cells could be sufficient to allow their incorporation within particles which then would be able to vehicle all the components of the CRISPR machinery. To check these hypothesis, we designed gRNAs expressing plasmids to target the YFP gene and attempted to incorporate the gRNAs into Cas9-VLPs produced from HEK293T cells. A schema recapitulating this approach and the constructs used is depicted in FIG. 1. VLP-containing supernatants were next introduced in the medium of murine L929 cells expressing a stable version of YFP and cleavage of the fluorescent gene was next investigated by a surveyor assay. Results shown in FIG. 2 indicates that Cas9-VLPs delivered the CRISPR machinery and allowed the cleavage of the YFP gene at the expected position defined by the incorporated gRNA. This disruption of the gene was associated with a dramatic and irreversible loss of fluorescence in the treated population resulting from the expected rupture of the YFP-reading frame (FIG. 3). These observations validated the use of Cas9-VLPs as a potent delivery agent of the CRISPR components.

Example 2: Disruption of the Myd88 Gene in HEK293T and Hela Recipient Cells

We further explored the capacity of VLPs to incorporate several gRNAs in order to mediate the deletion of the hMyd88 gene. Myd88 is a crucial adapter protein transmitting the signal of most TLRs to activate the transcription of nuclear factors and is notably implicated in the survival of macrophages in certain conditions (Lombardo et al., 2007, J Immunol Baltim Md. 1950, Vol. 178: 3731-3739). Two gRNAs were designed to mediate two distinct cleavages in the human Myd88 gene resulting in a deletion of the endogenous gene (FIG. 4A-B). Cas9-Myd88VLPs were produced upon transfection of different combinations of plasmids (described in Material and method). Released particles were next concentrated and used to alter the Myd88 gene in different recipient cells including Hela and HEK293T. Results shown FIGS. 4 C and D indicate that all Cas9-VLPs types loaded with Myd88 gRNAs were efficient in deleting the expected portion of the Myd88 gene in HEK293T cells. However, Hela cells seemed more reluctant and were poorly modified by particular VLP species. Notably, we noted that VLPs devoid of protease (R4) were inefficient in Hela cells while remaining fully active in HEK293T target cells. These data suggest that the VLP recipe should be optimized for each targeted cell type. Additional experiments show that the effect of Cas9-Myd88VLPs was dose dependent (FIG. 5) and is potentiated by polybrene addition (FIG. 6).

Figure 7A:
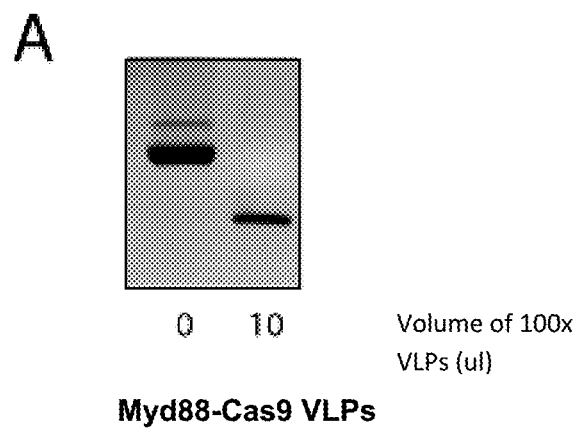
Figure 7B:
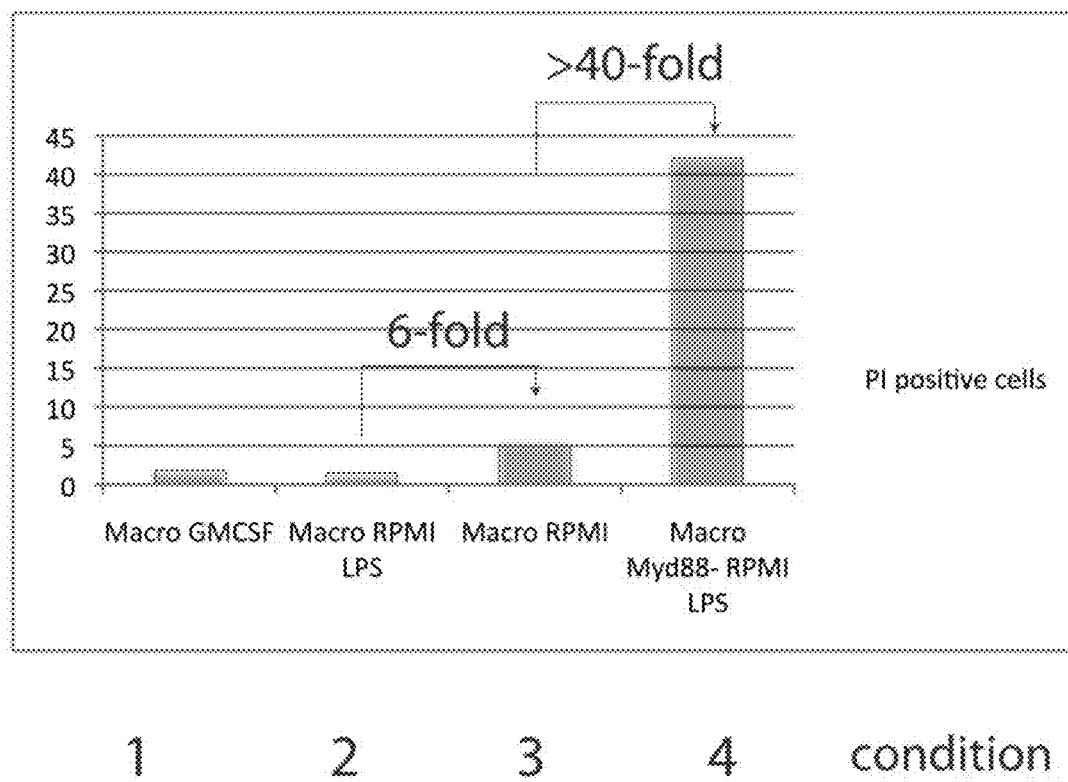

Example 3: VLP-Mediated Disruption of the Myd88 Gene in Primary Cells of Human and Murine Origin A more challenging issue is to deliver CRISPRs components into primary cells which are hardly permissive to conventional methods of transfection and may be difficult to transduce by viral vectors. Efficacy of Cas9-Myd88VLPs was thus monitored in different cell types freshly isolated from living organisms including human macrophages derived from human monocytes. Genotype analyses of treated cells reveals an obvious and very efficient cleavage of the Myd88 gene by a single administration of Cas9-Myd88VLPs in cultured macrophages (FIG. 7A). Beyond the genotype PCR-based assay which ascertains the cleavage of the gene, Myd88 disruption was responsible for a strong phenotype as revealed in FIG. 7B, confirming the inactivation of the Myd88 function. The amazing efficiency of VLPs to deliver CRISPRs in primary cells was further verified in human non activated-lymphocytes typically reluctant to most existing gene-modification techniques (FIG. 8). To generalize our observations, we designed another couple of gRNAs targeting the murine Myd88 gene and prepared a VLP batch dedicated to murine cells. This new VLP batch was used to deliver the CRISPRs RNPc in macrophages of murine origin with a high efficacy as indicated in FIG. 9. Altogether these results validate Cas9-VLPs as efficient agents to introduce the functional CRISPRs machinery in primary cells.

Figure 10A:
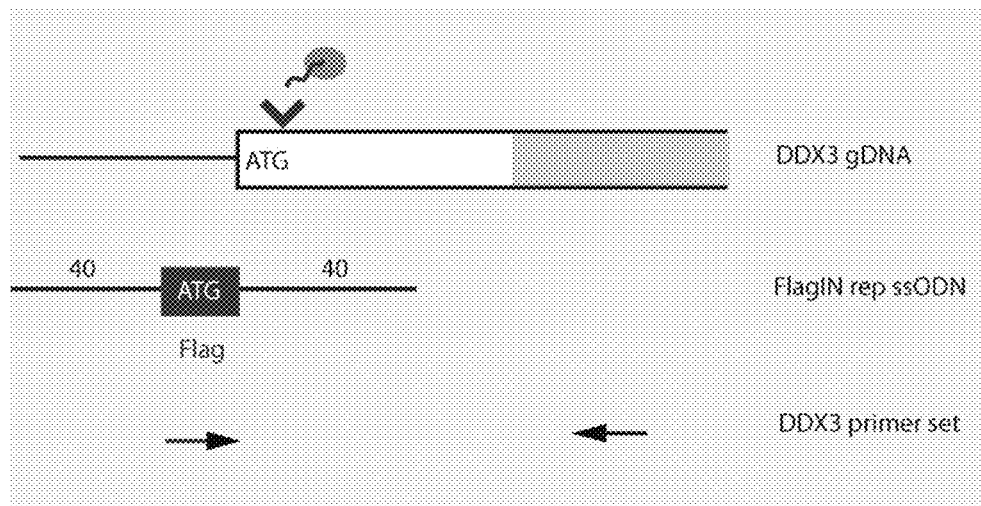
Figure 10B:
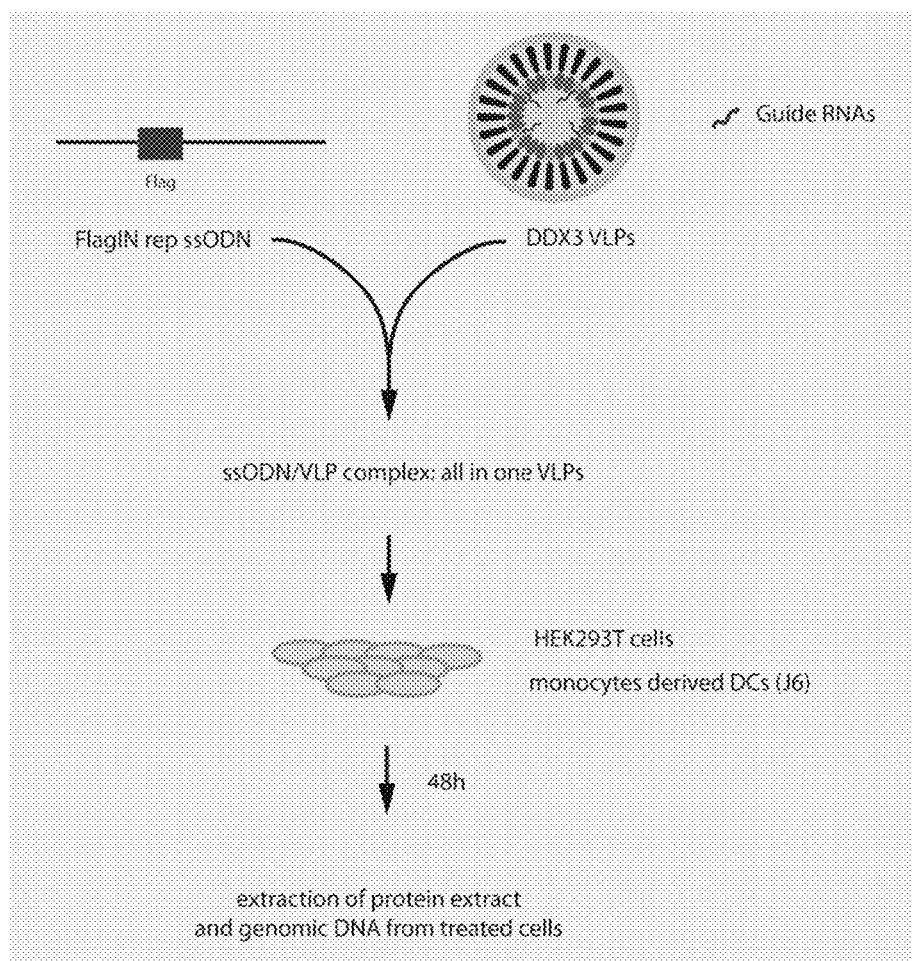
Figure 10C:
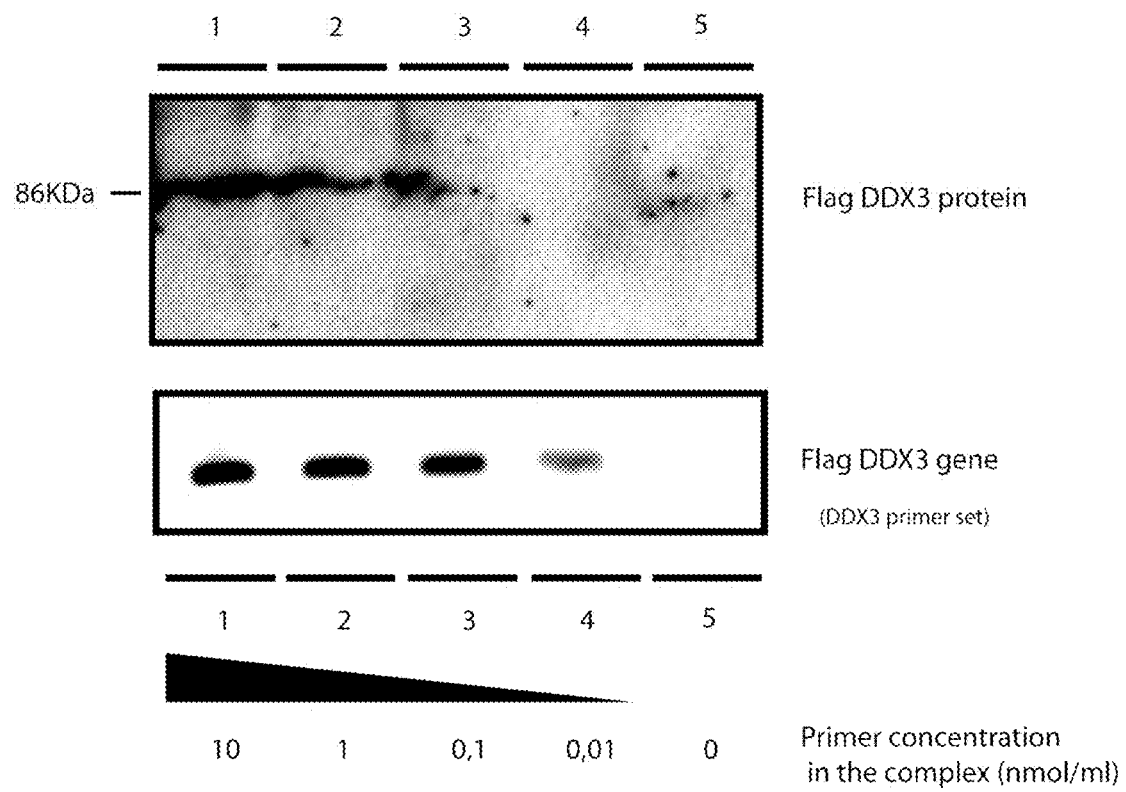
Figure 10D:
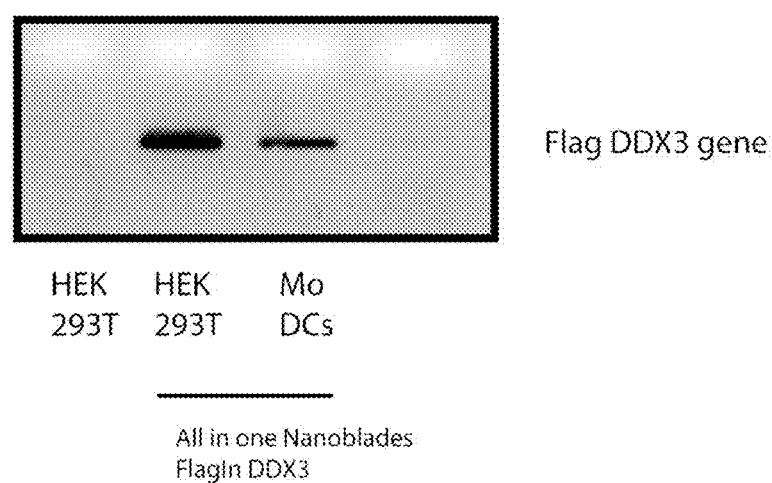

Example 4: Cas9-VLP can Mediate the Transfer of a Reparation Template: Generation of 'all in One' VLPs Complexes Previous works related the ability of MLV-derived VLPs and other VSV-G-induced particles to mediate the delivery of plasmids into human cells and to serve as viral-derived transfection agent. (Okimoto et al., 2001, Mol Ther J Am Soc Gene Ther, Vol. 4: 232-238). Since particles can be combined with dsDNA molecules, we reasoned that MLV-derived Cas9-VLPs could support a combination with ssDNA and mediate their delivery into cells. We took advantage of this knowledge and tried to combine Cas9-VLPs with a reparation primer composed of ssDNA. By this approach we propose to use VLPs to cleave an endogenous gene and to have it repaired in the cell by a homologous recombination-like mechanism (HR) using the provided reparation template. This was investigated using the DDX3 human gene as a model and a reparation primer designed to insert the FLAG sequence upstream of the ATG codon of the endogenous DDX3 gene. FIG. 10 depicts the principle of this 'All in one' VLP strategy that we have directly investigated both in transformed cells and primary cells. Cas9-DDX3VLPs combined with the Flag reparation primer successfully cleaved the DDX3 gene (not shown) and allowed the genetic targeted insertion of the flag sequence at the correct predicted site in the 5'-sequence of DDX3. This was checked by a PCR-based genotyping assay and the detection of the flagged DDX3 protein by Western Blot (FIG. 10C). This result was also verified at the genetic level in primary human dendritic cells exposed to a single treatment of Cas9-DDX3VLPs.

Example 5: Characterization of CAS9 Virus-Derived Particles

CAS9 VLPS were produced as disclosed in the Materials and Methods section and concentrated by a first Ultracentrifugation on a 20% sucrose cushion. Resulting pellet was next resuspended in PBS and recentrifuged on two sucrose cushions: a 50% sucrose cushion at the bottom of the tube and a 20%-sucrose cushion separating the 50% cushion from the sample. After 2 h of centrifugation the interface separating the 50% and the 20% was harvested and recentrifuged to obtain highly pure CAS9-VLPs resuspended in PBS. 10 ug of VLPs were lysed in Laemlli buffer and heat at 95° C. during 5 min before western blot analysis.

Western blot analysis is represented in FIG. 12A (Mug per lane). Antibodies used were directed against GAGmlv (ABCAM R187), against VSVG (ABCAM P5D4), against CAS9 (7A9-3A3 clone Cell SIgnaling), against the Flag sequence engrafted on Cas9 (Sigma). Different forms of mlv GAG are revealed, corresponding to the cleaved products processed by the viral Protease. VSVG is clearly detected in the particle preparation at its expected size. CAS9 antibody reveals a higher product above 200 KDa which corresponds to the GAG-CAS9 fusion (225 KDA expected), a protein that is also detected by the Flag antibody (left panel). Both CAS9 and FLAG antibodies reveals smaller CAS9 products (ranging from 160 to 200 KDa) that might corresponds to the free CAS9 protein or cleaved CAS9 products, released from GAG after protease processing.

As it is illustrated in FIG. 12B, 30 ug of total highly pure VLPs were loaded on a discontinuous sucrose gradient (10%-60% sucrose in PBS) in a total volume of 12 ml. After 16 h of centrifugation (25000 rpm SW41), 500 ul fractions were collected from the top of the tube and named 1-24. 2 ul of each fraction were next spotted onto a nitrocellulose membrane immediately blocked by milk addition (TBST 5% low-fat Milk). Similar antibodies described above were next used to detect VSVG CAS9 and GAG MLV for each fractions. Results indicate that CAS9 VLPs sedimented at a density between 1.14 and 1.21 with a peak at 1.17.

Example 6: Loading of Guide RNAs in the CAS9 Virus-Derived Particles

Example 6 shows that the CAS9 virus-derived particles efficiently integrate guide RNAs. Northern blot directed against the conserved region of the guideRNA using total RNA extracted from producer cells (lanes 2 to 4) or the corresponding purified VLPs (lanes 5 to 7). Lane 1. Control sample corresponding to total RNA of cells that do not produce VLPs. Lane 2. Total RNA from cells expressing the Gag/Cas9 fusion, viral envelope and guideRNA. Lane 3. Total RNA from cells expressing the Gag/Cas9 fusion, viral envelope and a modified guideRNA with a longer stem structure. Lane 4. Total RNA from cells expressing wild-type Cas9 and the guideRNA in absence of Gag. Lanes 5, 6 and 7. Total RNA extracted from the supernatant of the corresponding producer cells (Lane 5 corresponds to the supernatant of cells from lane 2 and so on) after clearing cellular debris and filtrating on a 0.8 μm filter. Lane 7 shows that when the Gag/Cas9 fusion is not expressed, the guideRNA is not efficiently incorporated within particles. Interestingly, the modified guideRNA with a longer stem structure (lanes 3 and 6) does not appear to be incorporated more efficiently into VLPs than the wild-type guideRNA (lanes 2 and 5).

Example 7: Comparison of MLV-Based Virus-Derived Particles with HIV-Based Virus-Derived Particles FIG. 14A illustrates a schematic representation of the coding cassettes designed for the production of MLV-based VLPs or HIV-1-based VLPs. Both cassettes were incorporated in an eucaryotic expression vector equipped with the early hCMV promoter, the rabbit-Bglobin intron and the rabbit pA signal. Both systems were optimized by exploration and test of diverse proteolytic sites separating the GAG cassette from the Cas9 gene. MLV based VLPs were produced as described in the Materials and Methods section while HIV-1 based VLPs were produced similarly except that an HIV-1 helper construct (construct of SEQ ID NO. 33) encoding GAG POL Tat Rev proteins was transfected instead of the MLV GAG POL plasmid. Production of HIV-1 VLPs follows the same procedure as compared with MLV-based VLPs.

FIG. 14B illustrates the test of concentrated VLPs engineered to incorporate a guide RNA targeting the GFP gene were used to transduce 30000 HEK293T cells expressing GFP. HIV-1 and MLV-based particles were produced with the same loaded gRNA (target sequence: CGAG-GAGCTGTTCACCGGGG—SEQ ID NO. 35). Recipient cells were plated the day before in a 96-w plate. Transduction medium was supplemented with polybrene (4 ug/ml). 72 hours after treatment with 3 increasing doses of each VLP-batch, fluorescence intensities were measured by a Fluorometer (Excitation 488, Emission 535). Fluorescence decrease was evident in VLPs-treated cells as compared with control non-treated cells (C), revealing the cleavage of the GFP gene within recipient cells. Results indicate that HIV-1 based VLPs are efficient in delivering the CRISPR/CAS9 system to a level slightly less efficient than MLV-based VLPs in these recipient cells (1,5-2 fold less efficient).

FIG. 14C illustrates the cleavage of the WASP gene in primary human T cells stimulated with IL7. For this experiment, two guide RNAs targeting the human WASP gene were incorporated within HIV-1 or MLV-based VLPs before treatment of freshly purified T-cells stimulated with IL7. WASP deletion by CRISPR-CAS9 was next measured by PCR in recipient cells 24 hours after treatment. Gel analysis performed using the ImageJ software allowed a quantification of double-cutting efficiencies for MLV-based VLPs (32%) and HIV-1-based VLPs (6%).

Example 8: CRISPR Delivery into Thy1-GFP Mouse Embryos by Cas9-Containing Virus-Derived Particles Cas9 VLPs incorporating a guide RNA targeting the GFP gene were produced and highly purified before injection into the zona pellucida of mouse embryos (stage 1-cell). Heterozygous embryos were all carrying the Thy1-GFP allele responsible for GFP expression in motoneurons. The aim of the study is to evaluate the capacity of VLPs to cleave GFP within embryos and to generate animals altered in their Thy1-GFP cassette after reimplantation of VLP-treated embryos into female mice. Few nanoliters of a preparation (6.5 uM Cas9) were used for two rounds of injections performed without performing the cell membrane as depicted in A. No embryo died upon this injection protocol. After reimplantion we obtained a total of 20 animals (F0). Genomic DNAs from new borns-fingers were extracted and analysed by a T7-endonuclease assay revealing the cleavage of the GFP cassette. As shown in B, 6 animals amongst 20 were positive for the assay (arrow) and 4/9 for the first injection experiment (left panel): animals 5, 7, 8, 12 and animal 40 and 45 (weak) for the second injection. Animals 7 8 and 12 were next crossed with wt-057B6 animals to evaluate the transmission of the cleaved GFP allele to descendants. Roughly half of the F1-descendance was noted to be heterozygous for the Thy1-GFP allele (for all 3 founders) as expected. The state of the Thy1-GFP allele in heterozygous F1 mice was next measured by a T7-endonuclease assay shown in C*.GFP was shown to be altered in all F1 heterozygous descendants of mice 7 and mice 12 and 33% of descendants of mice 8. Sequencing of the Thy1-GFP allele was next performed on the allele of animals #78 #79 #21 and #22 and chromatograms were compared to a sequence obtained for a Thy1-GFP non treated animal TIDE software was used for this purpose and provided histograms describing the nature of indels for each animal and the % of sequence alteration. Results given in D E F and G indicate the % of GFP alteration in F1-mice*. Altogether these date show that Cas9-VLPs can assist animal transgenesis and be used as CRISPR-delivering agents to alter genes into mammal embryos without transfer of genetic material nor harming the egg-cell.

Protocol of T7-Endonuclease Assay:

Mouse genomic DNAs were extracted from mouse fingers using the Nucleospin Tissue Kit (Macherey Nagel). 3 ul of DNA template were next used in a 50 ul-PCR reaction (PCR conditions are: 95° C. 5 min followed by 3 cycles of (95° 30 sec-64° 30 sec-72° 30 sec) and 25 cycles of (95° 30 sec-57° 30 sec-72° 30 sec) followed by 5 min at 72° C. using primers:

Forward: 5'-TCTGAGTGGCAAAGGACCTTAGG (Thy1 primer—SEQ ID NO. 39)

Reverse: 5'-GAAGTCGTGCTGCTTCATGTGGTCGG (GFP primer—SEQ ID NO. 40)

Thy1-GFP Amplicons were next submitted to the T7endonuclease assay (NEB) as described by the manufacturer in a 40 ul reaction tube. (neb.com/protocols/2014/08/11/determining-genome-targeting-efficiency-using-t7-endonuclease-i) Digestions were finally loaded on a 2.5%-agarose gel.

** TIDE software is a free online tool: tide.nki.nl/. Chromatograms sequence (abi files) were uploaded into the software and the TIDE runs performed without modification of default settings. TIDE histograms are given

*** % is never complete due to the fact that the chosen Thy1-GFP line carries several copies of GFP/allele (6 to 10). Results should be reproduced in a mouse line bearing one single constitutive GFP copy per allele, which is under preparation.

---

Other sequences

GAG-Cas9 Amino acid sequence; (SEQ ID NO. 22)

```
MGQAVTTPLSLTLDHWKDVERTAHNLSVEVRKRRWVTFCSAEWPTFNVGWPRDGTFNP
DIITQVKIKVFSPGPHGHPDQVPYIVTWEAIAVDPPPWVRPFVHPKPPLSLPPSAPSLPPEPP
LSTPPQSSLYPALTSPLNTKPRPQVLPDSGGPLIDLLTEDPPPYRDPGPPSPDGNGDSGEVA
PTEGAPDPSPMVSRLRGRKEPPVADSTTSQAFPLRLGGNGQYQYWPFSSSDLYNWKNNN
PSFSEDPAKLTALIESVLLTHQPTWDDCQQLLGTLLTGEEKQRVLLEARKAVRGEDGRPT
QLPNDINDAFPLERPDWDYNTQRGRNHLVHYRQLLLAGLQNAGRSPTNLAKVKGITQGP
NESPSAFLERLKEAYRRYTPYDPEDPGQETNVAMSFIWQSAPDIGRKLERLEDLKSKTLG
DLVREAEKIFNKRETPEEREERIRRETEEKEERRAEDVQREKERDRRRHREMSKLLATV
VSGQRQDRQGGERRRPQLDHDQCAYCKEKGHWARDCPKKPRGPRGPRPQASLLTRSSL
YPALTPTGDYKDDDDKMAPKKKRKVGIHGVPAADKKYSIGLDIGTNSVGWAVITDEYK
VPSKKFKVLGNTDRHSIKKNLIGALLFDSGETAEATRLKRTARRRYTRRKNRICYLQEIFS
NEMAKVDDSFFHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFEENPINASGVDA
KAILS ARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEHH
QDLTLLKALVRQQLPEKYKEIFFDQSKNGYAGYIDGGASQEEFYKFIKPILEKMDGTEELL
VKLNREDLLRKQRTFDNGSIPHQIHLGELHAILRRQEDFYPFLKDNREKIEKILTFRIPYYV
GPLARGNSRFAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIE
ERLKTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSKES
ILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELAL
PSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQ
SITGLYETRIDLSQLGGDKRPAATKKAGQAKKKKARA
```

VSV-G Amino acid sequence : (SEQ ID NO. 23)

```
MKCLLYLAFLFIGVNCKFTIVFPHNQKGNWKNVPSNYHYCPSSSDLNWHNDLIGTAIQV
KMPKSHKAIQADGWMCHASKWVTTCDFRWYGPKYITQSIRSFTPSVEQCKESIEQTKQG
TWLNPGFPPQSCGYATVTDAEAVIVQVTPHHVLVDEYTGEWVDSQFINGKCSNYICPTV
HNSTTWHSDYKVKGLCDSNLISMDITFFSEDGELSSLGKEGTGFRSNYFAYETGGKACK
MQYCKHWGVRLPSGVWFEMADKDLFAAARFPECPEGSSISAPSQTSVDVSLIQDVERILD
YSLCQETWSKIRAGLPISPVDLSYLAPKNPGTGPAFTIINGTLKYFETRYIRVDIAAPILSRM
VGMISGTTTERELWDDWAPYEDVEIGPNGVLRTSSGYKFPLYMIGHGMLDSDLHLSSKA
QVFEHPHIQDAASQLPDDESLFFGDTGLSKNPIELVEGWFSSWKSSIASFFFIIGLIIGLFLVL
RVGIHLCIKLKHTKKRQIYTDIEMNRLGK
```

GAG PRO POL Amino acid sequence : (SEQ ID NO. 24)

```
MGQAVTTPLSLTLDHWKDVERTAHNLSVEVRKRRWVTFCSAEWPTFNVGWPRDGTFNP
DIITQVKIKVFSPGPHGHPDQVPYIVTWEAIAVDPPPWVRPFVHPKPPLSLPPSAPSLPPEPP
LSTPPQSSLYPALTSPLNTKPRPQVLPDSGGPLIDLLTEDPPPYRDPGPPSPDGNGDSGEVA
PTEGAPDPSPMVSRLRGRKEPPVADSTTSQAFPLRLGGNGQYQYWPFSSSDLYNWKNNN
PSFSEDPAKLTALIESVLLTHQPTWDDCQQLLGTLLTGEEKQRVLLEARKAVRGEDGRPT
QLPNDINDAFPLERPDWDYNTQRGRNHLVHYRQLLLAGLQNAGRSPTNLAKVKGITQGP
NESPSAFLERLKEAYRRYTPYDPEDPGQETNVAMSFIWQSAPDIGRKLERLEDLKSKTLG
DLVREAEKIFNKRETPEEREERIRRETEEKEERRAEDVQREKERDRRRHREMSKLLATV
VSGQRQDRQGGERRRPQLDHDQCAYCKEKGHWARDCPKKPRGPRGPRPQASLLTLDDT
```

| Other sequences |
|---|
| LDDQGGQGQEPPPEPRITLRVGGQPVTFLVDTGAQHSVLTQNPGPLSDKSAWVQGATGG<br>KRYRWTTDRRVHLATGKVTHSFLHVPDCPYPLLGRDLLTKLKAQIHFEGSGAQVVGPM<br>GQPLQVTLTLNIEDEYRLHETSKGPDVPLGSTWLSDFPQAWAETGGMGLAVRQAPLIIPLK<br>ATSTPVSIKQYPMSQEARLGIKPHIQRLLDQGILVPCQSPWNTPLLPVKKPGTNDYRPVQD<br>LREVNKRVEDIHPTVPNPYNLLSGLPPSHQWYTVLDLKDAFFCLRLHPTSQSLFAFEWRD<br>PEMGISGQLTWTRLPQGFKNSPTLFDEALHRDLADFRIQHPDLILLQYVDDLLLAATSELD<br>CQQGTRALLQTLGDLGYRASAKKAQICQKQVKYLGYLLKEGQRWLTEARKETVMGQP<br>TPKTPRQLREFLGTAGFCRLWIPGFAEMAAPLYPLTKTGTLFEWGPDQQKAYQEIKQALL<br>TAPALGLPDLTKPFELFVDEKQGYAKGVLTQKLGPWRRPVAYLSKKLDPVAAGWPPCL<br>RMVAAIAVLTKDAGKLTMGQPLVILAPHAVEALVKQPPDRWLSNARMTHYQALLLDTD<br>RVQFGPIVALNPATLLPLPEEGLQHDCLDILAEAHGTRPDLTDQPLPDADHTWYTDGSSF<br>LQEGQRKAGAAVTTETEVVWAKALPAGTSAQRAELIALTQALKMAEGKKLNVYTDSRY<br>AFATAHIHGEIYRRRGLLTSEGKEIKNKDEILALLKALFLPKRLSIIHCPGHQKGNRAEARG<br>NRMADQAAREVATRETPETSTLLIENSAPYTHEHFHYTVTDIKDLTKLGATYDDAKKCW<br>VYQGKPVMPDQFTFELLDFLHQLTHLSFSKTKALLERNYCPYYMLNRDRTLKDITETCQ<br>ACAQVNASKSAVKQGTRVRGHRPGTHWEIDFTEVKPGLYGYKYLLVFIDTFSGWVEAFP<br>TKKETAKVVTKKLLEEIFPRFGMPQVLGTDNGPAFVSKVSQTVADLLGVDWKLHCAYRP<br>QSSGQVERMNRTIKETLTKLTLATGSRDWVLLLPLALYRARNTPGPHGLTPYEILYGAPP<br>PLVNFPDPDMAKVTHNPSLQAHLQALYLVQHEVWRPLAAAYQEQLDRPVVPHPFRVGD<br>TVWVRRHQTKNLEPRWKGPYTVLLTTPTALKVDGIAAWIHAAHVKAADTRIEPPSESTW<br>RVQRSQNPLKIRLTRGTS* |

BAEV-G Amino acid sequence (SEQ ID NO. 25)

```
MGFTTKIIFLYNLVLVYAGFDDPRKAIELVQKRYGRPCDCSGGQVSEPPSDRVSQVTCSG
KTAYLMPDQRWKCKSIPKDTSPSGPLQECPCNSYQSSVHSSCYTSYQQCRSGNKTYYTA
TLLLKTQTGGTSDVQVLGSTNKLIQSPCNGIKGQSICWSTTAPIHVSDGGGPLDTTRIKSVQ
RKLEEIHKALYPELQYHPLAIPKVRDNLMVDAQTLNILNATYNLLLMSNTSLVDDCWLC
LKLGPPTPLAIPNFLLSYVTRSSDNISCLIIPPLLVQPMQFSNSSCLFSPSYNSTEEIDLGHVA
FSNCTSITNVTGPICAVNGSVFLCGNNMAYTYLPTNWTGLCVLATLLPDIDIIPGDEPVPIP
AIDHFIYRPKRAIQFIPLLAGLGITAAFTTGATGLGVSVTQYTKLSNQLISDVQILSSTIQDL
QDQVDSLAEVVLQNRRGLDLLTAEQGGICLALQEKCCFYVNKSGIVRDKIKTLQEELERR
RKDLASNPLWTGLQGLLPYLLPFLGPLLTLLLLLTIGPCIFNRLTAFINDKLNIIHAM
```

GAGmlv-CAS9 sequence :

(SEQ ID NO. 26)

```
ATGGGCCAGGCTGTTACCACCCCCTTAAGTTTGACTTTAGACCACTGGAAGGATGTCGAACGGACAGCCCACA
ACCTGTCGGTAGAGGTTAGAAAAAGGCGCTGGGTTACATTCTGCTCTGCAGAATGGCCAACCTTAACGTCGG
ATGGCCACGAGACGGCACTTTTAACCCAGACATTATTACACAGGTTAAGATCAAGGTCTTCTCACCTGGCCAC
ATGGACATCCGGATCAGGTCCCCTACATCGTGACCTGGGAAGCTATAGCAGTAGACCCCCCTCCCTGGGTCAG
ACCCTTCGTGCACCCTAAACCTCCCCTCTCTCTTCCCCCTTCAGCCCCCTCTCTCCCACCTGAACCCCACTCTCGA
CCCCGCCCCAGTCCTCCCTCTATCCGGCTCTCACTTCTCCTTTAAACACCAAACCTAGGCCTCAAGTCCTTCCTGA
TAGCGGAGGACCACTCATTGATCTACTCACGGAGGACCCTCCGCCTTACCGGGACCCAGGGCCACCCTCTCCT
GACGGGAACGGCGATAGCGGAGAAGTGGCCCCTACAGAAGGACCCCTGACCCTTCCCAATGGTATCCCGC
CTGCGGGGAAGAAAAGAACCCCCCGTGGCGGATTCTACTACCTCTCAGGCGTTCCCCCTTCGCCTGGGAGGGA
ATGGACAGTATCAATACTGGCCATTTTCCTCCTCTGACCTCTATAACTGGAAAATAACAACCCCTCTTTCTCCG
AGGACCCAGCTAAATTGACAGCTTTGATCGAGTCCGTTCTCCTTACTCATCAGCCCCACTTGGGATGACTGCCAA
CAGCTATTAGGGACCCTGCTGACGGGAGAAGAAAACAGCGAGTTGCTCCTAGAGGCCCCGAAAGGCGGTTCG
AGGGGAGGACGGACGCCCAACTCAGCTGCCCAATGACATTAATGATGCTTTTCCCTTGGAACGTCCCGACTGG
GACTACAACACCCAACGAGGTAGGAACCACCTAGTCCACTATCGCCAGTTGCTCCTAGCGGGTCTCCAAAACG
CGGGCAGAAGCCCCACCAATTTGGCCAAGGTAAAAGGGATAAACCCAGGGACCTAATGAGTCTCCCTCAGCCTT
TTTAGAGAGACTCAAGGAGGCCTATCGCAGATACACTTCCTTATGACCCTGAGGACCCAGGGCAAGAAACCAAT
GTGGCCATGTCATTCATCTGGCAGTCCGCCCCgGATATCGGGCGAAAGTTAGAGCGGTTAGAAGATTTGAAGA
GTAAGACCTTAGGAGACTTAGTGAGGGAAGCTGAAAAGATCTTTAATAAACGAGAAACCCCGGAAGAAAGAG
AGGAACGTATTAGGAGAGAAACAGAGGAAAAGGAAGAACGCCGTAGGGCAGAGGATGTGCAGAGAGAGAA
GGAGAGGGACCGCAGAAGACATAGAGAAATGAGTAAGTTGCTGGTACTGTCGTTAGCGGGCAAGAAGAGG
ATAGACAGGGAGGAGAGCGAAGGAGGCCCCAACTCGACCACGACCAGTGTGCCTACTGCAAAGAAAAGGGA
CATTGGGCTAGAGATTGCCCCAAGAAGCCAAGAGGACCCCGGGGACCACGACCCCAGGCCTCCTCCTGacgc
gtagttccctgtatccagccctcacacctaccggtGATTACAAAGACGATGACGATAAGATGGCCCCAAAGAAGAAGCGGA
AGGTCGGTATCCACGGAGTCCCAGCAGCCGACAAGAAGTACAGCATCGGCCTGGACATCGGCACCAACTCTG
TGGGCTGGGCCGTGATCACCGACGAGTACAAGGTGCCCAGCAAGAAATTCAAGGTGCTGGGCAACACCGACC
GGCACAGCATCAAGAAGAACCTGATCGGAGCCCTGCTGTTCGACAGCGGCGAAACAGCCGAGGCCACCCGGC
TGAAGAGAACCGCCAGAAGAAGATACACCAGACGGAAGAACCGGATCTGCTATCTGCAAGAGATCTTCAGCA
ACGAGATGGCCAAGGTGGACGACAGCTTCTTCCACAGACTGGAAGAGTCCTTCCTGGTGGAAGAGGATAAGA
AGCACGAGCGGCACCCCATCTTCGGCAACATCGTGGACGAGGTGGCCTACCACGAGAAGTACCCCACCATCTA
CCACCTGAGAAAGAAACTGGTGGACAGCACCGACAAGGCCGACCTGCGGCTGATCTATCTGGCCCTGGCCCA
CATGATCAAGTTCCGGGGCCACTTCCTGATCGAGGGCGACCTGAACCCCGACAACAGCGACGTGGACAAGCT
GTTCATCCAGCTGGTGCAGACCTACAACCAGCTGTTCGAGGAAAACCCCATCAACGCCAGCGGCGTGGACGCC
AAGGCCATCCTGTCTGCCAGACTGAGCAAGAGCAGACGGCTGGAAAATCTGATCGCCCAGCTGCCCGGCGAG
AAGAAGAATGGCCTGTTCGGCAACCTGATTGCCCTGAGCCTGGGCCTGACCCCCAACTTCAAGAGCAACTTCG
ACCTGGCCGAGGATGCCAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCCATCCTGCTGAGCGACAT
CCTGAGAGTGAACACCGAGATCACCAAGGCCCCCCTGAGCGCCTCTATGATCAAGAGATACGACGAGCACCAC
CAGGACCTGACCCTGCTGAAAGCTCTCGTGCGGCAGCAGCTGCCTGAAGTACAAAGAGATTTTCTTCGACC
AGAGCAAGAACGGCTACGCCGGCTACATTGACGGCGGAGCCAGCCAGGAAGAGTTCTACAAGTTCATCAAGC
CCATCCTGGAAAAGATGGACGGCACCGAGGAACTGCTCGTGAAGCTGAACAGAGAGGACCTGCTGCGCAAG
```

-continued

Other sequences

CAGCGGACCTTCGACAACGGCAGCATCCCCCACCAGATCCACCTGGGAGAGCTGCACGCCATTCTGCGGCGGC
AGGAAGATTTTTACCCATTCCTGAAGGACAACCGGGAAAAGATCGAGAAGATCCTGACCTTCCGCATCCCCTA
CTACGTGGGCCCTCTGGCCAGGGGAAACAGCAGATTCGCCTGGATGACCAGAAAGAGCGAGGAAACCATCAC
CCCCTGGAACTTCGAGGAAGTGGTGGACAAGGGCGCTTCCGCCCAGAGCTTCATCGAGCGGATGACCAACTTC
GATAAGAACCTGCCCAACGAGAAGGTGCTGCCCAAGCACAGCCTGCTGTACGAGTACTTCACCGTGTATAACG
AGCTGACCAAAGTGAAATACGTGACCGAGGGAATGAGAAAGCCCGCCTTCCTGAGCGGCGAGCAGAAAAAG
GCCATCGTGGACCTGCTGTTCAAGACCAACCGGAAAGTGACCGTGAAGCAGCTGAAAGAGGACTACTTCAAG
AAAATCGAGTGCTTCGACTCCGTGGAAATCTCCGGCGTGGAAGATCGGTTCAACGCCTCCCTGGGCACATACC
ACGATCTGCTGAAAATTATCAAGGACAAGGACTTCCTGGACAATGAGGAAAACGAGGACATTCTGGAAGATA
TCGTGCTGACCCTGACACTGTTTGAGGACAGAGAGATGATCGAGGAACGGCTGAAAACCTATGCCCACCTGTT
CGACGACAAAGTGATGAAGCAGCTGAAGCGGCGGAGATACACCGGCTGGGGCAGGCTGAGCCGGAAGCTGA
TCAACGGCATCCGGGACAAGCAGTCCGGCAAGACAATCCTGGATTTCCTGAAGTCCGACGGCTTCGCCAACAG
AAACTTCATGCAGCTGATCCACGACGACAGCCTGACCTTTAAAGAGGACATCCAGAAAGCCCAGGTGTCCGGC
CAGGGCGATAGCCTGCACGAGCACATTGCCAATCTGGCCGGCAGCCCCGCCATTAAGAAGGGCATCCTGCAG
ACAGTGAAGGTGGTGGACGAGCTCGTGAAAGTGATGGGCCGGCACAAGCCCGAGAACATCGTGATCGAAAT
GGCCAGAGAGAACCAGACCACCCAGAAGGGACAGAAGAACAGCCGCGAGAGAATGAAGCGGATCGAAGAG
GGCATCAAAGAGCTGGGCAGCCAGATCCTGAAAGAACACCCCGTGGAAAACACCCAGCTGCAGAACGAGAA
GCTGTACCTGTACTACCTGCAGAATGGGCGGGATATGTACGTGGACCAGGAACTGGACATCAACCGGCTGTCC
GACTCGATGTGGACCATATCGTGCCTCAGAGCTTTCTGAAGGACGACTCCATCGACAACAAGGTGCTGACCA
GAAGCGACAAGAACCGGGGCAAGAGCGACAACGTGCCCTCCGAAGAGGTCGTGAAGAAGATGAAGAACTAC
TGGCGGCAGCTGCTGAACGCCAAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAAACCCGGCAGATCACAAAGCAC
GTGGCACAGATCCTGGACTCCCGGATGAACACTAAGTACGACGAGAATGACAAGCTGATCCGGGAAGTGAAA
GTGATCACCCTGAAGTCCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTGATCAAAAAGTACCCTAA
GCTGGAAAGCGAGTTCGTGTACGGCGACTACAAGGTGTACGACGTGCGGAAGATGATCGCCAAGAGCGAGC
AGGAAATCGGCAAGGCTACCGCCAAGTACTTCTTCTACAGCAACATCATGAACTTTTTCAAGACCGAGATTACC
CTGGCCAACGGCGAGATCCGGAAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAGTGAATATCGTGAAAAAGACCGA
GGTGCAGACAGGCGGCTTCAGCAAAGAGTCTATCCTGCCCAAGAGGAACAGCGATAAGCTGATCGCCAGAAA
GAAGGACTGGGACCCTAAGAAGTACGGCGGCTTCGACAGCCCCACCGTGGCCTATTCTGTGCTGGTGGTGGC
CAAAGTGGAAAAGGGCAAGTCCAAGAAACTGAAGAGTGTGAAAGAGCTGCTGGGGATCACCATCATGGAAA
GAAGCAGCTTCGAGAAGAATCCCATCGACTTTCTGGAAGCCAAGGGCTACAAAGAAGTGAAAAAGGACCTGA
TCATCAAGCTGCCTAAGTACTCCCTGTTCGAGCTGGAAAACGGCCGGAAGAGAATGCTGGCCTCTGCCGGCGA
ACTGCAGAAGGGAAACGAACTGGCCCTGCCCTCCAAATATGTGAACTTCCTGTACCTGGCCAGCCACTATGAG
AAGCTGAAGGGCTCCCCCGAGGATAATGAGCAGAAACAGCTGTTTGTGGAACAGCACAAGCACTACCTGGAC
GAGATCATCGAGCAGATCAGCGAGTTCTCCAAGAGAGTGATCCTGGCCGACGCTAATCTGGACAAAGTGCTGT
CCGCCTACAACAAGCACCGGGATAAGCCCATCAGAGAGCAGGCCGAGAATATCATCCACCTGTTTACCCTGAC
CAATCTGGGAGCCCCTGCCGCCTTCAAGTACTTTGACACCACCATCGACCGGAAGAGGTACACCAGCACCAAA
GAGGTGCTGGACGCCACCCTGATCCACCAGAGCATCACCGGCCTGTACGAGACACGGATCGACCTGTCTCAGC
TGGGAGGCGACAAGCGTCCTGCTGCTACTAAGAAAGCTGGTCAAGCTAAGAAAAAGAAAGCTAGAGCTTGA

BAEV-G Baboon envelope RLESS variant BAEVRIess: (also noted BRL in the text and figures) referenced in Girard-GagnepainAet al. 2014. Blood. 2014 Aug 21 ;124(8):1221 -31. doi: 10.1182/blood-2014-02-558163. Epub 2014 Jun 20).

SEQ ID NO. 27 atgggctttaccaccaagattattttctgtataacctggtgctggtgtatgcgggctttgatgatccgcgcaaagcgattgaactggtgcagaaac
gctatggccgcccgtgcgattgcagcggcggccaggtgagcgaaccgccgagcgatcgcgtgagccaggtgacctgcagcggcaaaaccgcgt
atctgatgccggatcagcgctggaaatgcaaaagcattccgaaagataccagcccgagcggcccgctgcaggaatgcccgtgcaacagctatc
agagcagcgtgcatagcagctgctataccagctatcagcagtgccgcagcggcaacaaaacctattataccgcgaccctgctgaaaacccagac
cggcggcaccagcgatgtgcaggtgctgggcagcaccaacaaactgattcagagcccgtgcaacggcattaaaggccagagcatttgctggag
cacca ccgcgccgattcatgtgagcgatggcggcggcccgctggataccacccgcattaaaagcgtgcagcgcaaactggaagaaattcataa
agcgctgtatccggaactgcagtatcatccgctggcgattccgaaagtgcgcgataacctgatggtggatgcgcagaccctgaacattctgaacg
cgacctataacctgctgctgatgagcaacaccagcctggtggatgattgctggctgtgcctgaaactgggcccgccgaccccgctggcgattccg
aactttctgctgagctatgtgacccgcagcagcgataacattagctgcctgattattccgccgctgctggtgcagccgatgcagtttagcaacagc
agctgcctgtttagcccgagctataacagcaccgaagaaattgatctgggccatgtggcgtttagcaactgcaccagcattaccaacgtgaccgg
cccgatttgcgcggtgaacggcagcgtgtttctgtgcggcaacaacatggcgtatacctatctgccgaccaactggaccggcctgtgcgtgctggc
gaccctgctgccggatattgatattattccgggcgatgaaccggtgccgattccggcgattgatcattttatttatcgcccgaaacgcgcgattcag
tttattccgctgctggcgggcctgggcattaccgcggcgtttaccaccggcgcgaccggcctgggcgtgagcgtgacccagtataccaaactgag
caaccagctgattagcgatgtgcagattctgagcagcaccattcaggatctgcaggatcaggtggatagcctggcggaagtggtgctgcagaac
cgccgcggcctggatctgctgaccgcggaacagggcggcatttgcctggcgctgcaggaaaaatgctgcttttatgtgaacaaaagcggcattgt
gcgcgataaaattaaaaccctgcaggaagaactggaacgccgccgcaaagatctggcgagcaacccgctgtggaccggcctgcagggcctgct
gccgtatctgctgccgtttctgggcccgctgctgaccctgctgctgctgctgaccattggcccgtgcatttttaaccgcctgaccgcgtttattaacga
taaactgaacattattcatgcgatgtaa VSV-G sequence:

(SEQ ID NO 28)

ATGAAGTGCCTTTTGTACTTAGCCTTTTTATTCATTGGGGTGAATTGCAAGTTCACCATAGTTTTTCCACACAAC
CAAAAAGGAAACTGGAAAAATGTTCCTTCTAATTACCATTATTGCCCGTCAAGCTCAGATTTAAATTGGCATAA
TGACTTAATAGGCACAGCCTTACAAGTCAAAATGCCCAAGAGTCACAAGGCTATTCAAGCAGACGGTTGGATG
TGTCATGCTTCCAAATGGGTCACTACTTGTGATTTCCGCTGGTATGGACCGAAGTATATAACACATTCCATCCG
ATCCTTCACTCCATCTGTAGAACAATGCAAGGAAAGCATTGAACAAACGAAACAAGGAACTTGGCTGAATCCA
GGCTTCCCTCCTCAAAGTTGTGGATATGCAACTGTGACGGATGCCGAAGCAGTGATTGTCCAGGTGACTCCTC
ACCATGTGCTGGTTGATGAATACACAGGAGAATGGGTTGATTCACAGTTCATCAACGGAAAATGCAGCAATTA
CATATGCCCCACTGTCCATAACTCTACAACCTGGCATTCTGACTATAAGGTCAAAGGGCTATGTGATTCTAACCT
CATTTCCATGGACATCACCTTCTTCTCAGAGGACGGAGAGCTATCATCCCTGGGAAAAGGAGGGCACAGGGTTC

| Other sequences |
|---|
| AGAAGTAACTACTTTGCTTATGAAACTGGAGGCAAGGCCTGCAAAATGCAATACTGCAAGCATTGGGGAGTCA<br>GACTCCCATCAGGTGTCTGGTTCGAGATGGCTGATAAGGATCTCTTTGCTGCAGCCAGATTCCCTGAATGCCCA<br>GAAGGGTCAAGTATCTCTGCTCCATCTCAGACCTCAGTGGATGTAAGTCTAATTCAGGACGTTGAGAGGATCTT<br>GGATTATTCCCTCTGCCAAGAAACCTGGAGCAAAATCAGAGCGGGTCTTCCAATCTCTCCAGTGGATCTCAGCT<br>ATCTTGCTCCTAAAAACCCAGGAACCGGTCCTGCTTTCACCATAATCAATGGTACCCTAAAATACTTTGAGACCA<br>GATACATCAGAGTCGATATTGCTGCTCCAATCCTCTCAAGAATGGTCGGAATGATCAGTGGAACTACCACAGA<br>AAGGGAACTGTGGGATGACTGGGCACCATATGAAGACGTGGAAATTGAAGCCCAATGGAGTTCTGAGGACCA<br>GTTCAGGATATAAGTTTCCTTTATACATGATTGGACATGGTATGTTGGACTCCGATCTTCATCTTAGCTCAAAGG<br>CTCAGGTGTTCGAACATCCTCACATTCAAGACGCTGCTTCGCAACTTCCTGATGATGAGAGTTTATTTTTTGGTG<br>ATACTGGGCTATCCAAAAATCCAATCGAGCTTGTAGAAGGTTGGTTCAGTAGTTGGAAAAGCTCTATTGCCTCT<br>TTTTTCTTTATCATAGGGTTAATCATTGGACTATTCTTGGTTCTCCGAGTTGGTATCCATCTTTGCATTAAATTAA<br>AGCACACCAAGAAAAGACAGATTTATACAGACATAGAGATGAACCGACTTGGAAAGTAA |

Cleavage site:

Amino acid: SSLYPALTP (SEQ. ID NO 29)

Nucleic acid: agttcctgtatccagccctcacacct (SEQ ID NO 30)

Cas9 Amino acid sequence (SEQ ID NO. 31)

MAPKKKRKVGIHGVPAADKKYSIGLDIGTNSVGWAVITDEYKVPSKKFKVLGNTDRHSIKKNLIGALLFDSGETAEAT
RLKRTARRRYTRRKNRICYLQEIFSNEMAKVDDSFFHRLEESFLVEEDKKHERHPIFGNIVDEVAYHEKYPTIYHLRKKL
VDSTDKADLRLIYLALAHMIKFRGHFLIEGDLNPDNSDVDKLFIQLVQTYNQLFEENPINASGVDAKAILSARLSKSRR
LENLIAQLPGEKKNGLFGNLIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKHSLLYEYFTVYNELTKVKYVTEGMRKP
AFLSGEQKKAIVDLLFKTNRKVTVKQLKEDYFKKIECFDSVEISGVEDRFNASLGTYHDLLKIIKDKDFLDNEENEDILED
IVLTLTLFEDREMIEERLKTYAHLFDDKVMKQLKRRRYTGWGRLSRKLINGIRDKQSGKTILDFLKSDGFANRNFMQL
IHDDSLTFKEDIQKAQVSGQGDSLHEHIANLAGSPAIKKGILQTVKVVDELVKVMGRHKPENIVIEMARENQTTQKG
QKNSRERMKRIEEGIKELGSQILKEHPVENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNLTKAERGGLSELDKAGFIKRQLVETRQI
TKHVAQILDSRMNTKYDENDKLIREVKVITLKSKLVSDFRKDFQFYKVREINNYHHAHDAYLNAVVGTALIKKYPKLE
SEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVK
ELLGITIMERSSFEKNPIDFLEAKGYKEVKKDLIIKLPKYSLFELENGRKRMLASAGELQKGNELALPSKYVNFLYLASHY
EKLKGSPEDNEQKQLFVEQHKYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGDKRPAATKKAGQAKKKKA

Cas9 Nucleic acid sequence (SEQ ID NO. 32)

ATGGCCCCAAAGAAGAAGCGGAAGGTCGGTATCCACGGAGTCCCAGCAGCCGACAAGAAGTACAGCATCGG
CCTGGACATCGGCACCAACTCTGTGGGCTGGGCCGTGATCACCGACGAGTACAAGGTGCCCAGCAAGAAATT
CAAGGTGCTGGGCAACACCGACCGGCACAGCATCAAGAAGAACCTGATCGGAGCCCTGCTGTTCGACAGCGG
CGAAACAGCCGAGGCCACCCGGCTGAAGAGAACCGCCAGAAGAAGATACACCAGACGGAAGAACCGGATCT
GCTATCTGCAAGAGATCTTCAGCAACGAGATGGCCAAGGTGGACGACAGCTTCTTCCACAGACTGGAAGAGTC
CTTCCTGGTGGAAGAGGATAAGAAGCACGAGCGGCACCCCATCTTCGGCAACATCGTGGACGAGGTGGCCTA
CCACGAGAAGTACCCCACCATCTACCACCTGAGAAAGAAACTGGTGGACAGCACCGACAAGGCCGACCTGCG
GCTGATCTATCTGGCCCTGGCCCACATGATCAAGTTCCGGGGCCACTTCCTGATCGAGGGCGACCTGAACCCC
GACAACAGCGACGTGGACAAGCTGTTCATCCAGCTGGTCCAGACCTACAACCAGCTGTTCGAGGAAAACCCCA
TCAACGCCAGCGGCGTGGACGCCAAGGCCATCCTGTCTGCCAGACTGAGCAAGAGCAGACGGCTGGAAAATC
TGATCGCCCAGCTGCCCGGCGAGAAGAAGAATGGCCTGTTCGGCAACCTGATTGCCCTGAGCCTGGGCCTGAC
CCCCAACTTCAAGAGCAACTTCGACCTGGCCGAGGATGCCAAACTGCAGCTGAGCAAGGACACCTACGACGAC
GACCTGGACAACCTGCTGGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCCCTGAGCGCCTCTATGAT
CAAGAGATACGACGAGCACCACCAGGACCTGACCCTGCTGAAAGCCCTCGTGCGGCAGCAGCTGCCTGAGAA
GTACAAAGAGATTTTCTTCGACCAGAGCAAGAACGGCTACGCCGGCTACATTGACGGCGGAGCCAGCCAGGA
AGAGTTCTACAAGTTCATCAAGCCCATCCTGGAAAAGATGGACGGCACCGAGGAACTGCTCGTGAAGCTGAAC
AGAGAGGACCTGCTGCGGAAGCAGCGGACCTTCGACAACGGCAGCATCCCCCACCAGATCCACCTGGGAGAG
CTGCACGCCATTCTGCGGCGGCAGGAAGATTTTTACCCATTCCTGAAGGACAACCGGGAAAAGATCGAGAAG
ATCCTGACCTTCCGCATCCCCTACTACGTGGGCCCTCTGGCCAGGGGAAACAGCAGATTCGCCTGGATGACCA
GAAAGAGCGAGGAAACCATCACCCCCTGGAACTTCGAGGAAGTGGTGGACAAGGGCGCTTCCGCCCAGAGCT
TCATCGAGCGGATGACCAACTTCGATAAGAACCTGCCCAACGAGAAGGTGCTGCCCAAGCACAGCCTGCTGTA
CGAGTACTTCACCGTGTATAACGAGCTGACCAAAGTGAAATACGTGACCGAGGGAATGAGAAAGCCCGCCTTC
CTGAGCGGCGAGCAGAAAAAGGCCATCGTGGACCTGCTGTTCAAGACCAACCGGAAAGTGACCGTGAAGCAG
CTGAAAGAGGACTACTTCAAGAAAATCGAGTGCTTCGACTCCGTGGAAATCTCCGGCGTGGAAGATCGGTTCA
ACGCCTCCCTGGGCACATACCACGATCTGCTGAAAATTATCAAGGACAAGGACTTCCTGGACAATGAGGAAAA
CGAGGACATTCTGGAAGATATCGTGCTGACCCTGACACTGTTTGAGGACAGAGAGATGATCGAGGAACGGCT
GAAAACCTATGCCCACCTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCTGGAAAGACAATCCTGGATTTCCTGAA
GTCCGACGGCTTCGCCAACAGAAACTTCATGCAGCTGATCCACGACGACAGCCTGACCTTTAAAGAGGACATC
CAGAAAGCCCAGGTGTCCGGCCAGGGCGATAGCCTGCACGAGCACATTGCCAATCTGGCCGGCAGCCCCGCC
ATTAAGAAGGGCATCCTGCAGACAGTGAAGGTGGTGGACGAGCTCGTGAAAGTGATGGGCCGGCACAAGCC
CGAGAACATCGTGATCGAAATGGCCAGAGAGAACCAGACCACCCAGAAGGGACAGAAGAACAGCCGCGAGA
GAATGAAGCGGATCGAAGAGGGCATCAAAGAGCTGGGCAGCCAGATCCTGAAAGAACACCCCGTGGAAAAC
ACCCAGCTGCAGAACGAGAAGCTGTACCTGTACTACCTGCAGAATGGGCGGGATATGTACGTGGACCAGGAA

-continued

| Other sequences |
|---|
| CTGGACATCAACCGGCTGTCCGACTACGATGTGGACCATATCGTGCCTCAGAGCTTTCTGAAGGACGACTCCAT
CGACAACAAGGTGCTGACCAGAAGCGACAAGAACCGGGGCAAGAGCGACAACGTGCCCTCCGAAGAGGTCG
TGAAGAAGATGAAGAACTACTGGCGGCAGCTGCTGAACGCCAAGCTGATTACCCAGAGAAAGTTCGACAATC
TGACCAAGGCCGAGAGAGGCGGCCTGAGCGAACTGGATAAGGCCGGCTTCATCAAGAGACAGCTGGTGGAA
ACCCGGCAGATCACAAAGCACGTGGCACAGATCCTGGACTCCCGGATGAACACTAAGTACGACGAGAATGAC
AAGCTGATCCGGGAAGTGAAAGTGATCACCCTGAAGTCCAAGCTGGTGTCCGATTTCCGGAAGGATTTCCAGT
TTTACAAAGTGCGCGAGATCAACAACTACCACCACGCCCACGACGCCTACCTGAACGCCGTCGTGGGAACCGC
CCTGATCAAAAAGTACCCTAAGCTGGAAAGCGAGTTCGTGTACGGCGACTACAAGGTGTACGACGTGCGGAA
GATGATCGCCAAGAGCGAGCAGGAAATCGGCAAGGCTACCGCCAAGTACTTCTTCTACAGCAACATCATGAAC
TTTTTCAAGACCGAGATTACCCTGGCCAACGGCGAGATCCGGAAGCGGCCTCTGATCGAGAcAAACGGCGAA
ACCGGGGAGATCGTGTGGGATAAGGGCCGGGATTTTGCCACCGTGCGGAAAGTGCTGAGCATGCCCCAAGTG
AATATCGTGAAAAAGACCGAGGTGCAGACAGGCGGCTTCAGCAAAGAGTCTATCCTGCCCAAGAGGAACAGC
GATAAGCTGATCGCCAGAAAGAAGGACTGGGACCCTAAGAAGTACGGCGGCTTCGACAGCCCCACCGTGGCC
TATTCTGTGCTGGTGGTGGCCAAAGTGGAAAAGGGCAAGTCCAAGAAACTGAAGAGTGTGAAAGAGCTGCTG
GGGGATCACCATCATGGAAAGAAGCAGCTTCGAGAAGAATCCCATCGACTTTCTGGAAGCCAAGGGCTACAA
GAAGTGAAAAAGGACCTGATCATCAAGCTGCCTAAGTACTCCCTGTTCGAGCTGGAAAACGGCCGGAAGAGA
ATGCTGGCCTCTGCCGGCGAACTGCAGAAGGGAAACGAACTGGCCCTGCCCTCCAAATATGTGAACTTCCTGT
ACCTGGCCAGCCACTATGAGAAGCTGAAGGGCTCCCCCGAGGATAATGAGCAGAAACAGCTGTTTGTGGAAC
AGCACAAGCACTACCTGGACGAGATCATCGAGCAGATCAGCGAGTTCTCCAAGAGAGTGATCCTGGCCGACG
CTAATCTGGACAAAGTGCTGTCCGCCTACAACAAGCACCGGGATAAGCCCATCAGAGAGCAGGCCGAGAATA
TCATCCACCTGTTTACCCTGACCAATCTGGGAGCCCCTGCCGCCTTCAAGTACTTTGACACCACCATCGACCGGA
AGAGGTACACCAGCACCAAAGAGGTGCTGGACGCCACCCTGATCCACCAGAGCATCACCGGCCTGTACGAGA
CACGGATCGACCTGTCTCAGCTGGGAGGCGACAAGCGTCCTGCTGCTACTAAGAAAGCTGGTCAAGCTAAGA
AAAGAAAGCTAG |

HIV-1 encapsidation construct "p8.91" (encoding HIV-1 Gag-Pol-Tat-Rev)
(SEQ ID NO. 33)

ttgattattgactagttattaatagtaatcaattacggggtcattagttcatagcccatatatggagttccgcgttacataacttacggtaaatggcc
cgcctggctgaccgcccaacgacccccgcccattgacgtcaataatgacgtatgttcccatagtaacgccaatagggactttccattgacgtcaat
gggtggagtatttacggtaaactgcccacttggcagtacatcaagtgtatcatatgccaagtacgccccctattgacgtcaatgacggtaaatggc
ccgcctggcattatgcccagtacatgaccttatgggactttcctacttggcagtacatctacgtattagtcatcgctattaccatggtgatgcggtttt
ggcagtacatcaatgggcgtggatagcggtttgactcacggggatttccaagtctccaccccattgacgtcaatgggagtttgttttggcaccaaa
atcaacgggactttccaaaatgtcgtaacaactccgccccattgacgcaaatgggcggtaggcgtgtacggtgggaggtctatataagcagagct
cgtttagtgaaccgtcagatcgcctggagacgccatccacgctgttttgacctccatagaagacaccgggaccgatccagcctccgcggccggga
acggtgcattggaacgcggattccccgtgccaagagtgacgtaagtaccgcctatagagtctataggcccacccccttggcttcttatgcgacgga
tcgatcccgtaataagcttcgaggtccgcggccggccgcgttgacgcgcacggcaagaggcgaggggcggcgactggtgagagatgggtgcga
gagcgtcagtattaagcggggagaattagatcgatgggaaaaaattcggttaaggccaggggaaagaaaaaatataaattaaaacatata
gtatgggcaagcagggagctagaacgattcgcagttaatcctggcctgttagaaacatcagaaggctgtagacaaatactgggacagctacaac
catccccttcagacaggatcagaagaacttagatcattatataatacagtagcaaccctctattgtgtgcatcaaaggatagagataaaagacacc
aaggaagctttagacaagatagaggaagagcaaaacaaaagtaagaaaaaagcacagcaagcagcagctgacacaggacacagcaatcag
gtcagccaaaattaccctatagtgcagaacatccagggcaaatggtacatcaggccatatcacctagaactttaaatgcatgggtaaaagtagt
agaagagaaggcttcagcccagaagtgatacccatgttttcagcattatcagaaggagccaccccacaagatttaaacaccatgctaaacaca
gtggggggacatcaagcagccatgcaaatgttaaaagagaccatcaatgaggaagctgcagaatgggatagagtgcatccagtgcatgcagg
gcctattgcaccaggccagatgagagaaccaaggggaagtgacatagcaggaactactagtacccttcaggaacaaataggatggatgacaca
taatccacctatcccagtaggagaaatctataaaagatggataatcctgggattaaataaaatagtaagaatgtatagccctaccagcattctgg
acataagacaaggaccaaaggaaccctttagagactatgtagaccggttctataaaactctaagagccgagcaagcttcacaagaggtaaaaa
attggatgacagaaaccttgttggtccaaaatgcgaacccagattgtaagactattttaaaagcattgggaccaggagcgacactagaagaaat
gatgacagcatgtcagggagtggggggacccggccataaagcaagagttttggctgaagcaatgagccaagtaacaaatccagctaccataat
gatacagaaaggcaattttaggaaccaaagaaagactgttaagtgtttcaattgtggcaaagaagggcacatagccaaaaattgcagggcccct
aggaaaaagggctgttggaaatgtggaaaggaaggacaccaaatgaaagattgtactgagagacaggctaattttttagggaagatctggcctt
cccacaagggaaggccagggaattttcttcagagcagaccagagccaacagccccaccagaagagagcttcaggtttggggaagagacaaca
actccctctcagaagcaggagccgatagacaaggaactgtatcctttagcttccctcagatcactctttggcagcgacccctcgtcacaataaaga
taggggggcaattaaaggaagctctattagatacaggagcagatgatacagtattagaagaaatgaatttgccaggaagatggaaaccaaaaa
tgatagggggaattggaggttttatcaaagtaagacagtatgatcagatactcatagaaatctgcggacataaagctataggtacagtattagta
ggacctacacctgtcaacataattggaagaaatctgttgactcagattggctgcactttaaattttcccattagtcctattgagactgtaccagtaa
aattaaagccaggaatggatggcccaaaagttaaacaatggccattgacagaagaaaaaataaaagcattagtagaaatttgtacagaaatgg
aaaaggaagggaaaatttcaaaaattgggcctgaaaatccatacaatactccagtatttgccataaagaaaaaagacagtactaaatggagaa
aattagtagatttcagagaacttaataagagaactcaagatttctgggaagttcaattaggaataccacatcctgcagggttaaaacagaaaaa
atcagtaacagtactgatgtgggcgatgcatatttttcagttcccttagataaagacttcaggaagtatactgcatttaccatacctagtataaac
aatgagacaccagggattagatatcagtacaatgtgcttccacagggatggaaaggatcaccagcaatattccagtgtagcatgacaaaatct
tagagccttttagaaaacaaaatccagacatagtcatctatcaatacatggatgatttgtatgtaggatctgacttagaaatagggcagcataga
acaaaaatagaggaactgagacaactgttgagggggcaagttcaccacccagacaaaaaacatcagaaagaacctccattcctttggatggg
gttatgaactccatcctgataaatggacagtacagcctatagtgctgccagaaaaggacagctggactgtcaatgacatacagaaattagtggg
aaaattgaattgggcaagtcagatttatgcagggattaaagtaaggcaattatgtaaactccttaggggaaccaaagcactaacagaagtagta
ccactaacagaagaagcagagctagaactggcagaaaacagggagattctaaaagaaccggtacatggagtgtattatgacccatcaaaaga
cttaatagcagaaatacagaagcaggggcaaggccaatggacatatcaaatttatcaagagccatttaaaaatctgaaaacaggaaagtatgc
aagaatgaagggtgcccacactaatgatgtgaaacaattaacagaggcagtgcaaaaaatagccacagaaagcatagtaatatggggaaaga
ctcctaaatttaaattacccatacaaaaggaaacatgggaagcatggtggacagagtattggcaagccacctggattcctgagtgggagtttgtc
aatacccctcccttagtgaagttatggtaccagttagagaaagaacccataataggagcagaaacttcatgtagatggggcagcaataggg
aaactaaattaggaaaagcaggatatgtaactgacagaggaagacaaaaagttgtccccctaacggacacaacaaatcagaagactgagtta
caagcaattcatctagctttgcaggattcgggattagaagtaaacatagtgacagactcacaatatgcattgggaatcattcaagcacaaccaga
taagagtgaatcagagttagtcagtcaaataatagagcagttaataaaaaaggaaaaggtctacctggcatgggtaccagcacacaaaggaat
tggaggaaatgaacaagtagataaattggtcagtgctggaatcaggaaagtactatttttagatggaatagataaggcccaagaagaacatga
gaaatatcacagtaattggagagcaatggctagtgattttaacctaccacctgtagtagcaaaagaaatagtagccagctgtgataaatgtcagc
taaaaggggaagccatgcatggacaagtagactgtagcccaggaatatggcagctagattgtacacatttagaaggaaaagttatcttggtagc
agttcatgtagccagtggatatatagaagcagaagttattccagcagagacagggcaagaaacagcatacttcctcttaaaattagcaggaaga
tggccagtaaaaacagtacatacagacaatggcagcaatttcaccagtactacagttaaggccgcctgttggtgggcggggatcaagcaggaat -continued

| Other sequences |
|---|
| ttggcattccctacaatccccaaagtcaaggagtaatagaatctatgaataaagaattaaagaaaattataggacaggtaagagatcaggctga
acatcttaagacagcagtacaaatggcagtattcatccacaattttaaaagaaaagggggattgggggtacagtgcagggaaagaatagt
agacataatagcaacagacatacaaactaaagaattacaaaaacaaattacaaaaattcaaaattttcggggtttattacagggacagcagaga
tccagtttggaaaggaccagcaaagctcctctgaaaggtgaaggggcagtagtaatacaagataatagtgacataaaagtagtgccaagaag
aaaagcaaagatcatcagggattatggaaaacagatggcaggtgatgattgtgtggcaagtagacaggatgaggattaacacatggaattctg
caacaactgctgtttatccatttcagaattgggtgtcgacatagcagaataggcgttactcgacagaggagagcaagaaatggagccagtagat
cctagactagagccctggaagcatccaggaagtcagcctaaaactgcttgtaccaattgctattgtaaaaagtgttgcttttcattgccaagtttgtt
tcatgacaaaagccttaggcatctcctatggcaggaagaagcggagacagcgacgaagagctcatcagaacagtcagactcatcaagcttctct
atcaaagcagtaagtagtacatgtaatgcaacctataatagtagcaatagtagcattagtagtagcaataataatagcaatagttgtgtggtcca
tagtaatcatagaatataggaaaatggccgctgatcttcagacctggaggaggagatatgagggacaattggagaagtgaattatataaatata
aagtagtaaaaattgaaccattaggagtagcacccaccaaggcaaagaagaagtggtgcagagagaaaaaagagcagtgggaataggagc
tttgttccttgggttcttgggagcagcaggaagcactatgggcgcagcgtcaatgacgctgacggtacaggccagacaattattgtctggtatagt
gcagcagcagaacaatttgctgagggctattgaggcgcaacagcatcttgttgcaactcacagtctggggcatcaagcagctccaggcaagaatc
ctggctgtgaaagatacctaaaggatcaacagctcctggggatttggggttgctctggaaaactcatttgcaccactgctgtgccttggaatgct
agttggagtaataaatctctggaacagatttggaatcacacgacctggatggagtgggacagagaaattaacaattacacaagcttaatacact
ccttaattgaagaatcgcaaaaccagcaagaaaagaatgaacaagaatttattggaattagataaatgggcaagtttgtggaattggtttaacat
aacaaattggctgtggtatataaaattattcataatgatagtaggaggcttggtaggtttaagaatagtttttgctgtactttctatagtgaatagag
ttaggcagggatattcaccattatcgtttcagacccacctcccaaccccgagggacccgacaggcccgaaggaatagaagaagaaggtggag
agagagacagagacagatccattcgattagtgaacggatccttggcacttatctgggacgatctgcggagcctgtgcctcttcagctaccaccgct
tgagagacttactcttgattgtaacgaggattgtggaacttctggtaacgccgtcccgcaccgggaaatggtcagcgaaccaatc
agcagggtcatcgctagccagatcctctacgccggacgcatcgtggccggcatcaccggcgccacaggtgcggttgctggcgcctatatcgccga
catcaccgatggggaagatcgggctcgccacttcgggctcatgagcgcttgtttcggcgtgggtatggtggcaggcccgtggccggggactgt
tgggcgccatctccttgcatgcaccattccttgcggcggcggtgctcaacggcctcaacctactactgggctgcttcctaatgcaggagtcgcataa
gggagagcgtcgaatggtgcactctcagtacaatctgctctgatgccgcatagttaagccagccccgacacccgccaacacccgctgacgcgccc
tgacgggcttgtctgctcccggcatccgcttacagacaagctgtgaccgtctcgggagctgcatgtgtcagaggttttcaccgtcatcaccgaaa
cgcgcgagacgaaagggcctcgtgatacgcctatttttataggttaatgtcatgataataatggtttcttagacgtcaggtggcacttttcggggaa
atgtgcgcggaacccctatttgtttatttttctaaatacattcaaatatgtatccgctcatgagacaataaccctgataaatgcttcaataatattga
aaaaggaagagtatgagtattcaacatttccgtgtcgcccttattccctttttttgcggcattttgccttcctgtttttgctcacccagaaacgctggtg
aaagtaaaagatgctgaagatcagttgggtgcacgagtgggttacatcgaactggatctcaacagcggtaagatccttgagagttttcgccccga
agaacgttttccaatgatgagcactttaaagttctgctatgtggcgcggtattatcccgtattgacgccgggcaagagcaactcggtcgccgcata
cactattctcagaatgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaacatgggggatcatg
taactcgccttgatcgttgggaaccggagctgaatgaagccataccaaacgacgagcgtgacaccacgatgcctgtagcaatggcaacaacgtt
gcgcaaactattaactggcgaactacttactctagcttcccggcaacaattaatagactggatgaggcggataaagttgcaggaccacttctgc
gctcggcccttccggctggctggtttattgctgataaatctggagccggtgagcgtgggtctcgcggtatcattgcagcactggggccagatggta
agccctcccgtatcgtagttatctacacgacggggagtcaggcaactatgatgaacgaaatagacagatcgctgagataggtgcctcactgatt
aagcattggtaactgtcagaccaagtttactcatatatactttagattgatttaaaacttcattttttaatttaaaaggatctaggtgaagatcctttttt
gataatctcatgaccaaaatcccttaacgtgagttttcgttccactgagcgtcagacccgtagaaaagatcaaaggatcttcttgagatccttttt
tctgcgcgtaatctgctgcttgcaaacaaaaaaaccaccgctaccagcggtggtttgtttgccggatcaagagctaccaactctttttccgaaggt
aactggcttcagcagagcgcagataccaaatactgttcttctagtgtagccgtagttaggccaccacttcaagaactctgtagcaccgcctacata
cctcgctctgctaatcctgttaccagtggctgctgccagtggcgataagtcgtgtcttaccgggttggactcaagacgatagttaccggataaggcg
cagcggtcgggctgaacggggggttcgtgcacacagcccagcttggagcgaacgacctacaccgaactgagatacctacagcgtgagctatga
gaaagcgccacgcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtcaggggggcggagccatg
gaaaaacgccagcaacgcggcctttttacggttcctggccttttgctggccttttgctcacatgttctttcctgcgttatccctgattctgtggataac
cgtattaccgcctttgagtgagctgataccgctcgccgcagccgaacgaccgagcgcagcgagtcagtgagcgaggaagcggaagagcgccca
atacgcaaaccgcctctccccgcgcgttggccgattcattaatgcagctggcacgacaggtttcccgactggaaagcgggcagtgagcgcaacgca
attaatgtgagttagctcactcattaggcaccccaggctttacactttatgcttccggctcgtatgttgtgtggaattgtgagcggataacaatttc
acacaggaaacagctatgaccatgattacgccaagcgcgcaattaaccctcactaaagggaacaaaagctggagctccaccgcggtggcggcc
gctctagaactagtggatcccccgggctgcaggaattcgatatcaagcttatcgataccgtcgacctcgagggggggcccggtacccagcttttg
ttccctttagtgagggttaattgcgcgcttggcgtaatcatggtcatagctgtttcctgtgtgaaattgttatccgctcacaattccacacaacata
cgagccggaagcataaagtgtaaagcctggggtgcctaatgagtgagctaactcacattaattgcgttgcgctcactgcccgctttccagtcggg
aaacctgtcgtgccagctgcattaatgaatcggccaacgcgcggggagaggcggtttgcgtattgggcgctcttccgcttcctcgctcactgactc
gctgcgctcggtcgttcggctgcggcgagcggtatcagctcactcaaaggcggtaatacggttatccacagaatcaggggataacgcaggaaag
aacatgtgagcaaaaggccagcaaaaggccaggaaccgtaaaaaggccgcgttgctggcgtttttccataggctccgcccccctgacgagcatc
acaaaaatcgacgctcaagtcagaggtggcgaaacccgacaggactataaagataccaggcgtttccccctggaagctccctcgtgcgctctcc
tgttccgaccctgccgcttaccggatacctgtccgcctttctcccttcgggaagcgtggcgctttctcatagctcacgctgtaggtatctcagttcgg
tgtaggtcgttcgctccaagctgggctgtgtgcacgaaccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttcttgaagtg
gtggcctaactacggctacactagaagaacagtatttggtatctgcgctctgctgaagccagttaccttcggaaaaagagttggtagctcttgatc
cggcaaacaaaccaccgctggtagcggtggtttttttgtttgcaagcagcagattacgcgcagaaaaaaaggatctcaagaagatcctttgatc
ttttctacggggtctgacgctcagtggaacgaaaactcacgttaagggattttggtcatgagattatcaaaaaggatcttcacctagatccttttaaa
ttaaaaatgaagttttaaatcaatctaaagtatatatgagtaaacttggtctgacagttaccaatgcttaatcagtgaggcacctatctcagcgatct
gtctatttcgttcatccatagttgcctgactccccgtcgtgtagataactacgatacgggagggcttaccatctggccccagtgctgcaatgatacc
gcgagacccacgctcaccggctccagatttatcagcaataaaccagccagccggaagggccgagcgcagaagtggtcctgcaactttatccgcc
tccatccagtctattaattgttgccgggaagctagagtaagtagttcgccagttaatagtttgcgcaacgttgttgccattgctacaggcatcgtggt
gtcacgctcgtcgtttggtatggcttcattcagctccggttcccaacgatcaaggcgagttacatgatcccccatgttgtgcaaaaaagcggttagc
tccttcggtcctccgatcgttgtcagaagtaagttggccgcagtgttatcactcatggttatggcagcactgcataattctcttactgtcatgccatc
cgtaagatgcttttctgtgactggtgagtactcaaccaagtcattctgagaatagtgtatgcggcgaccgagttgctcttgcccggcgtcaatacggg
ataataccgcgccacatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacaggaaggcaaaatg
ccgcaaaaaagggaataagggcgacacggaaatgttgaatactcatactcttcctttttcaatattattgaagcatttatcagggttattgtctcat
gagcggatacatatttgaatgtatttagaaaaataaacaaataggggttccgcgcacatttccccgaaaagtgccacctgacgtctaagaaacc
attattatcatgacattaacctataaaaataggcgtatcacgaggccctttcgtcttcac |

-continued

Other sequences tttttcttactccacacaggcatagagtgtctgctattaataactatgctcaaaaattgtgtacctttagcttttaatttgtaaaggggttaataag
gaatatttgatgtatagtgccttgactagagatcataatcagccataccacatttgtagaggttttacttgctttaaaaaacctcccacacctcccc
tgaacctgaaacataaaatgaatgcaattgttgttgttgggctgcaggaattaattcgagctcgcccgaca HIV-1 GAG-CAS9-encoding nucleic acid "KLAP229"

(SEQ ID NO. 34)

GCGGCCGCTCTAGAGAGCTTGGCCCATTGCATACGTTGTATCCATATCATAATATGTACATTTATATTGGCTCAT
GTCCAACATTACCGCCATGTTGACATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTACGCCCCCTATTGACG
TCAATGACGGTAAATGGCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATGGGCGTGGATAGCGGTT
TGACTCACGGGGATTTCCAAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCATAGAA
GACACCGGGACCGATCCAGCCTCCGGTCGACCGATCCTGAGAACTTCAGGGTGAGTTTGGGGACCCTTGATTG
TTCTTTCTTTTTCGCTATTGTAAAATTCATGTTATATGGAGGGGCAAAGTTTTCAGGGTGTTGTTTAGAATGGG
AAGATGTCCCTTGTATCACCATGGACCCTCATGATAATTTTGTTTCTTTCACTTTCTACTCTGTTGACAACCATTG
TCTCCTCTTTATTTTCTTTTCATTTTCTTGTAACTTTTCGTTAAACTTTAGCTTGCATTTGTAACGAATTTTTAAATT
CACTTTTGTTTATTTTGTCAGATTGTAAGTACTTTCTCTAATCACTTTTTTTTCAAGGCAATCAGGGTATATTATATT
GTACTTCAGCACAGTTTTAGAGAACATTGTTATAATTAAATGATAAGGTAGAATATTTCTGCATATAAATTCTG
GCTGGCGTGGAAATATTCTTATTGGTAGAAACAACTACATCCTGGTCATCATCCTGCCTTTCTCTTTATGGTTAC
AATGATATACACTGTTTGAGATGAGGATAAAATACTCTGAGTCCAAACCGGGCCCTCTGCTAACCATGTTCAT
GCCTTCTTCTTTTTCCTACAGCTCCTGGGCAACGTGCTGGTTATTGTGCTGTCTCATCATTTTGGCAAAGAATTCc
tcgagatgggtgcgagagcgtcggtattaagcgggggagaattagataaatgggaaaaaattcggttaaggccaggggaaagaaacaatat
aaactaaaacatatagtatgggcaagcagggagctagaacgattcgcagttaatcctggccttttagagacatcagaaggctgtagacaaatac
tgggacagctacaaccatccctcagacaggatcagaagaacttagatcattatataataacaatagcagtcctctattgtgtgcatcaaaggata
gatgtaaaagacaccaaggaagccttagataagatagaggaagagcaaaacaaaagtaagaaaaaggcacagcaagcagcagctgacaca
ggaaacaacagccagtCAGCCAAAATTACCCTATAGTGCAGAACctccaggggcaaatggtacatcaggccatatcacctagaa
ctttaaatgcatgggtaaaagtagtagaagagaaggcttcagccagaagtaatacccatgttttcagcattatcagaaggagccaccccacaa
gatttaaataccatgctaaacacagtgggggggacatcaagcagccatgcaaatgttaaaagagaccatcaatgaggaagctgcagaatgggat
agattgcatccagtgcatgcagggcctattgcaccaggccagatgagagaaccaaggggaagtgacatagcaggaactactagtacccttcag
gaacaaataggatggatgacacataatccacctatcccagtaggagaaatctataaagatggataatcctgggattaaataaaatagtaaga
atgtatagccctaccagcattctggacataagacaaggaccaaaggaacccttagagactatgtagaccgattctataaaactctaagagccg
agcaagcttcacaagaggtaaaaaattggatgacagaaaccttgttggtccaaaatgcgaaccagattgtaagactattttaaaagcattggg
accaggagcgacactagaagaaatgatgacagcatgtcagggagtgggggggacccggccataAAAGCAAGAGTTTTGGCTGAAGCA
ATGAGCcaagtaacaaatccagctaccataatgatacagaaaggcaattttaggaaccaaagaaagactgttaagtgtttcaattgtggcaa
agaagggcacatagccaaaaattgcagggcccctaggaaaaagggctgttggaaatgtggaaaggaaggacaccaaatgaaagattgtactG
AGAGACAGGCTAATTTTTTAGGGAAGATCtggccttcccacaagggaAGGCCAGGGAATTTTCTTCAGAGCAGACCA
gagccaacagccccaccagaagagagcttcaggtttggggaagagacaacaactccctctcagaagcaggagccgatagacaaggaactgta
tcctttagcttccctcagatcactctttggcagcgaccccctcgtcacaaCCGGGGACCACGACCCCAGGcAAAGCAAGAGTTTTG
GCTGAAGCAATGAGCaccggtGATTACAAAGACGATGACGATAAGATGGCCCCAAAGAAGAAGCGGAAGGTCG
GTATCCACGGAGTCCCAGCAGCCGACAAGAAGTACAGCATCGGCCTGGACATCGGCACCAACTCTGTGGGCT
GGGCCGTGATCACCGACGAGTACAAGGTGCCCAGCAAGAAATTCAAGGTGCTGGGCAACACCGACCGGCACA
GCATCAAGAAGAACCTGATCGGAGCCCTGCTGTTCGACAGCGGCGAAACAGCCGAGGCCACCCGGCTGAAGA
GAACCGCCAGAAGAAGATACACCAGACGGAAGAACCGGATCTGCTATCTGCAAGAGATCTTCAGCAACGAGA
TGGCCAAGGTGGACGACAGCTTCTTCCACAGACTGGAAGAGTCCTTCCTGGTGGAAGAGGATAAGAAGCACG
AGCGGCACCCCATCTTCGGCAACATCGTGGACGAGGTGGCCTACCACGAGAAGTACCCCACCATCTACCACCT
GAGAAAGAAACTGGTGGACAGCACCGACAAGGCCGACCTGCGGCTGATCTATCTGGCCCTGGCCCACATGAT
CAAGTTCCGGGGCCACTTCCTGATCGAGGGCGACCTGAACCCCGACAACAGCGACGTGGACAAGCTGTTCATC
CAGCTGGTGCAGACCTACAACCAGCTGTTCGAGGAAAACCCCATCAACGCCAGCGGCGTGGACGCCAAGGCC
ATCCTGTCTGCCAGACTGAGCAAGAGCAGACGGCTGGAAAATCTGATCGCCCAGCTGCCCGGCGAGAAGAAG
AATGGCCTGTTCGGCAACCTGATTGCCCTGAGCCTGGGCCTGACCCCCAACTTCAAGAGCAACTTCGACCTGG
CCGAGGATGCCAAACTGCAGCTGAGCAAGGACACCTACGACGACGACCTGGACAACCTGCTGGCCCAGATCGG
CGACCAGTACGCCGACCTGTTTCTGGCCGCCAAGAACCTGTCCGACGCCATCCTGCTGAGCGACATCCTGAGA
GTGAACACCGAGATCACCAAGGCCCCCCTGAGCGCCTCTATGATCAAGAGATACGACGAGCACCACCAGGACC
TGACCCTGCTGAAAGCTCTCGTGCGGCAGCAGCTGCCTGAGAAGTACAAAGAGATTTTCTTCGACCAGAGCAA
GAACGGCTACGCCGGCTACATTGACGGCGGAGCCAGCCAGGAAGAGTTCTACAAGTTCATCAAGCCCATCCTG
GAAAAGATGGACGGCACCGAGGAACTGCTCGTGAAGCTGAACAGAGAGGACCTGCTGCGCAAGCAGCGGAC
CTTCGACAACGGCAGCATCCCCCACCAGATCCACCTGGGAGCTGCACGCCATTCTGCGGCGGCAGGAAGAT
TTTTACCCATTCCTGAAGGACAACCGGGAAAAGATCGAGAAGATCCTGACCTTCCGCATCCCCTACTACGTGGG
CCCTCTGGCCAGGGGAAACAGCAGATTCGCCTGGATGACCAGAAAGAGCGAGGAAACCATCACCCCCTGGAA
CTTCGAGGAAGTGGTGGACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCGTGTATAACGAGCTGACC
AAAGTGAAATACGTGACCGAGGGAATGAGAAAGCCCGCCTTCCTGAGCGGCGAGCAGAAAAAGGCCATCGT
GGACCTGCTGTTCAAGACCAACCGGAAAGTGACCGTGAAGCAGCTGAAAGAGGACTACTTCAAGAAAATCGA
GTGCTTCGACTCCGTGGAAATCTCCGGCGTGGAAGATCGGTTCAACGCCTCCCTGGGCACATACCACGATCTG
CTGAAAATTATCAAGGACAAGGACTTCCTGGACAATGAGGAAAACGAGGACATTCTGGAAGATATCGTGCTG
ACCCTGACACTGTTTGAGGACAGAGAGATGATCGAGGAACGGCTGAAAACCTATGCCCACCTGTTCGACGACA
AAGTGATGAAGCAGCTGAAGCGGCGGAGATACACCGGCTGGGGCAGGCTGAGCCGGAAGCTGATCAACGGA
ATCCGGGACAAGCAGTCCGGCAAGACAATCCTGGATTTCCTGAAGTCCGACGGCTTCGCCAACAGAAACTTCA
TGCAGCTGATCCACGACGACAGCCTGACCTTTAAAGAGGACATCCAGAAAGCCCAGGTGTCCGGCCAGGGCG
ATAGCCTGCACGAGCACATTGCCAATCTGGCCGGCAGCCCCGCCATTAAGAAGGGCATCCTGCAGACAGTGAA
GGTGGTGGACGAGCTCGTGAAAGTGATGGGCCGGCACAAGCCCGAGAACATCGTGATCGAAATGGCCAGAG
AGAACCAGACCACCCAGAAGGGACAGAAGAACAGCCGCGAGAGAATGAAGCGGATCGAAGAGGGCATCAA
AGAGCTGGGCAGCCAGATCCTGAAAGAACACCCCGTGGAAAACACCCAGCTGCAGAACGAGAAGCTGTACCT

| Other sequences |
|---|
| GTACTACCTGCAGAATGGGCGGGATATGTACGTGGACCAGGAACTGGACATCAACCGGCTGTCCGACTACGA |
| TGTGGACCATATCGTGCCTCAGAGCTTTCTGAAGGACGACTCCATCGACAACAAGGTGCTGACCAGAAGCGAC |
| AAGAACCGGGGCAAGAGCGACAACGTGCCCTCCGAAGAGGTCGTGAAGAAGATGAAGAACTACTGGCGGCA |
| GCTGCTGAACGCCAAGCTGATTACCCAGAGAAAGTTCGACAATCTGACCAAGGCCGAGAGAGGCGGCCTGAG |
| CGAACTGGATAAGGCCGGCTTCATCAAGAGACAGCTGGTGGAAACCCGGCAGATCACAAAGCACGTGGCACA |
| GATCCTGGACTCCGGATGAACACTAAGTACGACGAGAATGACAAGCTGATCCGGGAAGTGAAAGTGATCAC |
| CCTGAAGTCCAAGCTGGTGTCCGATTTCCGGAAGGATTTCCAGTTTTACAAAGTGCGCGAGATCAACAACTACC |
| ACCACGCCCACGACGCCTACCTGAACGCCGTCGTGGGAACCGCCCTGATCAAAAAGTACCCTAAGCTGGAAAG |
| CGAGTTCGTGTACGGCGACTACAAGGTGTACGACGTGCGGAAGATGATCGCCAAGAGCGAGCAGGAAATCG |
| GCAAGGCTACCGCCAAGTACTTCTTCTACAGCAACATCATGAACTTTTTCAAGACCGAGATTACCCTGGCCAAC |
| GGCGAGATCCGGAAGCGGCCTCTGATCGAGACAAACGGCGAAACCGGGGAGATCGTGTGGGATAAGGGCCG |
| GGATTTTGCCACCGTGCGGAAAGTGCTGAGCATGCCCCAAGTGAATATCGTGAAAAAGACCGAGGTGCAGAC |
| AGGCGGCTTCAGCAAAGAGTCTATCCTGCCCAAGAGGAACAGCGATAAGCTGATCGCCAGAAAGAAGGACTG |
| GGACCCTAAGAAGTACGGCGGCTTCGACAGCCCCACCGTGGCCTATTCTGTGCTGGTGGTGGCCAAAGTGGA |
| AAAGGGCAAGTCCAAGAAACTGAAGAGTGTGAAAGAGCTGCTGGGGATCACCATCATGGAAAGAAGCAGCT |
| TCGAGAAGAATCCCATCGACTTTCTGGAAGCCAAGGGCTACAAAGAAGTGAAAAAGGACCTGATCATCAAGCT |
| GCCTAAGTACTCCCTGTTCGAGCTGGAAAACGGCCGGAAGAGAATGCTGGCCTCTGCCGGCGAACTGCAGAA |
| GGGAAACGAACTGGCCCTGCCCTCCAAATATGTGAACTTCCTGTACCTGGCCAGCCACTATGAGAAGCTGAAG |
| GGCTCCCCCGAGGATAATGAGCAGAAACAGCTGTTTGTGGAACAGCACAAGCACTACCTGGACGAGATCATC |
| GAGCAGATCAGCGAGTTCTCCAAGAGAGTGATCCTGGCCGACGCTAATCTGGACAAAGTGCTGTCCGCCTACA |
| ACAAGCACCGGGATAAGCCCATCAGAGAGCAGGCCGAGAATATCATCCACCTGTTTACCCTGACCAATCTGGG |
| AGCCCCTGCCGCCTTCAAGTACTTTGACACCACCATCGACCGGAAGAGGTACACCAGCACCAAAGAGGTGCTG |
| GACGCCACCCTGATCCACCAGAGCATCACCGGCCTGTACGAGACACGGATCGACCTGTCTCAGCTGGGAGGC |
| GACAAGCGTCCTGCTGCTACTAAGAAAGCTGGTCAAGCTAAGAAAAAGAAAGCTAGAGCTTGATATCCTGCAG |
| ACGCGTAGGATCCGTCGAGGAATTCACTCctCAGGTGCAGGCTGCCTATCAGAAGGTGGTGGCTGGTGTGGCC |
| AATGCCCTGGCTCACAAATACCACTGAGATCTTTTTCCCTCTGCCAAAAATTATGGGGACATCATGAAGCCCCTT |
| GAGCATCTGACTTCTGGCTAATAAAGGAAATTTATTTTCATTGCAATAGTGTGTTGGAATTTTTTGTGTCTCTCA |
| CTCGGAAGGACATATGGGAGGGCAAATCATTTAAAACATCAGAATGAGTATTTGGTTTAGAGTTTGGCAACAT |
| ATGCCCATATGCTGGCTGCCATGAACAAAGGTTGGCTATAAAGAGGTCATCAGTATATGAAACAGCCCCCTGC |
| TGTCCATTCCTTTATTCCATAGAAAAGCCTTGACTTGAGGTTAGATTTTTTTTATATTTTGTTTTGTGTTATTTTTTT |
| CTTTAACATCCCTAAAATTTTCCTTACATGTTTTACTAGCCAGATTTTTCCTCCTCTCCTGACTACTCCCAGTCATA |
| GCTGTCCCTCTTCTCTTATGGAGATCCCTCGACGGATCGGCCGCAATTCGTAATCATGTCATAGCTGTTTCCTGT |
| GTGAAATTGTTATCCGCTCACAATTCCACACAACATACGAGCCGGAAGCATAAAGTGTAAAGCCTGGGGTGCC |
| TAATGAGTGAGCTAACTCACATTAATTGCGTTGCGCTCACTGCCCGCTTTCCAGTCGGGAAACCTGTCGTGCCA |
| GCTGCATTAATGAATCGGCCAACGCGCGGGGAGAGGCGGTTTGCGTATTGGGCGCTCTTCCGCTTCCTCGCTC |
| ACTGACTCGCTGCGCTCGGTCGTTCGGCTGCGGCGAGCGGTATCAGCTCACTCAAAGGCGGTAATACGGTTAT |
| CCACAGAATCAGGGGATAACGCAGGAAAGAACATGTGAGCAAAAGGCCAGCAAAAGGCCAGGAACCGTAAA |
| AAGGCCGCGTTGCTGGCGTTTTTCCATAGGCTCCGCCCCCCTGACGAGCATCACAAAAATCGACGCTCAAGTCA |
| GAGGTGGCGAAACCCGACAGGACTATAAAGATACCAGGCGTTTCCCCCTGGAAGCTCCCTCGTGCGCTCTCCT |
| GTTCCGACCCTGCCGCTTACCGGATACCTGTCCGCCTTTCTCCCTTCGGGAAGCGTGGCGCTTTCTCATAGCTCA |
| CGCTGTAGGTATCTCAGTTCGGTGTAGGTCGTTCGCTCCAAGCTGGGCTGTGTGCACGAACCCCCCGTTCAGCC |
| CGACCGCTGCGCCTTATCCGGTAACTATCGTCTTGAGTCCAACCCGGTAAGACACGACTTATCGCCACTGGCAG |
| CAGCCACTGGTAACAGGATTAGCAGAGCGAGGTATGTAGGCGGTGCTACAGAGTTCTTGAAGTGGTGGCCTA |
| ACTACGGCTACACTAGAAGAACAGTATTTGGTATCTGCGCTCTGCTGAAGCCAGTTACCTTCGGAAAAAGAGT |
| TGGTAGCTCTTGATCCGGCAAACAAACCACCGCTGGTAGCGGTGGTTTTTTTGTTTGCAAGCAGCAGATTACGC |
| GCAGAAAAAAAGGATCTCAAGAAGATCCTTTGATCTTTTCTACGGGGTCTGACGCTCAGTGGAACGAAAACTC |
| ACGTTAAGGGATTTTGGTCATGAGATTATCAAAAAGGATCTTCACCTAGATCCTTTTAAATTAAAAATGAAGTT |
| TTAAATCAATCTAAAGTATATATGAGTAAACTTGGTCTGACAGTTACCAATGCTTAATCAGTGAGGCACCTATC |
| TCAGCGATCTGTCTATTTCGTTCATCCATAGTTGCCTGACTCCCCGTCGTGTAGATAACTACGATACGGGAGGG |
| CTTACCATCTGGCCCCAGTGCTGCAATGATACCGCGAGACCCACGCTCACCGGCTCCAGATTTATCAGCAATAA |
| ACCAGCCAGCCGGAAGGGCCGAGCGCAGAAGTGGTCCTGCAACTTTATCCGCCTCCATCCAGTCTATTAATTG |
| TTGCCGGGAAGCTAGAGTAAGTAGTTCGCCAGTTAATAGTTTGCGCAACGTTGTTGCCATTGCTACAGGCATC |
| GTGGTGTCACGCTCGTCGTTTGGTATGGCTTCATTCAGCTCCGGTTCCCAACGATCAAGGCGAGTTACATGATC |
| CCCCATGTTGTGCAAAAAAGCGGTTAGCTCCTTCGGTCCTCCGATCGTTGTCAGAAGTAAGTTGGCCGCAGT |
| GTTATCACTCATGGTTATGGCAGCACTGCATAATTCTCTTACTGTCATGCCATCCGTAAGATGCTTTTCTGTGAC |
| TGGTGAGTACTCAACCAAGTCATTCTGAGAATAGTGTATGCGGCGACCGAGTTGCTCTTGCCCGGCGTCAATA |
| CGGGATAATACCGCGCCACATAGCAGAACTTTAAAAGTGCTCATCATTGGAAAACGTTCTTCGGGGCGAAAAC |
| TCTCAAGGATCTTACCGCTGTTGAGATCCAGTTCGATGTAACCCACTCGTGCACCCAACTGATCTTCAGCATCTT |
| TTACTTTCACCAGCGTTTCTGGGTGAGCAAAAACAGGAAGGCAAAATGCCGCAAAAAAGGGAATAAGGGCGA |
| CACGGAAATGTTGAATACTCATACTCTTCCTTTTTCAATATTATTGAAGCATTTATCAGGGTTATTGTCTCATGA |
| GCGGATACATATTTGAATGTATTTAGAAAAATAAACAAATAGGGGTTCCGCGCACATTTCCCCGAAAAGTGCC |
| ACCTAAATTGTAAGCGTTAATATTTTGTTAAAATTCGCGTTAAATTTTTGTTAAATCAGCTCATTTTTTAACCAAT |
| AGGCCGAAATCGGCAAAATCCCTTATAAATCAAAAGAATAGACCGAGATAGGGTTGAGTGTTGTTCCAGTTTG |
| GAACAAGAGTCCACTATTAAAGAACGTGGACTCCAACGTCAAAGGGCGAAAAACCGTCTATCAGGGCGATGG |
| CCCACTACGTGAACCATCACCCTAATCAAGTTTTTTGGGGTCGAGGTGCCGTAAAGCACTAAATCGGAACCCTA |
| AAGGGAGCCCCCGATTTAGAGCTTGACGGGGAAAGCCGGCGAACGTGGCGAGAAAGGAAGGGAAGAAAGC |
| GAAAGGAGCGGGCGCTAGGGCGCTGGCAAGTGTAGCGGTCACGCTGCGCGTAACCACCACACCCGCCGCGCT |
| TAATGCGCCGCTACAGGGCGCGTCCCATTCGCCATTCAGGCTGCGCAACTGTTGGGAAGGGCGATCGGTGCG |
| GGCCTCTTCGCTATTACGCCAGCTGGCGAAAGGGGGATGTGCTGCAAGGCGATTAAGTTGGGTAACGCCAGG |
| GTTTTCCCAGTCACGACGTTGTAAAACGACGGCCAGTGAGCGCGCGTAATACGACTCACTATAGGGCGAATTG |
| GAGCTCCACCGCGGTG |

| SEQ ID NO. | Type | Description |
|---|---|---|
| 1 | Nucleic acid | YFPgRNA1f primer |
| 2 | Nucleic acid | YFPgRNA1r primer |
| 3 | Nucleic acid | YFPgRNA2f primer |
| 4 | Nucleic acid | YFPgRNA2r primer |
| 5 | Nucleic acid | hMyd88gRNA1f primer |
| 6 | Nucleic acid | hMyd88gRNA1r primer |
| 7 | Nucleic acid | hMyd88gRNA2f primer |
| 8 | Nucleic acid | hMyd88gRNA2r primer |
| 9 | Nucleic acid | mMyd88gRNA1f primer |
| 10 | Nucleic acid | mMyd88gRNA1r primer |
| 11 | Nucleic acid | mMyd88gRNA2f primer |
| 12 | Nucleic acid | mMyd88gRNA2r primer |
| 13 | Nucleic acid | DDX3gRNA1f primer |
| 14 | Nucleic acid | DDX3gRNA1r primer |
| 15 | Nucleic acid | YFPf primer |
| 16 | Nucleic acid | YFPr primer |
| 17 | Nucleic acid | hMyd88f2 primer |
| 18 | Nucleic acid | hMyd88r1 primer |
| 19 | Nucleic acid | mMyd88f2 primer |
| 20 | Nucleic acid | mMyd88r2 primer |
| 21 | Nucleic acid | Flag-DDX3 primer |
| 22 | Amino acid | GAG-Cas9 fusion protein |
| 23 | Amino acid | VSV-G protein |
| 24 | Amino acid | GAG PRO POL polyprotein |
| 25 | Amino acid | BAEV-G protein |
| 26 | Nucleic acid | encoding Gag-Cas9 fusion protein |
| 27 | Nucleic acid | encoding BAEV-G |
| 28 | Nucleic acid | encoding VSV-G protein |
| 29 | Amino acid | cleavage sequence |
| 30 | Nucleic acid | encoding the cleavage sequence of SEQ ID NO. 29 |
| 31 | Amino acid | Cas9 protein |
| 32 | Nucleic acid | encoding Cas9 protein |
| 33 | Nucleic acid | HIV encapsidation construct (may be termed "p8.91") |
| 34 | Nucleic acid | encoding HIV-1 GAG-CAS9 polypeptide (may be termed "KLAP229") |
| 35 | Nucleic acid | target sequence |
| 36 | Nucleic acid | primer |
| 37 | Nucleic acid | primer |
| 38 | Nucleic acid | target sequence |
| 39 | Nucleic acid | primer |
| 40 | Nucleic acid | primer |

The invention claimed is:

1. A method of producing a retrovirus-derived particle comprising a Cas protein, the method comprising:
   a) providing a cell that comprises a nucleic acid sequence encoding a fusion protein comprising (i) a GAG protein and (ii) a Cas protein;
   b) culturing the cell under conditions that allow for production of a retrovirus-derived particle; and
   c) separating the retrovirus-derived particle from the cell, wherein the retrovirus-derived particle comprises the Cas protein contained within said particle.

2. The method of claim 1, wherein the cell comprises a nucleic acid sequence encoding the GAG protein and a nucleic acid sequence encoding a viral envelope protein, wherein the viral envelope protein is from the same virus as the GAG protein.

3. The method of claim 1, wherein the cell comprises a nucleic acid sequence encoding the GAG protein and a nucleic acid sequence encoding a viral envelope protein, wherein the viral envelope protein is a pseudotyped protein that is from a different virus than the GAG protein.

4. The method of claim 3, wherein the pseudotyped protein is a glycoprotein derived from another enveloped virus.

5. The method of claim 3, wherein the Cas protein is Cas9 or a homolog or derivative thereof.

6. The method of claim 3, wherein the Cas protein is Cas9.

7. The method of claim 3, wherein the fusion protein is a cleavable fusion protein comprising a proteolysis cleavage site located between the GAG protein and the Cas protein.

8. The method of claim 7, wherein the retrovirus-derived particle comprises the Cas protein as a free Cas protein resulting from the cleavage of the cleavable fusion protein.

9. A method of producing a retrovirus-derived particle comprising a Cas protein, the method comprising:
   a) providing a cell that comprises a nucleic acid sequence encoding a GAG-Cas9 fusion protein;
   b) culturing the cell under conditions that allow for production of a retrovirus-derived particle; and
   c) separating the retrovirus-derived particle from the cell, wherein the retrovirus-derived particle comprises the Cas9 protein contained within said particle.

10. The method of claim 9, wherein the GAG-Cas9 fusion protein is a cleavable fusion protein comprising a proteolysis cleavage site located between GAG and Cas9.

11. The method of claim 10, wherein the retrovirus-derived particle comprises the Cas9 protein as a free Cas9 protein within the particle resulting from the cleavage of the cleavable fusion protein.

12. The method of claim 9, wherein the cell comprises a nucleic acid sequence encoding one or more viral structural protein that is a Gag-Pro-Pol fusion protein.

13. The method of claim 12, wherein the cell comprises a nucleic acid sequence encoding one or more viral envelope protein that is a pseudotyped protein from the same virus as the one or more viral structural protein.

14. The method of claim 9, wherein the cell comprises a nucleic acid sequence encoding one or more viral structural protein and one or more viral envelope protein that is a pseudotyped protein that is from a different virus than the one or more viral structural protein.

15. The method of claim 14, wherein the pseudotyped protein comprises a viral envelope protein selected from the group consisting of a VSV-G protein, a Measles virus F protein, an Influenza virus HA protein, a Moloney virus MLV-A protein, a Moloney virus MLV-E protein, a Baboon Endogenous retrovirus (BAEV) envelope protein, an Ebola virus glycoprotein and foamy virus envelope protein, or a combination thereof.

16. The method of claim 1, wherein the retrovirus-derived particle is devoid of any encoding nucleic acids.

17. The method of claim 9, wherein the retrovirus derived particle is devoid of any encoding nucleic acids.

18. The method of claim 1, wherein the retrovirus-derived particle is a lentivirus-derived particle.

19. The method of claim 1, wherein the retrovirus-derived particle is selected from the group consisting of Moloney murine leukemia virus-derived vector particles, Bovine immunodeficiency virus-derived particles, Simian immunodeficiency virus-derived vector particles, Feline immunodeficiency virus-derived vector particles, Human immunodeficiency virus-derived vector particles, Equine infection anemia virus-derived vector particles, Caprine arthritis encephalitis virus-derived vector particles, and Baboon endogenous virus-derived vector particles.

20. The method of claim 9, wherein the retrovirus-derived particle is a lentivirus-derived particle.

21. The method of claim 9, wherein the retrovirus-derived particle is selected from the group consisting of Moloney murine leukemia virus-derived vector particles, Bovine immunodeficiency virus-derived particles, Simian immunodeficiency virus-derived vector particles, Feline immunodeficiency virus-derived vector particles, Human immunodeficiency virus-derived vector particles, Equine infection anemia virus-derived vector particles, Caprine arthritis encephalitis virus-derived vector particles, and Baboon endogenous virus-derived vector particles.

22. The method of claim 1, wherein the nucleic acid sequence encoding the fusion protein is placed under the control of a regulatory sequence for over-expression of the Cas protein in the cell.

23. The method of claim 9, wherein the nucleic acid sequence encoding the GAG-Cas9 fusion protein is placed under the control of a regulatory sequence for over-expression of the Cas9 protein in the cell.

24. The method of claim 1, wherein the cell further comprises one or more CRISPR-Cas guide RNAs, wherein the retrovirus-derived particle comprises the Cas protein complexed with a CRISPR-Cas system guide RNA.

25. The method of claim 24, wherein the CRISPR-Cas system guide RNA comprises a) a first CRISPR-Cas system guide RNA that hybridizes with a first target sequence of a target nucleic acid, and b) a second CRISPR-Cas system guide RNA that hybridizes with a second target sequence of said target nucleic acid.

26. The method of claim 25, wherein the retrovirus-derived particles comprise a CRISPR-Cas ribonucleoprotein complex comprising a complex of the Cas protein with a guide RNA.

27. The method of claim 9, wherein the cell further comprises one or more CRISPR-Cas guide RNAs, wherein the retrovirus-derived particle comprises the Cas9 protein complexed with a CRISPR-Cas system guide RNA.

28. The method of claim 27, wherein the CRISPR-Cas system guide RNA comprises a) a first CRISPR-Cas system guide RNA that hybridizes with a first target sequence of a target nucleic acid, and b) a second CRISPR-Cas system guide RNA that hybridizes with a second target sequence of said target nucleic acid.

29. The method of claim 27, wherein the retrovirus-derived particle comprises a CRISPR-Cas9 ribonucleoprotein complex which is a complex of the Cas9 protein with a guide RNA.

30. The method of claim 24, wherein the cell further comprises one or more targeting nucleic acids.

31. The method of claim 27, wherein the cell further comprises one or more targeting nucleic acids.

32. The method of claim 1, wherein the cell is a mammalian cell.

33. The method of claim 9, wherein the cell is a mammalian cell.

34. A virus-derived particle produced by the method of claim 1.

35. A virus-derived particle produced by the method of claim 8.

36. A virus-derived particle produced by the method of claim 9.

37. A virus-derived particle produced by the method of claim 11.

38. The method of claim 1, wherein the cell comprises a nucleic acid sequence encoding one or more viral structural protein that is a Gag-Pro-Pol fusion protein.

39. The method of claim 1, wherein the Cas protein is Cpf1.

40. The method of claim 3, wherein the pseudotyped protein comprises a viral envelope protein selected from the group consisting of a VSV-G protein, a Measles virus F protein, an Influenza virus HA protein, a Moloney virus MLV-A protein, a Moloney virus MLV-E protein, a Baboon Endogenous retrovirus (BAEV) envelope protein, an Ebola virus glycoprotein and foamy virus envelope protein, or a combination thereof.

41. The method of claim 1, wherein the retrovirus-derived particle is a Moloney murine leukemia virus-derived vector particle.

42. The method of claim 1, wherein the retrovirus-derived particle is a Human immunodeficiency virus-derived vector particle.

43. The method of claim 9, wherein the retrovirus-derived particle is a Moloney murine leukemia virus-derived vector particle.

44. The method of claim 9, wherein the retrovirus-derived particle is a Human immunodeficiency virus-derived vector particle.

45. The method of claim 1, wherein the GAG protein is derived from Moloney murine leukemia virus.

46. The method of claim 1, wherein the GAG protein is derived from Human immunodeficiency virus.

47. The method of claim 9, wherein GAG is derived from Moloney murine leukemia virus.

48. The method of claim 9, wherein GAG is derived from Human immunodeficiency virus.

* * * * *